(12) United States Patent
Mack et al.

(10) Patent No.: US 8,283,363 B2
(45) Date of Patent: *Oct. 9, 2012

(54) CARBOXAMIDE COMPOUNDS AND THEIR USE AS CALPAIN INHIBITORS

(75) Inventors: Helmut Mack, Ludwigshafen (DE);
Andreas Kling, Ludwigshafen (DE);
Katja Jantos, Ludwigshafen (DE);
Achim Moeller, Grunstadt (DE);
Wilfried Hornberger, Ludwigshafen (DE); Charles W. Hutchins, Green Oaks, IL (US)

(73) Assignees: Abbott Laboratories, Abbott Park, IL (US); Abbott GmbH & Co. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/940,339

(22) Filed: Nov. 5, 2010

(65) Prior Publication Data

US 2011/0086879 A1  Apr. 14, 2011

Related U.S. Application Data

(63) Continuation-in-part of application No. 12/768,226, filed on Apr. 27, 2010.

(60) Provisional application No. 61/289,753, filed on Dec. 23, 2009, provisional application No. 61/176,138, filed on May 7, 2009.

(51) Int. Cl.
| | |
|---|---|
| *A61P 35/00* | (2006.01) |
| *A61P 25/00* | (2006.01) |
| *A61P 29/00* | (2006.01) |
| *A61P 31/00* | (2006.01) |
| *A61P 9/00* | (2006.01) |
| *A61P 27/02* | (2006.01) |
| *A61K 31/425* | (2006.01) |
| *A61K 31/451* | (2006.01) |
| *A61K 31/4015* | (2006.01) |
| *A61K 31/4439* | (2006.01) |
| *A61K 31/4164* | (2006.01) |
| *C07D 211/40* | (2006.01) |
| *C07D 207/12* | (2006.01) |
| *C07D 401/02* | (2006.01) |
| *C07D 233/02* | (2006.01) |
| *C07D 275/03* | (2006.01) |

(52) U.S. Cl. ........ 514/315; 514/343; 514/372; 514/392; 514/423; 546/242; 548/213; 548/316.4; 548/518; 548/537

(58) Field of Classification Search ........................ None
See application file for complete search history.

(56) References Cited

FOREIGN PATENT DOCUMENTS
| | | |
|---|---|---|
| WO | 98/16512 | 4/1998 |
| WO | 98/25883 | 6/1998 |
| WO | 98/25899 | 6/1998 |
| WO | 99/17775 | 4/1999 |
| WO | 99/54294 | 10/1999 |
| WO | 99/54304 | 10/1999 |
| WO | 99/54305 | 10/1999 |
| WO | 99/54310 | 10/1999 |
| WO | 99/54320 | 10/1999 |
| WO | 99/61423 | 12/1999 |
| WO | 03/080182 | 10/2003 |
| WO | 2007/016589 | 2/2007 |
| WO | 2008/080969 | 7/2008 |
| WO | 2008/106130 | 9/2008 |

OTHER PUBLICATIONS

Liebergurg, caplus an 2005:1123789.*
Kato et al., caplus an 1973:84162.*
Neffe, A.T., et al., "Developments in the design and synthesis of calpain inhibitors," Current Opinion in Drug Discovery & Development, 2005, vol. 8, Issue 6, pp. 684-700.
Saez, M.E., Drug Discovery Today, 2006,11 (19/20), pp. 917-923.
Suzuki, K., et al., Biol. Chem. Hoppe-Seyler 1995, 376(9), pp. 523-529.
Barrett, M.J., et al. Life Sci. 1991, 48, pp. 1659-1669.
Wang, K., et al., Trends in Pharmacal. Sci. 1994, 15, pp. 412-419.
Medana, M., et al., Neuropath. and Appl. Neurobiol. 2007, 33, pp. 179-192.
Hong, Seung-Chyul, et al., Stroke 1994, 25(3), pp. 663-669.
Bartus, R.T., et al. Neurological Res. 1995, 17, pp. 249-258.
Saatman, K.E., et al. Proc. Natl. Acad. Sci. USA 1996, 93, pp. 3428-3433.
Edelstein, C.L., et al., Proc. Natl. Acad. Sci. USA 1995, 92, pp. 7662-7666.
Yoshida, Ken Ischi, et al., Jap. Circ. J. 1995,59(1), pp. 40-48.
Li, X., et al., Mol. Biochem. Parasitol. 2007,155(1), pp. 26-32.
Peltier, J., et al., J. Am. Soc. Nephrol. 2006,17, pp. 3415-3423.
Groshong, J.S., et al., J. Clin. Invest. 2007,117(10), pp. 2903-2912.
Takano, J., et al., J. Biol. Chem. 2005, 280(16), pp. 16175-16184.
Spencer, M.J., et al., Hum. Mol. Gen. 2002, 11 (21), pp. 2645-2655.
Patrick, G., et al. Nature 1999, 402, pp. 615-622.
Monaco, E.A., et al., Curro Alzheimer Res. 2004, 1(1), pp. 33-38.
Higuchi, et al., J. Biol. Chem. 2005, 280(15), pp. 15229-15237.
Mokhtarian, F., et al. J. Neuroimrnunology 2006,180, pp. 135-146.
Park, et al., J. Neurosci. 2005, 25, pp. 5365-5375.
Higaki, J., et al., Neuron 1995, 14, pp. 651-659.
Watanabe, N., et al., Cytokine 1994, 6(6), pp. 597-601.
Shiba, E., et al. 20th Meeting Int. Association Breast Cancer Res. Sandal Jp., Sep. 25-28, 1994, Int. J. Oncol. S (Suppl.), 381.
O'Donnell, et al., J. Neurosci. 2006, 26(3), pp. 981-990.
Teranishi, Et Al.., Biochem. Biophys. Res. Comm. 2003, 303(3), pp. 940-946.
Kunz, et al., Pain 2004,110, pp. 409-418.
Wang, et al., Brain 2004, 127, pp. 671-679.
Cuzzocrea, et ai, American Journal of Pathology 2000, 157(6), pp. 2065-2079.
Shi, Y., et al., Am. J. Physiol. Renal Physiol. 2000, 279, pp. 509-517.
Dnyanmote, Et Al.., Toxicology and Applied Pharmacology 2006, 215, pp. 146-157.
Chatterjee, P., et al., Biochem. Pharmacol. 2005, 7, pp. 1121-1131.
Carragher, N. O., Curr. Pharm. Design 2006,12, pp. 615-638.
Wang, K.K., et al., Drugs of the Future, 1998, 23(7), pp. 741-749 and Trends in Pharmacol. Sci. 1994, 15, pp. 412-419.
Fehrentz, J.A., Synthesis 1983, pp. 676-678.
Pietsch, M. et al. Current Topics in Medicinal Chemistry, 2010, 10, pp. 270-293.

* cited by examiner

*Primary Examiner* — Sun Jae Loewe
(74) *Attorney, Agent, or Firm* — Lisa V. Mueller; Michael Best & Friedrich LLP

(57) ABSTRACT

The present invention relates to novel carboxamide compounds and their use for the manufacture of a medicament. The carboxamide compounds are inhibitors of calpain (calcium dependant cysteine proteases). The invention therefore also relates to the use of these carboxamide compounds for treating a disorder associated with an elevated calpain activity.

The carboxamide compounds are compounds of the general formula I

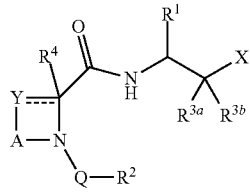

(I)

in which $R^1$, $R^2$, $R^{3a}$, $R^{3b}$, $R^4$, Q, Y, A and X have the meanings mentioned in the claims and the description, the tautomers thereof and the pharmaceutically suitable salts thereof. In particular, the compounds have the general formula Ia and Ib

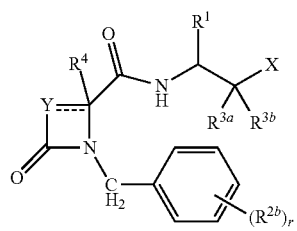

(Ia)

-continued

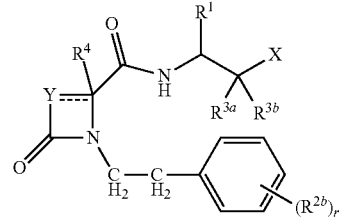

(Ib)

in which $R^1$, r, $R^{2b}$, $R^{3a}$, $R^{3b}$, $R^4$, Y and X have the meanings mentioned in the claims, including the tautomers thereof and the pharmaceutically suitable salts thereof. Of these compounds those are preferred wherein Y is a moiety $CH_2$—$CH_2$, $CH_2$—$CH_2$—$CH_2$, $N(R^{y\#})$—$CH_2$, $N(R^{y\#})$—$CH_2$—$CH_2$ or CH=CH—CH=, each optionally having 1 or 2 H-atoms replaced with identical or different radicals $R^y$, wherein $R^y$ and $R^{y\#}$ have the meanings mentioned in the claims.

21 Claims, No Drawings

CARBOXAMIDE COMPOUNDS AND THEIR USE AS CALPAIN INHIBITORS

RELATED APPLICATION INFORMATION

This application is a continuation-in-part of U.S. application Ser. No. 12/768,226, filed on Apr. 27, 2010 which claims the benefit of U.S. Application No. 61/176,138, filed May 7, 2009 and U.S. Application No. 61/289,753, filed Dec. 23, 2009, the contents of each of which are herein incorporated by reference.

The present invention relates to novel carboxamide compounds and their use for the manufacture of a medicament. The carboxamide compounds are inhibitors of calpain (calcium dependant cysteine proteases). The invention therefore also relates to the use of these carboxamide compounds for treating a disorder associated with an elevated calpain activity.

Calpains are intracellular, proteolytic enzymes from the cysteine protease group and are found in many cells. The enzyme calpain is activated by elevated calcium concentration, with a distinction being made between calpain I or μ-calpain, which is activated by n-molar concentrations of calcium ions, and calpain II or m-calpain, which is activated by m-molar concentrations of calcium ions. Currently, further calpain isoenzymes are also postulated (M. E. Saez et al.; Drug Discovery Today 2006, 11 (19/20), pp. 917-923; K. Suzuki et al., Biol. Chem. Hoppe-Seyler 1995, 376 (9), pp. 523-529).

Calpains play an important role in various physiological processes. These processes include the cleavage of different regulatory proteins such as protein kinase C, cytoskeletal proteins such as MAP 2 and spectrin, and muscle proteins, protein degradation in rheumatoid arthritis, proteins in the activation of platelets, neuropeptide metabolism, proteins in mitosis, and others which are listed in: M. J. Barrett et al., Life Sci. 1991, 48, pp. 1659-69; K. Wang et al., Trends in Pharmacol. Sci. 1994, 15, pp. 412-419.

Elevated calpain levels have been measured in various pathophysiological processes, for example: ischemias of the heart (e.g. myocardial infarction), the kidney, the lung, the liver or the central nervous system (e.g. stroke), inflammations, muscular dystrophies, cataracts of the eyes, diabetes, HIV disorders, injuries to the central nervous system (e.g. brain trauma), Alzheimer's, Huntington's, Parkinson's diseases, multiple sclerosis etc. (see K. K. Wang, above) and infectious diseases such as malaria (I. M. Medana et al., Neuropath. and Appl. Neurobiol. 2007, 33, pp. 179-192). It is assumed that there is a connection between these diseases and generally or persistently elevated intracellular calcium levels. This results in calcium-dependent processes becoming hyperactivated and no longer being subject to normal physiological control. A corresponding hyperactivation of calpains can also trigger pathophysiological processes.

For this reason, it was postulated that inhibitors of calpain could be of use for treating these diseases. This postulate was confirmed by a variety of investigations. Thus, Seung-Chyul Hong et al., Stroke 1994, 25 (3), pp. 663-669, and R. T. Bartus et al., Neurological Res. 1995, 17, pp. 249-258, have demonstrated that calpain inhibitors have a neuroprotective effect in acute neurodegenerative impairments or ischemias such as occur after cerebral stroke. K. E. Saatman et al., Proc. Natl. Acad. Sci. USA 1996, 93, pp. 3428-3433, describe that following experimental brain trauma, calpain inhibitors also improved recovery from the memory performance deficits and neuromotor impairments. C. L. Edelstein et al., Proc. Natl. Acad. Sci. USA 1995, 92, pp. 7662-6, found that calpain inhibitors have a protective effect on hypoxia-damaged kidneys. Yoshida, Ken Ischi et al., Jap. Circ. J. 1995, 59 (1), pp. 40-48, pointed out that calpain inhibitors had favorable effects following cardiac damage which was produced by ischemia or reperfusion. The calpain inhibitor BDA-410 delayed the progression of malaria infection in a mouse model of malaria pathogenesis as shown by X. Li et al., Mol. Biochem. Parasitol. 2007, 155 (1), pp 26-32.

More recent studies have shown in calpastatin transgenic animals that the expression of the natural inhibitor of calpain significantly attenuates the pathophysiological effects of activated calpain in experimental glomerulonephritis shown by J. Peltier et al., J. Am. Soc. Nephrol. 2006, 17, pp. 3415-3423, in cardiovascular remodeling in angiotensin II-induced hypertension, in impaired synaptic transmission in slow-channel congenital myasthenic syndrome shown by J. S. Groshong et al., J. Clin. Invest. 2007, 117 (10), pp 2903-2912, in excitotoxic DNA fragmentation via mitochondrial pathways shown by J. Takano et al., J. Biol. Chem. 2005, 280 (16), pp 16175-16184, and in necrotic processes in dystrophic muscles shown by M. J. Spencer et al., Hum. Mol. Gen. 2002, 11(21), pp 2645-2655.

It has been shown in recent years that both the function and the metabolism of a number of important proteins involved in the development of Alzheimer's disease are modulated by calpain. Various external influences such as, for example, excitotoxins, oxidative stress or else the action of amyloid protein lead to hyperactivation of calpain in the nerve cell, causing, as cascade, a dysregulation of the CNS-specific kinase cdk5 and subsequently a hyperphosphorylation of the so-called tau protein. Whereas the actual task of the tau protein consists of stabilizing the microtubules and thus the cytoskeleton, phosphorylated tau is no longer able to fulfill this function; the cytoskeleton collapses, axonal transport of matter is impaired and thus eventually the nerve cell degenerates (G. Patrick et al., Nature 1999, 402, pp 615-622; E. A. Monaco et al., Curr. Alzheimer Res. 2004, 1 (1), pp 33-38). Accumulation of phosphorylated tau additionally leads to the formation of so-called neurofibrillary tangles (NFTs) which, together with the well-known amyloid plaques, represent a pathological hallmark of Alzheimer's disease. Similar changes in the tau protein, generally referred to important feature of as tauopathies are also observed in other (neuro) degenerative disorders such as, for example, following stroke, inflammations of the brain, Parkinsonism, in normal-pressure hydrocephalus and Creutzfeldt-Jakob disease.

The involvement of calpain in neurodegenerative processes has been demonstrated in transgenic mice with the aid of calpastatin, a specific and natural inhibitor of calpains (Higuchi et al.; J. Biol. Chem. 2005, 280 (15), pp 15229-15237). It was possible with the aid of a calpain inhibitor to reduce markedly the clinical signs of acute autoimmune encephalomyelitis in a mouse model of multiple sclerosis (F. Mokhtarian et al.; J. Neuroimmunology 2006, 180, pp 135-146). It has further been shown that calpain inhibitors on the one hand block the Ab-induced degeneration of neurons (Park et al.; J. Neurosci. 2005, 25, pp 5365-5375), and in addition reduce the release of the β-amyloid precursor protein (β APP) (J. Higaki et al., Neuron 1995, 14, pp 651-659). With this background, calpain inhibitors having sufficient CNS availability represent a novel therapeutic principle for the treatment of neurodegenerative disorders in general and in particular also of Alzheimer's disease.

The release of interleukin-1α is likewise inhibited by calpain inhibitors (N. Watanabe et al., Cytokine 1994, 6(6), pp 597-601). It has additionally been found that calpain inhibitors show cytotoxic effects on tumor cells (E. Shiba et al. 20th Meeting Int. Ass. Breast Cancer Res., Sendai Jp., 1994, 25.-28. Sep., Int. J. Oncol. S(Suppl.), 1994, 381).

The involvement of calpain in HIV disorders has only recently been shown. Thus, it has been demonstrated that the HIV-induced neurotoxicity is mediated by calpain (O'Donnell et al.; J. Neurosci. 2006, 26 (3), pp 981-990). Calpain involvement in the replication of the HIV virus has also been shown (Teranishi et al.; Biochem. Biophys. Res. Comm 2003, 303 (3), pp 940-946).

Recent investigations indicate that calpain plays a part in so-called nociception, the perception of pain. Calpain inhibitors showed a distinctly beneficial effect in various preclinically relevant models of pain, e.g. in the thermally induced hyperalgesia in rats (Kunz et al., Pain 2004, 110, pp 409-418), in Taxol-induced neuropathy (Wang et al.; Brain 2004, 127, pp 671-679) and in acute and chronic inflammatory processes (Cuzzocrea et al.; American Journal of Pathololgy 2000, 157 (6), pp 2065-2079).

The involvement of calpain in the development of kidney diseases, such as chronic kidney diseases, e.g. diabetic nephropathy, has also been shown recently. Thus, it has been demonstrated by Y. Shi et al. in animal models that the natural calpain inhibitor calpastatin is down regulated during renal ischemia reperfusion (Am. J. Physiol. Renal Physiol. 2000, 279, pp 509-517). Furthermore, A. Dnyanmote et al., Toxicology and Applied Pharmacology 2006, 215, pp 146-157, have shown that inhibition of calpain via overexpression of calpastatin reduces the progression of DCVC-induced renal injury in a model of acute renal failure. In addition, Peltier et al. have demonstrated that calpain activation and secretion promotes glomerular injury in experimental glomerulonephritis (J. Am. Soc. Nephrol. 2006, 17, pp 3415-3423). It has also been shown that calpain inhibitors reduce renal dysfunction and injury caused by renal ischemia-reperfusion and thus may be useful in enhancing the tolerance of the kidney against renal injury associated with aortovascular surgery or renal transplantation (P. Chatterjee et al., Biochem. Pharmacol. 2005, 7, pp 1121-1131).

Calpain has also been identified as a central mediator essential for parasitic activity. Parasites like *Plasmodium falciparum* and *Toxoplasma gondii* exploit host cell calpains to facilitate escape from the intracellular parasitophorous vacuole and/or host plasma membrane Inhibition of calpain-1 in hypotonically lysed and resealed erythrocytes prevented the escape of *P. falciparum* parasites, which was restored by adding purified calpain-1. Similarly, efficient egress of *T. gondii* from mammalian fibroblasts was blocked by either small interfering RNA-mediated suppression or genetic deletion of calpain activity and could be restored by genetic complementation (D. Greenbaum et al., Science 324, 794 (2009). Because parasites that fail to escape from their host cells are unable to proliferate, suggesting a strategy for anti-parasitic therapeutics. Pharmacological inhibition of calpain has been shown to exert anti-malarial activity, and hence presents a novel strategy for anti-parasitic strategy such as diseases caused by protest infections like malaria or toxoplasmosis (Li et al., *Mol Biochem Parasitol.* 2007; 155(1): 26-32; Jung et al. Archives of Pharmacal Research (2009), 32(6), 899-906, Chandramohanadas et al. Science (2009), 324, 794).

Further possible applications of calpain inhibitors are detailed in: M. Pietsch et al. Current Topics in Medicinal Chemistry, 2010, 10, 270-293; M. E. Saez et al., Drug Discovery Today 2006, 11 (19/20), pp 917-923; N, O. Carragher, Curr. Pharm. Design 2006, 12, pp 615-638; K. K. Wang et al., Drugs of the Future 1998, 23 (7), pp 741-749; and Trends in Pharmacol. Sci. 1994, 15, pp. 412-419.

With the calpain inhibitors described to date a general distinction is made between irreversible and reversible inhibitors, and peptide and non-peptide inhibitors.

Irreversible inhibitors are usually alkylating substances. They have the disadvantage that they firstly react unselectively and/or are unstable in the body. Thus, corresponding inhibitors often show unwanted side effects such as toxicity, and application thereof is therefore markedly restricted. The irreversible inhibitors include for example epoxides such as E64, α-halo ketones, and disulfides.

A large number of known reversible calpain inhibitors are peptide aldehydes which are derived in particular from di- or tripeptides such as, for example, Z-Val-Phe-H (MDL 28170). Derivatives and prodrugs structurally derived from aldehydes are also described, especially corresponding acetals and hemiacetals (e.g. hydroxytetrahydro-furans, hydroxyoxazolindines, hydroxymorpholines and the like), but also imines or hydrazones. However, under physiological conditions, peptide aldehydes and related compounds usually have the disadvantage that, owing to their reactivity, they are frequently unstable, are rapidly metabolized and are prone to unspecific reactions which may likewise cause toxic effects (J. A. Fehrentz and B. Castro, *Synthesis* 1983, pp 676-78).

In recent years, a number of non-peptide carboxamides having a β-keto function in the amine moiety and inhibiting calpain have been described. Thus, WO-98/16512 describes 3-amino-2-oxo carboxylic acid derivatives whose amino group is amidated with a 4-piperidinecarboxylic acid compound. WO-99/17775 describes similar compounds which are amidated with a quinolinecarboxylic acid. WO-98/25883, WO-98/25899 and WO-99/54294 describe 3-amino-2-oxo carboxylic acid derivatives whose amino group is amidated with a substituted benzoic acid. WO-99/61423 describes 3-amino-2-oxo carboxylic acid derivatives whose amino group is amidated with an aromatic carboxylic acid carrying a tetrahydroquinoline/isoquinoline and 2,3-dihydroindole/isoindole residue Similar compounds in which the aromatic carboxylic acid residue carries a heterocyloalkyl radical or (hetero)aryl radical which is optionally connected via a linker are described in WO-99/54320, WO-99/54310, WO-99/54304 and WO-99/54305. Likewise, WO-08/080,969 describes nicotinamides of 3-amino-2-oxo carboxylic acid derivatives that in position 2 of the pyridine ring are linked to a substituted pyrazole via a nitrogen atom. WO-03/080182 describes the use of the aforementioned amides for the treatment of pulmonary diseases. The nonpeptide calpain inhibitors mentioned therein also have a number of disadvantages, in particular a low or absent selectivity in respect of related cysteine proteases, such as various cathepsins, likewise possibly leading to unwanted side effects.

WO-07/016,589 and WO-08/106,130 describe 2-oxo carboxylic acid derivatives carrying a N-acylated 2-pyrrolidinecarboxylamido group in the 3-position. Also disclosed is their use for treating hepatitis C virus infections.

The present invention is thus based on the object of providing compounds which inhibit, in particular selectively, calpain even at low serum concentrations. The compounds were intended in particular to display a high selectivity in relation to the inhibition of calpain, i.e. inhibit other cystein proteases, e.g. cathepsin, not at all or only at higher concentrations.

This object and further objects are achieved by the carboxamide compounds of the general formula I described below, the tautomers thereof and the pharmaceutically suitable salts thereof:

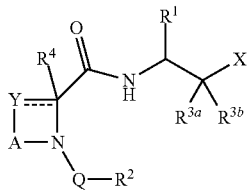

(I)

in which ⸺ indicates a single bond or, if $R^4$ is absent, indicates a double bond;

$R^1$ is hydrogen, $C_1$-$C_{10}$-alkyl, $C_2$-$C_{10}$-alkenyl, $C_2$-$C_{10}$-alkynyl, where the last 3 radicals mentioned may be partly or completely halogenated and/or have 1, 2 or 3 substituents $R^{1a}$, $C_3$-$C_7$-cycloalkyl, $C_3$-$C_7$-cycloalkyl-$C_1$-$C_4$-alkyl, where a $CH_2$ group in the cycloalkyl moiety of the last two radicals mentioned may be replaced by O, NH, or S, or two adjacent C atoms may form a double bond, where the cycloalkyl moiety may further have 1, 2, 3 or 4 radicals $R^{1b}$, aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, where aryl and hetaryl in the last 6 radicals mentioned may be unsubstituted or carry 1, 2, 3 or 4 identical or different radicals $R^{1c}$; where $R^{1a}$ is selected independently of one another from OH, SH, COOH, CN, $OCH_2COOH$, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, $COOR^{a1}$, $CONR^{a2}R^{a3}$, $SO_2NR^{a2}R^{a3}$, $-NR^{a2}-SO_2-R^{a4}$, $NR^{a2}-CO-R^{a5}$, $SO_2-R^{a4}$ and $NR^{a6}R^{a7}$, $R^{1b}$ is selected independently of one another from OH, SH, COOH, CN, $OCH_2COOH$, halogen, phenyl which optionally has 1, 2 or 3 substituents $R^{1d}$, $C_1$-$C_6$-alkyl, $C_1$-$C_6$-alkoxy, $C_1$-$C_6$-alkylthio, where the alkyl moieties in the last 3 substituents mentioned may be partly or completely halogenated and/or have 1, 2 or 3 substituents $R^{1a}$, $COOR^{b1}$, $CONR^{b2}R^{b3}$, $SO_2NR^{b2}R^{b3}$, $NR^{b2}-SO_2-R^{b4}$, $NR^{b2}-SO_2-R^{b4}$, $-CO-R^{b5}$, $SO_2-R^{b4}$ and $NR^{b6}R^{b7}$, in addition two $R^{1b}$ radicals may together form a $C_1$-$C_4$-alkylene group, or 2 $R^{1b}$ radicals bonded to adjacent C atoms of cycloalkyl may form together with the carbon atoms to which they are bonded also a benzene ring, $R^{1c}$ is selected independently of one another from OH, SH, halogen, $NO_2$, $NH_2$, CN, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the alkyl moieties in the last 4 substituents mentioned may be partly or completely halogenated and/or have 1, 2 or 3 substituents $R^{1a}$, $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 $R^{1b}$ radicals, and where 1 or 2 $CH_2$-groups in the cycloalkyl moiety may be replaced by O, NH or S, aryl, hetaryl, O-aryl, $O-CH_2$-aryl, where the last three radicals mentioned are unsubstituted in the aryl moiety or may carry 1, 2, 3 or 4 radicals $R^{1d}$, $COOR^{c1}$, $CONR^{c2}R^{c3}$, $SO_2NR^{c2}R^{c3}$, $NR^{c2}-SO_2-R^{c4}$, $NR^{c2}-CO-R^{c5}$, $SO_2-R^{c4}$, $-(CH_2)_p-NR^{c6}R^{c7}$ with p=0, 1, 2, 3, 4, 5 or 6 and $O-(CH_2)_q-NR^{c6}R^{c7}$ with q=2, 3, 4, 5 or 6; where $R^{a1}$, $R^{b1}$ and $R^{c1}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, $R^{a2}$, $R^{b2}$ and $R^{c2}$ are independently of one another H, $C_1$-$C_6$-alkyl, $C_1$-$C_6$-haloalkyl, $C_1$-$C_6$-alkyl which has 1, 2 or 3 substituents $R^{1a}$ or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1a}$, and $R^{a3}$, $R^{b3}$ and $R^{c3}$ are independently of one another H, $C_1$-$C_6$-alkyl, haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, or the two radicals $R^{a2}$ and $R^{a1}$, or $R^{b2}$ and $R^{b3}$ or $R^{c2}$ and $R^{c3}$ form together with the N atom a 3 to 7-membered, optionally substituted nitrogen heterocycle which may optionally have 1, 2 or 3 further different or identical heteroatoms from the group of O, N, S as ring members, $R^{a4}$, $R^{b4}$ and $R^{c4}$ are independently of one another $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, and $R^{a5}$, $R^{b5}$ and $R^{c5}$ have independently of one another one of the meanings mentioned for $R^{a1}$, $R^{b1}$ and $R^{c1}$, $R^{a6}$, $R^{b6}$ and $R^{c6}$ are independently of one another H, $C_1$-$C_6$-alkyl, $C_1$-$C_6$-alkoxy, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, $CO$-$C_1$-$C_6$-alkyl, $CO$-$O$-$C_1$-$C_6$-alkyl, $SO_2$-$C_1$-$C_6$-alkyl, aryl, hetaryl, O-aryl, $OCH_2$-aryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO-O-aryl, CO-O-hetaryl, CO-(aryl-$C_1$-$C_4$-alkyl), CO-O-(hetaryl-$C_1$-$C_4$-alkyl), $SO_2$-aryl, $SO_2$-hetaryl, $SO_2-$ (aryl-$C_1$-$C_4$-alkyl) or $SO_2-$ (hetaryl-$C_1$-$C_4$-alkyl), where aryl and hetaryl in the last 18 radicals mentioned are unsubstituted or have 1, 2 or 3 substituents $R^{1d}$, and $R^{a7}$, $R^{b7}$ and $R^{c7}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, or the two radicals $R^{a6}$ and $R^{a7}$, or $R^{b6}$ and $R^{b7}$ or $R^{c6}$ and $R^{c7}$ form together with the N atom a 3 to 7-membered, optionally substituted nitrogen heterocycle which may optionally have 1, 2 or 3 further different or identical heteroatoms from the group of O, N and S as ring members, or two radicals $R^{1b}$ or $R^{1c}$ bonded to adjacent C atoms form together with the C atoms to which they are bonded a 4-, 5-, 6- or 7-membered, optionally substituted carbocycle or an optionally substituted heterocycle which has 1, 2 or 3 different or identical heteroatoms from the group of O, N and S as ring members;

$R^{1d}$ is selected from halogen, OH, SH, NO$_2$, COOH, C(O)NH$_2$, CHO, CN, NH$_2$, OCH$_2$COOH, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—C(O)$C_1$-$C_6$-alkyl, and SO$_2$—$C_1$-$C_6$-alkyl or two radicals $R^{1d}$ bonded to adjacent carbon atoms may together form a moiety —O-Alk"-O— where Alk" is linear $C_1$-$C_2$-alkandiyl, which is unsubstituted or wherein 1 or 2 hydrogen atoms may be replaced by fluorine, chlorine or methyl, e.g. Alk" is CH$_2$, CF$_2$, CHF, CHCH$_3$ or C(CH$_3$)$_2$, in particular CH$_2$;

$R^2$ is $C_3$-$C_7$-cycloalkyl, where a CH$_2$ group in the cycloalkyl moiety may be replaced by O, NH, or S, or two adjacent C atoms may form a double bond, where the cycloalkyl moiety may additionally have 1, 2, 3 or 4 $R^{2a}$ radicals, aryl, or hetaryl, where aryl and hetaryl may be unsubstituted or carry 1, 2, 3 or 4 identical or different $R^{2b}$ radicals; where $R^{2a}$ has one of the meanings indicated for $R^{1b}$, and $R^{2b}$ has one of the meanings indicated for $R^{1c}$;

$R^{3a}$ and $R^{3b}$ are independently of one another hydroxy or $C_1$-$C_4$-alkoxy, or together with the carbon atom to which they are bonded are C=O or C=NR$^3$; or $R^{3a}$ and $R^{3b}$ together form a moiety S-Alk-S, O-Alk-S or O-Alk-0, wherein Alk is linear $C_2$-$C_5$-alkandiyl, which may be unsubstituted or substituted with 1, 2, 3 or 4 radicals selected from $C_1$-$C_4$-alkyl or halogen;

$R^3$ is H, $C_1$-$C_6$-alkyl, $C_1$-$C_6$-alkoxy, $C_2$-$C_6$-alkenyl, $C_3$-$C_6$-cycloalkyl, $C_3$-$C_6$-cycloalkyl-$C_1$-$C_4$-alkyl, $C_2$-$C_6$-alkenyloxy, $C_3$-$C_6$-cycloalkyloxy or $C_3$-$C_6$-cycloalkyl-$C_1$-$C_4$-alkyloxy;

$R^4$ is absent or indicates hydrogen;

A is C=O, S(=O) or S(=O)$_2$;

Q is a single bond or a moiety Alk'-Z, wherein

Z is bound to $R^2$ and selected from a single bond, O, S, S(=O), S(=O)$_2$ and NR$^q$, where $R^q$ is selected from hydrogen, $C_1$-$C_4$-alkyl and $C_1$-$C_4$-haloalkyl;

Alk' is linear $C_1$-$C_3$-alkandiyl, wherein 1, 2 or 3 hydrogen atoms may be replaced by $C_1$-$C_4$-alkyl, $C_1$-$C_4$-haloalkyl or halogen;

X is hydrogen or a radical of the formulae C(=O)—O—$R^{x1}$, C(=O)—NR$^{x2}$R$^{x3}$, C(=O)—N(R$^{x4}$)—(C$_1$-C$_6$-alkylene)-NR$^{x2}$R$^{x3}$ or C(=O)—N(R$^{x4}$)NR$^{x2}$R$^{x3}$, in which $R^{x1}$ is hydrogen, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, where alkyl, alkenyl, alkoxy, alkynyl, cycloalkyl, heterocycloalkyl in the last 6 radicals mentioned are unsubstituted or have 1, 2 or 3 substituents $R^{xa}$, or aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{xd}$, $R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, SO$_2$—$C_1$-$C_6$-alkyl, O—$C_1$-$C_6$-alkyl, where alkyl, alkoxy, alkenyl, alkynyl, cycloalkyl, heterocycloalkyl in the last 10 radicals mentioned are unsubstituted or have 1, 2 or 3 substituents $R^{xa}$, aryl, O-aryl, O—CH$_2$-aryl, hetaryl, O—CH$_2$-hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O—(hetaryl-$C_1$-$C_4$-alkyl), SO$_2$-aryl, SO$_2$-hetaryl, SO$_2$—(aryl-$C_1$-$C_4$-alkyl) or SO$_2$—(hetaryl-$C_1$-$C_4$-alkyl), where aryl and hetaryl in the last 19 radicals mentioned are unsubstituted or have 1, 2 or 3 substituents $R^{xd}$, and $R^{x3}$ is H, $C_1$-$C_6$-alkyl, $C_1$-$C_6$-haloalkyl, $C_1$-$C_6$-alkyl which has 1, 2 or 3 substituents lea, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, where alkyl, alkenyl, alkoxy, alkynyl, cycloalkyl, heterocycloalkyl in the last 6 radicals mentioned are unsubstituted or have 1, 2 or 3 substituents $R^{xa}$, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{xd}$, or the two radicals $R^{x2}$ and $R^{x3}$ form together with the N atom a 3 to 7-membered nitrogen heterocycle which may optionally have 1, 2 or 3 further different or identical heteroatoms from the group of O, N, S as ring members, and which may have 1, 2 or 3 substituents $R^{xb}$, $R^{x4}$ is H, OH, CN, $C_1$-$C_6$-alkyl, $C_1$-$C_6$-haloalkyl, $C_1$-$C_6$-alkyl which has 1, 2 or 3 substituents lea, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, SO$_2$—$C_1$-$C_6$-alkyl, where alkyl, alkenyl, alkoxy, alkynyl, cycloalkyl, heterocycloalkyl in the last 9 radicals mentioned are unsubstituted or have 1, 2 or 3 substituents $R^{xa}$, aryl, O-aryl, O—CH$_2$-aryl, hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), SO$_2$-aryl, SO$_2$-hetaryl, SO$_2$—(aryl-$C_1$-$C_4$-alkyl) or SO$_2$—(hetaryl-$C_1$-$C_4$-alkyl), where aryl and hetaryl in the last 18 radicals mentioned are unsubstituted or have 1, 2 or 3 substituents $R^{xd}$, and where $R^{xa}$ has one of the meanings indicated for $R^{1a}$, $R^{xb}$ has one of the meanings indicated for $R^{1b}$, and le has one of the meanings indicated for $R^{1a}$;

Y is $CH_2$, $CH_2$—$CH_2$, $CH_2$—$CH_2$—$CH_2$, $N(R^{y\#})$—$CH_2$ or $N(R^{y\#})$—$CH_2$—$CH_2$ or, if $R^4$ is absent, a moiety $CH$=$CH$—$CH$=, where in the 6 aforementioned moieties, 1 or 2 hydrogen atoms may be replaced by a radical $R^y$, $R^y$ is selected independently of one another from hydrogen, OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{ya}$, $C_3$-$C_7$-cycloalkyl, $C_3$-$C_7$-cycloalkyl-$C_1$-$C_4$-alkyl, $C_3$-$C_7$-cycloalkyl-O, where the cycloalkyl moiety in the last three radicals mentioned may have 1, 2, 3 or 4 $R^{yb}$ radicals, and where 1 or 2 $CH_2$-groups in the cycloalkyl moiety may be replaced by O, NH or S, aryl, hetaryl, O-aryl, $CH_2$-aryl, O—$CH_2$-aryl, where the last 4 radicals mentioned are unsubstituted in the aryl moiety or may carry 1, 2, 3 or 4 radicals $R^{yd}$, $COOR^{y1}$, $CONR^{y2}R^{y3}$, $SO_2NR^{y2}R^{y3}$, —NH—$SO_2$—$R^{y4}$, NH—CO—$R^{y5}$, $SO_2$—$R^{y4}$, $(CH_2)_p$—$NR^{y6}R^{y7}$ with p=0, 1, 2, 3, 4, 5 or 6 and O—$(CH_2)_q$—$NR^{y6}R^{y7}$ with q=2, 3, 4, 5 or 6; where $R^{ya}$ has one of the meanings indicated for $R^{1a}$,
$R^{yb}$ has one of the meanings indicated for $R^{1b}$,
$R^{yd}$ has one of the meanings indicated for $R^{1d}$,
$R^{y1}$ has one of the meanings indicated for $R^{c1}$,
$R^{y2}$ has one of the meanings indicated for $R^{c2}$,
$R^{y3}$ has one of the meanings indicated for $R^{c3}$,
$R^{y4}$ has one of the meanings indicated for $R^{c4}$,
$R^{y5}$ has one of the meanings indicated for $R^{c5}$,
$R^{y6}$ has one of the meanings indicated for $R^{c6}$, and
$R^{y7}$ has one of the meanings indicated for $R^{c7}$;

$R^{y\#}$ is selected independently of one another from hydrogen, $NH_2$, CN, $CF_3$, $CHF_2$, $CH_2F$, O—$CF_3$, O—$CHF_2$, O—$CH_2F$, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{ya}$, $C_3$-$C_7$-cycloalkyl, $C_3$-$C_7$-cycloalkyl-$C_1$-$C_4$-alkyl, $C_3$-$C_7$-cycloalkyl-O, where the cycloalkyl moiety in the last three radicals mentioned may have 1, 2, 3 or 4 $R^{yb}$ radicals, and where 1 or 2 $CH_2$-groups in the cycloalkyl moiety may be replaced by O, NH or S, aryl, hetaryl, O-aryl, $CH_2$-aryl, O—$CH_2$-aryl, where the last 4 radicals mentioned are unsubstituted in the aryl moiety or may carry 1, 2, 3 or 4 radicals $R^{yd}$, $COOR^{y1}$, $CONR^{y2}R^{y3}$, $SO_2NR^{y2}R^{y3}$, —NH—$SO_2$—$R^{y4}$, NH—CO—$R^{y5}$, $SO_2$—$R^{y4}$, —$(CH_2)_p$—$NR^{y6}R^{y7}$ with p=0, 1, 2, 3, 4, 5 or 6 and O—$(CH_2)_q$—$NR^{y6}R^{y7}$ with q=2, 3, 4, 5 or 6.

The present invention therefore relates to the carboxamide compounds of the general formula I, their tautomers and the pharmaceutically suitable salts of the carboxamide compounds I.

The carboxamide compounds of the invention of the formula I, their salts and their tautomers effectively inhibit calpain even at low concentrations. They are additionally distinguished by a high selectivity in relation to the inhibition of the calpain compared with other cysteine proteases such as cathepsin B, cathepsin K, cathepsin L and cathepsin S.

The carboxamide compounds of the invention of the formula I, their salts and their tautomers are therefore particularly suitable for treating disorders and conditions in creatures, especially human creatures, which are associated with an elevated calpain activity.

The invention therefore also relates to the use of carboxamide compounds of the formula I, their tautomers and their pharmaceutically suitable salts for the manufacture of a medicament, in particular of a medicament which is suitable for the treatment of a disorder or a condition which is associated with an elevated calpain activity.

The invention further relates to a medicament, in particular a medicament which is suitable for the treatment of a disorder or a condition which is associated with an elevated calpain activity. The medicament comprises at least one carboxamide compound of the formula I, as described herein, a tautomer or a pharmaceutically suitable salt of the compound I.

The carboxamide compounds of the formula I may be in the form of β-keto compounds, i.e. the radicals $R^{3a}$ and $R^{3b}$ in the compounds of the formula I form together with the carbon atom to which they are bonded a carbonyl group as shown in the formula on the left in Scheme A. The compounds of the invention may also be in the form of a hydrate, i.e. the radicals $R^{3a}$ and $R^{3b}$ are each OH, as shown in the formula on the right in Scheme A. $R^1$, $R^2$, $R^4$, Q, X, A and Y in Scheme A have the aforementioned meanings.

Scheme A:

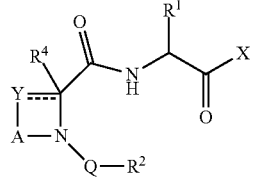

(I) for $R^{3a}/R^{3b}$ = O

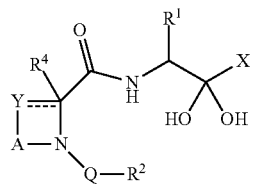

(I) for $R^{3a}$ = $R^{3b}$ = OH

In the presence of water, especially under physiological conditions, usually both the β-keto form and the hydrate form are present in a mixture.

Where only the β-keto form is indicated in the following formulae and descriptions, this is intended to include also the hydrate and mixtures thereof with the β-keto form unless indicated otherwise. Hydrates and β-keto forms are equally suitable as calpain inhibitors.

The carboxamide compounds of the invention of the formula I are also able to form tautomers when $R^{3a}$ and $R^{3b}$ form a carbonyl group together with the carbon atom to which they are bonded. The tautomers are equally suitable as calpain inhibitors. Particular examples of tautomers to be mentioned are the compounds of the formula I-T:

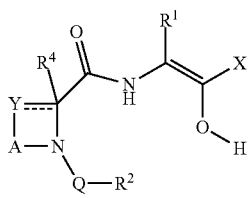
(I-T)

$R^1$, $R^2$, $R^4$, Q, A, X and Y in formula I-T have the aforementioned meanings.

The carboxamide compounds of the invention of the formula I can also form hemiacetals, hemiketals, acetals or ketals with alkanols or imines with primary amines or ammonia. These compounds are equally suitable as calpain inhibitors as they are prodrugs of the compounds I, where $CR^{3a}R^{3b}$ is a carbonyl group (i.e. C=O) or $C(OH)_2$. Accordingly, compounds where one or both radicals $R^{3a}$ and $R^{3b}$ are a radical derived from an alkanol, and especially $C_1$-$C_4$-alkoxy, can also be used according to the invention.

The term prodrug, as used herein refers to a compound which is transformed under metabolic conditions into a compound of the formula I. Apart from the aforementioned hemiacetals, hemiketals, acetals and ketals, prodrugs of the compounds I include the compounds of the formula I, wherein $R^{3a}$ and $R^{3b}$ together form a group O-Alk-O, S-Alk-O or S-Alk-S, where Alk is linear $C_2$-$C_5$-alkandiyl, which may be unsubstituted or substituted with 1, 2, 3 or 4 radicals selected from $C_1$-$C_4$-alkyl or halogen, examples for such groups including $O(CH_2)_2O$, $O(CH_2)_5O$, $O(CH_2)_4O$, $S(CH_2)_2O$, $S(CH_2)_5O$, $S(CH_2)_4O$, etc. Further prodrugs of the compounds I include the compounds of the formula I, wherein $R^{3a}$ and $R^{3b}$ together with the carbon atom form a group $C=NR^3$, where $R^3$ is selected from H, $C_1$-$C_6$-alkyl, $C_1$-$C_6$-alkoxy, $C_2$-$C_6$-alkenyl, $C_3$-$C_6$-cycloalkyl, $C_3$-$C_6$-cycloalkyl-$C_1$-$C_4$-alkyl, $C_2$-$C_6$-alkenyloxy, $C_3$-$C_6$-cycloalkyloxy, $C_3$-$C_6$-cycloalkyl-$C_1$-$C_4$-alkyloxy. Under metabolic conditions, the aforementioned prodrugs are transformed into the corresponding β-keto compounds of the formula I ($CR^{3a}R^{3b}$ is C=O) or into the hydrates thereof ($CR^{3a}R^{3b}$ is $C(OH)_2$). Likewise compounds wherein $R^{3a}$ and $R^{3b}$ are $C_1$-$C_4$-alkoxy are useful as prodrugs.

It is equally possible to use pharmaceutically suitable salts of the carboxamide compounds of the formula I, of their tautomers or of their prodrugs, especially acid addition salts with physiologically tolerated organic or inorganic acids. Examples of suitable physiologically tolerated organic and inorganic acids are hydrochloric acid, hydrobromic acid, phosphoric acid, nitric acid, sulfuric acid, organic sulfonic acids having 1 to 12 carbon atoms, e.g. $C_1$-$C_4$-alkylsulfonic acids such as methanesulfonic acid, cycloaliphatic sulfonic acids such as S-(+)-10-camphorsulfonic acids, and aromatic sulfonic acids such as benzenesulfonic acid and toluenesulfonic acid, di- and tricarboxylic acids and hydroxy carboxylic acids having 2 to 10 carbon atoms, such as oxalic acid, malonic acid, maleic acid, fumaric acid, mucic acid, lactic acid, tartaric acid, citric acid, glycolic acid and adipic acid, as well as cis- and trans-cinnamic acid, furan-2-carboxylic acid and benzoic acid. Further suitable acids are described in "Fortschritte der Arzneimittelforschung", Volume 10, pages 224 et seq., Birkhäuser Verlag, Basel and Stuttgart, 1966. The physiologically tolerated salts of the compounds of the formula I may be in the form of mono-, di-, tri- or tetrasalts, meaning that they may comprise 1, 2, 3 or 4 of the aforementioned acid molecules per molecule of the formula I. The acid molecules may be present in their acidic form or as anion.

The compounds of the invention may be in the form of a mixture of diastereomers, or of a mixture of diastereomers in which one of the two diastereomers is enriched, or of essentially diastereomerically pure compounds (diastereomeric excess de>90%). The compounds are preferably in the form of essentially diastereomerically pure compounds (diastereomeric excess de>90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee>90%). However, the compounds of the invention are frequently prone to epimerization in relation to the configuration of the carbon atom which carries the radical $R^1$, so that mixtures are frequently obtained in relation to this carbon atom, or compounds which exhibit a uniform configuration in relation to this C atom form mixtures under physiological conditions. However, in relation to other stereocenters and the occurrence, associated therewith, of enantiomers and diastereomers, it is preferred to employ the compounds enantiomerically pure or diastereomerically pure. In particular, the compounds of formula I, where ⎓ indicates a single bond will have a center of chirality at the carbon atom carrying $R^4$.

In the context of the present description, unless stated otherwise, the terms "alkyl", "alkoxy", "alkylthio", "haloalkyl", "haloalkoxy", "haloalkylthio", "alkenyl", "alkynyl", "alkylene" and radicals derived therefrom always include both unbranched and branched "alkyl", "alkoxy", "alkylthio", "haloalkyl", "haloalkoxy", "haloalkylthio", "alkenyl", "alkynyl" and "alkylene", respectively.

The prefix $C_n$-$C_m$— indicates the respective number of carbons in the hydrocarbon unit. Unless indicated otherwise, halogenated substituents preferably have one to five identical or different halogen atoms, especially fluorine atoms or chlorine atoms. $C_0$-Alkylene or $(CH_2)_0$ or similar expressions in the context of the description designate, unless indicated otherwise, a single bond.

The term "halogen" designates in each case, fluorine, bromine, chlorine or iodine, specifically fluorine, chlorine or bromine.

Examples of other meanings are:

Alkyl, and the alkyl moieties for example in alkoxy, alkylthio, arylalkyl, hetarylalkyl, cycloalkylalkyl or alkoxyalkyl: saturated, straight-chain or branched hydrocarbon radicals having one or more C atoms, e.g. 1 to 4, 1 to 6 or 1 to 10 carbon atoms, e.g. $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. In one embodiment of the invention, alkyl stands for small alkyl groups such as $C_1$-$C_4$-alkyl. In another embodiment of the invention, alkyl stands for larger alkyl groups such as $C_5$-$C_{10}$-alkyl.

Haloalkyl: an alkyl radical having ordinarily 1 to 6 or 1 to 4 C atoms as mentioned above, whose hydrogen atoms are partly or completely replaced by halogen atoms such as fluorine, chlorine, bromine and/or iodine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl.

Cycloalkyl, and the cycloalkyl moieties for example in cycloalkoxy or cycloalkyl-$C_1$-$C_6$-alkyl: monocyclic, saturated hydrocarbon groups having three or more C atoms, e.g. 3, 4, 5, 6 or 7 carbon ring members, such as cyclopropyl, cyclobutyl, cyclopentyl, cyclohexyl.

Alkenyl, and alkenyl moieties for example in aryl-($C_2$-$C_6$)-alkenyl: monounsaturated, straight-chain or branched hydrocarbon radicals having two or more C atoms, e.g. 2 to 4, 2 to 6 or 2 to 10 carbon atoms and one double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl.

Alkynyl: straight-chain or branched hydrocarbon groups having two or more C atoms, e.g. 2 to 4, 2 to 6 or 2 to 10 carbon atoms and one or two triple bonds in any position but nonadjacent, e.g. $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl.

Alkoxy or alkoxy moieties for example in alkoxyalkyl:
Alkyl as defined above having preferably 1 to 6 or 1 to 4 C atoms, which is linked via an O atom: e.g. methoxy, ethoxy, n-propoxy, 1-methylethoxy, butoxy, 1-methylpropoxy, 2-methylpropoxy or 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

Haloalkoxy: alkoxy as described above, in which the hydrogen atoms of these groups are partly or completely replaced by halogen atoms, i.e. for example $C_1$-$C_6$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, specifically chloromethoxy, fluoromethoxy, difluoromethoxy, trifluoromethoxy, 2-fluoroethoxy, 2-chloroethoxy or 2,2,2-trifluoroethoxy.

Alkoxyalkyl: an alkyl radical ordinarily having 1 to 4 C atoms, in which one hydrogen atom is replaced by an alkoxy radical ordinarily having 1 to 6 or 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methyl-propoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkylthio: alkyl as defined above preferably having 1 to 6 or 1 to 4 C atoms, which is linked via an S atom, e.g. methylthio, ethylthio, n-propylthio and the like.

Haloalkylthio: haloalkyl as defined above preferably having 1 to 6 or 1 to 4 C atoms, which is linked via an S atom, e.g. fluoromethylthio, difluoromethylthio, trifluoromethylthio, 2-fluoroethylthio, 2,2-difluoroethylthio, 2,2,2-trifluoroethylthio, pentafluoroethylthio, 2-fluoropropylthio, 3-fluoropropylthio, 2,2-difluoropropylthio, 2,3-difluoropropylthio, and heptafluoropropylthio.

Aryl: a mono-, bi- or tricyclic aromatic hydrocarbon radical such as phenyl or naphthyl, especially phenyl.

Heterocyclyl: a heterocyclic radical which may be saturated or partly unsaturated and which ordinarily has 3, 4, 5, 6, 7 or 8 ring atoms, where ordinarily 1, 2, 3 or 4, in particular 1, 2 or 3, of the ring atoms are heteroatoms such as N, S or O, besides carbon atoms as ring members.

Examples of saturated heterocycles are in particular:

Heterocycloalkyl: i.e. a saturated heterocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:

C-bonded, 3-4-membered saturated rings such as 2-oxiranyl, 2-oxetanyl, 3-oxetanyl, 2-aziridinyl, 3-thiethanyl, 1-azetidinyl, 2-azetidinyl.

C-bonded, 5-membered saturated rings such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as:

tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as:

tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as:

piperidin-1-yl, hexahydropyrimidin-1-yl, hexahydropyrazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heterocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as:

2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as:

2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydro-pyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetra-hydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as:

2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as:

1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Hetaryl: a 5- or 6-membered aromatic heterocyclic radical which ordinarily has 1, 2, 3 or 4 nitrogen atoms or a heteroatom selected from oxygen and sulfur and, optionally, 1, 2 or 3 nitrogen atoms as ring members besides carbon atoms as ring members: for example C-bonded, 5-membered heteroaromatic radicals having 1, 2, 3 or 4 nitrogen atoms or a heteroatom selected from oxygen and sulfur and, if appropriate, having 1, 2 or 3 nitrogen atoms as ring members, such as:

2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2- yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered heteroaromatic radicals having 1, 2, 3 or 4 nitrogen atoms as ring members, such as:

pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:

pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles which have one of the aforementioned 5- or 6-membered heterocyclic rings and a further saturated, unsaturated or aromatic carbocycle fused thereto, for example a benzene, cyclohexane, cyclohexene or cyclohexadiene ring, or a further 5- or 6-membered heterocyclic ring fused thereto, where the latter may likewise be saturated, unsaturated or aromatic. These include for example quinolinyl, isoquinolinyl, indolyl, indolizynyl, isoindolyl, indazolyl, benzofuryl, benzothienyl, benzolblthiazolyl, benzoxazolyl, benzthiazolyl and benzimidazolyl. Examples of 5- to 6-membered heteroaromatic compounds comprising a fused benzene ring include dihydroindolyl, dihydroindolizynyl, dihydroisoindolyl, dihydroquinolinyl, dihydroisoquinolinyl, chromenyl and chromanyl.

Arylalkyl: an aryl radical as defined above which is linked via an alkylene group, in particular via a methylene, 1,1-ethylene or 1,2-ethylene group, e.g. benzyl, 1-phenyl-ethyl and 2-phenylethyl.

Arylalkenyl: an aryl radical as defined above, which is linked via an alkenylene group, in particular via a 1,1-ethenyl, 1,2-ethenyl or 1,3-propenyl group, e.g. 2-phenylethen-1-yl and 1-phenylethen-1-yl.

Cycloalkoxy: a cycloalkyl radical as defined above which is linked via an oxygen atom, e.g. cyclopropyloxy, cyclobutyloxy, cyclopentyloxy or cyclohexyloxy.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl or cyclohexylmethyl.

Heterocyclylalkyl and hetarylalkyl: a heterocyclyl or hetaryl radical as defined above which is linked via an alkylene group, in particular via a methylene, 1,1-ethylene or 1,2-ethylene group.

The expression "optionally substituted" means in the context of the present invention that the respective moiety is substituted or has 1, 2 or 3, in particular 1, substituents which are selected from halogen, $C_1$-$C_4$-alkyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl and NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

In relation to their use as calpain inhibitors, the variables $R^1$, $R^2$, $R^4$, Q, A, Y and X preferably have the following meanings, where these represent, both considered on their own and in combination with one another, special embodiments of the compounds of the formula I:

$R^1$ $C_1$-$C_{10}$-alkyl, preferably $C_3$-$C_{10}$-alkyl, which may be partly or completely halogenated and/or have 1, 2 or 3 substituents $R^{1a}$, in particular unsubstituted $C_1$-$C_{10}$-alkyl, specifically unsubstituted $C_3$-$C_{10}$-alkyl or $C_3$-$C_{10}$-alkyl which is partly or completely halogenated and/or has 1, 2 or 3 substituents $R^{1a}$, $C_3$-$C_7$-cycloalkyl-$C_1$-$C_4$-alkyl, specifically $C_3$-$C_7$-cycloalkylmethyl, 1-($C_3$-$C_7$-cycloalkyl)ethyl or 2-($C_3$-$C_7$-cycloalkyl)ethyl, where the cycloalkyl moiety may have 1, 2, 3 or 4 radicals $R^{1b}$, very specifically cyclohexylmethyl, phenyl-$C_1$-$C_4$-alkyl and hetaryl-$C_1$-$C_4$-alkyl, in particular benzyl, 1-phenylethyl, 2-phenylethyl, hetarylmethyl, 1-hetarylethyl, 2-hetarylethyl such as thienylmethyl, pyridinylmethyl, where phenyl and hetaryl in the last radicals mentioned may be unsubstituted or carry 1, 2, 3 or 4 identical or different radicals $R^{1c}$.

Preferred among these are compounds of the general formula I where $R^1$ is $C_3$-$C_{10}$-alkyl which is unsubstituted or may be partly or completely halogenated and/or have 1, 2 or 3 substituents $R^{1a}$, in particular $C_3$-$C_{10}$-alkyl and most preferred $C_3$-$C_8$-alkyl.

Likewise preferred among these are compounds of the general formula I where $R^1$ is phenyl-$C_1$-$C_4$-alkyl or hetaryl-$C_1$-$C_4$-alkyl, where phenyl and hetaryl in the last 2 radicals mentioned is unsubstituted or carries 1, 2, 3 or 4 identical or different radicals $R^{1c}$. In hetaryl-$C_1$-$C_4$-alkyl, the hetaryl moiety is preferably pyridyl or thienyl.

In a particular preferred embodiment $R^1$ is phenyl-$C_1$-$C_4$-alkyl and most preferred benzyl, wherein the phenyl ring in phenyl-$C_1$-$C_4$-alkyl or benzyl is unsubstituted or carries 1, 2, 3 or 4 identical or different radicals $R^{1c}$.

In this connection, $R^{1a}$, $R^{1b}$ and $R^{1c}$, where present, have the aforementioned meanings. In particular:

$R^{1a}$ is $C_1$-$C_4$-alkoxy or $C_1$-$C_4$-haloalkoxy;

$R^{1b}$ is halogen, $C_1$-$C_4$-alkyl, $C_1$-$C_4$-haloalkyl, $C_1$-$C_4$-alkoxy or $C_1$-$C_4$-haloalkoxy; and $R^{1c}$ is halogen, $C_1$-$C_4$-alkyl, $C_1$-$C_4$-haloalkyl, OH, SH, CN, COOH, O—$CH_2$—COOH, $C_1$-$C_6$-alkoxy, $C_1$-$C_4$-haloalkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl, NH—CO-hetaryl where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy, —($CH_2$)$_p$—$NR^{c6}R^{c7}$ with p=0, 1, 2, 3, 4, 5 or 6, in particular 0, and —O—($CH_2$)$_q$—$NR^{c6}R^{c7}$ with q=2, 3, 4, 5 or 6, in particular 2, where $R^{c6}$, $R^{c7}$ are independently of one another hydrogen or $C_1$-$C_6$-alkyl, or together with the nitrogen atom to which they are bonded, are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy. $R^{1c}$ is in particular halogen, $C_1$-$C_4$-alkyl, $C_1$-$C_4$-haloalkyl, especially $C_1$-$C_2$-fluoroalkyl such as $CF_3$, $CHF_2$, $CH_2F$, specially $CF_3$, $C_1$-$C_4$-alkoxy or $C_1$-$C_4$-haloalkoxy, especially $C_1$-$C_2$-fluoroalkoxy such as O—$CF_3$, O—$CHF_2$ or O—$CH_2F$, specially $OCF_3$.

$R^2$ is, in particular:

aryl or hetaryl, where aryl and hetaryl in the last 2 radicals mentioned may be unsubstituted or carry 1, 2, 3 or 4 identical or different radicals $R^{2b}$.

Preferred among these are those compounds of the general formula I in which $R^2$ is selected from aryl and hetaryl, specifically from phenyl, naphthyl, thienyl and pyridyl, and most preferred from phenyl and naphthyl, where aryl and hetaryl (or phenyl, naphthyl, thienyl and pyridyl) may be unsubstituted or carry 1, 2, 3 or 4, in particular 1 or 2, identical or different radicals $R^{2b}$.

In this connection $R^{2b}$, where present, has the aforementioned meanings. In particular:

$R^{2b}$ is halogen, $C_1$-$C_4$-alkyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl, NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy, —$(CH_2)_p$—$NR^{c6}R^{c7}$ with p=0, 1, 2, 3, 4, 5 or 6, in particular 0, and —O—$(CH_2)_q$—$NR^{c6}R^{c7}$ with q=2, 3, 4, 5 or 6, in particular 2, where $R^{c6}$, $R^{c7}$ are independently of one another hydrogen or $C_1$-$C_6$-alkyl, or together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

$R^{3a}$, $R^{3b}$ in particular OH or the group $CR^{3a}R^{3b}$ is a carbonyl group, wherein the latter is most preferred.

Q is a single bond or a moiety Alk'-Z, wherein

Z is bound to $R^2$ and preferably selected from a single bond, O, S and $NR^q$, where $R^q$ is selected from hydrogen, $C_1$-$C_4$-alkyl and $C_1$-$C_4$-haloalkyl; and Alk' is preferably a linear $C_1$-$C_3$-alkandiyl.

Particular preference is given to compounds of the formula I, wherein Q is a single bond, $CH_2$ or $CH_2$—$CH_2$ and specifically $CH_2$ or $CH_2$—$CH_2$.

X is a radical C(=O)—$NR^{x2}R^{x3}$ in which $R^{x2}$ and $R^{x3}$ have one of the aforementioned meanings. Compounds preferred among these are those in which:

$R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$. In particular, $R^{x2}$ is hydrogen, $C_1$-$C_6$-alkyl, $C_1$-$C_6$-haloalkyl, $C_1$-$C_6$-alkyl which has 1 or 2 substituents $R^{xa}$, $C_3$-$C_7$-cycloalkyl-$C_1$-$C_4$-alkyl, $C_3$-$C_7$-heterocycloalkyl-$C_1$-$C_4$-alkyl, aryl, hetaryl, aryl-$C_1$-$C_4$-alkyl or hetaryl-$C_1$-$C_4$-alkyl.

$R^{x3}$ is H, $C_1$-$C_6$-alkyl, $C_1$-$C_6$-haloalkyl or $C_1$-$C_6$-alkyl which has 1, 2 or 3 substituents $R^{xa}$. In particular, $R^{x3}$ is hydrogen, $C_1$-$C_6$-alkyl, $C_1$-$C_6$-haloalkyl, $C_1$-$C_6$-alkyl which has 1 or 2 substituents $R^{xa}$. $R^{x3}$ is very particularly preferably hydrogen.

Compounds of the formula I which are likewise preferred are those in which the group $NR^{x2}R^{x3}$ is a nitrogen heterocycle of the following formulae:

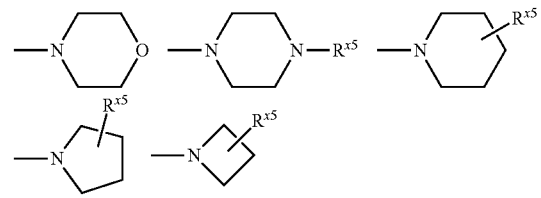

in which $R^{x5}$ is hydrogen or has the meaning indicated for $R^{xb}$. In particular, $R^{x5}$ is $C_1$-$C_6$-alkyl, $C_1$-$C_6$-haloalkyl, $C_1$-$C_6$-alkyl which has 1, 2 or 3 substituents $R^{xa}$, or $C_1$-$C_6$-alkoxy-$C_1$-$C_4$-alkyl, or COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_6$-alkyl, CONH-phenyl, $SO_2NH$-phenyl, CONH-hetaryl, $SO_2NH$-hetaryl, where phenyl and hetaryl in the last 4 radicals mentioned are unsubstituted or may have 1, 2 or 3 substituents which are selected from the halogen, $C_1$-$C_4$-alkyl, $C_1$-$C_4$-haloalkyl, $C_1$-$C_4$-alkoxy and $C_1$-$C_4$-haloalkoxy. In particular, $R^{x5}$ is hydrogen or $C_1$-$C_4$-alkyl. In this embodiment the group $NR^{x2}R^{x3}$ is preferably morpholin-4-yl.

In a particularly preferred embodiment of the invention, X is C(O)—$NH_2$.

In another particularly preferred embodiment of the invention, X is C(O)—$NHR^{x22}$ in which $R^{x22}$ is preferably selected from $C_1$-$C_4$-alkyl, $C_1$-$C_4$-alkoxy-$C_1$-$C_4$-alkyl, hydroxy-$C_1$-$C_4$-alkyl, hydroxy-$C_1$-$C_4$-alkoxy, phenyl, wherein phenyl is unsubstituted or substituted by one, two or three radicals $R^{xd}$, phenyl-$C_1$-$C_4$-alkyl, wherein the phenyl moiety of phenyl-$C_1$-$C_4$-alkyl is unsubstituted or substituted by one, two or three radicals $R^{xd}$, hetaryl, $C_3$-$C_7$-cycloalkyl and $C_3$-$C_7$-cycloalkyl-$C_1$-$C_4$-alkyl. In another particularly preferred embodiment of the invention, X is C(O)—$NHR^{x22}$ in which $R^{x22}$ is $C_3$-$C_7$-heterocycloalkyl-$C_1$-$C_4$-alkyl or hetaryl-$C_1$-$C_4$-alkyl where heterocyclyl is a 5-, 6- or 7-membered heterocyclic radical which has as ring members 1 or 2 heteroatoms selected from O, S and N and hetaryl is a 5- or 6-membered heteroaromatic radical which has as ring members 1 or 2 heteroatoms selected from O, S and N and wherein the hetaryl moiety of hetaryl-$C_1$-$C_4$-alkyl is unsubstituted or substituted by one, two or three radicals $R^{xd}$. Preferred examples of $C_3$-$C_7$-heterocycloalkyl-$C_1$-$C_4$-alkyl are tetrahydrofuran-2-ylmethyl or tetrahydrofuran-2-ylethyl. Preferred examples of hetaryl-$C_1$-$C_4$-alkyl are pyridin-2-ylmethyl, pyridin-3-ylmethyl, pyridin-4-ylmethyl, pyridin-2-ylethyl, pyridin-3-ylethyl, pyridin-4-ylethyl, pyridin-2-ylpropyl, pyridin-3- ylpropyl, pyridin-4-ylpropyl, thiophen-2-ylmethyl, thiophen-2-ylethyl, furan-2-ylmethyl, furan-2-ylethyl, oxazo-2-ylmethyl, oxazol-2-ylethyl, thiazol-5-ylmethyl, thiazol-2-ylmethyl, thiazol-5-ylethyl, thiazol-2-ylethyl, thiazol-4-ylmethyl, thiazol-4-ylmethyl, benzothiazol-2-ylmethyl or benzothiazol-2-ylethyl.

In particular $R^{x22}$ is $C_1$-$C_4$-alkyl, $C_3$-$C_6$-cycloalkyl, heterocycloalkyl-$C_1$-$C_4$-alkyl, phenyl, phenyl-$C_1$-$C_4$-alkyl or hetaryl-$C_1$-$C_4$-alkyl, where phenyl and hetaryl in the last 3 radicals mentioned are unsubstituted or have 1, 2 or 3 substituents $R^{x\ d}$, hetaryl is a 5- or 6-membered heteroaromatic radical which has as ring members 1 or 2 heteroatoms selected from O, S and N and heterocyclyl is a 5-, 6- or 7-membered heterocyclic radical which has as ring members 1 or 2 heteroatoms selected from O, S and N. $R^{xd}$ is preferably halogen such as chlorine or fluorine, $C_1$-$C_4$-haloalkyl, especially $C_1$-$C_2$-fluoroalkyl such trifluoromethyl or $C_1$-$C_4$-alkyl such as methyl or ethyl or two radicals $R^{xd}$ bonded to adjacent C atoms form together a moiety —O—$CH_2$—O—.

Particularly preferred are compounds of formula I, wherein $R^{x22}$ is methyl, ethyl, cyclopropyl, cyclobutyl, cyclohexyl, benzyl, 2-chlorobenzyl, 4-trifluoromethylbenzyl, 1,3-benzodioxol-5-ylmethyl, 2-phenylethyl, 3-phenylpropyl, pyridin-2-ylmethyl, pyridin-2-ylethyl, pyridin-2-ylpropyl, pyridin-4-ylmethyl, thiophen-2-ylmethyl, furan-2-ylmethyl, oxazol-2-ylmethyl, thiazol-5-ylmethyl, thiazol-2-ylmethyl, benzothiazol-2-ylmethyl, oxazol-2-ylmethyl or tetrahydrofuran-2-yl.

In another embodiment of the invention, X is C(=O)—N($R^{x4}$)$NR^{x2}R^{x3}$ in which $R^{x4}$ is preferably hydrogen or $C_1$-$C_6$-alkyl, especially hydrogen. In this embodiment $R^{x3}$ is preferably hydrogen. $R^{x2}$ is preferably CO-aryl, especially benzoyl or aryl-$C_1$-$C_4$-alkyl, especially benzyl.

In another embodiment of the invention, X is hydrogen.

In another embodiment of the invention, X is $C(O)OR^{x1}$ in which $R^{x1}$ has the aforementioned meanings. In particular, $R^{x1}$ is $C_1$-$C_6$-alkyl, $C_1$-$C_6$-haloalkyl, $C_1$-$C_6$-alkyl which has 1, 2 or 3 substituents $R^{xa}$, or $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl stands, where aryl and hetaryl in the last 4 radicals mentioned are unsubstituted or have 1, 2 or 3 substituents $R^{xd}$.

In this connection, $R^{xa}$ has the aforementioned meanings and is in particular OH, $C_1$-$C_4$-alkoxy, or $C_1$-$C_4$-haloalkoxy. In this connection, $R^{xd}$ has the aforementioned meanings and is preferably F, Cl, OH, COOH, C(O)$NH_2$, CN, $NH_2$, $OCH_2COOH$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, CO—$C_1$-$C_4$-alkyl, CO—O—$C_1$-$C_4$-alkyl, NH—$C_1$-$C_4$-alkyl, NH—C(O)$C_1$-$C_4$-alkyl or $SO_2$—$C_1$-$C_4$-alkyl.

A is selected from C=O, S(=O) and S(=O)$_2$.

In a preferred embodiment of the invention, A is C=O.

$R^4$ is hydrogen. In a preferred embodiment of the invention, the carbon atom carrying the radical $R^4$ has predominantly R-configuration.

In another preferred embodiment of the invention, $R^4$ is absent.

Y is a moiety $CH_2$—$CH_2$, $CH_2CH_2CH_2$, $N(R^{y\#})$—$CH_2$ or $N(R^{y\#})$—$CH_2$—$CH_2$ or, if $R^4$ is absent, a moiety CH=CH—CH=, each of which may have 1 or 2 hydrogen atoms replaced by a radical $R^y$, wherein the radicals $R^y$, which may be identical or different, and the radical $R^{y\#}$ have one of the aforementioned meanings.

In a preferred embodiment of the invention Y is a moiety $CH_2$—$CH_2$ or $CH_2CH_2CH_2$ and particular preferred a moiety $CH_2$—$CH_2$, each of which may have 1 or 2 hydrogen atoms replaced by a radical $R^y$, wherein the radicals $R^y$ may be identical or different, each having one of the aforementioned meanings.

In another preferred embodiment of the invention Y is a moiety $N(R^{y\#})$—$CH_2$ or $N(R^{y\#})$—$CH_2$—$CH_2$, each of which may have 1 or 2 hydrogen atoms replaced by a radical $R^y$, wherein the radicals $R^y$, which may be identical or different, and the radical $R^{y\#}$ have one of the aforementioned meanings. Preferably, $N(R^{y\#})$—$CH_2$ and $N(R^{y\#})$—$CH_2$—$CH_2$, respectively, are bonded to the variable A via the nitrogen atom.

In a preferred embodiment of the invention Y is a moiety CH=CH—CH=, which may have 1 or 2 hydrogen atoms replaced by a radical $R^y$, wherein the radicals $R^y$ may be identical or different, each having one of the aforementioned meanings.

The cyclic radical of formula I that includes the variable Y preferably has 0, 1 or 2 identical or different substituents $R^y$ other than hydrogen and more preferably 0 or 1 substituent $R^y$ other than hydrogen. Particularly preferred are compounds of formula I, wherein all substituents $R^y$ are hydrogen.

Where a substituent $R^y$ is present that is not hydrogen, it is preferably selected from OH, F, Cl, $NH_2$, CN, $CF_3$, $CHF_2$, O—$CF_3$, O—$CHF_2$, O—$CH_2F$, $C_1$-$C_6$-alkyl, $C_3$-$C_7$-cycloalkyl, $C_1$-$C_6$-alkylamino, $C_1$-$C_6$-dialkylamino, pyrrolidinyl, piperidinyl, morpholinyl, imidazolyl, $C_1$-$C_4$-alkoxy, $C_1$-$C_4$-alkoxy-$C_1$-$C_4$-alkyl, $CONR^{y2}R^{y3}$, $SO_2NR^{y2}R^{y3}$, NH—$SO_2$—$R^{y4}$, —$(CH_2)_p$—$NR^{y6}R^{y7}$, NH—CO—$R^{y5}$, in which p is 0, 1, 2, 3, 4, or 5, and in which $R^{y2}$, $R^{y3}$, $R^{y4}$, $R^{y5}$, $R^{y6}$, $R^{y7}$ have the aforementioned meanings, preferably the meanings mentioned as preferred below, and are in particular H and $C_1$-$C_6$-alkyl, phenyl, benzyl and O-benzyl, where the phenyl ring in the last 3 groups mentioned may have 1, 2 or 3 substituents selected from halogen, OH, SH, $NO_2$, COOH, C(O)$NH_2$, CHO, CN, $NH_2$, $OCH_2COOH$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—C(O)$C_1$-$C_6$-alkyl, and $SO_2$—$C_1$-$C_6$-alkyl.

In particular, $R^y$ that is not hydrogen, is OH, F, Cl, $NH_2$, CN, $CF_3$, $CHF_2$, O—$CF_3$, O—$CHF_2$, O—$CH_2F$, $C_1$-$C_6$-alkyl, $C_3$-$C_7$-cycloalkyl, $C_1$-$C_6$-alkylamino, $C_1$-$C_6$-dialkylamino, pyrrolidinyl, piperidinyl, morpholinyl, imidazolyl, $C_1$-$C_4$-alkoxy, $C_1$-$C_4$-alkoxy-$C_1$-$C_4$-alkyl, CONH—$C_1$-$C_6$-alkyl, $SO_2N(C_1$-$C_6$-alkyl$)_2$, NH—$SO_2$—$C_1$-$C_6$-alkyl, NH—CO—$C_1$-$C_6$-alkyl, $(CH_2)_p$—$N(C_1$-$C_6$-alkyl$)_2$, in which p is 2, 3 or 4.

$R^y$ that is not hydrogen, is particularly preferably F, Cl, CN, $CF_3$, $CHF_2$, O—$CF_3$, O—$CHF_2$, O—$CH_2F$ or $C_1$-$C_3$-alkyl.

Where a substituent $R^{y\#}$ is present that is not hydrogen, it is preferably selected from $NH_2$, CN, $CF_3$, $CHF_2$, O—$CF_3$, O—$CHF_2$, O—$CH_2F$, $C_1$-$C_6$-alkyl, $C_3$-$C_7$-cycloalkyl, $C_1$-$C_6$-alkylamino, $C_1$-$C_6$-dialkylamino, pyrrolidinyl, piperidinyl, morpholinyl, imidazolyl, $C_1$-$C_4$-alkoxy, $C_1$-$C_4$-alkoxy-$C_1$-$C_4$-alkyl, $CONR^{y2}R^{y3}$, $SO_2NR^{y2}R^{y3}$, NH—$SO_2$—$R^{y4}$, —$(CH_2)_p$—$NR^{y6}R^{y7}$, NH—CO—$R^{y5}$, in which p is 0, 1, 2, 3, 4, or 5, and in which $R^{y2}$, $R^{y3}$, $R^{y4}$, $R^{y5}$, $R^{y6}$, $R^{y7}$ have the aforementioned meanings, preferably the meanings mentioned as preferred below, and are in particular H and $C_1$-$C_6$-alkyl, phenyl, benzyl and O-benzyl, where the phenyl ring in the last 3 groups mentioned may have 1, 2 or 3 substituents selected from halogen, OH, SH, $NO_2$, COOH, C(O) $NH_2$, CHO, CN, $NH_2$, $OCH_2COOH$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—C(O)$C_1$-$C_6$-alkyl, and $SO_2$—$C_1$-$C_6$-alkyl.

In particular, $R^{y\#}$ that is not hydrogen, is $NH_2$, CN, $CF_3$, $CHF_2$, O—$CF_3$, O—$CHF_2$, O—$CH_2F$, $C_1$-$C_6$-alkyl, $C_3$-$C_7$-cycloalkyl, $C_1$-$C_6$-alkylamino, $C_1$-$C_6$-dialkylamino, pyrrolidinyl, piperidinyl, morpholinyl, imidazolyl, $C_1$-$C_4$-alkoxy, $C_1$-$C_4$-alkoxy-$C_1$-$C_4$-alkyl, CONH—$C_1$-$C_6$-alkyl, $SO_2N(C_1$-$C_6$-alkyl$)_2$, NH—$SO_2$—$C_1$-$C_6$-alkyl, NH—CO—$C_1$-$C_6$-alkyl, $(CH_2)_p$—$N(C_1$-$C_6$-alkyl$)_2$, in which p is 2, 3 or 4.

$R^{y\#}$ that is not hydrogen, is particularly preferably $CF_3$, $CHF_2$ or $C_1$-$C_3$-alkyl.

More preferred are compounds of the formula I wherein:
Y is a moiety $CH_2$—$CH_2$ or $CH_2$—$CH_2$—$CH_2$, each optionally having 1 or 2H-atoms replaced with identical or different radicals $R^y$,
Q is a single bond, a moiety $CH_2$ or $CH_2$—$CH_2$,
A is C═O,
$R^1$ is phenyl-$C_1$-$C_4$-alkyl, which is unsubstituted or carries 1, 2, 3 or 4 identical or different radicals $R^{1c}$,
$R^2$ is phenyl or naphthyl, where phenyl and naphthyl may be unsubstituted or substituted with 1 or 2 identical or different radicals $R^{2b}$,
X is $CONH_2$ or $CONHR^{x22}$, and
$R^{3a}$ and $R^{3b}$ are each OH or the group $CR^{3a}R^{3b}$ is a carbonyl group.

Also more preferred are compounds of the formula I wherein:
Y is a moiety $CH_2$—$CH_2$ or $CH_2$—$CH_2$—$CH_2$, each optionally having 1 or 2H-atoms replaced with identical or different radicals $R^y$,
Q is a single bond, a moiety $CH_2$ or $CH_2$—$CH_2$,
A is C═O,
$R^1$ is $C_3$-$C_8$-alkyl,
$R^2$ is phenyl or naphthyl, where phenyl and naphthyl may be unsubstituted or substituted with 1 or 2 identical or different radicals $R^{2b}$,
X is $CONH_2$ or $CONHR^{x22}$, and
$R^{3a}$ and $R^{3b}$ are each OH or the group $CR^{3a}R^{3b}$ is a carbonyl group.

Also more preferred are compounds of the formula I wherein:
Y is a moiety $CH_2$—$CH_2$ or $CH_2$—$CH_2$—$CH_2$, each optionally having 1 or 2H-atoms replaced with identical or different radicals $R^y$,
Q is a single bond, a moiety $CH_2$ or $CH_2$—$CH_2$,
A is C═O,
$R^1$ is phenyl-$C_1$-$C_4$-alkyl, which is unsubstituted or carries 1, 2, 3 or 4 identical or different radicals $R^{1c}$,
$R^2$ is phenyl or naphthyl, where phenyl and naphthyl may be unsubstituted or substituted with 1 or 2 identical or different radicals $R^{2b}$,
X is C(═O)—N($R^{x4}$)$NR^{x2}R^{x3}$, and
$R^{3a}$ and $R^{3b}$ are each OH or the group $CR^{3a}R^{3b}$ is a carbonyl group Also more preferred are compounds of the formula I wherein:
Y is a moiety $CH_2$—$CH_2$ or $CH_2$—$CH_2$—$CH_2$, each optionally having 1 or 2H-atoms replaced with identical or different radicals $R^y$,
Q is a single bond, a moiety $CH_2$ or $CH_2$—$CH_2$,
A is C═O,
$R^1$ is $C_3$-$C_8$-alkyl,
$R^2$ is phenyl or naphthyl, where phenyl and naphthyl may be unsubstituted or substituted with 1 or 2 identical or different radicals $R^{2b}$,
X is C(═O)—N($R^{x4}$)$NR^{x2}R^{x3}$, and
$R^{3a}$ and $R^{3b}$ are each OH or the group $CR^{3a}R^{3b}$ is a carbonyl group.

Also more preferred are compounds of the formula I wherein:
Y is a moiety $N(R^{y\#})$—$CH_2$ or $N(R^{y\#})$—$CH_2$—$CH_2$, each optionally having 1 or 2H-atoms replaced with identical or different radicals $R^y$,
Q is a single bond, a moiety $CH_2$ or $CH_2$—$CH_2$,
A is C═O,
$R^1$ is phenyl-$C_1$-$C_4$-alkyl, which is unsubstituted or carries 1, 2, 3 or 4 identical or different radicals $R^{1c}$,
$R^2$ is phenyl or naphthyl, where phenyl and naphthyl may be unsubstituted or substituted with 1 or 2 identical or different radicals $R^{2b}$,
X is $CONH_2$ or $CONHR^{x22}$, and
$R^{3a}$ and $R^{3b}$ are each OH or the group $CR^{3a}R^{3b}$ is a carbonyl group.

Also more preferred are compounds of the formula I wherein:
Y is a moiety $N(R^{y\#})$—$CH_2$ or $N(R^{y\#})$—$CH_2$—$CH_2$, each optionally having 1 or 2H-atoms replaced with identical or different radicals $R^y$, wherein $N(R^{y\#})$—$CH_2$ and $N(R^{y\#})$—$CH_2$—$CH_2$, respectively, are preferably bonded to the variable A via the nitrogen atom,
Q is a single bond, a moiety $CH_2$ or $CH_2$—$CH_2$,
A is C═O,
$R^1$ is $C_3$-$C_8$-alkyl,
$R^2$ is phenyl or naphthyl, where phenyl and naphthyl may be unsubstituted or substituted with 1 or 2 identical or different radicals $R^{2b}$,
X is $CONH_2$ or $CONHR^{x22}$, and
$R^{3a}$ and $R^{3b}$ are each OH or the group $CR^{3a}R^{3b}$ is a carbonyl group.

Also more preferred are compounds of the formula I wherein:
Y is a moiety CH═CH—CH═, optionally having 1 or 2H-atoms replaced with identical or different radicals $R^y$,
Q is a single bond, a moiety $CH_2$ or $CH_2$—$CH_2$,
A is C═O,
$R^1$ is phenyl-$C_1$-$C_4$-alkyl, which is unsubstituted or carries 1, 2, 3 or 4 identical or different radicals $R^{1c}$,
$R^2$ is phenyl or naphthyl, where phenyl and naphthyl may be unsubstituted or substituted with 1 or 2 identical or different radicals $R^{2b}$,
X is $CONH_2$ or $CONHR^{x22}$, and
$R^{3a}$ and $R^{3b}$ are each OH or the group $CR^{3a}R^{3b}$ is a carbonyl group.

Also more preferred are compounds of the formula I wherein:
Y is a moiety CH═CH—CH═, optionally having 1 or 2H-atoms replaced with identical or different radicals $R^y$,
Q is a single bond, a moiety $CH_2$ or $CH_2$—$CH_2$,
A is C═O,
$R^1$ is $C_3$-$C_8$-alkyl, R² is phenyl or naphthyl, where phenyl and naphthyl may be unsubstituted or substituted with 1 or 2 identical or different radicals R$^{2b}$, X is CONH$_2$ or CONHR$^{x22}$, and R$^{3a}$ and R$^{3b}$ are each OH or the group CR$^{3a}$R$^{3b}$ is a carbonyl group.

Otherwise, the radicals R$^{ya}$, R$^{yb}$, R$^{yd}$, R$^{a1}$, R$^{b1}$, R$^{c1}$, R$^{y1}$, R$^{a2}$, R$^{b2}$, R$^{c2}$, R$^{y2}$, R$^{a3}$, R$^{b3}$, R$^{c3}$, R$^{y3}$, R$^{a4}$, R$^{b4}$, R$^{c4}$, R$^{y4}$, R$^{a5}$, R$^{b5}$, R$^{c5}$, R$^{y5}$, R$^{a6}$, R$^{b6}$, R$^{c6}$, R$^{y6}$, R$^{a7}$, R$^{b7}$, R$^{c7}$ and R$^{y7}$ have, unless otherwise indicated, independently of one another preferably one of the following meanings:

R$^{ya}$: C$_1$-C$_4$-alkoxy or C$_1$-C$_4$-haloalkoxy.

R$^{yb}$: halogen, C$_1$-C$_4$-alkyl, C$_1$-C$_4$-haloalkyl, C$_1$-C$_4$-alkoxy or C$_1$-C$_4$-haloalkoxy.

R$^{yd}$: F, Cl, OH, COOH, C(O)NH$_2$, CN, NH$_2$, OCH$_2$COOH, C$_1$-C$_4$ alkyl, C$_1$-C$_4$-haloalkyl, C$_1$-C$_4$-alkoxy, C$_1$-C$_4$-haloalkoxy, C$_1$-C$_4$-alkylthio, C$_1$-C$_4$-haloalkylthio, CO—C$_1$-C$_4$-alkyl, CO—O—C$_1$-C$_4$-alkyl, NH—C$_1$-C$_4$-alkyl, NH—C(O)C$_1$-C$_4$-alkyl or SO$_2$—C$_1$-C$_4$-alkyl.

R$^{a1}$, R$^{b1}$, R$^{c1}$, R$^{y1}$ independently of one another: hydrogen, C$_1$-C$_6$-alkyl, C$_1$-C$_6$-haloalkyl, phenyl, benzyl, hetaryl and hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$ haloalkyl, C$_1$-C$_4$-alkoxy and C$_1$-C$_4$-haloalkoxy.

R$^{a2}$, R$^{b2}$, R$^{c2}$, R$^{y2}$ independently of one another: hydrogen, C$_1$-C$_6$-alkyl, phenyl, benzyl, hetaryl and hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a3}$, R$^{b3}$, R$^{c3}$, R$^{y3}$ independently of one another: hydrogen or C$_1$-C$_6$-alkyl, or R$^{a2}$ with R$^{a3}$ (and likewise R$^{b2}$ with R$^{b3}$, R$^{c2}$ with R$^{c3}$ and R$^{2}$ with R$^{y3}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from C$_1$-C$_4$-alkyl, C$_1$-C$_4$-haloalkyl, C$_1$-C$_4$-alkoxy or C$_1$-C$_4$-haloalkoxy.

R$^{a4}$, R$^{b4}$, R$^{c4}$, R$^{y4}$ independently of one another: C$_1$-C$_6$-alkyl, phenyl, benzyl, hetaryl and hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a5}$, R$^{b5}$, R$^{c5}$, R$^{y5}$ independently of one another: hydrogen, C$_1$-C$_6$-alkyl, phenyl, benzyl, hetaryl and hetarylmethyl, where phenyl and hetaryl in the last 4 radicals mentioned are unsubstituted or have 1, 2 or 3 substituents which are selected from halogen, C$_1$-C$_4$-alkyl C$_1$-C$_4$-haloalkyl, C$_1$-C$_4$-alkoxy and C$_1$-C$_4$-haloalkoxy.

R$^{a6}$, R$^{b6}$, R$^{c6}$, R$^{y6}$ independently of one another: hydrogen, C$_1$-C$_6$-alkyl, phenyl, benzyl, hetaryl and hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a7}$, R$^{b7}$, R$^{c7}$, R$^{y7}$ independently of one another: hydrogen or C$_1$-C$_6$-alkyl, or R$^{a6}$ with R$^{a7}$ (and likewise R$^{b6}$ with R$^{b7}$, R$^{c6}$ with R$^{c7}$ and R$^{y6}$ with R$^{y7}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from C$_1$-C$_4$-alkyl, C$_1$-C$_4$-haloalkyl, C$_1$-C$_4$-alkoxy or C$_1$-C$_4$-haloalkoxy.

Preferred among the carboxamide compounds of the invention of the formula I are those compounds which correspond to the general formula Ia,

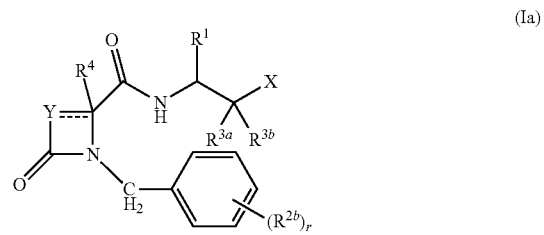

(Ia)

in which X, Y, R$^1$, R$^{3a}$, R$^{3b}$, R$^4$ and R$^{2b}$ have the aforementioned meanings, in particular the meanings mentioned as preferred, and r is an integer from 0 to 4, preferably from 0 to 2, and particularly from 0 to 1. In formula Ia the variable Y is preferably a moiety CH$_2$—CH$_2$, CH$_2$—CH$_2$—CH$_2$, N(R$^{Y\#}$)—CH$_2$, N(R$^{y\#}$)—CH$_2$—CH$_2$ or CH=CH—CH=, each optionally having 1 or 2, and preferably 1, H-atoms replaced with identical or different radicals R$^y$. Also preferred are the tautomers of Ia, the pharmaceutically suitable salts thereof and the tautomers thereof.

Also preferred among the carboxamide compounds of the invention of the formula I are those compounds which correspond to the general formula Ib,

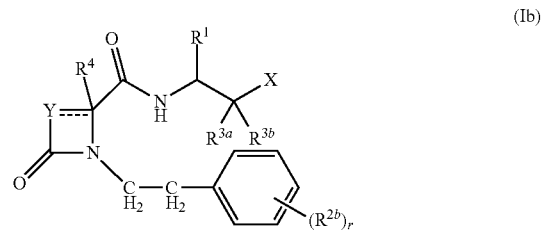

(Ib)

in which X, Y, R$^1$, R$^{3a}$, R$^{3b}$, R$^4$ and R$^{2b}$ have the aforementioned meanings, in particular the meanings mentioned as preferred, and r is an integer from 0 to 4, preferably from 0 to 2, and particularly from 0 to 1. In formula Ib the variable Y is preferably a moiety CH$_2$—CH$_2$, CH$_2$—CH$_2$—CH$_2$, N(R$^{y\#}$)—CH$_2$, N(R$^{y\#}$)—CH$_2$—CH$_2$ or CH=CH—CH=, each optionally having 1 or 2, and preferably 1, H-atoms replaced with identical or different radicals R$^y$. Also preferred are the tautomers of Ib, the pharmaceutically suitable salts thereof and the tautomers thereof.

Also preferred among the carboxamide compounds of the invention of the formula I are those compounds which correspond to the general formula I-A,

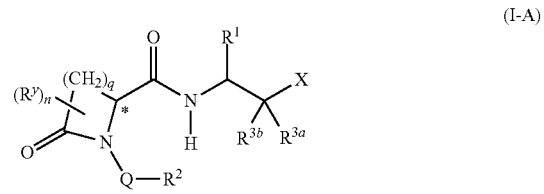

(I-A)

in which X, Q, R$^1$, R$^2$, R$^{3a}$, R$^{3b}$ and R$^y$ have the aforementioned meanings, in particular the meanings mentioned as preferred, the variable n is 0, 1 or 2, preferably 0 or 1, and the variable q is 2 or 3, preferably 2. In formula I-A Q is preferably a single bond, a moiety CH$_2$ or CH$_2$—CH$_2$ and particularly preferred a moiety CH$_2$ or CH$_2$—CH$_2$. The variable R$^2$ is preferably phenyl, which is unsubstituted or carries 1 to 4, preferably 1 to 2, identical or different radicals R$^{2b}$. In preferred compounds of formula I-A the carbon atom indicated with an asterisk has predominantly R-configuration. Also preferred are the tautomers of I-A, the pharmaceutically suitable salts thereof and the tautomers thereof.

In the compounds of the formula I-A the carbon atom indicated with an asterisk (*) is a center of chirality. Thus, the compounds I-A may have R-configuration or S-configuration with regard to this center of chirality. Mixtures of the stereoisomers of I-A containing almost equal amounts of the compounds wherein this center has R-configuration and compounds wherein this center has S-configuration are denominated as rac-compounds, while compounds where one configuration significantly dominates are denominated as R-compound and S-compound, respectively.

Preferred examples of compounds of the formula I-A comprise:
rac-N-(4-amino-3,4-dioxo-1-phenylbutan-2-yl)-1-benzyl-5-oxopyrrolidine-2-carboxamide,
(2R)—N-(4-amino-3,4-dioxo-1-phenylbutan-2-yl)-1-benzyl-5-oxopyrrolidine-2-carboxamide,
(2S)—N-(4-amino-3,4-dioxo-1-phenylbutan-2-yl)-1-benzyl-5-oxopyrrolidine-2-carboxamide,
rac-N-(4-amino-3,4-dioxo-1-phenylbutan-2-yl)-1-(3-chlorobenzyl)-5-oxopyrrolidine-2-carboxamide,
(2R)—N-(4-amino-3,4-dioxo-1-phenylbutan-2-yl)-1-(3-chlorobenzyl)-5-oxopyrrolidine-2-carboxamide,
(2S)—N-(4-amino-3,4-dioxo-1-phenylbutan-2-yl)-1-(3-chlorobenzyl)-5-oxopyrrolidine-2-carboxamide,
rac-N-(4-amino-3,4-dioxo-1-phenylbutan-2-yl)-1-(4-fluorobenzyl)-5-oxopyrrolidine-2-carboxamide
(2R)—N-(4-amino-3,4-dioxo-1-phenylbutan-2-yl)-1-(4-fluorobenzyl)-5-oxopyrrolidine-2-carboxamide,
(2S)—N-(4-amino-3,4-dioxo-1-phenylbutan-2-yl)-1-(4-fluorobenzyl)-5-oxopyrrolidine-2-carboxamide,
rac-N-(4-amino-3,4-dioxo-1-phenylbutan-2-yl)-1-(3-methoxybenzyl)-5-oxopyrrolidine-2-carboxamide
(2R)—N-(4-amino-3,4-dioxo-1-phenylbutan-2-yl)-1-(3-methoxybenzyl)-5-oxopyrrolidine-2-carboxamide,
(2S)—N-(4-amino-3,4-dioxo-1-phenylbutan-2-yl)-1-(3-methoxybenzyl)-5-oxopyrrolidine-2-carboxamide,
rac-N-(4-amino-3,4-dioxo-1-phenylbutan-2-yl)-1-(3-trifluoromethyl-benzyl)-5-oxopyrrolidine-2-carboxamide,
(2R)—N-(4-amino-3,4-dioxo-1-phenylbutan-2-yl)-1-(3-trifluoromethyl-benzyl)-5-oxopyrrolidine-2-carboxamide,
(2S)—N-(4-amino-3,4-dioxo-1-phenylbutan-2-yl)-1-(3-trifluoromethyl-benzyl)-5-oxopyrrolidine-2-carboxamide,
rac-N-(4-amino-3,4-dioxo-1-phenylbutan-2-yl)-1-(3-fluorobenzyl)-5-oxopyrrolidine-2-carboxamide,
(2R)—N-(4-amino-3,4-dioxo-1-phenylbutan-2-yl)-1-(3-fluorobenzyl)-5-oxopyrrolidine-2-carboxamide,
(2S)—N-(4-amino-3,4-dioxo-1-phenylbutan-2-yl)-1-(3-fluorobenzyl)-5-oxopyrrolidine-2-carboxamide,
rac-N-(4-amino-3,4-dioxo-1-phenylbutan-2-yl)-5-oxo-1-[2-(trifluoromethoxy)-benzyl]pyrrolidine-2-carboxamide,
(2R)—N-(4-amino-3,4-dioxo-1-phenylbutan-2-yl)-5-oxo-1-[2-(trifluoromethoxy)-benzyl]pyrrolidine-2-carboxamide,
(2S)—N-(4-amino-3,4-dioxo-1-phenylbutan-2-yl)-5-oxo-1-[2-(trifluoromethoxy)-benzyl]pyrrolidine-2-carboxamide,
rac-N-(4-amino-3,4-dioxo-1-phenylbutan-2-yl)-1-(naphthalen-1-ylmethyl)-5-oxopyrrolidine-2-carboxamide,
(2R)—N-(4-amino-3,4-dioxo-1-phenylbutan-2-yl)-1-(naphthalen-1-ylmethyl)-5-oxopyrrolidine-2-carboxamide,
(2S)—N-(4-amino-3,4-dioxo-1-phenylbutan-2-yl)-1-(naphthalen-1-ylmethyl)-5-oxopyrrolidine-2-carboxamide,
rac-N-(4-amino-3,4-dioxo-1-phenylbutan-2-yl)-1-(naphthalen-2-ylmethyl)-5-oxopyrrolidine-2-carboxamide,
(2R)—N-(4-amino-3,4-dioxo-1-phenylbutan-2-yl)-1-(naphthalen-2-ylmethyl)-5-oxopyrrolidine-2-carboxamide,
(2S)—N-(4-amino-3,4-dioxo-1-phenylbutan-2-yl)-1-(naphthalen-2-ylmethyl)-5-oxopyrrolidine-2-carboxamide,
rac-N-(4-amino-3,4-dioxo-1-phenylbutan-2-yl)-5-oxo-1-[3-(trifluoromethoxy)benzyl]-pyrrolidine-2-carboxamide,
(2R)—N-(4-amino-3,4-dioxo-1-phenylbutan-2-yl)-5-oxo-1-[3-(trifluoromethoxy)benzyl]pyrrolidine-2-carboxamide,
(2S)—N-(4-amino-3,4-dioxo-1-phenylbutan-2-yl)-5-oxo-1-[3-(trifluoromethoxy)benzyl]pyrrolidine-2-carboxamide,
rac-N-(4-amino-3,4-dioxo-1-phenylbutan-2-yl)-1-benzyl-6-oxopiperidine-2-carboxamide,
(2R)—N-(4-amino-3,4-dioxo-1-phenylbutan-2-yl)-1-benzyl-6-oxopiperidine-2-carboxamide,
(2S)—N-(4-amino-3,4-dioxo-1-phenylbutan-2-yl)-1-benzyl-6-oxopiperidine-2-carboxamide,
rac-N-(4-amino-3,4-dioxo-1-phenylbutan-2-yl)-5-oxo-1-phenylpyrrolidine-2-carboxamide,
(2R)—N-(4-amino-3,4-dioxo-1-phenylbutan-2-yl)-5-oxo-1-phenylpyrrolidine-2-carboxamide,
(2S)—N-(4-amino-3,4-dioxo-1-phenylbutan-2-yl)-5-oxo-1-phenylpyrrolidine-2-carboxamide,
rac-N-(4-amino-3,4-dioxo-1-phenylbutan-2-yl)-1-(3-cyanobenzyl)-5-oxopyrrolidine-2-carboxamide
(2R)—N-(4-amino-3,4-dioxo-1-phenylbutan-2-yl)-1-(3-cyanobenzyl)-5-oxopyrrolidine-2-carboxamide,
(2S)—N-(4-amino-3,4-dioxo-1-phenylbutan-2-yl)-1-(3-cyanobenzyl)-5-oxopyrrolidine-2-carboxamide,
rac-N-(4-amino-3,4-dioxo-1-phenylbutan-2-yl)-5-oxo-1-[2-(trifluoromethyl)benzyl]-pyrrolidine-2-carboxamide,
(2R)—N-(4-amino-3,4-dioxo-1-phenylbutan-2-yl)-5-oxo-1-[2-(trifluoromethyl)benzyl]-pyrrolidine-2-carboxamide,
(2S)—N-(4-amino-3,4-dioxo-1-phenylbutan-2-yl)-5-oxo-1-[2-(trifluoromethyl)benzyl]-pyrrolidine-2-carboxamide,
(2RS,4S)—N-(4-amino-3,4-dioxo-1-phenylbutan-2-yl)-1-benzyl-4-methyl-5-oxopyrrolidine-2-carboxamide,
(2R,4S)—N-(4-amino-3,4-dioxo-1-phenylbutan-2-yl)-1-benzyl-4-methyl-5-oxopyrrolidine-2-carboxamide,
(2S,4S)—N-(4-amino-3,4-dioxo-1-phenylbutan-2-yl)-1-benzyl-4-methyl-5-oxopyrrolidine-2-carboxamide,
rac-1-benzyl-N-{3,4-dioxo-1-phenyl-4-[(pyridin-2-ylmethyl)amino]butan-2-yl}-5-oxopyrrolidine-2-carboxamide,
(2R)-1-benzyl-N-{3,4-dioxo-1-phenyl-4-[(pyridin-2-ylmethyl)amino]butan-2-yl}-5-oxopyrrolidine-2-carboxamide,
(2S)-1-benzyl-N-{3,4-dioxo-1-phenyl-4-[(pyridin-2-ylmethyl)amino]butan-2-yl}-5-oxopyrrolidine-2-carboxamide,
rac-1-benzyl-N-[4-(ethylamino)-3,4-dioxo-1-phenylbutan-2-yl]-5-oxopyrrolidine-2-carboxamide,
(2R)-1-benzyl-N-[4-(ethylamino)-3,4-dioxo-1-phenylbutan-2-yl]-5-oxopyrrolidine-2-carboxamide,
(2S)-1-benzyl-N-[4-(ethylamino)-3,4-dioxo-1-phenylbutan-2-yl]-5-oxopyrrolidine-2-carboxamide,
rac-N-(4-amino-3,4-dioxo-1-phenylbutan-2-yl)-1-(3,5-dimethoxybenzyl)-5-oxopyrrolidine-2-carboxamide,
(2R)—N-(4-amino-3,4-dioxo-1-phenylbutan-2-yl)-1-(3,5-dimethoxybenzyl)-5-oxopyrrolidine-2-carboxamide,
(2S)—N-(4-amino-3,4-dioxo-1-phenylbutan-2-yl)-1-(3,5-dimethoxybenzyl)-5-oxopyrrolidine-2-carboxamide,
rac-N-(4-amino-3,4-dioxo-1-phenylbutan-2-yl)-5-oxo-1-(pyridin-4-ylmethyl)pyrrolidine-2-carboxamide, (2R)—N-(4-amino-3,4-dioxo-1-phenylbutan-2-yl)-5-oxo-1-(pyridin-4-ylmethyl)pyrrolidine-2-carboxamide,
(2S)—N-(4-amino-3,4-dioxo-1-phenylbutan-2-yl)-5-oxo-1-(pyridin-4-ylmethyl)pyrrolidine-2-carboxamide,
rac-N-(4-amino-3,4-dioxo-1-phenylbutan-2-yl)-1-(3,5-difluorobenzyl)-5-oxopyrrolidine-2-carboxamide,
(2R)—N-(4-amino-3,4-dioxo-1-phenylbutan-2-yl)-1-(3,5-difluorobenzyl)-5-oxopyrrolidine-2-carboxamide,
(2S)—N-(4-amino-3,4-dioxo-1-phenylbutan-2-yl)-1-(3,5-difluorobenzyl)-5-oxopyrrolidine-2-carboxamide,
rac-1-benzyl-N-(4-(methylamino)-3,4-dioxo-1-phenylbutan-2-yl)-5-oxopyrrolidine-2-carboxamide,
(2R)-1-benzyl-N-(4-(methylamino)-3,4-dioxo-1-phenylbutan-2-yl)-5-oxopyrrolidine-2-carboxamide,
(2S)-1-benzyl-N-(4-(methylamino)-3,4-dioxo-1-phenylbutan-2-yl)-5-oxopyrrolidine-2-carboxamide,
rac-1-benzyl-N-(3,4-dioxo-1-phenyl-4-(propylamino)butan-2-yl)-5-oxopyrrolidine-2-carboxamide,
(2R)-1-benzyl-N-(3,4-dioxo-1-phenyl-4-(propylamino)butan-2-yl)-5-oxopyrrolidine-2-carboxamide,
(2S)-1-benzyl-N-(3,4-dioxo-1-phenyl-4-(propylamino)butan-2-yl)-5-oxopyrrolidine-2-carboxamide,
rac-1-benzyl-N-(4-(cyclopropylamino)-3,4-dioxo-1-phenylbutan-2-yl)-5-oxopyrrolidine-2-carboxamide,
(2R)-1-benzyl-N-(4-(cyclopropylamino)-3,4-dioxo-1-phenylbutan-2-yl)-5-oxopyrrolidine-2-carboxamide,
(2S)-1-benzyl-N-(4-(cyclopropylamino)-3,4-dioxo-1-phenylbutan-2-yl)-5-oxopyrrolidine-2-carboxamide,
rac-1-benzyl-N-(4-(isobutylamino)-3,4-dioxo-1-phenylbutan-2-yl)-5-oxopyrrolidine-2-carboxamide,
(2R)-1-benzyl-N-(4-(isobutylamino)-3,4-dioxo-1-phenylbutan-2-yl)-5-oxopyrrolidine-2-carboxamide,
(2S)-1-benzyl-N-(4-(isobutylamino)-3,4-dioxo-1-phenylbutan-2-yl)-5-oxopyrrolidine-2-carboxamide,
rac-1-benzyl-N-(4-(cyclobutylamino)-3,4-dioxo-1-phenylbutan-2-yl)-5-oxopyrrolidine-2-carboxamide,
(2R)-1-benzyl-N-(4-(cyclobutylamino)-3,4-dioxo-1-phenylbutan-2-yl)-5-oxopyrrolidine-2-carboxamide,
(2S)-1-benzyl-N-(4-(cyclobutylamino)-3,4-dioxo-1-phenylbutan-2-yl)-5-oxopyrrolidine-2-carboxamide,
rac-1-benzyl-N-(4-(methoxyamino)-3,4-dioxo-1-phenylbutan-2-yl)-5-oxopyrrolidine-2-carboxamide,
(2R)-1-benzyl-N-(4-(methoxyamino)-3,4-dioxo-1-phenylbutan-2-yl)-5-oxopyrrolidine-2-carboxamide,
(2S)-1-benzyl-N-(4-(methoxyamino)-3,4-dioxo-1-phenylbutan-2-yl)-5-oxopyrrolidine-2-carboxamide,
rac-1-benzyl-N-(3,4-dioxo-1-phenyl-4-(2-(pyridin-2-yl)ethylamino)butan-2-yl)-5-oxopyrrolidine-2-carboxamide,
(2R)-1-benzyl-N-(3,4-dioxo-1-phenyl-4-(2-(pyridin-2-yl)ethylamino)butan-2-yl)-5-oxopyrrolidine-2-carboxamide,
(2S)-1-benzyl-N-(3,4-dioxo-1-phenyl-4-(2-(pyridin-2-yl)ethylamino)butan-2-yl)-5-oxopyrrolidine-2-carboxamide,
rac-1-benzyl-N-(3,4-dioxo-1-phenyl-4-(3-(pyridin-2-yl)propylamino)butan-2-yl)-5-oxopyrrolidine-2-carboxamide,
(2R)-1-benzyl-N-(3,4-dioxo-1-phenyl-4-(3-(pyridin-2-yl)propylamino)butan-2-yl)-5-oxopyrrolidine-2-carboxamide,
(2S)-1-benzyl-N-(3,4-dioxo-1-phenyl-4-(3-(pyridin-2-yl)propylamino)butan-2-yl)-5-oxopyrrolidine-2-carboxamide,
rac-1-benzyl-N-(3,4-dioxo-1-phenyl-4-(3-phenylpropylamino)butan-2-yl)-5-oxopyrrolidine-2-carboxamide,
(2R)-1-benzyl-N-(3,4-dioxo-1-phenyl-4-(3-phenylpropylamino)butan-2-yl)-5-oxopyrrolidine-2-carboxamide,
(2S)-1-benzyl-N-(3,4-dioxo-1-phenyl-4-(3-phenylpropylamino)butan-2-yl)-5-oxopyrrolidine-2-carboxamide,
rac-1-benzyl-N-(4-(ethyl(methyl)amino)-3,4-dioxo-1-phenylbutan-2-yl)-5-oxopyrrolidine-2-carboxamide,
(2R)-1-benzyl-N-(4-(ethyl(methyl)amino)-3,4-dioxo-1-phenylbutan-2-yl)-5-oxopyrrolidine-2-carboxamide,
(2S)-1-benzyl-N-(4-(ethyl(methyl)amino)-3,4-dioxo-1-phenylbutan-2-yl)-5-oxopyrrolidine-2-carboxamide,
rac-1-benzyl-N-(4-(2-chlorobenzylamino)-3,4-dioxo-1-phenylbutan-2-yl)-5-oxopyrrolidine-2-carboxamide,
(2R)-1-benzyl-N-(4-(2-chlorobenzylamino)-3,4-dioxo-1-phenylbutan-2-yl)-5-oxopyrrolidine-2-carboxamide,
(2S)-1-benzyl-N-(4-(2-chlorobenzylamino)-3,4-dioxo-1-phenylbutan-2-yl)-5-oxopyrrolidine-2-carboxamide,
rac-N-(4-(cyclopropylamino)-3,4-dioxo-1-phenylbutan-2-yl)-5-oxo-1-(2-(trifluoromethyl)benzyl)pyrrolidine-2-carboxamide,
(2R)—N-(4-(cyclopropylamino)-3,4-dioxo-1-phenylbutan-2-yl)-5-oxo-1-(2-(trifluoromethyl)benzyl)pyrrolidine-2-carboxamide,
(2S)—N-(4-(cyclopropylamino)-3,4-dioxo-1-phenylbutan-2-yl)-5-oxo-1-(2-(trifluoromethyl)benzyl)pyrrolidine-2-carboxamide,
rac-N-(4-(ethylamino)-3,4-dioxo-1-phenylbutan-2-yl)-5-oxo-1-(2-(trifluoromethyl)benzyl)pyrrolidine-2-carboxamide,
(2R)—N-(4-(ethylamino)-3,4-dioxo-1-phenylbutan-2-yl)-5-oxo-1-(2-(trifluoromethyl)benzyl)pyrrolidine-2-carboxamide,
(2S)—N-(4-(ethylamino)-3,4-dioxo-1-phenylbutan-2-yl)-5-oxo-1-(2-(trifluoromethyl)benzyl)pyrrolidine-2-carboxamide,
rac-N-(4-(benzylamino)-3,4-dioxo-1-phenylbutan-2-yl)-5-oxo-1-(2-(trifluoromethyl)benzyl)pyrrolidine-2-carboxamide,
(2R)—N-(4-(benzylamino)-3,4-dioxo-1-phenylbutan-2-yl)-5-oxo-1-(2-(trifluoromethyl)benzyl)pyrrolidine-2-carboxamide,
(2S)—N-(4-(benzylamino)-3,4-dioxo-1-phenylbutan-2-yl)-5-oxo-1-(2-(trifluoromethyl)benzyl)pyrrolidine-2-carboxamide,
rac-N-(4-(isopropylamino)-3,4-dioxo-1-phenylbutan-2-yl)-5-oxo-1-(2-(trifluoromethyl)benzyl)pyrrolidine-2-carboxamide,
(2R)—N-(4-(isopropylamino)-3,4-dioxo-1-phenylbutan-2-yl)-5-oxo-1-(2-(trifluoromethyl)benzyl)pyrrolidine-2-carboxamide,
(2S)—N-(4-(isopropylamino)-3,4-dioxo-1-phenylbutan-2-yl)-5-oxo-1-(2-(trifluoromethyl)benzyl)pyrrolidine-2-carboxamide,
rac-N-(3,4-dioxo-1-phenyl-4-(2-(pyridin-2-yl)-ethylamino)butan-2-yl)-5-oxo-1-(2-(trifluoromethyl)benzyl)pyrrolidine-2-carboxamide,
(2R)—N-(3,4-dioxo-1-phenyl-4-(2-(pyridin-2-yl)-ethylamino)butan-2-yl)-5-oxo-1-(2-(trifluoromethyl)benzyl)pyrrolidine-2-carboxamide,
(2S)—N-(3,4-dioxo-1-phenyl-4-(2-(pyridin-2-yl)-ethylamino)butan-2-yl)-5-oxo-1-(2-(trifluoromethyl)benzyl)pyrrolidine-2-carboxamide,
rac-N-(3,4-dioxo-1-phenyl-4-(3-(pyridin-2-yl)propylamino)butan-2-yl)-5-oxo-1-(2-(trifluoromethyl)benzyl)pyrrolidine-2-carboxamide
(2R)—N-(3,4-dioxo-1-phenyl-4-(3-(pyridin-2-yl)propylamino)butan-2-yl)-5-oxo-1-(2-(trifluoromethyl)benzyl)pyrrolidine-2-carboxamide,
(2S)—N-(3,4-dioxo-1-phenyl-4-(3-(pyridin-2-yl)propylamino)butan-2-yl)-5-oxo-1-(2-(trifluoromethyl)benzyl)pyrrolidine-2-carboxamide, rac-N-(4-(ethylamino)-3,4-dioxo-1-phenylbutan-2-yl)-1-(2-methoxy-6-(trifluoromethyl)benzyl)-5-oxopyrrolidine-2-carboxamide,
(2R)—N-(4-(ethylamino)-3,4-dioxo-1-phenylbutan-2-yl)-1-(2-methoxy-6-(trifluoromethyl)benzyl)-5-oxopyrrolidine-2-carboxamide,
(2S)—N-(4-(ethylamino)-3,4-dioxo-1-phenylbutan-2-yl)-1-(2-methoxy-6-(trifluoromethyl)benzyl-5-oxopyrrolidine-2-carboxamide,
rac-N-(3,4-dioxo-1-phenyl-4-(pyridin-2-ylmethylamino)butan-2-yl)-1-(2-methoxy-6-(trifluoromethyl)benzyl)-5-oxopyrrolidine-2-carboxamide,
(2R)—N-(3,4-dioxo-1-phenyl-4-(pyridin-2-ylmethylamino)butan-2-yl)-1-(2-methoxy-6-(trifluoromethyl)benzyl)-5-oxopyrrolidine-2-carboxamide,
(2S)—N-(3,4-dioxo-1-phenyl-4-(pyridin-2-ylmethylamino)butan-2-yl)-1-(2-methoxy-6-(trifluoromethyl)benzyl)-5-oxopyrrolidine-2-carboxamide,
rac-N-(4-(benzylamino)-3,4-dioxo-1-phenylbutan-2-yl)-1-(2-methoxy-6-(trifluoromethyl)benzyl)-5-oxopyrrolidine-2-carboxamide,
(2R)—N-(4-(benzylamino)-3,4-dioxo-1-phenylbutan-2-yl)-1-(2-methoxy-6-(trifluoromethyl)benzyl)-5-oxopyrrolidine-2-carboxamide,
(2S)—N-(4-(benzylamino)-3,4-dioxo-1-phenylbutan-2-yl)-1-(2-methoxy-6-(trifluoromethyl)benzyl)-5-oxopyrrolidine-2-carboxamide,
rac-N-(3,4-dioxo-1-phenyl-4-(2-(pyridin-2-yl)-ethylamino)butan-2-yl)-5-oxo-1-(2-(trifluoromethoxy)benzyl)pyrrolidine-2-carboxamide,
(2R)—N-(3,4-dioxo-1-phenyl-4-(2-(pyridin-2-yl)-ethylamino)butan-2-yl)-5-oxo-1-(2-(trifluoromethoxy)benzyl)pyrrolidine-2-carboxamide,
(2S)—N-(3,4-dioxo-1-phenyl-4-(2-(pyridin-2-yl)-ethylamino)butan-2-yl)-5-oxo-1-(2-(trifluoromethoxy)benzyl)pyrrolidine-2-carboxamide,
rac-1-(2-chlorobenzyl)-N-(4-(cyclopropylamino)-3,4-dioxo-1-phenylbutan-2-yl)-5-oxopyrrolidine-2-carboxamide,
(2R)-1-(2-chlorobenzyl)-N-(4-(cyclopropylamino)-3,4-dioxo-1-phenylbutan-2-yl)-5-oxopyrrolidine-2-carboxamide,
(2S)-1-(2-chlorobenzyl)-N-(4-(cyclopropylamino)-3,4-dioxo-1-phenylbutan-2-yl)-5-oxopyrrolidine-2-carboxamide,
rac-1-(2-chlorobenzyl)-N-(4-(ethylamino)-3,4-dioxo-1-phenylbutan-2-yl)-5-oxopyrrolidine-2-carboxamide,
(2R)-1-(2-chlorobenzyl)-N-(4-(ethylamino)-3,4-dioxo-1-phenylbutan-2-yl)-5-oxopyrrolidine-2-carboxamide,
(2S)-1-(2-chlorobenzyl)-N-(4-(ethylamino)-3,4-dioxo-1-phenylbutan-2-yl)-5-oxopyrrolidine-2-carboxamide,
rac-N-(4-(cyclopropylamino)-3,4-dioxo-1-phenylbutan-2-yl)-1-(2,6-difluorobenzyl)-5-oxopyrrolidine-2-carboxamide,
(2R)—N-(4-(cyclopropylamino)-3,4-dioxo-1-phenylbutan-2-yl)-1-(2,6-difluorobenzyl)-5-oxopyrrolidine-2-carboxamide,
(2S)—N-(4-(cyclopropylamino)-3,4-dioxo-1-phenylbutan-2-yl)-1-(2,6-difluorobenzyl)-5-oxopyrrolidine-2-carboxamide,
rac-1-(2,6-difluorobenzyl)-N-(4-(ethylamino)-3,4-dioxo-1-phenylbutan-2-yl)-5-oxopyrrolidine-2-carboxamide,
(2R)-1-(2,6-difluorobenzyl)-N-(4-(ethylamino)-3,4-dioxo-1-phenylbutan-2-yl)-5-oxopyrrolidine-2-carboxamide,
(2S)-1-(2,6-difluorobenzyl)-N-(4-(ethylamino)-3,4-dioxo-1-phenylbutan-2-yl)-5-oxopyrrolidine-2-carboxamide,
rac-N-(4-amino-3,4-dioxo-1-phenylbutan-2-yl)-5-oxo-1-[2-methoxy-6-(trifluoromethyl)benzyl]pyrrolidine-2-carboxamide,
(2R)—N-(4-amino-3,4-dioxo-1-phenylbutan-2-yl)-5-oxo-1-[2-methoxy-6-(trifluoromethyl)benzyl]pyrrolidine-2-carboxamide,
(2S)—N-(4-amino-3,4-dioxo-1-phenylbutan-2-yl)-5-oxo-1-[2-methoxy-6-(trifluoromethyl)benzyl]pyrrolidine-2-carboxamide,
rac-N-(4-amino-3,4-dioxo-1-phenylbutan-2-yl)-5-oxo-1-(2,6-difluorobenzyl)pyrrolidine-2-carboxamide,
(2R)—N-(4-amino-3,4-dioxo-1-phenylbutan-2-yl)-5-oxo-1-(2,6-difluorobenzyl)pyrrolidine-2-carboxamide,
(2S)—N-(4-amino-3,4-dioxo-1-phenylbutan-2-yl)-5-oxo-1-(2,6-difluorobenzyl)pyrrolidine-2-carboxamide,
rac-1-benzyl-N-(3,4-dioxo-1-phenyl-4-(2-phenylethylamino)butan-2-yl)-5-oxopyrrolidine-2-carboxamide,
(2R)-1-benzyl-N-(3,4-dioxo-1-phenyl-4-(2-phenylethylamino)butan-2-yl)-5-oxopyrrolidine-2-carboxamide,
(2S)-1-benzyl-N-(3,4-dioxo-1-phenyl-4-(2-phenylethylamino)butan-2-yl)-5-oxopyrrolidine-2-carboxamide
rac-1-benzyl-N-(3,4-dioxo-1-phenyl-4-(thiazol-5-ylmethylamino)butan-2-yl)-5-oxopyrrolidine-2-carboxamide,
(2R)-1-benzyl-N-(3,4-dioxo-1-phenyl-4-(thiazol-5-ylmethylamino)butan-2-yl)-5-oxopyrrolidine-2-carboxamide
(2S)-1-benzyl-N-(3,4-dioxo-1-phenyl-4-(thiazol-5-ylmethylamino)butan-2-yl)-5-oxopyrrolidine-2-carboxamide,
rac-N-(4-(benzo[d]thiazol-2-ylmethylamino)-3,4-dioxo-1-phenylbutan-2-yl)-1-benzyl-5-oxopyrrolidine-2-carboxamide,
(2R)—N-(4-(benzo[d]thiazol-2-ylmethylamino)-3,4-dioxo-1-phenylbutan-2-yl)-1-benzyl-5-oxopyrrolidine-2-carboxamide,
(2S)—N-(4-(benzo[d]thiazol-2-ylmethylamino)-3,4-dioxo-1-phenylbutan-2-yl)-1-benzyl-5-oxopyrrolidine-2-carboxamide,
rac-1-benzyl-N-(4-morpholino-3,4-dioxo-1-phenylbutan-2-yl)-5-oxopyrrolidine-2-carboxamide,
(2R)-1-benzyl-N-(4-morpholino-3,4-dioxo-1-phenylbutan-2-yl)-5-oxopyrrolidine-2-carboxamide,
(2S)-1-benzyl-N-(4-morpholino-3,4-dioxo-1-phenylbutan-2-yl)-5-oxopyrrolidine-2-carboxamide,
rac-N-(4-(ethylamino)-3,4-dioxo-1-phenylbutan-2-yl)-5-oxo-1-(4-(trifluoromethyl)benzyl)pyrrolidine-2-carboxamide,
(2R)—N-(4-(ethylamino)-3,4-dioxo-1-phenylbutan-2-yl)-5-oxo-1-(4-(trifluoromethyl)benzyl)pyrrolidine-2-carboxamide,
(2S)—N-(4-(ethylamino)-3,4-dioxo-1-phenylbutan-2-yl)-5-oxo-1-(4-(trifluoromethyl)benzyl)pyrrolidine-2-carboxamide,
rac-1-benzyl-N-(4-(cyclohexylamino)-3,4-dioxo-1-phenylbutan-2-yl)-5-oxopyrrolidine-2-carboxamide,
(2R)-1-benzyl-N-(4-(cyclohexylamino)-3,4-dioxo-1-phenylbutan-2-yl)-5-oxopyrrolidine-2-carboxamide,
(2S)-1-benzyl-N-(4-(cyclohexylamino)-3,4-dioxo-1-phenylbutan-2-yl)-5-oxopyrrolidine-2-carboxamide,
rac-N-(4-(2-benzoylhydrazinyl)-3,4-dioxo-1-phenylbutan-2-yl)-1-benzyl-5-oxopyrrolidine-2-carboxamide,
(2R)—N-(4-(2-benzoylhydrazinyl)-3,4-dioxo-1-phenylbutan-2-yl)-1-benzyl-5-oxopyrrolidine-2-carboxamide,
(2S)—N-(4-(2-benzoylhydrazinyl)-3,4-dioxo-1-phenylbutan-2-yl)-1-benzyl-5-oxopyrrolidine-2-carboxamide,
rac-N-(4-(cyclopropylamino)-3,4-dioxo-1-phenylbutan-2-yl)-5-oxo-1-(4-(trifluoromethyl)benzyl)pyrrolidine-2-carboxamide, (2R)—N-(4-(cyclopropylamino)-3,4-dioxo-1-phenylbutan-2-yl)-5-oxo-1-(4-(trifluoromethyl)benzyl)pyrrolidine-2-carboxamide,
(2S)—N-(4-(cyclopropylamino)-3,4-dioxo-1-phenylbutan-2-yl)-5-oxo-1-(4-(trifluoromethyl)benzyl)pyrrolidine-2-carboxamide,
rac-1-benzyl-N-(3,4-dioxo-1-phenyl-4-(thiazol-2-ylmethylamino)butan-2-yl)-5-oxopyrrolidine-2-carboxamide,
(2R)-1-benzyl-N-(3,4-dioxo-1-phenyl-4-(thiazol-2-ylmethylamino)butan-2-yl)-5-oxopyrrolidine-2-carboxamide,
(2S)-1-benzyl-N-(3,4-dioxo-1-phenyl-4-(thiazol-2-ylmethylamino)butan-2-yl)-5-oxopyrrolidine-2-carboxamide,
rac-1-benzyl-N-(3,4-dioxo-1-phenyl-4-(thiophen-2-ylmethylamino)butan-2-yl)-5-oxopyrrolidine-2-carboxamide,
(2R)-1-benzyl-N-(3,4-dioxo-1-phenyl-4-(thiophen-2-ylmethylamino)butan-2-yl)-5-oxopyrrolidine-2-carboxamide,
(2S)-1-benzyl-N-(3,4-dioxo-1-phenyl-4-(thiophen-2-ylmethylamino)butan-2-yl)-5-oxopyrrolidine-2-carboxamide,
rac-N-(4-(cyclopropylamino)-3,4-dioxo-1-phenylbutan-2-yl)-1-(2,6-dichlorobenzyl)-5-oxopyrrolidine-2-carboxamide,
(2R)—N-(4-(cyclopropylamino)-3,4-dioxo-1-phenylbutan-2-yl)-1-(2,6-dichlorobenzyl)-5-oxopyrrolidine-2-carboxamide,
(2S)—N-(4-(cyclopropylamino)-3,4-dioxo-1-phenylbutan-2-yl)-1-(2,6-dichlorobenzyl)-5-oxopyrrolidine-2-carboxamide,
rac-1-(2,6-dichlorobenzyl)-N-(4-(ethylamino)-3,4-dioxo-1-phenylbutan-2-yl)-5-oxopyrrolidine-2-carboxamide,
(2R)-1-(2,6-dichlorobenzyl)-N-(4-(ethylamino)-3,4-dioxo-1-phenylbutan-2-yl)-5-oxopyrrolidine-2-carboxamide,
(2S)-1-(2,6-dichlorobenzyl)-N-(4-(ethylamino)-3,4-dioxo-1-phenylbutan-2-yl)-5-oxopyrrolidine-2-carboxamide,
rac-1-benzyl-N-(3,4-dioxo-1-phenyl-4-(pyridin-4-ylmethylamino)butan-2-yl)-5-oxopyrrolidine-2-carboxamide,
(2R)-1-benzyl-N-(3,4-dioxo-1-phenyl-4-(pyridin-4-ylmethylamino)butan-2-yl)-5-oxopyrrolidine-2-carboxamide,
(2S)-1-benzyl-N-(3,4-dioxo-1-phenyl-4-(pyridin-4-ylmethylamino)butan-2-yl)-5-oxopyrrolidine-2-carboxamide,
rac-1-benzyl-N-(4-(oxazol-2-ylmethylamino)-3,4-dioxo-1-phenylbutan-2-yl)-5-oxopyrrolidine-2-carboxamide,
(2R)-1-benzyl-N-(4-(oxazol-2-ylmethylamino)-3,4-dioxo-1-phenylbutan-2-yl)-5-oxopyrrolidine-2-carboxamide,
(2S)-1-benzyl-N-(4-(oxazol-2-ylmethylamino)-3,4-dioxo-1-phenylbutan-2-yl)-5-oxopyrrolidine-2-carboxamide,
rac-1-benzyl-N-(3,4-dioxo-1-phenyl-4-(phenylamino)butan-2-yl)-5-oxopyrrolidine-2-carboxamide,
(2R)-1-benzyl-N-(3,4-dioxo-1-phenyl-4-(phenylamino)butan-2-yl)-5-oxopyrrolidine-2-carboxamide,
(S)-1-benzyl-N-(3,4-dioxo-1-phenyl-4-(phenylamino)butan-2-yl)-5-oxopyrrolidine-2-carboxamide,
rac-N-(4-(benzo[d][1,3]dioxol-5-ylmethylamino)-3,4-dioxo-1-phenylbutan-2-yl)-1-benzyl-5-oxopyrrolidine-2-carboxamide,
(2R)—N-(4-(benzo[d][1,3]dioxol-5-ylmethylamino)-3,4-dioxo-1-phenylbutan-2-yl)-1-benzyl-5-oxopyrrolidine-2-carboxamide,
(2S)—N-(4-(benzo[d][1,3]dioxol-5-ylmethylamino)-3,4-dioxo-1-phenylbutan-2-yl)-1-benzyl-5-oxopyrrolidine-2-carboxamide,
rac-1-benzyl-N-(4-(4-fluorobenzylamino)-3,4-dioxo-1-phenylbutan-2-yl)-5-oxopyrrolidine-2-carboxamide,
(2R)-1-benzyl-N-(4-(4-fluorobenzylamino)-3,4-dioxo-1-phenylbutan-2-yl)-5-oxopyrrolidine-2-carboxamide,
(2S)-1-benzyl-N-(4-(4-fluorobenzylamino)-3,4-dioxo-1-phenylbutan-2-yl)-5-oxopyrrolidine-2-carboxamide,
rac-1-benzyl-N-(3,4-dioxo-1-phenyl-4-(4-(trifluoromethyl)benzylamino)butan-2-yl)-5-oxopyrrolidine-2-carboxamide,
(2R)-1-benzyl-N-(3,4-dioxo-1-phenyl-4-(4-(trifluoromethyl)benzylamino)butan-2-yl)-5-oxopyrrolidine-2-carboxamide,
(2S)-1-benzyl-N-(3,4-dioxo-1-phenyl-4-(4-(trifluoromethyl)benzylamino)butan-2-yl)-5-oxopyrrolidine-2-carboxamide,
rac-1-benzyl-N-(3,4-dioxo-1-phenyl-4-(((R)-tetrahydrofuran-2-yl)methylamino)butan-2-yl)-5-oxopyrrolidine-2-carboxamide,
(2R)-1-benzyl-N-(3,4-dioxo-1-phenyl-4-(((R)-tetrahydrofuran-2-yl)-methylamino)butan-2-yl)-5-oxopyrrolidine-2-carboxamide,
(2S)-1-benzyl-N-(3,4-dioxo-1-phenyl-4-(((R)-tetrahydrofuran-2-yl)-methylamino)butan-2-yl)-5-oxopyrrolidine-2-carboxamide,
rac-1-benzyl-N-(3,4-dioxo-1-phenyl-4-(((S)-tetrahydrofuran-2-yl)methylamino)butan-2-yl)-5-oxopyrrolidine-2-carboxamide,
(2R)-1-benzyl-N-(3,4-dioxo-1-phenyl-4-(((S)-tetrahydrofuran-2-yl)-methylamino)butan-2-yl)-5-oxopyrrolidine-2-carboxamide,
(2S)-1-benzyl-N-(3,4-dioxo-1-phenyl-4-(((S)-tetrahydrofuran-2-yl)methylamino)butan-2-yl)-5-oxopyrrolidine-2-carboxamide,
rac-1-benzyl-N-(3,4-dioxo-1-phenyl-4-(2-(thiophen-3-yl)-ethylamino)butan-2-yl)-5-oxopyrrolidine-2-carboxamide,
(2R)-1-benzyl-N-(3,4-dioxo-1-phenyl-4-(2-(thiophen-3-yl)-ethylamino)butan-2-yl)-5-oxopyrrolidine-2-carboxamide,
(2S)-1-benzyl-N-(3,4-dioxo-1-phenyl-4-(2-(thiophen-3-yl)-ethylamino)butan-2-yl)-5-oxopyrrolidine-2-carboxamide,
rac-1-benzyl-N-(4-(furan-2-ylmethylamino)-3,4-dioxo-1-phenylbutan-2-yl)-5-oxopyrrolidine-2-carboxamide,
(2R)-1-benzyl-N-(4-(furan-2-ylmethylamino)-3,4-dioxo-1-phenylbutan-2-yl)-5-oxopyrrolidine-2-carboxamide,
(2S)-1-benzyl-N-(4-(furan-2-ylmethylamino)-3,4-dioxo-1-phenylbutan-2-yl)-5-oxopyrrolidine-2-carboxamide,
rac-1-benzyl-N-(4-(2-benzylhydrazinyl)-3,4-dioxo-1-phenylbutan-2-yl)-5-oxopyrrolidine-2-carboxamide,
(2R)-1-benzyl-N-(4-(2-benzylhydrazinyl)-3,4-dioxo-1-phenylbutan-2-yl)-5-oxopyrrolidine-2-carboxamide,
(2S)-1-benzyl-N-(4-(2-benzylhydrazinyl)-3,4-dioxo-1-phenylbutan-2-yl)-5-oxopyrrolidine-2-carboxamide,
rac-N-(4-(cyclopropylamino)-3,4-dioxo-1-phenylbutan-2-yl)-1-(2-methoxy-6-(trifluoromethyl)benzyl)-5-oxopyrrolidine-2-carboxamide
(2R)—N-(4-(cyclopropylamino)-3,4-dioxo-1-phenylbutan-2-yl)-1-(2-methoxy-6-(trifluoromethyl)benzyl)-5-oxopyrrolidine-2-carboxamide,
(2S)—N-(4-(cyclopropylamino)-3,4-dioxo-1-phenylbutan-2-yl)-1-(2-methoxy-6-(trifluoromethyl)benzyl)-5-oxopyrrolidine-2-carboxamide.
rac-1-benzyl-N-(4-(ethoxyamino)-3,4-dioxo-1-phenylbutan-2-yl)-5-oxopyrrolidine-2-carboxamide,
(2R)-1-benzyl-N-(4-(ethoxyamino)-3,4-dioxo-1-phenylbutan-2-yl)-5-oxopyrrolidine-2-carboxamide,
(2S)-1-benzyl-N-(4-(ethoxyamino)-3,4-dioxo-1-phenylbutan-2-yl)-5-oxopyrrolidine-2-carboxamide,
rac-1-benzyl-N-(4-(isopropoxyamino)-3,4-dioxo-1-phenylbutan-2-yl)-5-oxopyrrolidine-2-carboxamide,
(2R)-1-benzyl-N-(4-(isopropoxyamino)-3,4-dioxo-1-phenylbutan-2-yl)-5-oxopyrrolidine-2-carboxamide,
(2S)-1-benzyl-N-(4-(isopropoxyamino)-3,4-dioxo-1-phenylbutan-2-yl)-5-oxopyrrolidine-2-carboxamide, rac-1-benzyl-N-(4-(cyclopropylmethoxyamino)-3,4-dioxo-1-phenylbutan-2-yl)-5-oxopyrrolidine-2-carboxamide,
(2R)-1-benzyl-N-(4-(cyclopropylmethoxyamino)-3,4-dioxo-1-phenylbutan-2-yl)-5-oxopyrrolidine-2-carboxamide,
(2S)-1-benzyl-N-(4-(cyclopropylmethoxyamino)-3,4-dioxo-1-phenylbutan-2-yl)-5-oxopyrrolidine-2-carboxamide
rac-1-(2-fluorobenzyl)-N-(4-(methoxyamino)-3,4-dioxo-1-phenylbutan-2-yl)-5-oxopyrrolidine-2-carboxamide,
(2R)-1-(2-fluorobenzyl)-N-(4-(methoxyamino)-3,4-dioxo-1-phenylbutan-2-yl)-5-oxopyrrolidine-2-carboxamide,
(2-S)-1-(2-fluorobenzyl)-N-(4-(methoxyamino)-3,4-dioxo-1-phenylbutan-2-yl)-5-oxopyrrolidine-2-carboxamide,
rac-1-(2-chlorobenzyl)-N-(4-(methoxyamino)-3,4-dioxo-1-phenylbutan-2-yl)-5-oxopyrrolidine-2-carboxamide,
(2R)-1-(2-chlorobenzyl)-N-(4-(methoxyamino)-3,4-dioxo-1-phenylbutan-2-yl)-5-oxopyrrolidine-2-carboxamide,
(2S)-1-(2-chlorobenzyl)-N-(4-(methoxyamino)-3,4-dioxo-1-phenylbutan-2-yl)-5-oxopyrrolidine-2-carboxamide,
rac-N-(4-(cyclopropylamino)-3,4-dioxo-1-phenylbutan-2-yl)-1-(2-fluorobenzyl)-5-oxopyrrolidine-2-carboxamide,
(2R)—N-(4-(cyclopropylamino)-3,4-dioxo-1-phenylbutan-2-yl)-1-(2-fluorobenzyl)-5-oxopyrrolidine-2-carboxamide,
(2S)—N-(4-(cyclopropylamino)-3,4-dioxo-1-phenylbutan-2-yl)-1-(2-fluorobenzyl)-5-oxopyrrolidine-2-carboxamide,
and the tautomers thereof, the hydrates thereof, the prodrugs thereof and the pharmaceutically suitable salts thereof.

Also preferred among the carboxamide compounds of the invention of the formula I are those compounds which correspond to the general formula I-B,

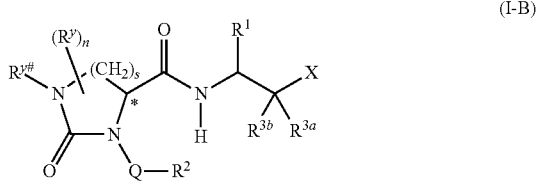

(I-B)

in which X, Q, $R^1$, $R^2$, $R^{3a}$, $R^{3b}$, $R^y$ and $R^{y\#}$ have the aforementioned meanings, in particular the meanings mentioned as preferred, the variable n is 0, 1 or 2, preferably 0 or 1, and the variable s is 1 or 2, preferably 1. In formula 1-B Q is preferably a single bond, a moiety $CH_2$ or $CH_2$—$CH_2$ and particularly preferred a moiety $CH_2$ or $CH_2$—$CH_2$. The variable $R^2$ is preferably phenyl, which is unsubstituted or carries 1 to 4, preferably 1 to 2, identical or different radicals $R^{2b}$. In preferred compounds of formula I-B the carbon atom indicated with an asterisk has predominantly R-configuration. Also preferred are the tautomers of 1-B, the pharmaceutically suitable salts thereof and the tautomers thereof.

In the compounds of the formula I-B the carbon atom indicated with an asterisk (*) is a center of chirality. Thus, the compounds I-B may have R-configuration or S-configuration with regard to this center of chirality. Mixtures of the stereoisomers of I-A containing almost equal amounts of the compounds wherein this center has R-configuration and compounds wherein this center has S-configuration are denominated as rac-compounds, while compounds where one configuration significantly dominates are denominated as R-compound and S-compound, respectively.

Preferred examples of compounds of the formula I-B comprise:
rac-N-(4-amino-3,4-dioxo-1-phenylbutan-2-yl)-3-benzyl-1-methyl-2-oxoimidazolidine-4-carboxamide,
(4R)—N-(4-amino-3,4-dioxo-1-phenylbutan-2-yl)-3-benzyl-1-methyl-2-oxoimidazolidine-4-carboxamide,
(4S)—N-(4-amino-3,4-dioxo-1-phenylbutan-2-yl)-3-benzyl-1-methyl-2-oxoimidazolidine-4-carboxamide.

Also preferred among the carboxamide compounds of the invention of the formula I are those compounds which correspond to the general formula I-C,

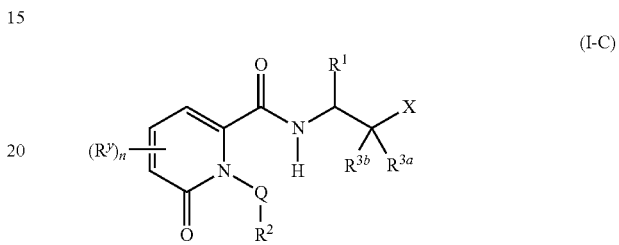

(I-C)

in which X, Q, $R^1$, $R^2$, $R^{3a}$, $R^{3b}$ and $R^y$ have the aforementioned meanings, in particular the meanings mentioned as preferred, the variable n is 0, 1 or 2, and preferably 0 or 1. In formula I-C Q is preferably a single bond, a moiety $CH_2$ or $CH_2$—$CH_2$ and particularly preferred a moiety $CH_2$ or $CH_2$—$CH_2$. The variable $R^2$ is preferably phenyl, which is unsubstituted or carries 1 to 4, preferably 1 to 2, identical or different radicals $R^{2b}$. Also preferred are the tautomers of 1-C, the pharmaceutically suitable salts thereof and the tautomers thereof.

Preferred examples of compounds of formula I-C comprise:
N-(4-amino-3,4-dioxo-1-phenylbutan-2-yl)-1-benzyl-6-oxo-1,6-dihydropyridine-2-carboxamide.

Preferred examples of compounds of formula I, wherein Y is $CH_2$—$CH_2$, A is $SO_2$ and Q is $CH_2$ comprise:
N-(4-amino-3,4-dioxo-1-phenylbutan-2-yl)-2-benzyl-isothiazolidine-3-carboxamide 1,1-dioxide,
(3R)—N-(4-amino-3,4-dioxo-1-phenylbutan-2-yl)-2-benzylisothiazolidine-3-carboxamide 1,1-dioxide and
(3S)—N-(4-amino-3,4-dioxo-1-phenylbutan-2-yl)-2-benzylisothiazolidine-3-carboxamide 1,1-dioxide.

In turn preferred among the carboxamide compounds of the invention of the formula I-A are compounds which correspond to the general formulae Ia-A, Ia-B or Ia-C,

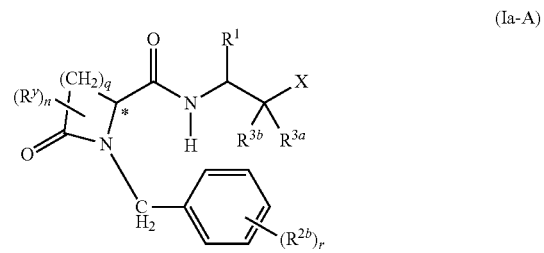

(Ia-A)

-continued

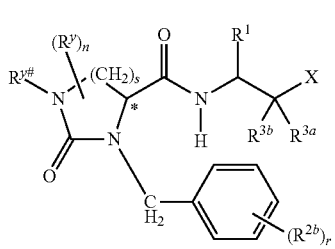
(Ia-B)

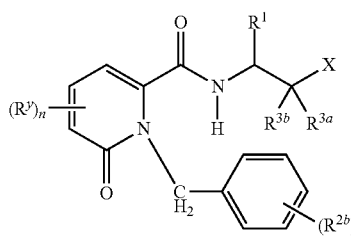
(Ia-C)

in which n, q, s, r, $R^y$, $R^{y\#}$, $R^{2b}$, X, $R^1$, $R^{3a}$ and $R^{3b}$ have the aforementioned meanings, in particular those mentioned as preferred.

In turn preferred among the carboxamide compounds of the invention of the formula I-B are compounds which correspond to the general formulae Ib-A, Ib-B or IB-C,

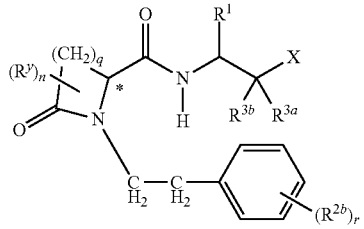
(Ib-A)

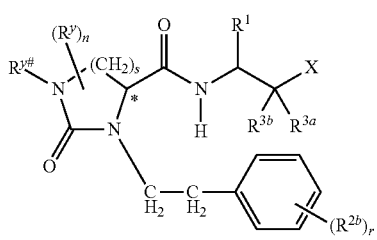
(Ib-B)

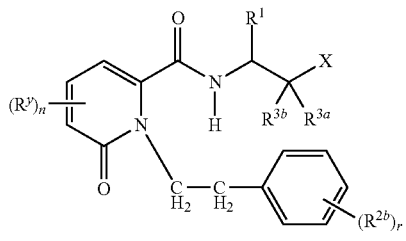
(Ib-C)

in which n, q, r, s, $R^y$, $R^{y\#}$, $R^{2b}$, X, $R^1$, $R^{3a}$ and $R^{3b}$ have the aforementioned meanings, in particular those mentioned as preferred.

The compounds of the general formulae I-A'.rac, I-A".R, I-A".rac, I-A".R, I-B'.rac, I-B'.R, I-B".rac, I-B".R and I-C', which are indicated in Tables 1 to 228 below and in which $CR^{3a}R^{3b}$ is a carbonyl function or a $C(OH)_2$ group, and their tautomers, prodrugs and pharmaceutically acceptable salts, represent per se preferred embodiments of the present invention. Formulae I-A'.rac, I-A".rac, I-B'.rac and I-B".rac depict carboxamide compounds I-A and I-B that have predominantly R/S-configuration at the carbon atom indicated with an asterisk, as illustrated by the zigzag lines. Formulae I-A'.R, I-A".R, I-B'.R and I-B".R, on the other hand, depict carboxamide compounds I-A and I-B that have predominantly R-configuration at the corresponding carbon atom, as illustrated by the dashed-wedged lines. The asterisk indicates the stereocenter. The meanings for $R^1$ and $R^2$ indicated in Table A below represent embodiments of the invention which are likewise preferred independently of one another and especially in combination.

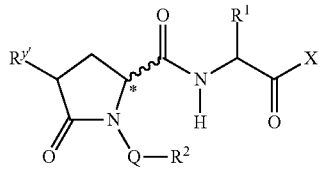
(I-A'.rac)

$CR^{3a}R^{3b} = C=O$

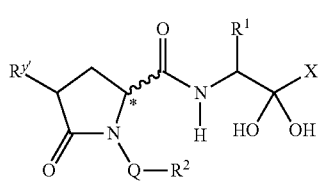

$CR^{3a}R^{3b} = C(OH)_2$

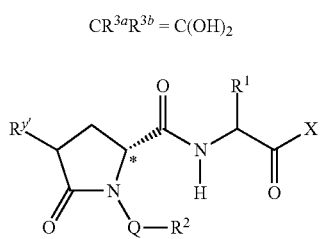
(I-A'.R)

$CR^{3a}R^{3b} = C=O$

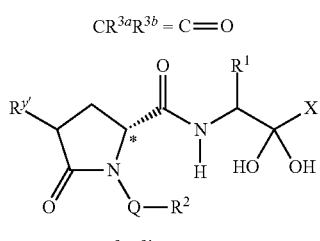

$CR^{3a}R^{3b} = C(OH)_2$

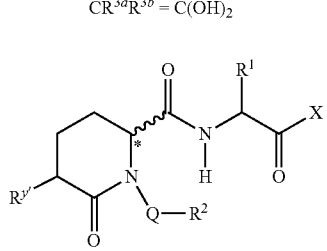
(I-A".rac)

$CR^{3a}R^{3b} = C=O$

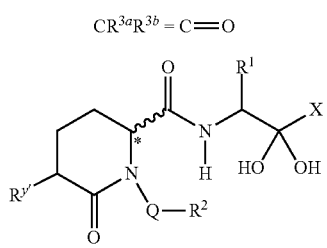

$CR^{3a}R^{3b} = C(OH)_2$

-continued

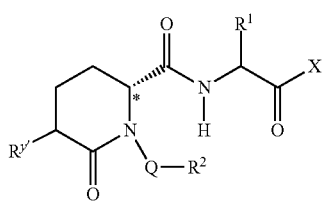

$CR^{3a}R^{3b} = C=O$

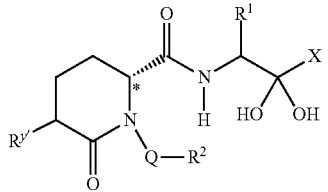

$CR^{3a}R^{3b} = C(OH)_2$

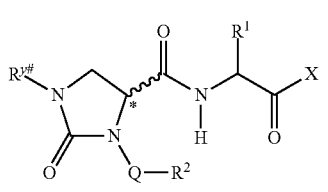

$CR^{3a}R^{3b} = C=O$

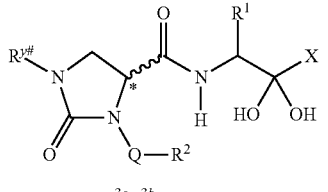

$CR^{3a}R^{3b} = C(OH)_2$ (I-B'.R)

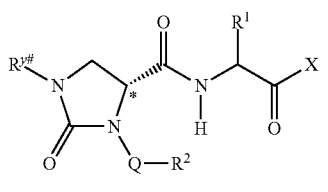

$CR^{3a}R^{3b} = C=O$

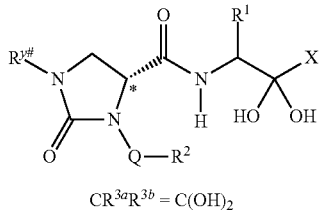

$CR^{3a}R^{3b} = C(OH)_2$ (I-B''.rac)

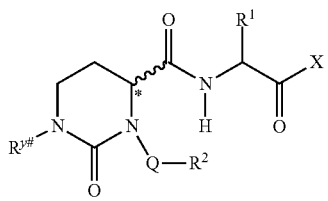

$CR^{3a}R^{3b} = C=O$ (I-A''.R)

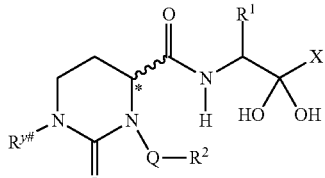

$CR^{3a}R^{3b} = C(OH)_2$ (I-B''.R)

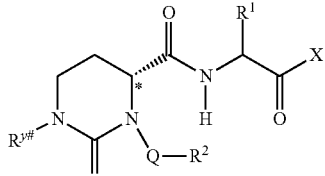

$CR^{3a}R^{3b} = C=O$

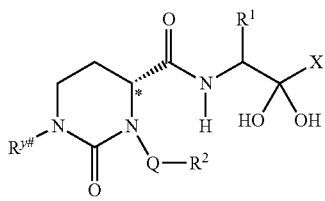

$CR^{3a}R^{3b} = C(OH)_2$ (I-C')

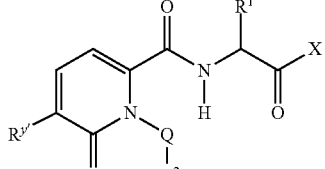

$CR^{3a}R^{3b} = C=O$

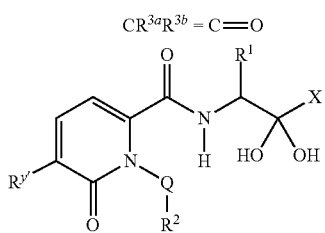

$CR^{3a}R^{3b} = C(OH)_2$

Table 1

Compounds of the formulae I-A'.rac, I-A'.R, I-A''.rac, I-A''.R, I-B'.rac, I-B'.R, I-B'' fac, I-B''.R and I-C', in which the group $C(R^{3a}R^{3b})$ is C=O, X is carbamoyl, $R^{y'}$ and $R^{y\#}$, respectively, is hydrogen, Q is a single bond, and the combination of $R^1$ and $R^2$ for a compound in each case corresponds to one line of Table A.

Table 2

Compounds of the formulae I-A'.rac, I-A'.R, I-A''.rac, I-A''.R, I-B'.rac, I-B'.R, I-B''.rac, I-B''.R and I-C', in which the group $C(R^{3a}R^{3b})$ is C=O, X is carbamoyl, $R^{y'}$ and $R^{y\#}$, respectively, is $CH_3$, Q is a single bond, and the combination of $R^1$ and $R^2$ for a compound in each case corresponds to one line of Table A.

Table 3

Compounds of the formulae I-A'.rac, I-A'.R, I-A''.rac, I-A''.R, I-B'.rac, I-B'.R, I-B''.rac, I-B''.R and I-C', in which the group $C(R^{3a}R^{3b})$ is C=O, X is carbamoyl, $R^{y'}$ and $R^{y\#}$, respectively, is CN, Q is a single bond, and the combination of $R^1$ and $R^2$ for a compound in each case corresponds to one line of Table A.

Table 4

Compounds of the formulae I-A' fac, I-A'.R, I-A" fac, I-A".R and I-C', in which the group $C(R^{3a}R^{3b})$ is C=O, X is carbamoyl, $R^{y'}$ is Cl, Q is a single bond, and the combination of $R^1$ and $R^2$ for a compound in each case corresponds to one line of Table A.

Table 5

Compounds of the formulae I-A'.rac, I-A'.R, I-A".rac, I-A".R and I-C', in which the group $C(R^{3a}R^{3b})$ is C=O, X is carbamoyl, $R^{y'}$ is F, Q is a single bond, and the combination of $R^1$ and $R^2$ for a compound in each case corresponds to one line of Table A.

Table 6

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is —C(O)NHCH$_3$, $R^{y'}$ and $R^{y\#}$, respectively, is hydrogen, Q is a single bond, and the combination of $R^1$ and $R^2$ for a compound in each case corresponds to one line of Table A.

Table 7

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is —C(O)NHCH$_3$, $R^{y'}$ and $R^{y\#}$, respectively, is CH$_3$, Q is a single bond, and the combination of $R^1$ and $R^2$ for a compound in each case corresponds to one line of Table A.

Table 8

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is —C(O)NHCH$_3$, $R^{y'}$ and $R^{y\#}$, respectively, is CN, Q is a single bond, and the combination of $R^1$ and $R^2$ for a compound in each case corresponds to one line of Table A.

Table 9

Compounds of the formulae I-A' fac, I-A'.R, I-A" fac, I-A".R and I-C', in which the group $C(R^{3a}R^{3b})$ is C=O, X is —C(O)NHCH$_3$, $R^{y'}$ is Cl, Q is a single bond, and the combination of $R^1$ and $R^2$ for a compound in each case corresponds to one line of Table A.

Table 10

Compounds of the formulae I-A'.rac, I-A'.R, I-A".rac, I-A".R and I-C', in which the group $C(R^{3a}R^{3b})$ is C=O, X is —C(O)NHCH$_3$, $R^{y'}$ is F, Q is a single bond, and the combination of $R^1$ and $R^2$ for a compound in each case corresponds to one line of Table A.

Table 11

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C(OH)$_2$, X is carbamoyl, $R^{y'}$ and $R^{y\#}$, respectively, is hydrogen, Q is a single bond, and the combination of $R^1$ and $R^2$ for a compound in each case corresponds to one line of Table A.

Table 12

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C(OH)$_2$, X is carbamoyl, $R^{y'}$ and $R^{y\#}$, respectively, is CH$_3$, Q is a single bond, and the combination of $R^1$ and $R^2$ for a compound in each case corresponds to one line of Table A.

Table 13

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C(OH)$_2$, X is carbamoyl, $R^{y'}$ and $R^{y\#}$, respectively, is CN, Q is a single bond, and the combination of $R^1$ and $R^2$ for a compound in each case corresponds to one line of Table A.

Table 14

Compounds of the formulae I-A' fac, I-A'.R, I-A".rac, I-A".R and I-C', in which the group $C(R^{3a}R^{3b})$ is C(OH)$_2$, X is carbamoyl, $R^{y'}$ is Cl, Q is a single bond, and the combination of $R^1$ and $R^2$ for a compound in each case corresponds to one line of Table A.

Table 15

Compounds of the formulae I-A'.rac, I-A'.R, I-A".rac, I-A".R and I-C', in which the group $C(R^{3a}R^{3b})$ is C(OH)$_2$, X is carbamoyl, $R^{y'}$ is F, Q is a single bond, and the combination of $R^1$ and $R^2$ for a compound in each case corresponds to one line of Table A.

Table 16

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C(OH)$_2$, X is —C(O)NHCH$_3$, $R^{y'}$ and $R^{y\#}$, respectively, is hydrogen, Q is a single bond, and the combination of $R^1$ and $R^2$ for a compound in each case corresponds to one line of Table A.

Table 17

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C(OH)$_2$, X is —C(O)NHCH$_3$, $R^{y'}$ and $R^{y\#}$, respectively, is CH$_3$, Q is a single bond, and the combination of $R^1$ and $R^2$ for a compound in each case corresponds to one line of Table A.

Table 18

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C(OH)$_2$, X is —C(O)NHCH$_3$, $R^{y'}$ and $R^{y\#}$, respectively, is CN, Q is a single bond, and the combination of $R^1$ and $R^2$ for a compound in each case corresponds to one line of Table A.

Table 19

Compounds of the formulae I-A'.rac, I-A'.R, I-A".rac, I-A".R and I-C', in which the group $C(R^{3a}R^{3b})$ is C(OH)$_2$, X is —C(O)NHCH$_3$, $R^{y'}$ is Cl, Q is a single bond, and the combination of $R^1$ and $R^2$ for a compound in each case corresponds to one line of Table A.

Table 20

Compounds of the formulae I-A'.rac, I-A'.R, I-A".rac, I-A".R and I-C', in which the group $C(R^{3a}R^{3b})$ is C(OH)$_2$, X is —C(O)NHCH$_3$, $R^{y'}$ is F, Q is a single bond, and the combination of $R^1$ and $R^2$ for a compound in each case corresponds to one line of Table A.

Table 21

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is carbamoyl, $R^{y'}$ and $R^{y\#}$, respectively, is hydrogen, Q is CH$_2$, and the combination of $R^1$ and $R^2$ for a compound in each case corresponds to one line of Table A.

Table 22

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is carbamoyl, $R^{y'}$ and $R^{y\#}$, respectively, is CH$_3$, Q is CH$_2$, and the combination of $R^1$ and $R^2$ for a compound in each case corresponds to one line of Table A.

Table 23

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is carbamoyl, $R^{y'}$ and $R^{y\#}$, respectively, is CN, Q is $CH_2$, and the combination of $R^1$ and $R^2$ for a compound in each case corresponds to one line of Table A.

Table 24

Compounds of the formulae I-A'.rac, I-A'.R, I-A".rac, I-A".R and I-C', in which the group $C(R^{3a}R^{3b})$ is $C=O$, X is carbamoyl, $R^{y'}$ is Cl, Q is $CH_2$, and the combination of $R^1$ and $R^2$ for a compound in each case corresponds to one line of Table A.

Table 25

Compounds of the formulae I-A'.rac, I-A'.R, I-A".rac, I-A".R and I-C', in which the group $C(R^{3a}R^{3b})$ is $C=O$, X is carbamoyl, $R^{y'}$ is F, Q is $CH_2$, and the combination of $R^1$ and $R^2$ for a compound in each case corresponds to one line of Table A.

Table 26

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C=O$, X is —$C(O)NHCH_3$, $R^{y'}$ and $R^{y\#}$, respectively, is hydrogen, Q is $CH_2$, and the combination of $R^1$ and $R^2$ for a compound in each case corresponds to one line of Table A.

Table 27

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C=O$, X is —$C(O)NHCH_3$, $R^{y'}$ and $R^{y\#}$, respectively, is $CH_3$, Q is $CH_2$, and the combination of $R^1$ and $R^2$ for a compound in each case corresponds to one line of Table A.

Table 28

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C=O$, X is —$C(O)NHCH_3$, $R^{y'}$ and $R^{y\#}$, respectively, is CN, Q is $CH_2$, and the combination of $R^1$ and $R^2$ for a compound in each case corresponds to one line of Table A.

Table 29

Compounds of the formulae I-A' fac, I-A'.R, I-A".rac, I-A".R and I-C', in which the group $C(R^{3a}R^{3b})$ is $C=O$, X is —$C(O)NHCH_3$, $R^{y'}$ is Cl, Q is $CH_2$, and the combination of $R^1$ and $R^2$ for a compound in each case corresponds to one line of Table A.

Table 30

Compounds of the formulae I-A' fac, I-A'.R, I-A".rac, I-A".R and I-C', in which the group $C(R^{3a}R^{3b})$ is $C=O$, X is —$C(O)NHCH_3$, $R^{y'}$ is F, Q is $CH_2$, and the combination of $R^1$ and $R^2$ for a compound in each case corresponds to one line of Table A.

Table 31

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is carbamoyl, $R^{y'}$ and $R^{y\#}$, respectively, is hydrogen, Q is $CH_2$, and the combination of $R^1$ and $R^2$ for a compound in each case corresponds to one line of Table A.

Table 32

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is carbamoyl, $R^{y'}$ and $R^{y\#}$, respectively, is $CH_3$, Q is $CH_2$, and the combination of $R^1$ and $R^2$ for a compound in each case corresponds to one line of Table A.

Table 33

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is carbamoyl, $R^{y'}$ and $R^{y\#}$, respectively, is CN, Q is $CH_2$, and the combination of $R^1$ and $R^2$ for a compound in each case corresponds to one line of Table A.

Table 34

Compounds of the formulae I-A'.rac, I-A'.R, I-A".rac, I-A".R and I-C', in which the group $C(R^{3a}R^{3b})$ is $C(OH)_2$, X is carbamoyl, $R^{y'}$ is Cl, Q is $CH_2$, and the combination of $R^1$ and $R^2$ for a compound in each case corresponds to one line of Table A.

Table 35

Compounds of the formulae I-A' fac, I-A'.R, I-A".rac, I-A".R and I-C', in which the group $C(R^{3a}R^{3b})$ is $C(OH)_2$, X is carbamoyl, $R^{y'}$ is F, Q is $CH_2$, and the combination of $R^1$ and $R^2$ for a compound in each case corresponds to one line of Table A.

Table 36

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is —$C(O)NHCH_3$, $R^{y'}$ and $R^{y\#}$, respectively, is hydrogen, Q is $CH_2$, and the combination of $R^1$ and $R^2$ for a compound in each case corresponds to one line of Table A.

Table 37

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is —$C(O)NHCH_3$, $R^{y'}$ and $R^{y\#}$, respectively, is $CH_3$, Q is $CH_2$, and the combination of $R^1$ and $R^2$ for a compound in each case corresponds to one line of Table A.

Table 38

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is —$C(O)NHCH_3$, $R^{y'}$ and $R^{y\#}$, respectively, is CN, Q is $CH_2$, and the combination of $R^1$ and $R^2$ for a compound in each case corresponds to one line of Table A.

Table 39

Compounds of the formulae I-A'.rac, I-A'.R, I-A".rac, I-A".R and I-C', in which the group $C(R^{3a}R^{3b})$ is $C(OH)_2$, X is —$C(O)NHCH_3$, $R^{y'}$ is Cl, Q is $CH_2$, and the combination of $R^1$ and $R^2$ for a compound in each case corresponds to one line of Table A.

Table 40

Compounds of the formulae I-A' fac, I-A'.R, I-A".rac, I-A".R and I-C', in which the group $C(R^{3a}R^{3b})$ is $C(OH)_2$, X is —$C(O)NHCH_3$, $R^{y'}$ is F, Q is $CH_2$, and the combination of $R^1$ and $R^2$ for a compound in each case corresponds to one line of Table A.

Table 41

Compounds of the formulae I-A' fac, I-A'.R, I-A".rac, I-A".R, I-B'.rac, I-B'.R, I-B".rac, I-B".R and I-C', in which the group $C(R^{3a}R^{3b})$ is $C=O$, X is carbamoyl, $R^{y'}$ and $R^{y\#}$, respectively, is hydrogen, Q is $CH_2$—$CH_2$, and the combination of $R^1$ and $R^2$ for a compound in each case corresponds to one line of Table A.

Table 42

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C=O$, X is carbamoyl, $R^{y'}$ and $R^{y\#}$, respectively, is $CH_3$, Q is $CH_2$—$CH_2$, and the combination of $R^1$ and $R^2$ for a compound in each case corresponds to one line of Table A.

Table 43

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C=O$, X is carbamoyl, $R^{y'}$ and $R^{y\#}$, respectively, is CN, Q is CH$_2$—CH$_2$, and the combination of R$^1$ and R$^2$ for a compound in each case corresponds to one line of Table A.

Table 44

Compounds of the formulae I-A'.rac, I-A'.R, I-A".rac, I-A".R and I-C', in which the group C(R$^{3a}$R$^{3b}$) is C=O, X is carbamoyl, R$^{y'}$ is Cl, Q is CH$_2$—CH$_2$, and the combination of R$^1$ and R$^2$ for a compound in each case corresponds to one line of Table A.

Table 45

Compounds of the formulae I-A' fac, I-A'.R, I-A".rac, I-A".R and I-C', in which the group C(R$^{3a}$R$^{3b}$) is C=O, X is carbamoyl, R$^{y'}$ is F, Q is CH$_2$—CH$_2$, and the combination of R$^1$ and R$^2$ for a compound in each case corresponds to one line of Table A.

Table 46

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is —C(O)NHCH$_3$, R$^{y'}$ and R$^{y\#}$, respectively, is hydrogen, Q is CH$_2$—CH$_2$, and the combination of R$^1$ and R$^2$ for a compound in each case corresponds to one line of Table A.

Table 47

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is —C(O)NHCH$_3$, R$^{y'}$ and R$^{y\#}$, respectively, is CH$_3$, Q is CH$_2$—CH$_2$, and the combination of R$^1$ and R$^2$ for a compound in each case corresponds to one line of Table A.

Table 48

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C=O, X is —C(O)NHCH$_3$, R$^{y'}$ and R$^{y\#}$, respectively, is CN, Q is CH$_2$—CH$_2$, and the combination of R$^1$ and R$^2$ for a compound in each case corresponds to one line of Table A.

Table 49

Compounds of the formulae I-A'.rac, I-A'.R, I-A" fac, I-A".R and I-C', in which the group C(R$^{3a}$R$^{3b}$) is C=O, X is —C(O)NHCH$_3$, R$^{y'}$ is Cl, Q is CH$_2$—CH$_2$, and the combination of R$^1$ and R$^2$ for a compound in each case corresponds to one line of Table A.

Table 50

Compounds of the formulae I-A'.rac, I-A'.R, I-A" fac, I-A".R and I-C', in which the group C(R$^{3a}$R$^{3b}$) is C=O, X is —C(O)NHCH$_3$, R$^{y'}$ is F, Q is CH$_2$—CH$_2$, and the combination of R$^1$ and R$^2$ for a compound in each case corresponds to one line of Table A.

Table 51

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is carbamoyl, R$^{y'}$ and R$^{y\#}$, respectively, is hydrogen, Q is CH$_2$—CH$_2$, and the combination of R$^1$ and R$^2$ for a compound in each case corresponds to one line of Table A.

Table 52

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is carbamoyl, R$^{y'}$ and R$^{y\#}$, respectively, is CH$_3$, Q is CH$_2$—CH$_2$, and the combination of R$^1$ and R$^2$ for a compound in each case corresponds to one line of Table A.

Table 53

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is carbamoyl, R$^{y'}$ and R$^{y\#}$, respectively, is CN, Q is CH$_2$—CH$_2$, and the combination of R$^1$ and R$^2$ for a compound in each case corresponds to one line of Table A.

Table 54

Compounds of the formulae I-A'.rac, I-A'.R, I-A".rac, I-A".R and I-C', in which the group C(R$^{3a}$R$^{3b}$) is C(OH)$_2$, X is carbamoyl, R$^{y'}$ is Cl, Q is CH$_2$—CH$_2$, and the combination of R$^1$ and R$^2$ for a compound in each case corresponds to one line of Table A.

Table 55

Compounds of the formulae I-A'.rac, I-A'.R, I-A".rac, I-A".R and I-C', in which the group C(R$^{3a}$R$^{3b}$) is C(OH)$_2$, X is carbamoyl, R$^{y'}$ is F, Q is CH$_2$—CH$_2$, and the combination of R$^1$ and R$^2$ for a compound in each case corresponds to one line of Table A.

Table 56

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is —C(O)NHCH$_3$, R$^{y'}$ and R$^{y\#}$, respectively, is hydrogen, Q is CH$_2$—CH$_2$, and the combination of R$^1$ and R$^2$ for a compound in each case corresponds to one line of Table A.

Table 57

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is —C(O)NHCH$_3$, R$^{y'}$ and R$^{y\#}$, respectively, is CH$_3$, Q is CH$_2$—CH$_2$, and the combination of R$^1$ and R$^2$ for a compound in each case corresponds to one line of Table A.

Table 58

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is —C(O)NHCH$_3$, R$^{y'}$ and R$^{y\#}$, respectively, is CN, Q is CH$_2$—CH$_2$, and the combination of R$^1$ and R$^2$ for a compound in each case corresponds to one line of Table A.

Table 59

Compounds of the formulae I-A' fac, I-A'.R, I-A".rac, I-A".R and I-C', in which the group C(R$^{3a}$R$^{3b}$) is C(OH)$_2$, X is —C(O)NHCH$_3$, R$^{y'}$ is Cl, Q is CH$_2$—CH$_2$, and the combination of R$^1$ and R$^2$ for a compound in each case corresponds to one line of Table A.

Table 60

Compounds of the formulae I-A'.rac, I-A'.R, I-A".rac, I-A".R and I-C', in which the group C(R$^{3a}$R$^{3b}$) is C(OH)$_2$, X is —C(O)NHCH$_3$, R$^{y'}$ is F, Q is CH$_2$—CH$_2$, and the combination of R$^1$ and R$^2$ for a compound in each case corresponds to one line of Table A.

Table 61

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is —C(O)NHcyclopropyl, R$^{y'}$ and R$^{y\#}$, respectively, is hydrogen, Q is a single bond, and the combination of R$^1$ and R$^2$ for a compound in each case corresponds to one line of Table A.

Table 62

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is —C(O)NHcyclopropyl, R$^{y'}$ and R$^{y\#}$, respectively, is CH$_3$, Q is a single bond, and the combination of R$^1$ and R$^2$ for a compound in each case corresponds to one line of Table A.

Table 63

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C=O, X is —C(O)NHcyclopropyl, R$^{y'}$ and R$^{y\#}$, respectively, is CN, Q is a single bond, and the Table 64

Compounds of the formulae I-A'.rac, I-A'.R, I-A" fac, I-A".R and I-C', in which the group $C(R^{3a}R^{3b})$ is C=O, X is —C(O)NHcyclopropyl$_3$, $R^{y'}$ is Cl, Q is a single bond, and the combination of $R^1$ and $R^2$ for a compound in each case corresponds to one line of Table A.

Table 65

Compounds of the formulae I-A'.rac, I-A'.R, I-A" fac, I-A".R and I-C', in which the group $C(R^{3a}R^{3b})$ is C=O, X is —C(O)NHcyclopropyl, $R^{y'}$ is F, Q is a single bond, and the combination of $R^1$ and $R^2$ for a compound in each case corresponds to one line of Table A.

Table 66

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is —C(O)NHcyclopropyl, $R^{y'}$ and $R^{y\#}$, respectively, is hydrogen, Q is a single bond, and the combination of $R^1$ and $R^2$ for a compound in each case corresponds to one line of Table A.

Table 67

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is —C(O)NHcyclopropyl, $R^{y'}$ and $R^{y\#}$, respectively, is $CH_3$, Q is a single bond, and the combination of $R^1$ and $R^2$ for a compound in each case corresponds to one line of Table A.

Table 68

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is —C(O)NHcyclopropyl, $R^{y'}$ and $R^{y\#}$, respectively, is CN, Q is a single bond, and the combination of $R^1$ and $R^2$ for a compound in each case corresponds to one line of Table A.

Table 69

Compounds of the formulae I-A'.rac, I-A'.R, I-A".rac, I-A".R and I-C', in which the group $C(R^{3a}R^{3b})$ is $C(OH)_2$, X is —C(O)NHcyclopropyl, $R^{y'}$ is Cl, Q is a single bond, and the combination of $R^1$ and $R^2$ for a compound in each case corresponds to one line of Table A.

Table 70

Compounds of the formulae I-A'.rac, I-A'.R, I-A".rac, I-A".R and I-C', in which the group $C(R^{3a}R^{3b})$ is $C(OH)_2$, X is —C(O)NHcyclopropyl, $R^{y'}$ is F, Q is a single bond, and the combination of $R^1$ and $R^2$ for a compound in each case corresponds to one line of Table A, Table 71

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is C(O)NHcyclopropyl, $R^{y'}$ and $R^{y\#}$, respectively, is hydrogen, Q is $CH_2$, and the combination of $R^1$ and $R^2$ for a compound in each case corresponds to one line of Table A.

Table 72

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is —C(O)NHcyclopropyl, $R^{y'}$ and $R^{y\#}$, respectively, is $CH_3$, Q is $CH_2$, and the combination of $R^1$ and $R^2$ for a compound in each case corresponds to one line of Table A.

Table 73

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is —C(O)NHcyclopropyl, $R^{y'}$ and $R^{y\#}$, respectively, is CN, Q is $CH_2$, and the combination of $R^1$ and $R^2$ for a compound in each case corresponds to one line of Table A.

Table 74

Compounds of the formulae I-A'.rac, I-A'.R, I-A".rac, I-A".R and I-C', in which the group $C(R^{3a}R^{3b})$ is C=O, X is —C(O)NHcyclopropyl, $R^{y'}$ is Cl, Q is $CH_2$, and the combination of $R^1$ and $R^2$ for a compound in each case corresponds to one line of Table A.

Table 75

Compounds of the formulae I-A'.rac, I-A'.R, I-A".rac, I-A".R and I-C', in which the group $C(R^{3a}R^{3b})$ is C=O, X is —C(O)NHcyclopropyl, $R^{y'}$ is F, Q is $CH_2$, and the combination of $R^1$ and $R^2$ for a compound in each case corresponds to one line of Table A.

Table 76

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is —C(O)NHcyclopropyl, $R^{y'}$ and $R^{y\#}$, respectively, is hydrogen, Q is $CH_2$, and the combination of $R^1$ and $R^2$ for a compound in each case corresponds to one line of Table A.

Table 77

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is —C(O)NHcyclopropyl, $R^{y'}$ and $R^{y\#}$, respectively, is $CH_3$, Q is $CH_2$, and the combination of $R^1$ and $R^2$ for a compound in each case corresponds to one line of Table A.

Table 78

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is —C(O)NHcyclopropyl, $R^{y'}$ and $R^{y\#}$, respectively, is CN, Q is $CH_2$, and the combination of $R^1$ and $R^2$ for a compound in each case corresponds to one line of Table A.

Table 79

Compounds of the formulae I-A' fac, I-A'.R, I-A".rac, I-A".R and I-C', in which the group $C(R^{3a}R^{3b})$ is $C(OH)_2$, X is —C(O)NHcyclopropyl, $R^{y'}$ is Cl, Q is $CH_2$, and the combination of $R^1$ and $R^2$ for a compound in each case corresponds to one line of Table A.

Table 80

Compounds of the formulae I-A'.rac, I-A'.R, I-A".rac, I-A".R and I-C', in which the group $C(R^{3a}R^{3b})$ is $C(OH)_2$, X is —C(O)NHcyclopropyl, $R^{y'}$ is F, Q is $CH_2$, and the combination of $R^1$ and $R^2$ for a compound in each case corresponds to one line of Table A.

Table 81

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is —C(O)NHcyclopropyl, $R^{y'}$ and $R^{y\#}$, respectively, is hydrogen, Q is $CH_2$—$CH_2$, and the combination of $R^1$ and $R^2$ for a compound in each case corresponds to one line of Table A.

Table 82

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is —C(O)NHcyclopropyl, $R^{y'}$ and $R^{y\#}$, respectively, is $CH_3$, Q is $CH_2$—$CH_2$, and the combination of $R^1$ and $R^2$ for a compound in each case corresponds to one line of Table A.

Table 83

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is C=O, X is —C(O)NHcyclopropyl, $R^{y'}$ and $R^{y\#}$, respectively, is CN, Q is $CH_2$—$CH_2$, and the combination of $R^1$ and $R^2$ for a compound in each case corresponds to one line of Table A.

Table 84

Compounds of the formulae I-A'.rac, I-A'.R, I-A".rac, I-A".R and I-C', in which the group $C(R^{3a}R^{3b})$ is C=O, X is —C(O)NHcyclopropyl, $R^{y'}$ is Cl, Q is $CH_2$—$CH_2$, and the combination of $R^1$ and $R^2$ for a compound in each case corresponds to one line of Table A.

Table 85

Compounds of the formulae I-A'.rac, I-A'.R, I-A".rac, I-A".R and I-C', in which the group $C(R^{3a}R^{3b})$ is C=O, X is —C(O)NHcyclopropyl, $R^{y'}$ is F, Q is $CH_2$—$CH_2$, and the combination of $R^1$ and $R^2$ for a compound in each case corresponds to one line of Table A.

Table 86

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C(OH)_2$, X is C(O)NHcyclopropyl, $R^{y'}$ and $R^{y\#}$, respectively, is hydrogen, Q is $CH_2$—$CH_2$, and the combination of $R^1$ and $R^2$ for a compound in each case corresponds to one line of Table A.

Table 87

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is C(O)NHcyclopropyl, $R^{y'}$ and $R^{y\#}$, respectively, is $CH_3$, Q is $CH_2$—$CH_2$, and the combination of $R^1$ and $R^2$ for a compound in each case corresponds to one line of Table A.

Table 88

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is C(O)NHcyclopropyl, $R^{y'}$ and $R^{y\#}$, respectively, is CN, Q is $CH_2$—$CH_2$, and the combination of $R^1$ and $R^2$ for a compound in each case corresponds to one line of Table A.

Table 89

Compounds of the formulae I-A'.rac, I-A'.R, I-A".rac, I-A".R and I-C', in which the group $C(R^{3a}R^{3b})$ is $C(OH)_2$, X is C(O)NHcyclopropyl, $R^{y'}$ is Cl, Q is $CH_2$—$CH_2$, and the combination of $R^1$ and $R^2$ for a compound in each case corresponds to one line of Table A.

Table 90

Compounds of the formulae I-A'.rac, I-A'.R, I-A".rac, I-A".R and I-C', in which the group $C(R^{3a}R^{3b})$ is $C(OH)_2$, X is C(O)NHcyclopropyl, $R^{y'}$ is F, Q is $CH_2$—$CH_2$, and the combination of $R^1$ and $R^2$ for a compound in each case corresponds to one line of Table A.

Table 91

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is C(O)NH(benzyl), $R^{y'}$ and $R^{y\#}$, respectively, is hydrogen, Q is a single bond, and the combination of $R^1$ and $R^2$ for a compound in each case corresponds to one line of Table A.

Table 92

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is C(O)NH(benzyl), $R^{y'}$ and $R^{y\#}$, respectively, is $CH_3$, Q is a single bond, and the combination of $R^1$ and $R^2$ for a compound in each case corresponds to one line of Table A.

Table 93

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is C(O)NH(benzyl), $R^{y'}$ and $R^{y\#}$, respectively, is CN, Q is a single bond, and the combination of $R^1$ and $R^2$ for a compound in each case corresponds to one line of Table A.

Table 94

Compounds of the formulae I-A'.rac, I-A'.R, I-A".rac, I-A".R and I-C', in which the group $C(R^{3a}R^{3b})$ is C=O, X is C(O)NH(benzyl), $R^{y'}$ is Cl, Q is a single bond, and the combination of $R^1$ and $R^2$ for a compound in each case corresponds to one line of Table A.

Table 95

Compounds of the formulae I-A'.rac, I-A'.R, I-A" fac, I-A".R and I-C', in which the group $C(R^{3a}R^{3b})$ is C=O, X is C(O)NH(benzyl), $R^{y'}$ is F, Q is a single bond, and the combination of $R^1$ and $R^2$ for a compound in each case corresponds to one line of Table A.

Table 96

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C(OH)_2$, X is C(O)NH(benzyl), $R^{y'}$ and $R^{y\#}$, respectively, is hydrogen, Q is a single bond, and the combination of $R^1$ and $R^2$ for a compound in each case corresponds to one line of Table A.

Table 97

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is C(O)NH(benzyl), $R^{y'}$ and $R^{y\#}$, respectively, is $CH_3$, Q is a single bond, and the combination of $R^1$ and $R^2$ for a compound in each case corresponds to one line of Table A.

Table 98

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C(OH)_2$, X is C(O)NH(benzyl), $R^{y'}$ and $R^{y\#}$, respectively, is CN, Q is a single bond, and the combination of $R^1$ and $R^2$ for a compound in each case corresponds to one line of Table A.

Table 99

Compounds of the formulae I-A'.rac, I-A'.R, I-A".rac, I-A".R and I-C', in which the group $C(R^{3a}R^{3b})$ is $C(OH)_2$, X is C(O)NH(benzyl), $R^{y'}$ is Cl, Q is a single bond, and the combination of $R^1$ and $R^2$ for a compound in each case corresponds to one line of Table A.

Table 100

Compounds of the formulae I-A'.rac, I-A'.R, I-A".rac, I-A".R and I-C', in which the group $C(R^{3a}R^{3b})$ is $C(OH)_2$, X is C(O)NH(benzyl), $R^{y'}$ is F, Q is a single bond, and the combination of $R^1$ and $R^2$ for a compound in each case corresponds to one line of Table A.

Table 101

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is C=O, X is C(O)NH(benzyl), $R^{y'}$ and $R^{y\#}$, respectively, is hydrogen, Q is $CH_2$, and the combination of $R^1$ and $R^2$ for a compound in each case corresponds to one line of Table A.

Table 102

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is C=O, X is C(O)NH(benzyl), $R^{y'}$ and $R^{y\#}$, respectively, is $CH_3$, Q is $CH_2$, and the combination of $R^1$ and $R^2$ for a compound in each case corresponds to one line of Table A.

Table 103

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is C(O)NH(benzyl), $R^{y'}$ and $R^{y\#}$, respectively, is CN, Q is CH$_2$, and the combination of R$^1$ and R$^2$ for a compound in each case corresponds to one line of Table A.

Table 104

Compounds of the formulae I-A'.rac, I-A'.R, I-A" fac, I-A".R and I-C', in which the group C(R$^{3a}$R$^{3b}$) is C=O, X is C(O)NH(benzyl), R$^{y'}$ is Cl, Q is CH$_2$, and the combination of R$^1$ and R$^2$ for a compound in each case corresponds to one line of Table A.

Table 105

Compounds of the formulae I-A'.rac, I-A'.R, I-A" fac, I-A".R and I-C', in which the group C(R$^{3a}$R$^{3b}$) is C=O, X is C(O)NH(benzyl), R$^{y'}$ is F, Q is CH$_2$, and the combination of R$^1$ and R$^2$ for a compound in each case corresponds to one line of Table A.

Table 106

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(benzyl), R$^{y'}$ and R$^{y\#}$, respectively, is hydrogen, Q is CH$_2$, and the combination of R$^1$ and R$^2$ for a compound in each case corresponds to one line of Table A.

Table 107

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is C(O)NH(benzyl), R$^{y'}$ and R$^{y\#}$, respectively, is CH$_3$, Q is CH$_2$, and the combination of R$^1$ and R$^2$ for a compound in each case corresponds to one line of Table A.

Table 108

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(benzyl), R$^{y'}$ and R$^{y\#}$, respectively, is CN, Q is CH$_2$, and the combination of R$^1$ and R$^2$ for a compound in each case corresponds to one line of Table A.

Table 109

Compounds of the formulae I-A'.rac, I-A'.R, I-A" fac, I-A".R and I-C', in which the group C(R$^{3a}$R$^{3b}$) is C(OH)$_2$, X is C(O)NH(benzyl), R$^{y'}$ is Cl, Q is CH$_2$, and the combination of R$^1$ and R$^2$ for a compound in each case corresponds to one line of Table A.

Table 110

Compounds of the formulae I-A'.rac, I-A'.R, I-A".rac, I-A".R and I-C', in which the group C(R$^{3a}$R$^{3b}$) is C(OH)$_2$, X is C(O)NH(benzyl), R$^{y'}$ is F, Q is CH$_2$, and the combination of R$^1$ and R$^2$ for a compound in each case corresponds to one line of Table A.

Table 111

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C=O, X is C(O)NH(benzyl), R$^{y'}$ and R$^{y\#}$, respectively, is hydrogen, Q is CH$_2$—CH$_2$, and the combination of R$^1$ and R$^2$ for a compound in each case corresponds to one line of Table A.

Table 112

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(benzyl), R$^{y'}$ and R$^{y\#}$, respectively, is CH$_3$, Q is CH$_2$—CH$_2$, and the combination of R$^1$ and R$^2$ for a compound in each case corresponds to one line of Table A.

Table 113

Compounds of the formulae I-A' fac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(benzyl), R$^{y'}$ and R$^{y\#}$, respectively, is CN, Q is CH$_2$—CH$_2$, and the combination of R$^1$ and R$^2$ for a compound in each case corresponds to one line of Table A.

Table 114

Compounds of the formulae I-A' fac, I-A'.R, I-A".rac, I-A".R and I-C', in which the group C(R$^{3a}$R$^{3b}$) is C=O, X is C(O)NH(benzyl), R$^{y'}$ is Cl, Q is CH$_2$—CH$_2$, and the combination of R$^1$ and R$^2$ for a compound in each case corresponds to one line of Table A.

Table 115

Compounds of the formulae I-A'.rac, I-A'.R, I-A".rac, I-A".R and I-C', in which the group C(R$^{3a}$R$^{3b}$) is C=O, X is C(O)NH(benzyl), R$^{y'}$ is F, Q is CH$_2$—CH$_2$, and the combination of R$^1$ and R$^2$ for a compound in each case corresponds to one line of Table A.

Table 116

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is C(O)NH(benzyl), R$^{y'}$ and R$^{y\#}$, respectively, is hydrogen, Q is CH$_2$—CH$_2$, and the combination of R$^1$ and R$^2$ for a compound in each case corresponds to one line of Table A.

Table 117

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is C(O)NH(benzyl), R$^{y'}$ and R$^{y\#}$, respectively, is CH$_3$, Q is CH$_2$—CH$_2$, and the combination of R$^1$ and R$^2$ for a compound in each case corresponds to one line of Table A.

Table 118

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is C(O)NH(benzyl), R$^{y'}$ and R$^{y\#}$, respectively, is CN, Q is CH$_2$—CH$_2$, and the combination of R$^1$ and R$^2$ for a compound in each case corresponds to one line of Table A.

Table 119

Compounds of the formulae I-A'.rac, I-A'.R, I-A".rac, I-A".R and I-C', in which the group C(R$^{3a}$R$^{3b}$) is C(OH)$_2$, X is C(O)NH(benzyl), R$^{y'}$ is Cl, Q is CH$_2$—CH$_2$, and the combination of R$^1$ and R$^2$ for a compound in each case corresponds to one line of Table A.

Table 120

Compounds of the formulae I-A'.rac, I-A'.R, I-A".rac, I-A".R and I-C', in which the group C(R$^{3a}$R$^{3b}$) is C(OH)$_2$, X is C(O)NH(benzyl), R$^{y'}$ is F, Q is CH$_2$—CH$_2$, and the combination of R$^1$ and R$^2$ for a compound in each case corresponds to one line of Table A.

Table 121

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(4-trifluoromethyl-benzyl), R$^{y'}$ and R$^{y\#}$, respectively, is hydrogen, Q is a single bond, and the combination of R$^1$ and R$^2$ for a compound in each case corresponds to one line of Table A.

Table 122

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(4-trifluoromethyl-benzyl), R$^{y'}$ and R$^{y\#}$, respectively, is CH$_3$, Q is a single bond, and the combination of R$^1$ and R$^2$ for a compound in each case corresponds to one line of Table A.

Table 123

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(4-trifluoromethyl-benzyl), R$^{y'}$ and R$^{y\#}$, respectively, is CN, Q is a single bond, and the combination of $R^1$ and $R^2$ for a compound in each case corresponds to one line of Table A.

Table 124

Compounds of the formulae I-A'.rac, I-A'.R, I-A".rac, I-A".R and I-C', in which the group $C(R^{3a}R^{3b})$ is C=O, X is C(O)NH(4-trifluoromethylbenzyl), $R^{y'}$ is Cl, Q is a single bond, and the combination of $R^1$ and $R^2$ for a compound in each case corresponds to one line of Table A.

Table 125

Compounds of the formulae I-A'.rac, I-A'.R, I-A" fac, I-A".R and I-C', in which the group $C(R^{3a}R^{3b})$ is C=O, X is C(O)NH(4-trifluoromethylbenzyl), $R^{y'}$ is F, Q is a single bond, and the combination of $R^1$ and $R^2$ for a compound in each case corresponds to one line of Table A.

Table 126

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C(OH)_2$, X is C(O)NH(4-trifluoromethylbenzyl), $R^{y'}$ and $R^{y\#}$, respectively, is hydrogen, Q is a single bond, and the combination of $R^1$ and $R^2$ for a compound in each case corresponds to one line of Table A.

Table 127

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is C(O)NH(4-trifluoromethylbenzyl), $R^{y'}$ and $R^{y\#}$, respectively, is $CH_3$, Q is a single bond, and the combination of $R^1$ and $R^2$ for a compound in each case corresponds to one line of Table A.

Table 128

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C(OH)_2$, X is C(O)NH(4-trifluoromethylbenzyl), $R^{y'}$ and $R^{y\#}$, respectively, is CN, Q is a single bond, and the combination of $R^1$ and $R^2$ for a compound in each case corresponds to one line of Table A.

Table 129

Compounds of the formulae I-A'.rac, I-A'.R, I-A" fac, I-A".R and I-C', in which the group $C(R^{3a}R^{3b})$ is $C(OH)_2$, X is C(O)NH(4-trifluoromethylbenzyl), $R^{y'}$ is Cl, Q is a single bond, and the combination of $R^1$ and $R^2$ for a compound in each case corresponds to one line of Table A.

Table 130

Compounds of the formulae I-A'.rac, I-A'.R, I-A".rac, I-A".R and I-C', in which the group $C(R^{3a}R^{3b})$ is $C(OH)_2$, X is C(O)NH(4-trifluoromethylbenzyl), $R^{y'}$ is F, Q is a single bond, and the combination of $R^1$ and $R^2$ for a compound in each case corresponds to one line of Table A.

Table 131

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is C=O, X is C(O)NH(4-trifluoromethylbenzyl), $R^{y'}$ and $R^{y\#}$, respectively, is hydrogen, Q is $CH_2$, and the combination of $R^1$ and $R^2$ for a compound in each case corresponds to one line of Table A.

Table 132

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is C(O)NH(4-trifluoromethylbenzyl), $R^{y'}$ and $R^{y\#}$, respectively, is $CH_3$, Q is $CH_2$, and the combination of $R^1$ and $R^2$ for a compound in each case corresponds to one line of Table A.

Table 133

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is C(O)NH(4-trifluoromethylbenzyl), $R^{y'}$ and $R^{y\#}$, respectively, is CN, Q is $CH_2$, and the combination of $R^1$ and $R^2$ for a compound in each case corresponds to one line of Table A.

Table 134

Compounds of the formulae I-A'.rac, I-A'.R, I-A" fac, I-A".R and I-C', in which the group $C(R^{3a}R^{3b})$ is C=O, X is C(O)NH(4-trifluoromethylbenzyl), $R^{y'}$ is Cl, Q is $CH_2$, and the combination of $R^1$ and $R^2$ for a compound in each case corresponds to one line of Table A.

Table 135

Compounds of the formulae I-A'.rac, I-A'.R, I-A".rac, I-A".R and I-C', in which the group $C(R^{3a}R^{3b})$ is C=O, X is C(O)NH(4-trifluoromethylbenzyl), $R^{y'}$ is F, Q is $CH_2$, and the combination of $R^1$ and $R^2$ for a compound in each case corresponds to one line of Table A.

Table 136

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C(OH)_2$, X is C(O)NH(4-trifluoromethylbenzyl), $R^{y'}$ and $R^{y\#}$, respectively, is hydrogen, Q is $CH_2$, and the combination of $R^1$ and $R^2$ for a compound in each case corresponds to one line of Table A.

Table 137

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is C(O)NH(4-trifluoromethylbenzyl), $R^{y'}$ and $R^{y\#}$, respectively, is $CH_3$, Q is $CH_2$, and the combination of $R^1$ and $R^2$ for a compound in each case corresponds to one line of Table A.

Table 138

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is C(O)NH(4-trifluoromethylbenzyl), $R^{y'}$ and $R^{y\#}$, respectively, is CN, Q is $CH_2$, and the combination of $R^1$ and $R^2$ for a compound in each case corresponds to one line of Table A.

Table 139

Compounds of the formulae I-A'.rac, I-A'.R, I-A" fac, I-A".R and I-C', in which the group $C(R^{3a}R^{3b})$ is $C(OH)_2$, X is C(O)NH(4-trifluoromethylbenzyl), $R^{y'}$ is Cl, Q is $CH_2$, and the combination of $R^1$ and $R^2$ for a compound in each case corresponds to one line of Table A.

Table 140

Compounds of the formulae I-A'.rac, I-A'.R, I-A".rac, I-A".R and I-C', in which the group $C(R^{3a}R^{3b})$ is $C(OH)_2$, X is C(O)NH(4-trifluoromethylbenzyl), $R^{y'}$ is F, Q is $CH_2$, and the combination of $R^1$ and $R^2$ for a compound in each case corresponds to one line of Table A.

Table 141

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is C=O, X is C(O)NH(4-trifluoromethylbenzyl), $R^{y'}$ and $R^{y\#}$, respectively, is hydrogen, Q is $CH_2$—$CH_2$, and the combination of $R^1$ and $R^2$ for a compound in each case corresponds to one line of Table A.

Table 142

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is C(O)NH(4-trifluoromethylbenzyl), $R^{y'}$ and $R^{y\#}$, respectively, is $CH_3$, Q is $CH_2$—$CH_2$, and the combination of $R^1$ and $R^2$ for a compound in each case corresponds to one line of Table A.

Table 143

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is C(O)NH(4-trifluoromethylbenzyl), $R^{y'}$ and $R^{y\#}$, respectively, is CN, Q is $CH_2$—$CH_2$, and the combination of $R^1$ and $R^2$ for a compound in each case corresponds to one line of Table A.

Table 144

Compounds of the formulae I-A'.rac, I-A'.R, I-A".rac, I-A".R and I-C', in which the group $C(R^{3a}R^{3b})$ is C=O, X is $C(O)NH(4$-trifluoromethylbenzyl), $R^{y'}$ is Cl, Q is $CH_2$—$CH_2$, and the combination of $R^1$ and $R^2$ for a compound in each case corresponds to one line of Table A.

Table 145

Compounds of the formulae I-A'.rac, I-A'.R, I-A" fac, I-A".R and I-C', in which the group $C(R^{3a}R^{3b})$ is C=O, X is $C(O)NH(4$-trifluoromethylbenzyl), $R^{y'}$ is F, Q is $CH_2$—$CH_2$, and the combination of $R^1$ and $R^2$ for a compound in each case corresponds to one line of Table A.

Table 146

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C(OH)_2$, X is $C(O)NH(4$-trifluoromethylbenzyl), $R^{y'}$ and $R^{y\#}$, respectively, is hydrogen, Q is $CH_2$—$CH_2$, and the combination of $R^1$ and $R^2$ for a compound in each case corresponds to one line of Table A.

Table 147

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is $C(O)NH(4$-trifluoromethylbenzyl), $R^{y'}$ and $R^{y\#}$, respectively, is $CH_3$, Q is $CH_2$—$CH_2$, and the combination of $R^1$ and $R^2$ for a compound in each case corresponds to one line of Table A.

Table 148

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is $C(O)NH(4$-trifluoromethylbenzyl), $R^{y'}$ and $R^{y\#}$, respectively, is CN, Q is $CH_2$—$CH_2$, and the combination of $R^1$ and $R^2$ for a compound in each case corresponds to one line of Table A.

Table 149

Compounds of the formulae I-A'.rac, I-A'.R, I-A".rac, I-A".R and I-C', in which the group $C(R^{3a}R^{3b})$ is $C(OH)_2$, X is $C(O)NH(4$-trifluoromethylbenzyl), $R^{y'}$ is Cl, Q is $CH_2$—$CH_2$, and the combination of $R^1$ and $R^2$ for a compound in each case corresponds to one line of Table A.

Table 150

Compounds of the formulae I-A'.rac, I-A'.R, I-A".rac, I-A".R and I-C', in which the group $C(R^{3a}R^{3b})$ is $C(OH)_2$, X is $C(O)NH(4$-trifluoromethylbenzyl), $R^{y'}$ is F, Q is $CH_2$—$CH_2$, and the combination of $R^1$ and $R^2$ for a compound in each case corresponds to one line of Table A.

Table 151

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is $C(O)NH($pyridin-4-ylmethyl), $R^{y'}$ and $R^{y\#}$, respectively, is hydrogen, Q is a single bond, and the combination of $R^1$ and $R^2$ for a compound in each case corresponds to one line of Table A.

Table 152

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is $C(O)NH($pyridin-4-ylmethyl), $R^{y'}$ and $R^{y\#}$, respectively, is $CH_3$, Q is a single bond, and the combination of $R^1$ and $R^2$ for a compound in each case corresponds to one line of Table A.

Table 153

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is $C(O)NH($pyridin-4-ylmethyl), $R^{y'}$ and $R^{y\#}$, respectively, is CN, Q is a single bond, and the combination of $R^1$ and $R^2$ for a compound in each case corresponds to one line of Table A.

Table 154

Compounds of the formulae I-A'.rac, I-A'.R, I-A".rac, I-A".R and I-C', in which the group $C(R^{3a}R^{3b})$ is C=O, X is $C(O)NH($pyridin-4-ylmethyl), $R^{y'}$ is Cl, Q is a single bond, and the combination of $R^1$ and $R^2$ for a compound in each case corresponds to one line of Table A.

Table 155

Compounds of the formulae I-A'.rac, I-A'.R, I-A" fac, I-A".R and I-C', in which the group $C(R^{3a}R^{3b})$ is C=O, X is $C(O)NH($pyridin-4-ylmethyl), $R^{y'}$ is F, Q is a single bond, and the combination of $R^1$ and $R^2$ for a compound in each case corresponds to one line of Table A.

Table 156

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C(OH)_2$, X is $C(O)NH($pyridin-4-ylmethyl), $R^{y'}$ and $R^{y\#}$, respectively, is hydrogen, Q is a single bond, and the combination of $R^1$ and $R^2$ for a compound in each case corresponds to one line of Table A.

Table 157

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is $C(O)NH($pyridin-4-ylmethyl), $R^{y'}$ and $R^{y\#}$, respectively, is $CH_3$, Q is a single bond, and the combination of $R^1$ and $R^2$ for a compound in each case corresponds to one line of Table A.

Table 158

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is $C(O)NH($pyridin-4-ylmethyl), $R^{y'}$ and $R^{y\#}$, respectively, is CN, Q is a single bond, and the combination of $R^1$ and $R^2$ for a compound in each case corresponds to one line of Table A.

Table 159

Compounds of the formulae I-A'.rac, I-A'.R, I-A".rac, I-A".R and I-C', in which the group $C(R^{3a}R^{3b})$ is $C(OH)_2$, X is $C(O)NH($pyridin-4-ylmethyl), $R^{y'}$ is Cl, Q is a single bond, and the combination of $R^1$ and $R^2$ for a compound in each case corresponds to one line of Table A.

Table 160

Compounds of the formulae I-A'.rac, I-A'.R, I-A".rac, I-A".R and I-C', in which the group $C(R^{3a}R^{3b})$ is $C(OH)_2$, X is $C(O)NH($pyridin-4-ylmethyl), $R^{y'}$ is F, Q is a single bond, and the combination of $R^1$ and $R^2$ for a compound in each case corresponds to one line of Table A.

Table 161

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is $C(O)NH($pyridin-4-ylmethyl), $R^{y'}$ and $R^{y\#}$, respectively, is hydrogen, Q is $CH_2$, and the combination of $R^1$ and $R^2$ for a compound in each case corresponds to one line of Table A.

Table 162

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is $C(O)NH($pyridin-4-ylmethyl), $R^{y'}$ and $R^{y\#}$, respectively, is $CH_3$, Q is $CH_2$, and the combination of $R^1$ and $R^2$ for a compound in each case corresponds to one line of Table A.

Table 163

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is $C(O)NH($pyridin-4-ylmethyl), $R^{y'}$ and $R^{y\#}$, respectively, is CN, Q is $CH_2$, and the combination of $R^1$ and $R^2$ for a compound in each case corresponds to one line of Table A.

Table 164

Compounds of the formulae I-A' fac, I-A'.R, I-A".rac, I-A".R and I-C', in which the group $C(R^{3a}R^{3b})$ is C=O, X is $C(O)NH(pyridin-4-ylmethyl)$, $R^{y'}$ is Cl, Q is $CH_2$, and the combination of $R^1$ and $R^2$ for a compound in each case corresponds to one line of Table A.

Table 165

Compounds of the formulae I-A'.rac, I-A'.R, I-A".rac, I-A".R and I-C', in which the group $C(R^{3a}R^{3b})$ is C=O, X is $C(O)NH(pyridin-4-ylmethyl)$, $R^{y'}$ is F, Q is $CH_2$, and the combination of $R^1$ and $R^2$ for a compound in each case corresponds to one line of Table A.

Table 166

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is $C(O)NH(pyridin-4-ylmethyl)$, $R^{y'}$ and $R^{y\#}$, respectively, is hydrogen, Q is $CH_2$, and the combination of $R^1$ and $R^2$ for a compound in each case corresponds to one line of Table A.

Table 167

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is $C(O)NH(pyridin-4-ylmethyl)$, $R^{y'}$ and $R^{y\#}$, respectively, is $CH_3$, Q is $CH_2$, and the combination of $R^1$ and $R^2$ for a compound in each case corresponds to one line of Table A.

Table 168

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is $C(O)NH(pyridin-4-ylmethyl)$, $R^{y'}$ and $R^{y\#}$, respectively, is CN, Q is $CH_2$, and the combination of $R^1$ and $R^2$ for a compound in each case corresponds to one line of Table A.

Table 169

Compounds of the formulae I-A'.rac, I-A'.R, I-A".rac, I-A".R and I-C', in which the group $C(R^{3a}R^{3b})$ is $C(OH)_2$, X is $C(O)NH(pyridin-4-ylmethyl)$, $R^{y'}$ is Cl, Q is $CH_2$, and the combination of $R^1$ and $R^2$ for a compound in each case corresponds to one line of Table A.

Table 170

Compounds of the formulae I-A'.rac, I-A'.R, I-A".rac, I-A".R and I-C', in which the group $C(R^{3a}R^{3b})$ is $C(OH)_2$, X is $C(O)NH(pyridin-4-ylmethyl)$, $R^{y'}$ is F, Q is $CH_2$, and the combination of $R^1$ and $R^2$ for a compound in each case corresponds to one line of Table A.

Table 171

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is $C(O)NH(pyridin-4-ylmethyl)$, $R^{y'}$ and $R^{y\#}$, respectively, is hydrogen, Q is $CH_2$—$CH_2$, and the combination of $R^1$ and $R^2$ for a compound in each case corresponds to one line of Table A.

Table 172

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is $C(O)NH(pyridin-4-ylmethyl)$, $R^{y'}$ and $R^{y\#}$, respectively, is $CH_3$, Q is $CH_2$—$CH_2$, and the combination of $R^1$ and $R^2$ for a compound in each case corresponds to one line of Table A.

Table 173

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is C=O, X is $C(O)NH(pyridin-4-ylmethyl)$, $R^{y'}$ and $R^{y\#}$, respectively, is CN, Q is $CH_2$—$CH_2$, and the combination of $R^1$ and $R^2$ for a compound in each case corresponds to one line of Table A.

Table 174

Compounds of the formulae I-A'.rac, I-A'.R, I-A".rac, I-A".R and I-C', in which the group $C(R^{3a}R^{3b})$ is C=O, X is $C(O)NH(pyridin-4-ylmethyl)$, $R^{y'}$ is Cl, Q is $CH_2$—$CH_2$, and the combination of $R^1$ and $R^2$ for a compound in each case corresponds to one line of Table A.

Table 175

Compounds of the formulae I-A'.rac, I-A'.R, I-A".rac, I-A".R and I-C', in which the group $C(R^{3a}R^{3b})$ is C=O, X is $C(O)NH(pyridin-4-ylmethyl)$, $R^{y'}$ is F, Q is $CH_2$—$CH_2$, and the combination of $R^1$ and $R^2$ for a compound in each case corresponds to one line of Table A.

Table 176

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is $C(O)NH(pyridin-4-ylmethyl)$, $R^{y'}$ and $R^{y\#}$, respectively, is hydrogen, Q is $CH_2$—$CH_2$, and the combination of $R^1$ and $R^2$ for a compound in each case corresponds to one line of Table A.

Table 177

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is $C(O)NH(pyridin-4-ylmethyl)$, $R^{y'}$ and $R^{y\#}$, respectively, is $CH_3$, Q is $CH_2$—$CH_2$, and the combination of $R^1$ and $R^2$ for a compound in each case corresponds to one line of Table A.

Table 178

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C(OH)_2$, X is $C(O)NH(pyridin-4-ylmethyl)$, $R^{y'}$ and $R^{y\#}$, respectively, is CN, Q is $CH_2$—$CH_2$, and the combination of $R^1$ and $R^2$ for a compound in each case corresponds to one line of Table A.

Table 179

Compounds of the formulae I-A'.rac, I-A'.R, I-A" fac, I-A".R and I-C', in which the group $C(R^{3a}R^{3b})$ is $C(OH)_2$, X is $C(O)NH(pyridin-4-ylmethyl)$, $R^{y'}$ is Cl, Q is $CH_2$—$CH_2$, and the combination of $R^1$ and $R^2$ for a compound in each case corresponds to one line of Table A.

Table 180

Compounds of the formulae I-A'.rac, I-A'.R, I-A".rac, I-A".R and I-C', in which the group $C(R^{3a}R^{3b})$ is $C(OH)_2$, X is $C(O)NH(pyridin-4-ylmethyl)$, $R^{y'}$ is F, Q is $CH_2$—$CH_2$, and the combination of $R^1$ and $R^2$ for a compound in each case corresponds to one line of Table A.

Table 181

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is C=O, X is $C(O)NH(phenylpropyl)$, $R^{y'}$ and $R^{y\#}$, respectively, is H, Q is a single bond, and the combination of $R^1$ and $R^2$ for a compound in each case corresponds to one line of Table A.

Table 182

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is C=O, X is $C(O)NH(phenylpropyl)$, $R^{y'}$ and $R^{y\#}$, respectively, is H, Q is $CH_2$, and the combination of $R^1$ and $R^2$ for a compound in each case corresponds to one line of Table A.

Table 183

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is C=O, X is $C(O)NH(phenylpropyl)$, $R^{y'}$ and R$^{y\#}$, respectively, is H, Q is CH$_2$—CH$_2$, and the combination of R$^1$ and R$^2$ for a compound in each case corresponds to one line of Table A.

Table 184

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(phenylpropyl), R$^{y'}$ and R$^{y\#}$, respectively, is H, Q is a single bond, and the combination of R$^1$ and R$^2$ for a compound in each case corresponds to one line of Table A.

Table 185

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(phenylpropyl), R$^{y'}$ and R$^{y\#}$, respectively, is H, Q is CH$_2$, and the combination of R$^1$ and R$^2$ for a compound in each case corresponds to one line of Table A.

Table 186

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(phenylpropyl), R$^{y'}$ and R$^{y\#}$, respectively, is H, Q is CH$_2$—CH$_2$, and the combination of R$^1$ and R$^2$ for a compound in each case corresponds to one line of Table A.

Table 187

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(phenylpropyl), R$^{y'}$ and R$^{y\#}$, respectively, is CH$_3$, Q is a single bond, and the combination of R$^1$ and R$^2$ for a compound in each case corresponds to one line of Table A.

Table 188

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(phenylpropyl), R$^{y'}$ and R$^{y\#}$, respectively, is CH$_3$, Q is CH$_2$, and the combination of R$^1$ and R$^2$ for a compound in each case corresponds to one line of Table A.

Table 189

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(phenylpropyl), R$^{y'}$ and R$^{y\#}$, respectively, is CH$_3$, Q is CH$_2$—CH$_2$, and the combination of R$^1$ and R$^2$ for a compound in each case corresponds to one line of Table A.

Table 190

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is C(O)NH(phenylpropyl), R$^{y'}$ and R$^{y\#}$, respectively, is CH$_3$, Q is a single bond, and the combination of R$^1$ and R$^2$ for a compound in each case corresponds to one line of Table A.

Table 191

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is C(O)NH(phenylpropyl), R$^{y'}$ and R$^{y\#}$, respectively, is CH$_3$, Q is CH$_2$, and the combination of R$^1$ and R$^2$ for a compound in each case corresponds to one line of Table A.

Table 192

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(phenylpropyl), R$^{y'}$ and R$^{y\#}$, respectively, is CH$_3$, Q is CH$_2$—CH$_2$, and the combination of R$^1$ and R$^2$ for a compound in each case corresponds to one line of Table A.

Table 193

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(pyridin-2-ylpropyl), R$^{y'}$ and R$^{y\#}$, respectively, is H, Q is a single bond, and the combination of R$^1$ and R$^2$ for a compound in each case corresponds to one line of Table A.

Table 194

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C=O, X is C(O)NH(pyridin-2-ylpropyl), R$^{y'}$ and R$^{y\#}$, respectively, is H, Q is CH$_2$, and the combination of R$^1$ and R$^2$ for a compound in each case corresponds to one line of Table A.

Table 195

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C=O, X is C(O)NH(pyridin-2-ylpropyl), R$^{y'}$ and R$^{y\#}$, respectively, is H, Q is CH$_2$—CH$_2$, and the combination of R$^1$ and R$^2$ for a compound in each case corresponds to one line of Table A.

Table 196

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(pyridin-2-ylpropyl), R$^{y'}$ and R$^{y\#}$, respectively, is H, Q is a single bond, and the combination of R$^1$ and R$^2$ for a compound in each case corresponds to one line of Table A.

Table 197

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(pyridin-2-ylpropyl), R$^{y'}$ and R$^{y\#}$, respectively, is H, Q is CH$_2$, and the combination of R$^1$ and R$^2$ for a compound in each case corresponds to one line of Table A.

Table 198

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(pyridin-2-ylpropyl), R$^{y'}$ and R$^{y\#}$, respectively, is H, Q is CH$_2$—CH$_2$, and the combination of R$^1$ and R$^2$ for a compound in each case corresponds to one line of Table A.

Table 199

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C=O, X is C(O)NH(pyridin-2-ylpropyl), R$^{y'}$ and R$^{y\#}$, respectively, is CH$_3$, Q is a single bond, and the combination of R$^1$ and R$^2$ for a compound in each case corresponds to one line of Table A.

Table 200

Compounds of the formulae I-A'.rac, I-A'.R, I-A" fac, I-A".R, I-B'.rac, I-B'.R, I-B" fac, I-B".R and I-C', in which the group C(R$^{3a}$R$^{3b}$) is C=O, X is C(O)NH(pyridin-2-ylpropyl), R$^{y'}$ and R$^{y\#}$, respectively, is CH$_3$, Q is CH$_2$, and the combination of R$^1$ and R$^2$ for a compound in each case corresponds to one line of Table A.

Table 201

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C=O, X is C(O)NH(pyridin-2-ylpropyl), R$^{y'}$ and R$^{y\#}$, respectively, is CH$_3$, Q is CH$_2$—CH$_2$, and the combination of R$^1$ and R$^2$ for a compound in each case corresponds to one line of Table A.

Table 202

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is C(O)NH(pyridin-2-ylpropyl), R^y′ and R^y#, respectively, is CH$_3$, Q is a single bond, and the combination of R$^1$ and R$^2$ for a compound in each case corresponds to one line of Table A.

Table 203

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is C(O)NH(pyridin-2-ylpropyl), R^y′ and R^y#, respectively, is CH$_3$, Q is CH$_2$, and the combination of R$^1$ and R$^2$ for a compound in each case corresponds to one line of Table A.

Table 204

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(pyridin-2-ylpropyl), R^y′ and R^y#, respectively, is CH$_3$, Q is CH$_2$—CH$_2$, and the combination of R$^1$ and R$^2$ for a compound in each case corresponds to one line of Table A.

Table 205

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C=O, X is C(O)NH(pyridin-3-ylpropyl), R^y′ and R^y#, respectively, is H, Q is a single bond, and the combination of R$^1$ and R$^2$ for a compound in each case corresponds to one line of Table A.

Table 206

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(pyridin-3-ylpropyl), R^y′ and R^y#, respectively, is H, Q is CH$_2$, and the combination of R$^1$ and R$^2$ for a compound in each case corresponds to one line of Table A.

Table 207

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(pyridin-3-ylpropyl), R^y′ and R^y#, respectively, is H, Q is CH$_2$—CH$_2$, and the combination of R$^1$ and R$^2$ for a compound in each case corresponds to one line of Table A.

Table 208

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(pyridin-3-ylpropyl), R^y′ and R^y#, respectively, is H, Q is a single bond, and the combination of R$^1$ and R$^2$ for a compound in each case corresponds to one line of Table A.

Table 209

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(pyridin-3-ylpropyl), R^y′ and R^y#, respectively, is H, Q is CH$_2$, and the combination of R$^1$ and R$^2$ for a compound in each case corresponds to one line of Table A.

Table 210

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(pyridin-3-ylpropyl), R^y′ and R^y#, respectively, is H, Q is CH$_2$—CH$_2$, and the combination of R$^1$ and R$^2$ for a compound in each case corresponds to one line of Table A.

Table 211

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(pyridin-3-ylpropyl), R^y′ and R^y#, respectively, is CH$_3$, Q is a single bond, and the combination of R$^1$ and R$^2$ for a compound in each case corresponds to one line of Table A.

Table 212

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(pyridin-3-ylpropyl), R^y′ and R^y#, respectively, is CH$_3$, Q is CH$_2$, and the combination of R$^1$ and R$^2$ for a compound in each case corresponds to one line of Table A.

Table 213

Compounds of the formulae I-A'.rac, I-A'.R, I-A" fac, I-A".R, I-B' fac, I-B'.R, I-B".rac, I-B".R and I-C', in which the group C(R$^{3a}$R$^{3b}$) is C=O, X is C(O)NH(pyridin-3-ylpropyl), R^y′ and R^y#, respectively, is CH$_3$, Q is CH$_2$—CH$_2$, and the combination of R$^1$ and R$^2$ for a compound in each case corresponds to one line of Table A.

Table 214

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(pyridin-3-ylpropyl), R^y′ and R^y#, respectively, is CH$_3$, Q is a single bond, and the combination of R$^1$ and R$^2$ for a compound in each case corresponds to one line of Table A.

Table 215

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C(OH)$_2$, X is C(O)NH(pyridin-3-ylpropyl), R^y′ and R^y#, respectively, is CH$_3$, Q is CH$_2$, and the combination of R$^1$ and R$^2$ for a compound in each case corresponds to one line of Table A.

Table 216

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is C(O)NH(pyridin-3-ylpropyl), R^y′ and R^y#, respectively, is CH$_3$, Q is CH$_2$—CH$_2$, and the combination of R$^1$ and R$^2$ for a compound in each case corresponds to one line of Table A.

Table 217

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(pyridin-4-ylpropyl), R^y′ and R^y#, respectively, is H, Q is a single bond, and the combination of R$^1$ and R$^2$ for a compound in each case corresponds to one line of Table A.

Table 218

Compounds of the formulae I-A'.rac, I-A'.R, I-A".rac, I-A".R, I-B'.rac, I-B'.R, I-B" fac, I-B".R and I-C', in which the group C(R$^{3a}$R$^{3b}$) is C=O, X is C(O)NH(pyridin-4-ylpropyl), R^y′ and R^y#, respectively, is H, Q is CH$_2$, and the combination of R$^1$ and R$^2$ for a compound in each case corresponds to one line of Table A.

Table 219

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C=O, X is C(O)NH(pyridin-4-ylpropyl), R^y′ and R^y#, respectively, is H, Q is CH$_2$—CH$_2$, and the combination of R$^1$ and R$^2$ for a compound in each case corresponds to one line of Table A.

Table 220

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is C(O)NH(pyridin-4-ylpropyl), R^y′ and R^y#, respectively, is H, Q is a single bond, and the combination of R$^1$ and R$^2$ for a compound in each case corresponds to one line of Table A.

Table 221

Compounds of the formulae I-A'.rac, I-A'.R, I-A".rac, I-A".R, I-B'.rac, I-B'.R, I-B".rac, I-B".R and I-C', in which the group C(R$^{3a}$R$^{3b}$) is C(OH)$_2$, X is C(O)NH(pyridin-4-ylpropyl), $R^{y'}$ and $R^{y\#}$, respectively, is H, Q is $CH_2$, and the combination of $R^1$ and $R^2$ for a compound in each case corresponds to one line of Table A.

Table 222

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is C(O)NH(pyridin-4-ylpropyl), $R^{y'}$ and $R^{y\#}$, respectively, is H, Q is $CH_2$—$CH_2$, and the combination of $R^1$ and $R^2$ for a compound in each case corresponds to one line of Table A.

Table 223

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is C=O, X is C(O)NH(pyridin-4-ylpropyl), $R^{y'}$ and $R^{y\#}$, respectively, is $CH_3$, Q is a single bond, and the combination of $R^1$ and $R^2$ for a compound in each case corresponds to one line of Table A.

Table 224

Compounds of the formulae I-A'.rac, I-A'.R, I-A" fac, I-A".R, I-B'.rac, I-B'.R, I-B".rac, I-B".R and I-C', in which the group $C(R^{3a}R^{3b})$ is C=O, X is C(O)NH(pyridin-4-ylpropyl), $R^{y'}$ and $R^{y\#}$, respectively, is $CH_3$, Q is $CH_2$, and the combination of $R^1$ and $R^2$ for a compound in each case corresponds to one line of Table A.

Table 225

Compounds of the formulae I-A'.rac, I-A'.R, I-A" fac, I-A".R, I-B' fac, I-B'.R, I-B".rac, I-B".R and I-C', in which the group $C(R^{3a}R^{3b})$ is C=O, X is C(O)NH(pyridin-4-ylpropyl), $R^{y'}$ and $R^{y\#}$, respectively, is $CH_3$, Q is $CH_2$—$CH_2$, and the combination of $R^1$ and $R^2$ for a compound in each case corresponds to one line of Table A.

Table 226

Compounds of the formulae I-A'.rac, I-A'.R, I-A".rac, I-A".R, I-B'.rac, I-B'.R, I-B".rac, I-B".R and I-C', in which the group $C(R^{3a}R^{3b})$ is $C(OH)_2$, X is C(O)NH(pyridin-4-ylpropyl), $R^{y'}$ and $R^{y\#}$, respectively, is $CH_3$, Q is a single bond, and the combination of $R^1$ and $R^2$ for a compound in each case corresponds to one line of Table A.

Table 227

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C(OH)_2$, X is C(O)NH(pyridin-4-ylpropyl), $R^{y'}$ and $R^{y\#}$, respectively, is $CH_3$, Q is $CH_2$, and the combination of $R^1$ and $R^2$ for a compound in each case corresponds to one line of Table A.

Table 228

Compounds of the formulae I-A'.rac, I-A'.R, I-A".rac, I-A".R, I-B'.rac, I-B'.R, I-B" fac, I-B".R and I-C', in which the group $C(R^{3a}R^{3b})$ is $C(OH)_2$, X is C(O)NH(pyridin-4-ylpropyl), $R^{y'}$ and $R^{y\#}$, respectively, is $CH_3$, Q is $CH_2$—$CH_2$, and the combination of $R^1$ and $R^2$ for a compound in each case corresponds to one line of Table A.

TABLE A

| No. | $R^1$ | $R^2$ |
| --- | --- | --- |
| A-1 | n-Butyl | Phenyl |
| A-2 | n-Butyl | 2-Methylphenyl |
| A-3 | n-Butyl | 2-Methoxyphenyl |
| A-4 | n-Butyl | 2-Chlorophenyl |
| A-5 | n-Butyl | 2-Fluorophenyl |
| A-6 | n-Butyl | 2-Trifluoromethylphenyl |
| A-7 | n-Butyl | 2-Trifluoromethoxyphenyl |
| A-8 | n-Butyl | 3-Methylphenyl |
| A-9 | n-Butyl | 3-Methoxyphenyl |
| A-10 | n-Butyl | 3-Chlorophenyl |
| A-11 | n-Butyl | 3-Fluorophenyl |
| A-12 | n-Butyl | 3-Trifluoromethylphenyl |
| A-13 | n-Butyl | 3-Trifluoromethoxyphenyl |
| A-14 | n-Butyl | 3-Cyanophenyl |
| A-15 | n-Butyl | 3-[(Phenylmethyl)oxy]phenyl |
| A-16 | n-Butyl | 3-Morpholin-4-ylphenyl |
| A-17 | n-Butyl | 3-Pyrrolidin-1-ylphenyl |
| A-18 | n-Butyl | 4-Methylphenyl |
| A-19 | n-Butyl | 4-(1-Methylethyl)phenyl |
| A-20 | n-Butyl | 4-Methoxyphenyl |
| A-21 | n-Butyl | 4-Chlorophenyl |
| A-22 | n-Butyl | 4-Fluorophenyl |
| A-23 | n-Butyl | 4-Trifluoromethylphenyl |
| A-24 | n-Butyl | 4-Diethylaminophenyl |
| A-25 | n-Butyl | 4-[(Diethylamino)methyl]phenyl |
| A-26 | n-Butyl | 4-Cyanophenyl |
| A-27 | n-Butyl | 4-(Piperidin-1-yl)phenyl |
| A-28 | n-Butyl | 4-(4-Methylpiperazin-1-yl)phenyl |
| A-29 | n-Butyl | 4-Pyrrolidin-1-ylphenyl |
| A-30 | n-Butyl | 4-(1H-Imidazol-1-yl)phenyl |
| A-31 | n-Butyl | 4-Morpholin-4-ylphenyl |
| A-32 | n-Butyl | 2,4-Difluorophenyl |
| A-33 | n-Butyl | 2,6-Difluorophenyl |
| A-34 | n-Butyl | 3,5-Difluorophenyl |
| A-35 | n-Butyl | 2,4-Dichlorophenyl |
| A-36 | n-Butyl | 2,6-Dichlorophenyl |
| A-37 | n-Butyl | 3,5-Dichlorophenyl |
| A-38 | n-Butyl | 2,4-Dimethoxyphenyl |
| A-39 | n-Butyl | 2,6-Dimethoxyphenyl |
| A-40 | n-Butyl | 3,5-Dimethoxyphenyl |
| A-41 | n-Butyl | 2-Chloro-4-fluorophenyl |
| A-42 | n-Butyl | 2-Chloro-4-morpholin-4-ylphenyl |
| A-43 | n-Butyl | 2-Fluoro-4-morpholin-4-ylphenyl |
| A-44 | n-Butyl | Naphth-1-yl |
| A-45 | n-Butyl | Naphth-2-yl |
| A-46 | n-Butyl | Pyridin-2-yl |
| A-47 | n-Butyl | Pyridin-4-yl |
| A-48 | n-Butyl | Thien-2-yl |
| A-49 | n-Butyl | 2,3-Dihydrobenzo[b]furan-5-yl |
| A-50 | Isobutyl | Phenyl |
| A-51 | Isobutyl | 2-Methylphenyl |
| A-52 | Isobutyl | 2-Methoxyphenyl |
| A-53 | Isobutyl | 2-Chlorophenyl |
| A-54 | Isobutyl | 2-Fluorophenyl |
| A-55 | Isobutyl | 2-Trifluoromethylphenyl |
| A-56 | Isobutyl | 2-Trifluoromethoxyphenyl |
| A-57 | Isobutyl | 3-Methylphenyl |
| A-58 | Isobutyl | 3-Methoxyphenyl |
| A-59 | Isobutyl | 3-Chlorophenyl |
| A-60 | Isobutyl | 3-Fluorophenyl |
| A-61 | Isobutyl | 3-Trifluoromethylphenyl |
| A-62 | Isobutyl | 3-Trifluoromethoxyphenyl |
| A-63 | Isobutyl | 3-Cyanophenyl |
| A-64 | Isobutyl | 3-[(Phenylmethyl)oxy]phenyl |
| A-65 | Isobutyl | 3-Morpholin-4-ylphenyl |
| A-66 | Isobutyl | 3-Pyrrolidin-1-ylphenyl |
| A-67 | Isobutyl | 4-Methylphenyl |
| A-68 | Isobutyl | 4-(1-Methylethyl)phenyl |
| A-69 | Isobutyl | 4-Methoxyphenyl |
| A-70 | Isobutyl | 4-Chlorophenyl |
| A-71 | Isobutyl | 4-Fluorophenyl |
| A-72 | Isobutyl | 4-Trifluoromethylphenyl |
| A-73 | Isobutyl | 4-Diethylaminophenyl |
| A-74 | Isobutyl | 4-[(Diethylamino)methyl]phenyl |
| A-75 | Isobutyl | 4-Cyanophenyl |
| A-76 | Isobutyl | 4-(Piperidin-1-yl)phenyl |
| A-77 | Isobutyl | 4-(4-Methylpiperazin-1-yl)phenyl |
| A-78 | Isobutyl | 4-Pyrrolidin-1-ylphenyl |
| A-79 | Isobutyl | 4-(1H-Imidazol-1-yl)phenyl |
| A-80 | Isobutyl | 4-Morpholin-4-ylphenyl |
| A-81 | Isobutyl | 2,4-Difluorophenyl |
| A-82 | Isobutyl | 2,6-Difluorophenyl |
| A-83 | Isobutyl | 3,5-Difluorophenyl |
| A-84 | Isobutyl | 2,4-Dichlorophenyl |
| A-85 | Isobutyl | 2,6-Dichlorophenyl |
| A-86 | Isobutyl | 3,5-Dichlorophenyl |
| A-87 | Isobutyl | 2,4-Dimethoxyphenyl |
| A-88 | Isobutyl | 2,6-Dimethoxyphenyl |
| A-89 | Isobutyl | 3,5-Dimethoxyphenyl |
| A-90 | Isobutyl | 2-Chloro-4-fluorophenyl |

TABLE A-continued

| No. | R¹ | R² |
|---|---|---|
| A-91 | Isobutyl | 2-Chloro-4-morpholin-4-ylphenyl |
| A-92 | Isobutyl | 2-Fluoro-4-morpholin-4-ylphenyl |
| A-93 | Isobutyl | Naphth-1-yl |
| A-94 | Isobutyl | Naphth-2-yl |
| A-95 | Isobutyl | Pyridin-2-yl |
| A-96 | Isobutyl | Pyridin-4-yl |
| A-97 | Isobutyl | Thien-2-yl |
| A-98 | Isobutyl | 2,3-Dihydrobenzo[b]furan-5-yl |
| A-99 | Benzyl | Phenyl |
| A-100 | Benzyl | 2-Methylphenyl |
| A-101 | Benzyl | 2-Methoxyphenyl |
| A-102 | Benzyl | 2-Chlorophenyl |
| A-103 | Benzyl | 2-Fluorophenyl |
| A-104 | Benzyl | 2-Trifluoromethylphenyl |
| A-105 | Benzyl | 2-Trifluoromethoxyphenyl |
| A-106 | Benzyl | 3-Methylphenyl |
| A-107 | Benzyl | 3-Methoxyphenyl |
| A-108 | Benzyl | 3-Chlorophenyl |
| A-109 | Benzyl | 3-Fluorophenyl |
| A-110 | Benzyl | 3-Trifluoromethylphenyl |
| A-111 | Benzyl | 3-Trifluoromethoxyphenyl |
| A-112 | Benzyl | 3-Cyanophenyl |
| A-113 | Benzyl | 3-[(Phenylmethyl)oxy]phenyl |
| A-114 | Benzyl | 3-Morpholin-4-ylphenyl |
| A-115 | Benzyl | 3-Pyrrolidin-1-ylphenyl |
| A-116 | Benzyl | 4-Methylphenyl |
| A-117 | Benzyl | 4-(1-Methylethyl)phenyl |
| A-118 | Benzyl | 4-Methoxyphenyl |
| A-119 | Benzyl | 4-Chlorophenyl |
| A-120 | Benzyl | 4-Fluorophenyl |
| A-121 | Benzyl | 4-Trifluoromethylphenyl |
| A-122 | Benzyl | 4-Diethylaminophenyl |
| A-123 | Benzyl | 4-[(Diethylamino)methyl]phenyl |
| A-124 | Benzyl | 4-Cyanophenyl |
| A-125 | Benzyl | 4-(Piperidin-1-yl)phenyl |
| A-126 | Benzyl | 4-(4-Methylpiperazin-1-yl)phenyl |
| A-127 | Benzyl | 4-Pyrrolidin-1-ylphenyl |
| A-128 | Benzyl | 4-(1H-Imidazol-1-yl)phenyl |
| A-129 | Benzyl | 4-Morpholin-4-ylphenyl |
| A-130 | Benzyl | 2,4-Difluorophenyl |
| A-131 | Benzyl | 2,6-Difluorophenyl |
| A-132 | Benzyl | 3,5-Difluorophenyl |
| A-133 | Benzyl | 2,4-Dichlorophenyl |
| A-134 | Benzyl | 2,6-Dichlorophenyl |
| A-135 | Benzyl | 3,5-Dichlorophenyl |
| A-136 | Benzyl | 2,4-Dimethoxyphenyl |
| A-137 | Benzyl | 2,6-Dimethoxyphenyl |
| A-138 | Benzyl | 3,5-Dimethoxyphenyl |
| A-139 | Benzyl | 2-Chloro-4-fluorophenyl |
| A-140 | Benzyl | 2-Chloro-4-morpholin-4-ylphenyl |
| A-141 | Benzyl | 2-Fluoro-4-morpholin-4-ylphenyl |
| A-142 | Benzyl | Naphth-1-yl |
| A-143 | Benzyl | Naphth-2-yl |
| A-144 | Benzyl | Pyridin-2-yl |
| A-145 | Benzyl | Pyridin-4-yl |
| A-146 | Benzyl | Thien-2-yl |
| A-147 | Benzyl | 2,3-Dihydrobenzo[b]furan-5-yl |
| A-148 | 4-Chlorobenzyl | Phenyl |
| A-149 | 4-Chlorobenzyl | 2-Methylphenyl |
| A-150 | 4-Chlorobenzyl | 2-Methoxyphenyl |
| A-151 | 4-Chlorobenzyl | 2-Chlorophenyl |
| A-152 | 4-Chlorobenzyl | 2-Fluorophenyl |
| A-153 | 4-Chlorobenzyl | 2-Trifluoromethylphenyl |
| A-154 | 4-Chlorobenzyl | 2-Trifluoromethoxyphenyl |
| A-155 | 4-Chlorobenzyl | 3-Methylphenyl |
| A-156 | 4-Chlorobenzyl | 3-Methoxyphenyl |
| A-157 | 4-Chlorobenzyl | 3-Chlorophenyl |
| A-158 | 4-Chlorobenzyl | 3-Fluorophenyl |
| A-159 | 4-Chlorobenzyl | 3-Trifluoromethylphenyl |
| A-160 | 4-Chlorobenzyl | 3-Trifluoromethoxyphenyl |
| A-161 | 4-Chlorobenzyl | 3-Cyanophenyl |
| A-162 | 4-Chlorobenzyl | 3-[(Phenylmethyl)oxy]phenyl |
| A-163 | 4-Chlorobenzyl | 3-Morpholin-4-ylphenyl |
| A-164 | 4-Chlorobenzyl | 3-Pyrrolidin-1-ylphenyl |
| A-165 | 4-Chlorobenzyl | 4-Methylphenyl |
| A-166 | 4-Chlorobenzyl | 4-(1-Methylethyl)phenyl |
| A-167 | 4-Chlorobenzyl | 4-Methoxyphenyl |
| A-168 | 4-Chlorobenzyl | 4-Chlorophenyl |
| A-169 | 4-Chlorobenzyl | 4-Fluorophenyl |
| A-170 | 4-Chlorobenzyl | 4-Trifluoromethylphenyl |
| A-171 | 4-Chlorobenzyl | 4-Diethylaminophenyl |
| A-172 | 4-Chlorobenzyl | 4-[(Diethylamino)methyl]phenyl |
| A-173 | 4-Chlorobenzyl | 4-Cyanophenyl |
| A-174 | 4-Chlorobenzyl | 4-(Piperidin-1-yl)phenyl |
| A-175 | 4-Chlorobenzyl | 4-(4-Methylpiperazin-1-yl)phenyl |
| A-176 | 4-Chlorobenzyl | 4-Pyrrolidin-1-ylphenyl |
| A-177 | 4-Chlorobenzyl | 4-(1H-Imidazol-1-yl)phenyl |
| A-178 | 4-Chlorobenzyl | 4-Morpholin-4-ylphenyl |
| A-179 | 4-Chlorobenzyl | 2,4-Difluorophenyl |
| A-180 | 4-Chlorobenzyl | 2,6-Difluorophenyl |
| A-181 | 4-Chlorobenzyl | 3,5-Difluorophenyl |
| A-182 | 4-Chlorobenzyl | 2,4-Dichlorophenyl |
| A-183 | 4-Chlorobenzyl | 2,6-Dichlorophenyl |
| A-184 | 4-Chlorobenzyl | 3,5-Dichlorophenyl |
| A-185 | 4-Chlorobenzyl | 2,4-Dimethoxyphenyl |
| A-186 | 4-Chlorobenzyl | 2,6-Dimethoxyphenyl |
| A-187 | 4-Chlorobenzyl | 3,5-Dimethoxyphenyl |
| A-188 | 4-Chlorobenzyl | 2-Chloro-4-fluorophenyl |
| A-189 | 4-Chlorobenzyl | 2-Chloro-4-morpholin-4-ylphenyl |
| A-190 | 4-Chlorobenzyl | 2-Fluoro-4-morpholin-4-ylphenyl |
| A-191 | 4-Chlorobenzyl | Naphth-1-yl |
| A-192 | 4-Chlorobenzyl | Naphth-2-yl |
| A-193 | 4-Chlorobenzyl | Pyridin-2-yl |
| A-194 | 4-Chlorobenzyl | Pyridin-4-yl |
| A-195 | 4-Chlorobenzyl | Thien-2-yl |
| A-196 | 4-Chlorobenzyl | 2,3-Dihydrobenzo[b]furan-5-yl |
| A-197 | 4-Methoxybenzyl | Phenyl |
| A-198 | 4-Methoxybenzyl | 2-Methylphenyl |
| A-199 | 4-Methoxybenzyl | 2-Methoxyphenyl |
| A-200 | 4-Methoxybenzyl | 2-Chlorophenyl |
| A-201 | 4-Methoxybenzyl | 2-Fluorophenyl |
| A-202 | 4-Methoxybenzyl | 2-Trifluoromethylphenyl |
| A-203 | 4-Methoxybenzyl | 2-Trifluoromethoxyphenyl |
| A-204 | 4-Methoxybenzyl | 3-Methylphenyl |
| A-205 | 4-Methoxybenzyl | 3-Methoxyphenyl |
| A-206 | 4-Methoxybenzyl | 3-Chlorophenyl |
| A-207 | 4-Methoxybenzyl | 3-Fluorophenyl |
| A-208 | 4-Methoxybenzyl | 3-Trifluoromethylphenyl |
| A-209 | 4-Methoxybenzyl | 3-Trifluoromethoxyphenyl |
| A-210 | 4-Methoxybenzyl | 3-Cyanophenyl |
| A-211 | 4-Methoxybenzyl | 3-[(Phenylmethyl)oxy]phenyl |
| A-212 | 4-Methoxybenzyl | 3-Morpholin-4-ylphenyl |
| A-213 | 4-Methoxybenzyl | 3-Pyrrolidin-1-ylphenyl |
| A-214 | 4-Methoxybenzyl | 4-Methylphenyl |
| A-215 | 4-Methoxybenzyl | 4-(1-Methylethyl)phenyl |
| A-216 | 4-Methoxybenzyl | 4-Methoxyphenyl |
| A-217 | 4-Methoxybenzyl | 4-Chlorophenyl |
| A-218 | 4-Methoxybenzyl | 4-Fluorophenyl |
| A-219 | 4-Methoxybenzyl | 4-Trifluoromethylphenyl |
| A-220 | 4-Methoxybenzyl | 4-Diethylaminophenyl |
| A-221 | 4-Methoxybenzyl | 4-[(Diethylamino)methyl]phenyl |
| A-222 | 4-Methoxybenzyl | 4-Cyanophenyl |
| A-223 | 4-Methoxybenzyl | 4-(Piperidin-1-yl)phenyl |
| A-224 | 4-Methoxybenzyl | 4-(4-Methylpiperazin-1-yl)phenyl |
| A-225 | 4-Methoxybenzyl | 4-Pyrrolidin-1-ylphenyl |
| A-226 | 4-Methoxybenzyl | 4-(1H-Imidazol-1-yl)phenyl |
| A-227 | 4-Methoxybenzyl | 4-Morpholin-4-ylphenyl |
| A-228 | 4-Methoxybenzyl | 2,4-Difluorophenyl |
| A-229 | 4-Methoxybenzyl | 2,6-Difluorophenyl |
| A-230 | 4-Methoxybenzyl | 3,5-Difluorophenyl |
| A-231 | 4-Methoxybenzyl | 2,4-Dichlorophenyl |
| A-232 | 4-Methoxybenzyl | 2,6-Dichlorophenyl |
| A-233 | 4-Methoxybenzyl | 3,5-Dichlorophenyl |
| A-234 | 4-Methoxybenzyl | 2,4-Dimethoxyphenyl |
| A-235 | 4-Methoxybenzyl | 2,6-Dimethoxyphenyl |
| A-236 | 4-Methoxybenzyl | 3,5-Dimethoxyphenyl |
| A-237 | 4-Methoxybenzyl | 2-Chloro-4-fluorophenyl |
| A-238 | 4-Methoxybenzyl | 2-Chloro-4-morpholin-4-ylphenyl |
| A-239 | 4-Methoxybenzyl | 2-Fluoro-4-morpholin-4-ylphenyl |
| A-240 | 4-Methoxybenzyl | Naphth-1-yl |
| A-241 | 4-Methoxybenzyl | Naphth-2-yl |
| A-242 | 4-Methoxybenzyl | Pyridin-2-yl |
| A-243 | 4-Methoxybenzyl | Pyridin-4-yl |
| A-244 | 4-Methoxybenzyl | Thien-2-yl |
| A-245 | 4-Methoxybenzyl | 2,3-Dihydrobenzo[b]furan-5-yl |
| A-246 | Cyclohexylmethyl | Phenyl |

TABLE A-continued

| No. | R¹ | R² |
|---|---|---|
| A-247 | Cyclohexylmethyl | 2-Methylphenyl |
| A-248 | Cyclohexylmethyl | 2-Methoxyphenyl |
| A-249 | Cyclohexylmethyl | 2-Chlorophenyl |
| A-250 | Cyclohexylmethyl | 2-Fluorophenyl |
| A-251 | Cyclohexylmethyl | 2-Trifluoromethylphenyl |
| A-252 | Cyclohexylmethyl | 2-Trifluoromethoxyphenyl |
| A-253 | Cyclohexylmethyl | 3-Methylphenyl |
| A-254 | Cyclohexylmethyl | 3-Methoxyphenyl |
| A-255 | Cyclohexylmethyl | 3-Chlorophenyl |
| A-256 | Cyclohexylmethyl | 3-Fluorophenyl |
| A-257 | Cyclohexylmethyl | 3-Trifluoromethylphenyl |
| A-258 | Cyclohexylmethyl | 3-Trifluoromethoxyphenyl |
| A-259 | Cyclohexylmethyl | 3-Cyanophenyl |
| A-260 | Cyclohexylmethyl | 3-[(Phenylmethyl)oxy]phenyl |
| A-261 | Cyclohexylmethyl | 3-Morpholin-4-ylphenyl |
| A-262 | Cyclohexylmethyl | 3-Pyrrolidin-1-ylphenyl |
| A-263 | Cyclohexylmethyl | 4-Methylphenyl |
| A-264 | Cyclohexylmethyl | 4-(1-Methylethyl)phenyl |
| A-265 | Cyclohexylmethyl | 4-Methoxyphenyl |
| A-266 | Cyclohexylmethyl | 4-Chlorophenyl |
| A-267 | Cyclohexylmethyl | 4-Fluorophenyl |
| A-268 | Cyclohexylmethyl | 4-Trifluoromethylphenyl |
| A-269 | Cyclohexylmethyl | 4-Diethylaminophenyl |
| A-270 | Cyclohexylmethyl | 4-[(Diethylamino)methyl]phenyl |
| A-271 | Cyclohexylmethyl | 4-Cyanophenyl |
| A-272 | Cyclohexylmethyl | 4-(Piperidin-1-yl)phenyl |
| A-273 | Cyclohexylmethyl | 4-(4-Methylpiperazin-1-yl)phenyl |
| A-274 | Cyclohexylmethyl | 4-Pyrrolidin-1-ylphenyl |
| A-275 | Cyclohexylmethyl | 4-(1H-Imidazol-1-yl)phenyl |
| A-276 | Cyclohexylmethyl | 4-Morpholin-4-ylphenyl |
| A-277 | Cyclohexylmethyl | 2,4-Difluorophenyl |
| A-278 | Cyclohexylmethyl | 2,6-Difluorophenyl |
| A-279 | Cyclohexylmethyl | 3,5-Difluorophenyl |
| A-280 | Cyclohexylmethyl | 2,4-Dichlorophenyl |
| A-281 | Cyclohexylmethyl | 2,6-Dichlorophenyl |
| A-282 | Cyclohexylmethyl | 3,5-Dichlorophenyl |
| A-283 | Cyclohexylmethyl | 2,4-Dimethoxyphenyl |
| A-284 | Cyclohexylmethyl | 2,6-Dimethoxyphenyl |
| A-285 | Cyclohexylmethyl | 3,5-Dimethoxyphenyl |
| A-286 | Cyclohexylmethyl | 2-Chloro-4-fluorophenyl |
| A-287 | Cyclohexylmethyl | 2-Chloro-4-morpholin-4-ylphenyl |
| A-288 | Cyclohexylmethyl | 2-Fluoro-4-morpholin-4-ylphenyl |
| A-289 | Cyclohexylmethyl | Naphth-1-yl |
| A-290 | Cyclohexylmethyl | Naphth-2-yl |
| A-291 | Cyclohexylmethyl | Pyridin-2-yl |
| A-292 | Cyclohexylmethyl | Pyridin-4-yl |
| A-293 | Cyclohexylmethyl | Thien-2-yl |
| A-294 | Cyclohexylmethyl | 2,3-Dihydrobenzo[b]furan-5-yl |
| A-295 | 2-Thienylmethyl | Phenyl |
| A-296 | 2-Thienylmethyl | 2-Methylphenyl |
| A-297 | 2-Thienylmethyl | 2-Methoxyphenyl |
| A-298 | 2-Thienylmethyl | 2-Chlorophenyl |
| A-299 | 2-Thienylmethyl | 2-Fluorophenyl |
| A-300 | 2-Thienylmethyl | 2-Trifluoromethylphenyl |
| A-301 | 2-Thienylmethyl | 2-Trifluoromethoxyphenyl |
| A-302 | 2-Thienylmethyl | 3-Methylphenyl |
| A-303 | 2-Thienylmethyl | 3-Methoxyphenyl |
| A-304 | 2-Thienylmethyl | 3-Chlorophenyl |
| A-305 | 2-Thienylmethyl | 3-Fluorophenyl |
| A-306 | 2-Thienylmethyl | 3-Trifluoromethylphenyl |
| A-307 | 2-Thienylmethyl | 3-Trifluoromethoxyphenyl |
| A-308 | 2-Thienylmethyl | 3-Cyanophenyl |
| A-309 | 2-Thienylmethyl | 3-[(Phenylmethyl)oxy]phenyl |
| A-310 | 2-Thienylmethyl | 3-Morpholin-4-ylphenyl |
| A-311 | 2-Thienylmethyl | 3-Pyrrolidin-1-ylphenyl |
| A-312 | 2-Thienylmethyl | 4-Methylphenyl |
| A-313 | 2-Thienylmethyl | 4-(1-Methylethyl)phenyl |
| A-314 | 2-Thienylmethyl | 4-Methoxyphenyl |
| A-315 | 2-Thienylmethyl | 4-Chlorophenyl |
| A-316 | 2-Thienylmethyl | 4-Fluorophenyl |
| A-317 | 2-Thienylmethyl | 4-Trifluoromethylphenyl |
| A-318 | 2-Thienylmethyl | 4-Diethylaminophenyl |
| A-319 | 2-Thienylmethyl | 4-[(Diethylamino)methyl]phenyl |
| A-320 | 2-Thienylmethyl | 4-Cyanophenyl |
| A-321 | 2-Thienylmethyl | 4-(Piperidin-1-yl)phenyl |
| A-322 | 2-Thienylmethyl | 4-(4-Methylpiperazin-1-yl)phenyl |
| A-323 | 2-Thienylmethyl | 4-Pyrrolidin-1-ylphenyl |
| A-324 | 2-Thienylmethyl | 4-(1H-Imidazol-1-yl)phenyl |
| A-325 | 2-Thienylmethyl | 4-Morpholin-4-ylphenyl |
| A-326 | 2-Thienylmethyl | 2,4-Difluorophenyl |
| A-327 | 2-Thienylmethyl | 2,6-Difluorophenyl |
| A-328 | 2-Thienylmethyl | 3,5-Difluorophenyl |
| A-329 | 2-Thienylmethyl | 2,4-Dichlorophenyl |
| A-330 | 2-Thienylmethyl | 2,6-Dichlorophenyl |
| A-331 | 2-Thienylmethyl | 3,5-Dichlorophenyl |
| A-332 | 2-Thienylmethyl | 2,4-Dimethoxyphenyl |
| A-333 | 2-Thienylmethyl | 2,6-Dimethoxyphenyl |
| A-334 | 2-Thienylmethyl | 3,5-Dimethoxyphenyl |
| A-335 | 2-Thienylmethyl | 2-Chloro-4-fluorophenyl |
| A-336 | 2-Thienylmethyl | 2-Chloro-4-morpholin-4-ylphenyl |
| A-337 | 2-Thienylmethyl | 2-Fluoro-4-morpholin-4-ylphenyl |
| A-338 | 2-Thienylmethyl | Naphth-1-yl |
| A-339 | 2-Thienylmethyl | Naphth-2-yl |
| A-340 | 2-Thienylmethyl | Pyridin-2-yl |
| A-341 | 2-Thienylmethyl | Pyridin-4-yl |
| A-342 | 2-Thienylmethyl | Thien-2-yl |
| A-343 | 2-Thienylmethyl | 2,3-Dihydrobenzo[b]furan-5-yl |
| A-344 | Pyridin-3-ylmethyl | Phenyl |
| A-345 | Pyridin-3-ylmethyl | 2-Methylphenyl |
| A-346 | Pyridin-3-ylmethyl | 2-Methoxyphenyl |
| A-347 | Pyridin-3-ylmethyl | 2-Chlorophenyl |
| A-348 | Pyridin-3-ylmethyl | 2-Fluorophenyl |
| A-349 | Pyridin-3-ylmethyl | 2-Trifluoromethylphenyl |
| A-350 | Pyridin-3-ylmethyl | 2-Trifluoromethoxyphenyl |
| A-351 | Pyridin-3-ylmethyl | 3-Methylphenyl |
| A-352 | Pyridin-3-ylmethyl | 3-Methoxyphenyl |
| A-353 | Pyridin-3-ylmethyl | 3-Chlorophenyl |
| A-354 | Pyridin-3-ylmethyl | 3-Fluorophenyl |
| A-355 | Pyridin-3-ylmethyl | 3-Trifluoromethylphenyl |
| A-356 | Pyridin-3-ylmethyl | 3-Trifluoromethoxyphenyl |
| A-357 | Pyridin-3-ylmethyl | 3-Cyanophenyl |
| A-358 | Pyridin-3-ylmethyl | 3-[(Phenylmethyl)oxy]phenyl |
| A-359 | Pyridin-3-ylmethyl | 3-Morpholin-4-ylphenyl |
| A-360 | Pyridin-3-ylmethyl | 3-Pyrrolidin-1-ylphenyl |
| A-361 | Pyridin-3-ylmethyl | 4-Methylphenyl |
| A-362 | Pyridin-3-ylmethyl | 4-(1-Methylethyl)phenyl |
| A-363 | Pyridin-3-ylmethyl | 4-Methoxyphenyl |
| A-364 | Pyridin-3-ylmethyl | 4-Chlorophenyl |
| A-365 | Pyridin-3-ylmethyl | 4-Fluorophenyl |
| A-366 | Pyridin-3-ylmethyl | 4-Trifluoromethylphenyl |
| A-367 | Pyridin-3-ylmethyl | 4-Diethylaminophenyl |
| A-368 | Pyridin-3-ylmethyl | 4-[(Diethylamino)methyl]phenyl |
| A-369 | Pyridin-3-ylmethyl | 4-Cyanophenyl |
| A-370 | Pyridin-3-ylmethyl | 4-(Piperidin-1-yl)phenyl |
| A-371 | Pyridin-3-ylmethyl | 4-(4-Methylpiperazin-1-yl)phenyl |
| A-372 | Pyridin-3-ylmethyl | 4-Pyrrolidin-1-ylphenyl |
| A-373 | Pyridin-3-ylmethyl | 4-(1H-Imidazol-1-yl)phenyl |
| A-374 | Pyridin-3-ylmethyl | 4-Morpholin-4-ylphenyl |
| A-375 | Pyridin-3-ylmethyl | 2,4-Difluorophenyl |
| A-376 | Pyridin-3-ylmethyl | 2,6-Difluorophenyl |
| A-377 | Pyridin-3-ylmethyl | 3,5-Difluorophenyl |
| A-378 | Pyridin-3-ylmethyl | 2,4-Dichlorophenyl |
| A-379 | Pyridin-3-ylmethyl | 2,6-Dichlorophenyl |
| A-380 | Pyridin-3-ylmethyl | 3,5-Dichlorophenyl |
| A-381 | Pyridin-3-ylmethyl | 2,4-Dimethoxyphenyl |
| A-382 | Pyridin-3-ylmethyl | 2,6-Dimethoxyphenyl |
| A-383 | Pyridin-3-ylmethyl | 3,5-Dimethoxyphenyl |
| A-384 | Pyridin-3-ylmethyl | 2-Chloro-4-fluorophenyl |
| A-385 | Pyridin-3-ylmethyl | 2-Chloro-4-morpholin-4-ylphenyl |
| A-386 | Pyridin-3-ylmethyl | 2-Fluoro-4-morpholin-4-ylphenyl |
| A-387 | Pyridin-3-ylmethyl | Naphth-1-yl |
| A-388 | Pyridin-3-ylmethyl | Naphth-2-yl |
| A-389 | Pyridin-3-ylmethyl | Pyridin-2-yl |
| A-390 | Pyridin-3-ylmethyl | Pyridin-4-yl |
| A-391 | Pyridin-3-ylmethyl | Thien-2-yl |
| A-392 | Pyridin-3-ylmethyl | 2,3-Dihydrobenzo[b]furan-5-yl |

The compounds of the invention of the general formula I and the required starting materials used to prepare them can be prepared in analogy to known processes of organic chemistry as are described in standard works of organic chemistry, e.g. Houben-Weyl, "Methoden der Organischen Chemie", Thieme-Verlag Stuttgart; Jerry March "Advanced Organic Chemistry", 5$^{th}$ edition, Wiley & Sons and the literature cited therein; and R. Larock, "Comprehensive Organic Transformations", 2$^{nd}$ edition, Weinheim 1999, and the literature cited therein. The compounds of the invention of the general formula I are advantageously prepared by the methods described below and/or in the experimental section.

In the following the variables $R^1$, $R^2$, Q, and X exhibit the aforementioned meanings and the variable W represents the diradical:

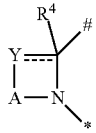
(W)

in which $R^4$, Y and A are as defined herein and wherein * indicates the point of attachment to Q, while # indicates the point of attachment to the carbonyl group.

The compounds of formula I can be prepared in analogy to the schemes and methods described in WO 99/54305 and WO 2008/080969.

Scheme 1:

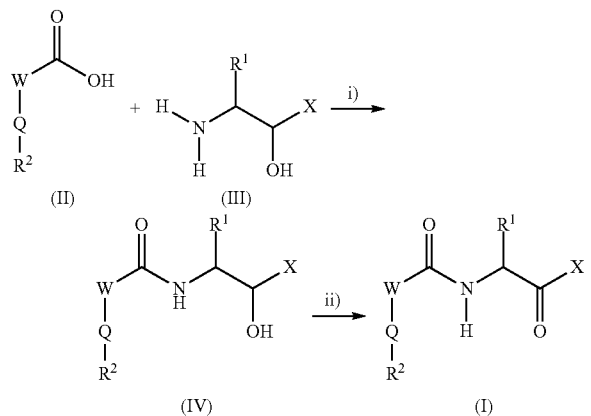

As shown in Scheme 1, in a first step i) a carboxylic acid II is converted by reaction with an amino alcohol III into a corresponding hydroxy amide IV. In this connection, conventional peptide coupling methods are ordinarily used, as are described for example in R. C. Larock, Comprehensive Organic Transformations, VCH Publisher, 1989, pages 972-976, or in Houben-Weyl, Methoden der organischen Chemie, 4$^{th}$ edition, E5, Chap. V. It may be advantageous to first activate the carboxylic acid II. For this purpose, for example, the carboxylic acid II is reacted with a carbodiimide such as dicyclohexylcarbodiimide (DCC) or 1-ethyl-3-(3-dimethylaminopropyl)-carbodiimide (EDC) in the presence of hydroxybenzotriazole (HOBt), nitrophenol, pentafluorophenol, 2,4,5-trichlorophenol or N-hydroxysuccinimide, to obtain an activated ester IIa. An alternative to the use of dicyclohexylcarbodiimide (DCC) or 1-ethyl-3-(3-dimethylaminopropyl)carbodiimide (EDC) is the use of 2-(7-aza-1H-benzotriazole-1-yl)-1,1,3,3-tetramethyluronium hexafluorophosphate (HATU). It may further be advantageous to prepare the activated ester IIa in the presence of a base, for example a tertiary amine. The activated ester IIa is subsequently reacted with the amino alcohol of the formula III or its hydrohalide salt to give the hydroxy amide IV. The reaction is normally performed in anhydrous inert solvents, such as chlorinated hydrocarbons, e.g. dichloromethane or dichloroethane, ethers, e.g. tetrahydrofuran or 1,4-dioxane or carboxamides, e.g. N,N-dimethylformamide, N,N-dimethylacetamide or N-methylpyrrolidone. Step i) is ordinarily carried out at temperatures in the range from −20° C. to +25° C.

Subsequently, in a second step ii), the hydroxy amide compound IV is oxidized to the carboxamide compound I. Various conventional oxidation reactions are suitable for this (see R. C. Larock, Comprehensive Organic Transformations, VCH Publisher, 1989, page 604 et seq.) such as, for example, Swern oxidation and Swern analogous oxidations (T. T. Tidwell, Synthesis 1990, pp. 857-870) or Pfitzner-Moffatt oxidation. Suitable oxidizing agents are dimethyl sulfoxide (DMSO) in combination with dicyclohexylcarbodiimide or 1-ethyl-3-(3-dimethylaminopropyl)carbodiimide, dimethyl sulfoxide in combination with the pyridine-SO$_3$ complex or dimethyl sulfoxide in combination with oxalyl chloride, sodium hypochloride/TEMPO(S. L. Harbenson et al., J. Med. Chem. 1994, 37, 2918-2929), and hypervalent iodine reagents like 2-iodoxybenzoic acid (IBX) (J. Org. Chem. 1995, 60, 7272), the Dess-Martin reagent (J. Org. Chem. 1983, 48, 4155) or polymer-supported IBX (H. S Jang, Tetrahedron Lett. 2007, 48, 3731-3734). Depending on the oxidizing agent used, the oxidation of the hydroxy amide compound IV is performed at temperatures of from −50 to +25° C.

If not commercially available the amino alcohols III can be prepared by processes disclosed in the literature (for amino hydroxy carboxylic acid derivatives, see, for example, S. L. Harbenson et al., J. Med. Chem. 1994, 37, 2918-2929 or J. P. Burkhardt et al., Tetrahedron Lett. 1988, 29, 3433-3436) or by the methods and procedures described in WO 2008/08969.

The carboxylic acid II can be prepared according to Scheme 2 by hydrolyzing the carboxylic ester V with acids or bases under generally customary conditions. The hydrolysis preferably takes place with bases such as alkali metal or alkaline earth metal hydroxides, for example lithium hydroxide, sodium hydroxide or potassium hydroxide in aqueous medium or in a mixture of water and organic solvents, e.g. alcohols such as methanol or ethanol, ethers such as tetrahydrofuran or dioxane, at room temperature or elevated temperature such as 25-100° C.

Scheme 2:

In Scheme 2 $R^2$, Q and W have the aforementioned meanings. In formula V, R' is e.g. alkyl, aryl or arylalkyl, preferably $C_1$-$C_6$-alkyl or benzyl.

In general, carboxylic acids of formula II or esters of formula V are commercially available or can be prepared using standard reactions for ring closure or general methods for alkylation or arylation employing the appropriate starting materials as depicted in Schemes 3, 5 and 6.

Scheme 3:

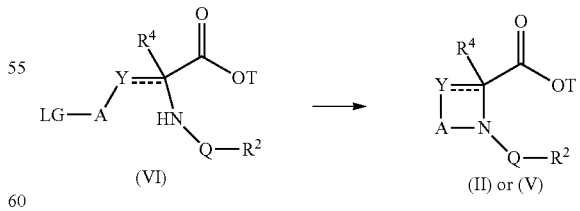

In Scheme 3 T is hydrogen or a variable R' as defined before and LG represents a leaving group such as halogen if A is CO, SO or SO$_2$, or, if A is CO, OH, OR''', O(C)O)R''', halogen or N-imidazole (R'' is e.g. an activating group of an active ester as described below and R''' is e.g. alkyl, aryl or arylalkyl). In case A-LG is CO—OH it may be advantageous to first activate the carboxylic acid VI using standard methods. For this purpose the carboxylic acid VI is e.g. reacted with a carbodiimide such as dicyclohexylcarbodiimide (DCC) or 1-ethyl-3-(3-dimethylaminopropyl)carbodiimide (EDC) in the presence of hydroxybenzotriazole (HOBt), nitrophenol, pentafluorophenol, 2,4,5-trichlorophenol or N-hydroxysuccinimide, to obtain an activated ester VIa, which usually cyclizes to the desired compound V. Representative cyclisation reactions are described in e.g. H. McAlonan et al., Tetrahedron Asymmetry 1995, 6(1), 239-244; S. Marchalin et al., Synthetic Communications 1998, 28(19), 3619-3624; B. Debnath et al., Internet Electronic Journal of Molecular Design 2005, 4(6), 393-412; S. Samanta et al., Bioorganic & Medicinal Chemistry 2004, 12(6), 1413-1423; K. Srikanth et al., Bioorganic & Medicinal Chemistry 2002, 10(7), 2119-2131; and D. Goswami et al., Pharmazie 2001, 56(5), 366-371.

Compounds of the formula VI', in which Q is a moiety Alk-Z, as defined before, and Y is $CH_2$—$CH_2$, $CH_2$—$CH_2$—$CH_2$ or $CH$=$CH$—$CH$=, can be prepared according to the synthesis depicted in Scheme 4.

Scheme 4:

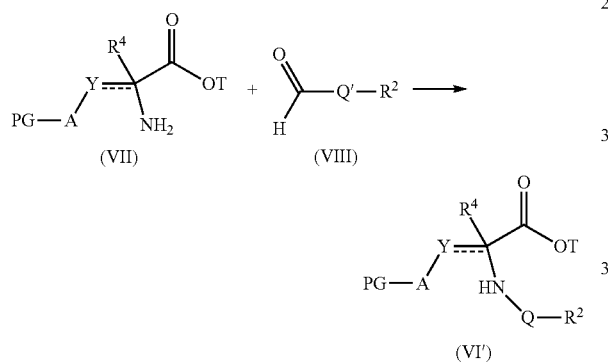

In Scheme 4 PG is a suitable protecting group and Q' represents a moiety Alk-Z with Alk' being Alk minus a methylene group. As shown in Scheme 4a 2-amino carboxylic acid derivative VII is converted by reductive amination with an aldehyde VIII to the secondary amine VI' using a reducing agent such like $NaBH_4$. The reaction may be carried out in a one-step process or, alternatively, in two separate steps by initially forming the Schiff base of educts VII and VIII followed by reduction. The appropriate starting materials of the formula VII, such as glutaminic acid, can either be purchased or prepared by generally known methods.

Alternatively, carboxylic ester of the formula V, in which Q is a moiety Alk'-Z, as defined before, can be prepared as outlined in Scheme 5 by alkylating the amino group of a precursor IX using standard methods.

Scheme 5:

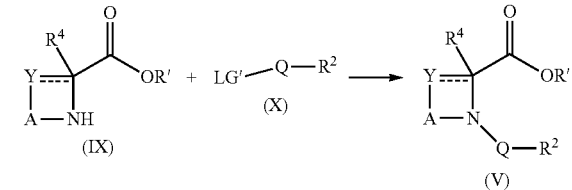

In Scheme 5, the variable LG' represents a leaving group, such as halogen, tosylate or triflate. In general the presence of an organic or inorganic base is required such as triethylamine, DIPEA, KOtBu, $K_2CO_3$, $Cs_2CO_3$ or NaH. As an example, an ester V with the substituent Q-$R^2$ being benzyl can be obtained by reacting the corresponding secondary amine IX with benzyl bromide X in the presence of potassium carbonate in DMF at room temperature. Representative methods for the conversion of a precursor IX are e.g. described in T. Simandan et al., Synth Commun 1996, 26(9), 1827; P. Cauliez et al., J. Heterocyclic Chem. 1991, 28(4), 1143-1146; R. F. Menezes et al., Tetrahedron Lett. 1989, 30(25), 3295-3298; T. Itoh et al., Tetrahedron 2003, 59(19), 3527-3536 and Tetrahedron 2001, 57(34), 7277-7289.

Compounds of formula V wherein Q is a single bond and $R^2$ is aryl or hetaryl, hereafter denoted as compounds of formula V', can be prepared using a transition metal-catalyzed C—N coupling reaction, employing the ester IX' and the (het)aryl compound X', as depicted in Scheme 6.

Scheme 6:

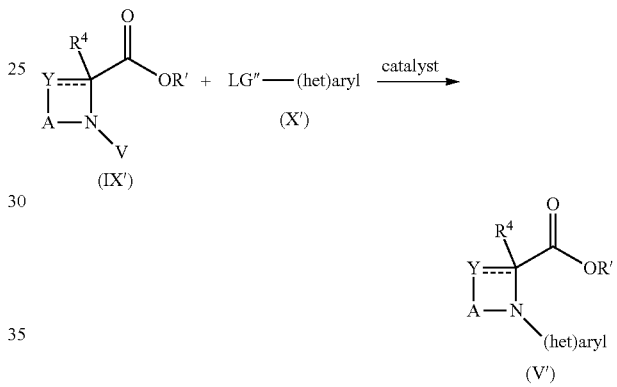

In Scheme 6, LG" represents a leaving group like halogen or triflate which is known to be displaceable in transition metal-catalyzed reactions. The variable V represents the required complementary group and is usually hydrogen. Suitable catalysts for these reactions are for example palladium complexes comprising Pd(0) or Pd(II) and a phosphine ligand such as 4,5-bis(diphenylphosphino)-9,9-dimethylxanthene (Xantphos), as described for example in Guram et al., Angew. Chem. Int. Ed. Eng. 1995, 34, 1348. Alternatively, Cu(I) complexes such as Cu(1,10-phenantroline)($PPh_3$)Br may also be used for catalyzing these reactions, as known for example from Gujadhur et al. Org. Lett. 2001, 2, 4315. Besides the catalyst the reactions according to Scheme 3 generally also include a base, such as potassium t-butoxylate or cesium carbonate, and are usually carried out at elevated temperatures.

Compounds of the formula I in which X is —C(O)N($R^{x4}$)—($C_1$-$C_6$-alkylene)-$NR^{x2}R^{x3}$ or —C(O)N($R^{x4}$)$NR^{x2}R^{x3}$, in which $R^{x2}$, $R^{x3}$ and $R^{x4}$ have the aforementioned meanings, can additionally be prepared by reacting compounds of the formula I, in which X is COOH, with hydrazine compounds of the formula NH($R^{x4}$)$NR^{x2}R^{x3}$ or diamines of the formula NH($R^{x4}$)—($C_1$-$C_6$-alkylene)-$NR^{x2}R^{x3}$. The reaction can be carried out using methods analogous to those described for the coupling reaction of step i) in Scheme 1.

Alternatively compounds of the formula I in which X is —C(O)—$NR^{x2}R^{x3}$, —C(O)—N($R^{x4}$)—($C_1$-$C_6$-alkylene)-$NR^{x2}R^{x3}$ or —C(O)—N($R^{x4}$)—$NR^{x2}R^{x3}$, can also be prepared according to Scheme 7.

Scheme 7:

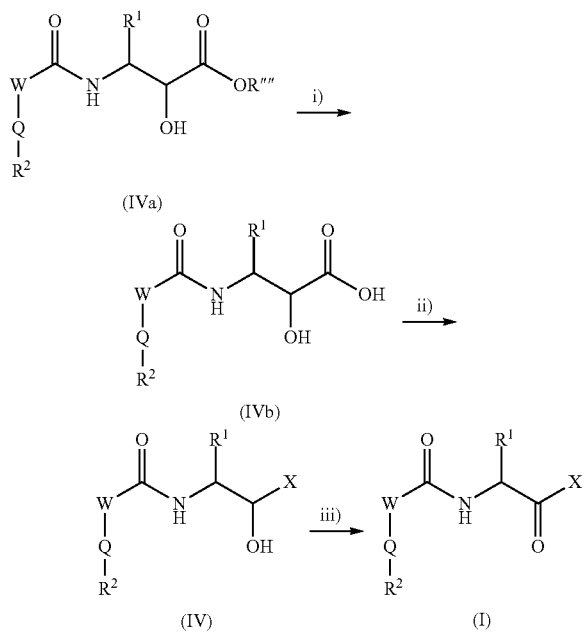

As shown in Scheme 7, in a first step i), a carboxylic ester of the formula IVa (R'''' is e.g. alkyl, aryl or arylalkyl, preferably $C_1$-$C_6$-alkyl or benzyl) prepared according to Scheme 1 is hydrolyzed to the corresponding carboxylic acid IVb, which in step ii) is reacted with an amine $HNR^{x2}R^{x3}$, $HN(R^{x4})$—$(C_1$-$C_6$-alkylene)-$NR^{x2}R^{x3}$ or $HN(R^{x4})$—$NR^{x2}R^{x3}$ to amides of the general formula IV using conventional coupling methods as described above. The final oxidation (step iii) is achieved as outlined above.

Furthermore, imidazolidinone derivatives of formulae V, IX or IX' in which Y is a moiety $N(R^{y\#})$—$CH_2$ or $N(R^{y\#})$—$CH_2$—$CH_2$ can for instance be prepared by reacting the corresponding precursors derived from 2,3-diamino propionic acid or 2,4-diamino butyric acid with phosgene or an equivalent thereof in the presence of a base, such as triethylamine. A substituent $R^{y\#}$ different from hydrogen may be introduced either before or after this ring closure reaction using well-established standard procedures. Suitable starting materials for this synthetic route to compounds VI' and VI are besides the mentioned diamino acid precursors also their derivates having two different or only one amino protective groups.

According to one aspect of the invention the hydrogen atom linked to the carbon atom carrying the radical $R^1$ of a compound I is replaced by a deuterium atom, as shown in formula I-D below. $R^1$, $R^2$, $R^{3a}$, $R^{3b}$, $R^4$, A, Y, Q and X in formula I-D have the aforementioned meanings.

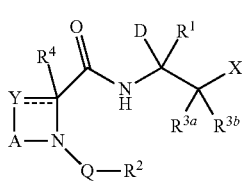

(I-D)

Compounds of formula I-D can be prepared in analogy to methods described by F. Maltais et al., J. Med. Chem. 2009, 52 (24), 7993-8001 (DOI 10.1021/jm901023f). The degree of deuteration at said position usually exceeds 80%, preferably exceeds 90% and in particular exceeds 95%. The deuterated compounds of formula I-D often show a markedly higher stability against racematisation than their counterparts of formula I, probably due to a kinetic isotope effect (see F. Maltais et al., J. Med. Chem. 2009, 52 (24), 7993-8001).

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

If individual compounds I are not obtainable by the routes described above, they can be prepared by derivatization of other compounds I.

The compounds of the invention exhibit extremely low Ki values in relation to the inhibition of calpain and thus permit efficient inhibition of calpain, especially calpain I, at low serum levels. The compounds of the invention ordinarily exhibit Ki values in relation to the inhibition of calpain in vitro of <600 nM, in particular <100 nM and specifically <50 nM. The compounds of the invention are therefore particularly suitable for the treatment of disorders associated with an elevated calpain activity.

In addition, the compounds of the invention are selective calpain inhibitors, i.e. the inhibition of other cysteine proteases such as cathepsin B, cathepsin K, cathepsin L or cathepsin S takes place only at concentrations which are distinctly higher than the concentrations necessary for inhibition of calpain. Accordingly, the compounds of the invention ought to show distinctly fewer side effects than the prior art compounds which are comparatively unselective in relation to inhibition of calpain and likewise inhibit other cysteine proteases.

Compounds preferred according to the invention accordingly have a selectivity in relation to inhibition of cathepsin B, expressed in the form of the ratio of the Ki for inhibition of cathepsin B to the Ki for inhibition of calpain of >5, preferably >10 and in particular >30.

Compounds preferred according to the invention accordingly have a selectivity in relation to inhibition of cathepsin K, expressed in the form of the ratio of the Ki for inhibition of cathepsin K to the Ki for inhibition of calpain of >5, preferably >10 and in particular >30.

Compounds preferred according to the invention accordingly have a selectivity in relation to inhibition of cathepsin L, expressed in the form of the ratio of the Ki for inhibition of cathepsin L to the Ki for inhibition of calpain of >5, preferably >10 and in particular >30.

Compounds preferred according to the invention accordingly have a selectivity in relation to inhibition of cathepsin S, expressed in the form of the ratio of the Ki for inhibition of cathepsin S to the Ki for inhibition of calpain of >10, preferably >30 and in particular >100.

In addition, the compounds of the present invention feature an improved stability in the cytosole of human cells, which markedly contributes to their good overall metabolic stability. The cytosolic stability can be measured for example by incubating a solution of a compound of the invention with liver cytosole from particular species (for example rat, dog, monkey or human) and determining the half-life of the compound under these conditions. It is possible to conclude from larger half-lives that the metabolic stability of the compound is improved. The stability in the presence of human liver cytosole is of particular interest because it makes it possible to predict the metabolic degradation of the compound in the human liver. Compounds with enhanced cytosolic stability therefore are likely to be degraded at reduced rates in the liver. Slower metabolic degradation in the liver in turn can lead to higher and/or longer-lasting concentrations (effective levels) of the compound in the body, so that the elimination half-life of the compounds of the invention is increased. Increased and/or longer-lasting effective levels may lead to a better efficacy of the compound in the treatment or prophylaxis of various calpain-dependent diseases. An improved metabolic stability may additionally lead to an increased bioavailability after oral administration, because the compound is subjected, after being absorbed in the intestine, to less metabolic degradation in the liver (termed the first pass effect). An increased oral bioavailability may, because the concentration (effective level) of the compound is increased, lead to a better efficacy of the compound after oral administration.

Accordingly, due to their improved cytosolic stability the compounds of the invention remain in the cytosol for extended periods, i.e. have a decreased cytosolic clearance, and therefore ought to show enhanced human pharmacokinetics.

Compounds preferred according to the invention accordingly have a cytosolic clearance in human liver cytosol of <30 μl/min/mg, in particular of <15 μl/min/mg.

The improved cytosolic stability of the compounds according to the present invention is probably primarily due to their reduced susceptibility to aldo-keto reductases (AKRs) which mediate the metabolic degradation of compounds having a carbonyl group in the liver cytosole of humans and monkeys. Thus, the AKR-catalyzed reduction of the ketoamides of formula I should be less pronounced than that of less stable ketoamides. Hence, the ratio of the concentration of the parent compound, i.e. the ketamide of formula I, to the concentration of the metabolite, i.e. the hydroxyamide stemming form the ketoamide, is a measure for the stability of the compounds of the invention.

Compounds preferred according to the invention accordingly have, after an incubation in human hepatocytes for 4 hours, a concentration ratio of the hydroxyamide metabolite to their corresponding parent compound of formula I of ≦5, in particular ≦2 and specifically ≦0.5.

Owing to their inhibitory effect on calpain and their selectivity for calpain by comparison with other cysteine proteases, the compounds of the invention of the formula I, their tautomers and their pharmaceutically suitable salts are particularly suitable for the treatment of a disorder or of a condition which is associated with an elevated calpain activity as are described for example in the prior art cited at the outset.

Disorders associated with an elevated calpain activity are in particular neurodegenerative disorders, especially those neurodegenerative disorders occurring as a result of a chronic brain supply deficit, of an ischemia (stroke) or of a trauma such as brain trauma, and the neurodegenerative disorders Alzheimer's disease, Parkinson's disease, amyotrophic lateral sclerosis and Huntington's disease, also multiple sclerosis and the damage to the nervous system associated therewith, especially damage to the optic nerve (optic neuritis) and the nerves which control the movement of the eye. Accordingly, preferred embodiments of the invention relate to the treatment of neurodegenerative disorders, especially of the aforementioned neurodegenerative disorders in humans, and to the use of the compounds of the invention of the formula I, their tautomers and their pharmaceutically suitable salts for the manufacture of a medicament for the treatment of these disorders.

Disorders associated with an elevated calpain activity also include epilepsy. Accordingly, preferred embodiments of the invention relate to the treatment of epilepsy in humans, and to the use of the compounds of the invention of the formula I, their tautomers and their pharmaceutically suitable salts for the manufacture of a medicament for the treatment of epilepsy.

The disorders or conditions associated with an elevated calpain activity also include pain and painful conditions. Accordingly, preferred embodiments of the invention relate to the treatment of pain and painful conditions in mammals, especially in humans, and to the use of the compounds of the invention of the formula I, their tautomers and their pharmaceutically suitable salts for the manufacture of a medicament for the treatment of pain and painful conditions.

The disorders or conditions associated with an elevated calpain activity also include damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty. Accordingly, preferred embodiments of the invention relate to the treatment of diseases or conditions associated with damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty in mammals, especially in humans, and to the use of the compounds of the invention of the formula I, their tautomers and their pharmaceutically suitable salts for the manufacture of a medicament for the treatment of these disorders.

It has further emerged that inhibition of calpain brings about cytotoxic effects on tumor cells. Accordingly, the compounds of the invention are suitable for the chemotherapy of tumors and metastasis thereof. Preferred embodiments of the invention therefore relate to the use of the compounds of the invention of the formula I, their tautomers and their pharmaceutically suitable salts in the therapy of tumors and metastases, and to their use for the manufacture of a medicament for the therapy of tumors and metastases.

It has further been found that various impairments associated with an HIV disorder, especially nerve damage (HIV-induced neurotoxicity), are mediated by calpain and therefore inhibition of calpain allows such impairments to be treated or alleviated. Accordingly, the compounds of the invention of the formula I, their tautomers and their pharmaceutically suitable salts are suitable for the treatment of HIV patients. Preferred embodiments of the invention therefore relate to the use of the compounds of the invention of the formula I, their tautomers and their pharmaceutically suitable salts for the treatment of HIV-infected patients, especially the treatment of those impairments caused by an HIV-induced neurotoxicity, and to their use for the manufacture of a medicament for the treatment of HIV patients.

It has further been found that the release of interleukin-I, TNF or beta-amyloid peptides (Aβ or Aβ-peptides) can be reduced or completely inhibited by calpain inhibitors. Accordingly, impairments or disorders associated with an elevated interleukin-I, TNF or Aβ level can be treated by using the compounds of the invention of the formula I, their tautomers and their pharmaceutically suitable salts. Preferred embodiments of the invention therefore relate to the use of the compounds of the invention of the formula I, their tautomers, their prodrugs and their pharmaceutically acceptable salts for the treatment of impairments or disorders associated with an elevated interleukin-I, TNF or Aβ level such as rheumatism, rheumatoid arthritis and to their use for the manufacture of a medicament for the treatment of such impairments or disorders.

It has further emerged that inhibition of calpain is suitable for the treatment of protozoan infection (protist infection) like malaria or toxoplasmosis (Li et al., *Mol Biochem Parasitol.* 2007; 155(1): 26-32; Jung et al. Archives of Pharmacal Research (2009), 32(6), 899-906). Hence, the compounds of the present invention are particularly suitable for treating protozoan infections like malaria or toxoplasmosis and to their use for the manufacture of a medicament for the treatment of such impairments or disorders.

The compounds of the general formula (I) are distinguished in particular also by a good metabolic stability. The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible to conclude from larger half-lives that the metabolic stability of the compound is improved. The stability in the presence of human liver microsomes is of particular interest because it makes it possible to predict the metabolic degradation of the compound in the human liver. Compounds with increased metabolic stability are therefore probably also degraded more slowly in the liver (measured in the liver microsome test). Slower metabolic degradation in the liver can lead to higher and/or longer-lasting concentrations (effective levels) of the compound in the body, so that the elimination half-life of the compounds of the invention is increased. Increased and/or longer-lasting effective levels may lead to a better efficacy of the compound in the treatment or prophylaxis of various calpain-dependent diseases. An improved metabolic stability may additionally lead to an increased bioavailability after oral administration, because the compound is subjected, after being absorbed in the intestine, to less metabolic degradation in the liver (termed the first pass effect). An increased oral bioavailability may, because the concentration (effective level) of the compound is increased, lead to a better efficacy of the compound after oral administration.

The compounds of the invention of the formula I are further distinguished by exhibiting an improved pharmacological activity, compared with the carboxamide compounds of the formula I disclosed in the prior art, in patients or relevant animal models allowing prognostic statements for use in treatment.

The present invention also relates to pharmaceutical compositions (i.e. medicaments) which comprise at least one compound of the invention of the formula I or a tautomer or a pharmaceutically suitable salt thereof and, where appropriate, one or more suitable drug carriers.

The drug carriers are chosen according to the pharmaceutical form and the desired mode of administration.

The compounds of the invention of the general formula I, their tautomers and the pharmaceutically suitable salts of these compounds can be used to manufacture pharmaceutical compositions for oral, sublingual, subcutaneous, intramuscular, intravenous, topical, intratracheal, intranasal, transdermal or rectal administration, and be administered to animals or humans in unit dose forms, mixed with conventional pharmaceutical carriers, for the prophylaxis or treatment of the above impairments or diseases.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active basic ingredient may vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered 1 to 5 times a day, so that a daily dose of from 0.5 to 25 000 mg, preferably 1 to 5000 mg, is administered.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their tautomers or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

The compounds of the invention also include those compounds in which one or more atoms have been replaced by their stable, non-radioactive isotopes, for example, a hydrogen atom by deuterium.

Stable isotopes (e.g., deuterium, $^{13}C$, $^{15}N$, $^{18}O$) are nonradioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999)).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet. Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann N.Y. Acad. Sci. 1960 84: 770; Thomson J F, Ann New York Acad. Sci. 1960 84: 736; Czakj a D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling 0 Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The following examples illustrate the invention without restricting it. Depending on the management of the reaction and working up, the compounds of the general formula I result as mixtures of carbonyl form and the corresponding hydrates. Conversion into the pure carbonyl compounds generally takes place by treating the substances with HCl in an inert solvent.

PREPARATION EXAMPLES

I. Preparation of Building Blocks of the General Formula II

The following building blocks II are commercially available:
(R)-1-Benzyl-5-oxo-pyrrolidine-2-carboxylic acid and (S)-1-benzyl-5-oxo-pyrrolidine-2-carboxylic acid.

Example A (R)-1-(3-methoxy-benzyl)-5-oxo-pyrrolidine-2-carboxylic acid

To the solution of (R)-2-aminopentanedioic acid (99% pure; 1000 mg, 6.37 mmol) in 6.37 ml of 2N NaOH (13.46 mmol) 3-methoxybenzaldehyde (0.827 ml; 925 mg, 6.37 mmol) in 1.8 ml ethanol was added, and the resulting mixture stirred overnight at room temperature to allow imine formation. Subsequent addition of $NaBH_4$ (309 mg; 8.07 mmol) resulted in a slightly exothermic reaction (temperature rise to about 40° C.), and the reaction was completed by stirring at room temperature. The mixture then was diluted with water and extracted twice with methyl tert-butylether (MTBE). The aqueous layer was acidified to pH 3 using concentrated HCl. The resulting precipitate was then filtered off, washed twice with water and dried under reduced pressure. The resulting (R)-2-(3-methoxybenzylamino)pentanedioic acid (1,075 g, 4.02 mmol; yield: 60%), obtained as white solid, was cyclized by heating in ethanol under reflux for 3 h. The solvent was evaporated under reduced pressure giving the desired product (R)-1-(3-methoxy-benzyl)-5-oxo-pyrrolidine-2-carboxylic acid (1.06 g; yield: 100%) as a white solid.
ESI-MS $[M+H]^+=250.1$ The compounds of Examples B to Q can be prepared in a manner analogous to the above described preparation of Example A.

Example B (R)-1-(3-Chloro-benzyl)-5-oxo-pyrrolidine-2-carboxylic acid

ESI-MS $[M+H]^+=254.1, 256.2$.

Example C (R)-1-(4-Fluoro-benzyl)-5-oxo-pyrrolidine-2-carboxylic acid

ESI-MS $[M+H]^+=238.1$.

Example D (R)-1-(3,5-Difluoro-benzyl)-5-oxo-pyrrolidine-2-carboxylic acid

ESI-MS $[M+H]^+=256.1$.

Example E (R)-1-(3-Trifluoromethyl-benzyl)-5-oxo-pyrrolidine-2-carboxylic acid

ESI-MS $[M+H]^+=288.1$.

Example F (R)-1-(3-Fluoro-benzyl)-5-oxo-pyrrolidine-2-carboxylic acid

ESI-MS $[M+H]^+=238.1$.

Example G (R)-1-(2-Trifluoromethoxy-benzyl)-5-oxo-pyrrolidine-2-carboxylic acid

ESI-MS $[M+H]^+=304.1$.

Example H (R)-1-(3-Trifluoromethoxy-benzyl)-5-oxo-pyrrolidine-2-carboxylic acid

ESI-MS $[M+H]^+=304.1$.

Example I (R)-1-Naphthalen-1-ylmethyl-5-oxo-pyrrolidine-2-carboxylic acid

ESI-MS $[M+H]^+=270.1$.

Example J (R)-1-Naphthalen-2-ylmethyl-5-oxo-pyrrolidine-2-carboxylic acid

ESI-MS $[M+H]^+=270.1$.

Example K (R)-5-Oxo-1-pyridin-4-ylmethyl-pyrrolidine-2-carboxylic acid

ESI-MS $[M+H^+]=221.1$.

Example L (R)-1-(3,5-Dimethoxy-benzyl)-5-oxo-pyrrolidine-2-carboxylic acid

ESI-MS $[M+H^+]=280.1$.

Example M (R)-1-Benzyl-6-oxo-piperidine-2-carboxylic acid

ESI-MS $[H+H]^+=234.1$.

Example N (R)-5-Oxo-1-(2-(trifluoromethoxy)benzyl)pyrrolidine-2-carboxylic acid

ESI-MS [M+H$^+$]=304.1.

Example O (R)-1-(2-Chlorobenzyl)-5-oxopyrrolidine-2-carboxylic acid

ESI-MS [M+H]$^+$=254.1.

Example P (R)-1-(2-Methoxy-6-(trifluoromethyl)benzyl)-5-oxopyrrolidine-2-carboxylic acid

ESI-MS [M+H]$^+$=318.1.

Example Q (R)-1-(2,6-Difluorobenzyl)-5-oxopyrrolidine-2-carboxylic acid

ESI-MS [M+H]$^+$=256.1.

Example R (R)-5-Oxo-1-(2-trifluoromethyl-benzyl)-pyrrolidine-2-carboxylic acid To the solution of (R)-ethyl 5-oxo-pyrrolidine-2-carboxylate (D-pyroglutamic acid ethyl ester; 99% pure; 1403 mg, 8.84 mmol) in 20 ml of DMF 1-(bromomethyl)-2-(trifluoromethyl)benzene (96% pure; 2200 mg, 8.84 mmol), K$_2$CO$_3$ (3660 mg, 26.5 mmol) and a small amount of each KI and 18-crown-6 were added, and the mixture was heated at 80° C. for 6 h. Subsequently the mixture was poured into water and extracted three times with MTBE. The organic layer was washed with brine, dried over MgSO$_4$ and the solvent removed under reduced pressure. Chromatography on silica gel using dichloromethane and dichloromethane/MeOH (99:1) resulted in (R)-5-oxo-1-(2-trifluoromethyl-benzyl)-pyrrolidine-2-carboxylic acid ethyl ester (410 mg, ESI-MS [M+H]$^+$=316.1; yield: 12%), which was hydrolyzed to the corresponding carboxylate by stirring overnight at room temperature in a solution of 15 ml ethanol and 1.56 mL 2N NaOH (aq). Evaporation of the solvent, followed by addition of water to the residue, extraction with ethyl acetate, subsequent acidification of the aqueous layer to pH 3 using concentrated HCl, extraction with dichloromethane, drying of the combined organic layers with MgSO$_4$ and removal of the solvent under reduced pressure led to the desired product as a white foam.

ESI-MS [M+H]$^+$=288.1.

Example S (R)-1-(3-Cyano-benzyl)-5-oxo-pyrrolidine-2-carboxylic acid

The title compound was prepared in a manner analogous to the above described preparation of Example R.

ESI-MS [M+H]$^+$=245.1.

Example T (R)-5-Oxo-1-phenyl-pyrrolidine-2-carboxylic acid

A mixture of (R)-ethyl 5-oxo-pyrrolidine-2-carboxylate (2760 mg, 17.56 mmol), bromobenzene (2.034 ml, 3030 mg, 19.32 mmol), Pd$_2$(dba)$_3$ (402 mg, 0.439 mmol), Cs$_2$CO$_3$ (8580 mg, 26.3 mmol), and 4,5-bis(diphenylphosphino)-9,9-dimethylxanthene (Xantphos, 254 mg, 0.439 mmol) in 70 ml of dioxane was stirred at 100° C. for 6 h under nitrogen atmosphere. Due to only partial reaction after this time additional Pd$_2$(dba)$_3$ (402 mg, 0.439 mmol), Cs$_2$CO$_3$ (2860 mg, 8.77 mmol) and Xantphos (254 mg, 0.439 mmol) were added and stirring at 100° C. was continued for additional 6 h. The reaction mixture was then filtered via a short celite column, the solvent was removed under reduced pressure, and the remaining residue was taken up in ethyl acetate, washed successively with an aq. sat. NaHCO$_3$ solution and an aq. citric acid solution (each 3×), then with water and brine. The organic layer was dried over Na$_2$SO$_4$, the solvent evaporated under reduced pressure, and the obtained residue purified by column chromatography on silica gel using dichloromethane to give (R)-ethyl 5-oxo-1-phenylpyrrolidine-2-carboxylate as a brown oil (715 mg, 3.07 mmol; yield: 17%; ESI-MS [M+H]$^+$=234.1). Saponification to the corresponding carboxylate was achieved by stirring at room temperature overnight in a solution of 4 ml ethanol and 1.84 ml 2N NaOH (aq). Subsequent evaporation of the solvent followed by addition of water, extraction with MTBE (3×), acidification of the aqueous layer to pH 3 using concentrated HCl, extraction with dichloromethane (3×), washing the combined organic layers with brine, drying over MgSO$_4$ and removing the solvent under reduced pressure yielded the title compound as a pale brown powder (0.5 g; yield: 79%).

ESI-MS [M+H]$^+$=206.1.

Example U (R)-3-Benzyl-1-methyl-2-oxo-imidazolidine-4-carboxylic acid

To the solution of (R)-benzyl 1-methyl-2-oxo-imidazolidine-4-carboxylate (1000 mg, 4.27 mmol) in 11 ml of DMF sodium hydride (129 mg, 5.12 mmol) was added, resulting in a slightly exothermic reaction (temperature rise to about 27° C.) and formation of a turbid solution. After stirring for 1 h at room temperature (bromomethyl)benzene (0.609 ml, 876 mg, 5.12 mmol) was added resulting again in a slightly exothermic reaction (temperature rise to about 29° C.). After stirring overnight the reaction mixture was poured into water and extracted three times with ethyl acetate. The combined organic layers were washed successively with a 10% citric acid solution, twice with saturated NaHCO$_3$ solution and brine, dried over Na$_2$SO$_4$ and the solvent was then removed under reduced pressure. Column chromatography on silica gel using dichloromethane and dichloromethane/methanol 98/2 gave (R)-benzyl 3-benzyl-1-methyl-2-oxoimidazolidine-4-carboxylate (425 mg, 1.38 mmol, yield: 31%, ESI-MS [M+H]$^+$=325.1), which was converted into to the corresponding carboxylate by stirring overnight at room temperature in a mixture of 2.7 ml of THF and 1.44 mL of 2N NaOH. Water was added to the reaction mixture followed by extraction with MTBE. The aqueous layer subsequently was acidified to pH 3 using 2M HCl, and extracted three times with dichloromethane. The combined organic layers were then washed with brine, dried over Na$_2$SO$_4$ and the solvent was removed under reduced pressure. The title compound was obtained as colorless oil which solidified by standing over time (245 mg, yield: 75%).

ESI-MS [M+H]$^+$=235.1.

Example V

(2R,4S)-1-Benzyl-4-methyl-5-oxo-pyrrolidine-2-carboxylic acid

To a solution of (R)-1-benzyl-5-oxopyrrolidine-2-carboxylic acid (1000 mg, 4.56 mmol) in 55 ml of THF 10.03 ml of a 1M lithium bis(trimethylsilyl)amide solution in THF (10.03 mmol) were added slowly at −10° C., and stirring was continued at this temperature for 1 h. Subsequently iodomethane (0.284 ml, 647 mg, 4.56 mmol) in 9 ml of THF were added (slight exothermic reaction), and the reaction was completed by stirring overnight at room temperature. The brown reaction mixture was acidified using 2M HCl, extracted three times with ethyl acetate. The combined organic layers were then washed with brine, dried over $Na_2SO_4$ and the solvent evaporated under reduced pressure. The title compound was obtained as a brown oil, which was reacted in the next step without further purification (890 mg of raw material, yield: 84%).

ESI-MS $[M+H]^+$=234.1.

Example W

2-Benzyl-1,1-dioxo-isothiazolidine-3-carboxylic acid

To the solution of 1,1-dioxo-isothiazolidine-3-carboxylic acid (97% pure; 1040 mg, 6.11 mmol) in 15 ml of DMF (bromomethyl)benzene (98% pure; 1.85 ml, 2660 mg, 15.27 mmol) and $K_2CO_3$ (2350 mg, 18.3 mmol) were added and the mixture stirred overnight at room temperature. Subsequently the reaction mixture was poured into water and extracted three times with MTBE. The combined organic layers were washed with brine, dried over $MgSO_4$ and the solvent was removed under reduced pressure. Chromatography on silica gel using dichloromethane resulted in 2-Benzyl-1,1-dioxo-isothiazolidine-3-carboxylic acid benzyl ester (1000 mg, 2.9 mmol; yield: 47%; ESI-MS $[M+H]^+$=346.1). Saponification to the corresponding carboxylate was achieved by stirring overnight at room temperature in a solution of 20 ml ethanol and 2.46 mL of 2N NaOH, and subsequent warming to 50° C. for 2 h. Evaporation of the solvent followed by addition of water, extraction with ethyl acetate, subsequent removal of water under reduced pressure and treatment with isopropanol resulted in the isolation of the sodium salt of the title compound (880 mg; containing some NaOH) as a white amorphous powder.

ESI-MS $[M+H]^+$=256.0.

Example X

1-Benzyl-6-oxo-1,6-dihydro-pyridine-2-carboxylic acid

To the suspension of 6-hydroxypicolinic acid (2500 mg, 17.97 mmol) in 37.75 ml of DMF were added (bromomethyl)benzene (6450 mg, 37.7 mmol) and $Cs_2CO_3$ (12300 mg, 37.7 mmol). The mixture was stirred overnight at room temperature (thin layer chromatography indicated nearly complete conversion with formation of two products, probably O- and N-alkylation). The reaction mixture was poured into water and extracted three times with ethyl acetate. The combined organic layers were successively washed with an aq. saturated $NaHCO_3$ solution (2×), water, 10% citric acid solution (2×), and brine, dried over $Na_2SO_4$ and the solvent was removed under reduced pressure. Column chromatography on silica gel using dichloromethane/heptane (3:1) followed by dichloromethane and dichloromethane/MeOH (99:1) resulted in 6-benzyloxy-pyridine-2-carboxylic acid benzyl ester (3030 mg, 9.41 mmol, yield: 53%; ESI-MS $[M+H]^+$=320.1) and 1-benzyl-6-oxo-1,6-dihydro-pyridine-2-carboxylic acid benzyl ester (containing minor impurities; 1920 mg, 6.01 mmol, yield: 34%; ESI-MS $[M+H]^+$=320.1). The latter compound was hydrolyzed to the corresponding carboxylate by stirring in a solution of 10.3 ml of ethanol and 5.17 mL 2N of aq. NaOH at room temperature for 3 h. Water was added to the reaction mixture followed by extraction with ethyl acetate (3×). The aqueous layer was acidified to pH 3 using 2M HCl and then extracted three times with dichloromethane. The combined organic layers were washed with brine and dried over $Na_2SO_4$. Afterwards the solvent was removed under reduced pressure giving of the title product as a pale brown powder (1230 mg, yield: 89%). ESI-MS $[M+H]^+$=230.1.

The compounds of Examples Y and Z can be prepared in a manner analogous to the above described preparation of Example A.

Example Y

(R)-5-Oxo-1-(4-(trifluoromethyl)benzyl)pyrrolidine-2-carboxylic acid

ESI-MS $[M+H]^+$=493.2.

Example Z

(R)-1-(2,6-Dichlorobenzyl)-5-oxopyrrolidine-2-carboxylic acid

ESI-MS $[M+H]^+$=493.2.

II. Preparation of Compounds of the General Formula I

Example 1

(2R)—N-(4-Amino-3,4-dioxo-1-phenylbutan-2-yl)-1-benzyl-5-oxopyrrolidine-2-carboxamide

1.1 (2R)—N-(4-Amino-3-hydroxy-4-oxo-1-phenylbutan-2-yl)-1-benzyl-5-oxopyrrolidine-2-carboxamide To the solution of (R)-1-benzyl-5-oxopyrrolidine-2-carboxylic acid (475 mg, 2.167 mmol) in a mixture of 15 ml of THF and 0.5 ml of DMF at 5° C. were successively added 1-hydroxybenzotriazole (365 mg, 2.383 mmol), 3-amino-2-hydroxy-4-phenylbutanamide (421 mg, 2.167 mmol), N-(3-dimethylaminopropyl)-N'-ethylcarbodiimide hydrochloride (EDC; 457 mg, 2.383 mmol) and DIPEA (0.416 mL; 308 mg, 2.383 mmol). After stirring overnight at room temperature the solvent was evaporated under reduced pressure, water was added to the remaining residue and after stirring for 30 minutes at about 5° C. the precipitate was filtered off. Drying under reduced pressure gave the title compound as an off-white powder (786 mg; yield: 92%) which was used without further purification in the next step.

ESI-MS $[M+H]^+$=396.2.

HPLC analysis revealed that the compound was isolated as mixture of diasteromers.

1.2 (2R)—N-(4-Amino-3,4-dioxo-1-phenylbutan-2-yl)-1-benzyl-5-oxopyrrolidine-2-carboxamide EDC (1543 mg, 8.05 mmol) and 2,2-dichloroacetic acid (0.446 ml; 696 mg, 5.4 mmol) were added to a solution of (2R)—N-(4-amino-3-hydroxy-4-oxo-1-phenylbutan-2-yl)-1-benzyl-5-oxopyrrolidine-2-carboxamide (400 mg, 1.012 mmol) in 8 ml of dry dimethylsulfoxide (DMSO), resulting in a slight exotheric reaction (40° C.). After stirring overnight at room temperature ethyl acetate and water were added, the formed precipitate filtered off and the remaining organic layer concentrated to dryness under reduced pressure. Precipitate and obtained residue were combined, and after addition of water and stirring at about 5° C. for 30 minutes the formed precipitate was filtered off and dried under reduced pressure. The title compound was obtained as an off-white powder (243 mg, yield: 61%).

ESI-MS [M+H]$^+$=394.2;
$^1$H-NMR (400 MHz DMSO), δ[ppm]: 8.62 (d, 1H), 8.09 and 8.11 (2s, 1H), 7.85 (s, 1H), 7.18-7.34 (m, 8H), 7.12 (d, 1H), 7.01 (d, 1H), 5.15-5.26 (m, 1H), 4.83 and 4.74 (2d, 1H), 3.84-3.88 (m, 1H), 3.48 and 3.34 (2d, 1H partially superimposed by water), 3.15-3.21 (m, 1H). 2.71-2.78 (m, 1H), 2.18-2.32 (m, 2H), 1.98-2.15 (m, 1H), 1.67-1.74 and 1.48-1.55 (2m, 1H).

The $^1$H-NMR analysis indicated a diastereomeric ratio of about 1:1.

The compounds of the following examples were prepared in a manner analogous to the preparation of Example 1:

Example 2

(2S)—N-(4-Amino-3,4-dioxo-1-phenylbutan-2-yl)-1-benzyl-5-oxopyrrolidine-2-carboxamide Coupling of (S)-1-benzyl-5-oxopyrrolidine-2-carboxylic acid with 3-amino-2-hydroxy-4-phenylbutanamide was followed by oxidation of the resulting hydroxyamide intermediate to the corresponding ketoamide.

$^1$H-NMR (400 MHz DMSO), δ [ppm]: 8.61 (d, 1H), 8.08 and 8.10 (2s, 1H), 7.84 (s, 1H), 7.18-7.34 (m, 8H), 7.12 (d, 1H), 7.01 (d, 1H), 5.15-5.26 (m, 1H), 4.83 and 4.74 (2d, 1H), 3.84-3.88 (m, 1H), 3.48 and 3.35 (2d, 1H partially superimposed by water), 3.15-3.21 (m, 1H), 2.71-2.78 (m, 1H), 2.18-2.32 (m, 2H), 1.98-2.15 (m, 1H), 1.67-1.74 and 1.48-1.55 (2m, 1H);

ESI-MS [M+H]$^+$=394.2.

Example 3

(2R)—N-(4-Amino-3,4-dioxo-1-phenylbutan-2-yl)-1-(3-chlorobenzyl)-5-oxopyrrolidine-2-carboxamide Coupling of (R)-1-(3-chloro-benzyl)-5-oxo-pyrrolidine-2-carboxylic acid with 3-amino-2-hydroxy-4-phenylbutanamide and oxidation of the resulting hydroxyamide intermediate to the corresponding ketoamide.

ESI-MS [M+H]$^+$=428.2, 430.2.

Example 4

N-(4-Amino-3,4-dioxo-1-phenylbutan-2-yl)-1-benzyl-6-oxo-1,6-dihydropyridine-2-carboxamide Coupling of 1-benzyl-6-oxo-1,6-dihydro-pyridine-2-carboxylic acid with 3-amino-2-hydroxy-4-phenylbutanamide and oxidation of the hydroxyamide intermediate to the corresponding ketoamide.

$^1$H-NMR (400 MHz DMSO), δ [ppm]: 9.32 (d, 1H), 8.09 (s, 1H), 7.83 (s, 1H), 7.45 (dd, 1H), 7,16-7.28 (m, 10H), 6.50 (d, 1H), 6.17 (d, 1H), 5.32-5.36 (m, 1H), 5.08 and 4.98 (2d, 2H), 3.19 and 2.74 (2dd, 2H);

ESI-MS [M+H]$^+$=404.2.

Example 5

(2R)—N-(4-Amino-3,4-dioxo-1-phenylbutan-2-yl)-1-(4-fluorobenzyl)-5-oxopyrrolidine-2-carboxamide Coupling of (R)-1-(4-fluoro-benzyl)-5-oxo-pyrrolidine-2-carboxylic acid with 3-amino-2-hydroxy-4-phenylbutanamide and oxidation of the resulting hydroxyamide intermediate to the corresponding ketoamide.

$^1$H-NMR (400 MHz DMSO), δ [ppm]: 8.63 (d, 1H), 8.09 and 8.11 (2s, 1H), 7.84 and 7.85 (2s, 1H), 7.01-7.32 (m, 9H), 5.15-5.23 (m, 1H), 4.77 and 4.67 (2d, 1H), 3.87 and 3.83 (2d, 1H), 3.51 and 3.36 (2d, 1H partially superimposed by water), 3.15-3.21 (m, 1H), 2.70-2.77 (m, 1H), 2.17-2.33 (m, 2H), 1.98-2.15 (m, 1H), 1.66-1.74 and 1.47-1.56 (2m, 1H);

ESI-MS [M+H]$^+$=412.2.

Example 6

(2R)—N-(4-Amino-3,4-dioxo-1-phenylbutan-2-yl)-1-(3-methoxybenzyl)-5-oxopyrrolidine-2-carboxamide Coupling of (R)-1-(3-methoxy-benzyl)-5-oxo-pyrrolidine-2-carboxylic acid with 3-amino-2-hydroxy-4-phenylbutanamide and oxidation of the resulting hydroxyamide intermediate to the corresponding ketoamide.

ESI-MS [M+H]$^+$=424.2.

Example 7

(2R)—N-(4-Amino-3,4-dioxo-1-phenylbutan-2-yl)-1-(3-trifluoromethyl-benzyl)-5-oxopyrrolidine-2-carboxamide Coupling of (R)-1-(3-trifluoromethyl-benzyl)-5-oxo-pyrrolidine-2-carboxylic acid with 3-amino-2-hydroxy-4-phenylbutanamide and oxidation of the resulting hydroxyamide intermediate to the corresponding ketoamide.

ESI-MS [M+H]$^+$=462.2.

Example 8

(2R)—N-(4-Amino-3,4-dioxo-1-phenylbutan-2-yl)-1-(3-fluorobenzyl)-5-oxopyrrolidine-2-carboxamide Coupling of (R)-1-(3-fluoro-benzyl)-5-oxo-pyrrolidine-2-carboxylic acid with 3-amino-2-hydroxy-4-phenylbutanamide and oxidation of the resulting hydroxyamide intermediate to the corresponding ketoamide.

ESI-MS [M+H]$^+$=412.1.

Example 9

(2R)—N-(4-Amino-3,4-dioxo-1-phenylbutan-2-yl)-5-oxo-1-[2-(trifluoromethoxy)-benzyl]pyrrolidine-2-carboxamide Coupling of (R)-1-(2-trifluoromethoxy-benzyl)-5-oxo-pyrrolidine-2-carboxylic acid with 3-amino-2-hydroxy-4-phenylbutanamide and oxidation of the resulting hydroxyamide intermediate to the corresponding ketoamide.

ESI-MS [M+H]$^+$=478.1.

Example 10

N-(4-Amino-3,4-dioxo-1-phenylbutan-2-yl)-2-benzylisothiazolidine-3-carboxamide 1,1-dioxide Coupling of the sodium salt of 2-benzyl-1,1-dioxo-isothiazolidine-3-carboxylic acid with 3-amino-2-hydroxy-4-phenylbutanamide and oxidation of the resulting hydroxyamide intermediate to the corresponding ketoamide.
ESI-MS [M+H]$^+$=430.1.

Example 11

(2R)—N-(4-Amino-3,4-dioxo-1-phenylbutan-2-yl)-1-(naphthalen-1-ylmethyl)-5-oxopyrrolidine-2-carboxamide Coupling of (R)-1-naphthalen-1-ylmethyl-5-oxo-pyrrolidine-2-carboxylic acid with 3-amino-2-hydroxy-4-phenylbutanamide and oxidation of the resulting hydroxyamide intermediate to the corresponding ketoamide.
ESI-MS [M+H]$^+$=444.2.

Example 12

(2R)—N-(4-Amino-3,4-dioxo-1-phenylbutan-2-yl)-1-(naphthalen-2-ylmethyl)-5-oxopyrrolidine-2-carboxamide Coupling of (R)-1-naphthalen-2-ylmethyl-5-oxo-pyrrolidine-2-carboxylic acid with 3-amino-2-hydroxy-4-phenylbutanamide and oxidation of the resulting hydroxyamide intermediate to the corresponding ketoamide.
ESI-MS [M+H]$^+$=444.2.

Example 13

(2R)—N-(4-Amino-3,4-dioxo-1-phenylbutan-2-yl)-5-oxo-1-[3-(trifluoromethoxy)-benzyl]pyrrolidine-2-carboxamide Coupling of (R)-1-(3-trifluoromethoxy-benzyl)-5-oxo-pyrrolidine-2-carboxylic acid with 3-amino-2-hydroxy-4-phenylbutanamide and oxidation of the resulting hydroxyamide intermediate to the corresponding ketoamide
ESI-MS [M+H]$^+$=478.1.

Example 14

(2R)—N-(4-Amino-3,4-dioxo-1-phenylbutan-2-yl)-1-benzyl-6-oxopiperidine-2-carboxamide Coupling of (R)-1-benzyl-6-oxo-piperidine-2-carboxylic acid with 3-amino-2-hydroxy-4-phenylbutanamide and oxidation of the resulting hydroxyamide intermediate to the corresponding ketoamide.
ESI-MS [M+H]$^+$=408.2.

Example 15

(2R)—N-(4-Amino-3,4-dioxo-1-phenylbutan-2-yl)-5-oxo-1-phenylpyrrolidine-2-carboxamide Coupling of (R)-5-Oxo-1-phenyl-pyrrolidine-2-carboxylic acid with 3-amino-2-hydroxy-4-phenylbutanamide and oxidation of the resulting hydroxyamide intermediate to the corresponding ketoamide.
ESI-MS [M+H]$^+$=380.2.

Example 16

(2R)—N-(4-Amino-3,4-dioxo-1-phenylbutan-2-yl)-1-(3-cyanobenzyl)-5-oxopyrrolidine-2-carboxamide Coupling of (R)-1-(3-cyano-benzyl)-5-oxo-pyrrolidine-2-carboxylic acid with 3-amino-2-hydroxy-4-phenylbutanamide and oxidation of the resulting hydroxyamide intermediate to the corresponding ketoamide.
ESI-MS [M+H]$^+$=419.1.

Example 17

(2R)—N-(4-Amino-3,4-dioxo-1-phenylbutan-2-yl)-5-oxo-1-[2-(trifluoromethyl)benzyl]-pyrrolidine-2-carboxamide Coupling of (R)-5-Oxo-1-(2-trifluoromethyl-benzyl)-pyrrolidine-2-carboxylic acid with 3-amino-2-hydroxy-4-phenylbutanamide and oxidation of the resulting hydroxyamide intermediate to the corresponding ketoamide.
ESI-MS [M+H]$^+$=462.1.

Example 18

(4R)—N-(4-Amino-3,4-dioxo-1-phenylbutan-2-yl)-3-benzyl-1-methyl-2-oxoimidazolidine-4-carboxamide Coupling of (R)-3-Benzyl-1-methyl-2-oxo-imidazolidine-4-carboxylic acid with 3-amino-2-hydroxy-4-phenylbutanamide and oxidation of the resulting hydroxyamide intermediate to the corresponding ketoamide.
ESI-MS [M+H]$^+$=409.2.

Example 19

(2R,4S)—N-(4-Amino-3,4-dioxo-1-phenylbutan-2-yl)-1-benzyl-4-methyl-5-oxopyrrolidine-2-carboxamide Coupling of (2R,4S)-1-Benzyl-4-methyl-5-oxo-pyrrolidine-2-carboxylic acid with 3-amino-2-hydroxy-4-phenylbutanamide and oxidation of the resulting hydroxyamide intermediate to the corresponding ketoamide.
ESI-MS [M+H]$^+$=408.1.

Example 20

(2R)-1-Benzyl-N-{3,4-dioxo-1-phenyl-4-[(pyridin-2-ylmethyl)amino]butan-2-yl}-5-oxopyrrolidine-2-carboxamide 20.1 Ethyl 3-((R)-1-benzyl-5-oxopyrrolidine-2-carboxamido)-2-hydroxy-4-phenyl-butanoate To a solution of (R)-1-benzyl-5-oxopyrrolidine-2-carboxylic acid (2440 mg, 11.13 mmol) in a mixture of 24 ml THF and 4 ml DMF were successively added at 5° C. 1-hydroxybenzotriazole (1875 mg, 12.24 mmol), ethyl 3-amino-2-hydroxy-4-phenylbutanoate (2485 mg, 11.13 mmol; preparation described in WO 98/25883, example 8a on page 24), EDC (2347 mg, 12.24 mmol) and DIPEA (6.41 mL; 4750 mg, 36.7 mmol). After stirring overnight at room temperature the reaction mixture was concentrated under reduced pressure, water was added and the obtained mixture was extracted three times with ethyl acetate. The organic layer was washed successively with aq. saturated NaHCO$_3$ (2×), 10% aq. citric acid solution (3×) and brine, dried over Na$_2$SO$_4$ and the solvent was then removed under reduced pressure. The title compound was obtained as a yellow oil (4550 mg, yield: 96%), which was used without further purification in the next step.
ESI-MS [M+H]$^+$=425.2.

20.2 3-((R)-1-Benzyl-5-oxopyrrolidine-2-carboxamido)-2-hydroxy-4-phenylbutanoic acid Ethyl 3-((R)-1-benzyl-5-oxopyrrolidine-2-carboxamido)-2-hydroxy-4-phenylbutanoate (4550 mg raw material from previous step 22.1; max. 10.72 mmol) dissolved in 13 ml of ethanol was treated with 6.43 ml 2N aq. NaOH overnight at room temperature. To complete the reaction, the mixture was then heated to 50° C. for 2 h. Water was added followed by extraction with MTBE (3×). The aqueous layer was acidified to pH 3 using 2M HCl and extracted three times with dichloromethane. The combined dichloromethane layers were then successively washed with water and brine, dried over Na$_2$SO$_4$ and the solvent was removed under reduced pressure. The title compound was obtained as a pale brown powder (2450 mg, yield: 58%). ESI-MS [M+H]$^+$=397.2.

20.3 (2R)-1-Benzyl-N-(3-hydroxy-4-oxo-1-phenyl-4-(pyridin-2-ylmethylamino)-butan-2-yl)-5-oxopyrrolidine-2-carboxamide 3-((R)-1-benzyl-5-oxopyrrolidine-2-carboxamido)-2-hydroxy-4-phenylbutanoic acid (300 mg, 0.757 mmol) and pyridin-2-ylmethanamine (94 µl, 98 mg, 0.908 mmol) were dissolved in 13 ml dichloromethane and cooled to 5° C. At this temperature 1-hydroxybenzotriazole hydrate (127 mg, 0.832 mmol), EDC (160 mg, 0.832 mmol) and triethylamine (1.58 ml, 127 mg, 1135 mmol) were successively added. After stirring overnight at room temperature the reaction mixture was concentrated under reduced pressure, water was added and the mixture extracted three times with ethyl acetate. The combined organic layers were successively washed with aq. saturated NaHCO$_3$ solution and brine, dried over Na$_2$SO$_4$ and the solvent was removed under reduced pressure. Column chromatography on silica gel using dichloromethane/MeOH (97/3), followed by dichloromethane/MeOH (95/5), resulted in the title compound (125 mg, yield: 34%) as a white powder.
ESI-MS [M+H]$^+$=487.2.

20.4 (2R)-1-Benzyl-N-{3,4-dioxo-1-phenyl-4-[(pyridin-2-ylmethyl)amino]butan-2-yl}-5-oxopyrrolidine-2-carboxamide (2R)-1-Benzyl-N-(3-hydroxy-4-oxo-1-phenyl-4-(pyridin-2-ylmethylamino)butan-2-yl)-5-oxopyrrolidine-2-carboxamide was converted into the corresponding ketoamide as described in step 1.2 of Example 1.
ESI-MS [M+H]$^+$=485.2.

Example 21

(2R)-1-Benzyl-N-[4-(ethylamino)-3,4-dioxo-1-phenylbutan-2-yl]-5-oxopyrrolidine-2-carboxamide Coupling of 3-((R)-1-benzyl-5-oxopyrrolidine-2-carboxamido)-2-hydroxy-4-phenyl-butanoic acid with ethylamine and oxidation of the resulting hydroxyamide intermediate to the corresponding ketoamide.
ESI-MS [M+H]$^+$=422.2.

Example 22

(2R)—N-(4-Amino-3,4-dioxo-1-phenylbutan-2-yl)-1-(3,5-dimethoxybenzyl)-5-oxopyrrolidine-2-carboxamide Coupling of (R)-1-(3,5-dimethoxy-benzyl)-5-oxo-pyrrolidine-2-carboxylic acid with 3-amino-2-hydroxy-4-phenylbutanamide and oxidation of the resulting hydroxyamide intermediate to the corresponding ketoamide.
ESI-MS [M+H]$^+$=454.2;
$^1$H-NMR (400 MHz DMSO), δ [ppm]: 8.60-8.57 (m, 1H), 8.03 (d, 1H, J=9.0 Hz), 7.12 (d, 1H, J=4.8 Hz), 7.29-7.18 (m, 5H), 6.39-6.22 (m, 3H), 5.22-5.17 (m, 1H), 4.75 (d, 0.5H, J=15.2 Hz), 4.70 (d, 0.5H, J=14.8 Hz), 3.94-3.89 (m, 1H), 3.40 (d, 0.5H, J=15.2 Hz), 3.31-2.26 (d, 0.5H, hidden under solvent peak), 3.19-3.14 (m, 1H), 3.81-2.66 (m, 1H), 2.32-1.99 (m, 3H), 1.74-1.69 (m, 0.5H), 1.55-1.50 (m, 0.5H). The $^1$H-NMR analysis indicated a diastereomeric ratio of about 1:1.

Example 23

(2R)—N-(4-Amino-3,4-dioxo-1-phenylbutan-2-yl)-5-oxo-1-(pyridin-4-ylmethyl)-pyrrolidine-2-carboxamide Coupling of (R)-5-oxo-1-pyridin-4-ylmethyl-pyrrolidine-2-carboxylic acid with 3-amino-2-hydroxy-4-phenylbutanamide and oxidation of the resulting hydroxyamide intermediate to the corresponding ketoamide using Dess Martin reagent.
ESI-MS [M+H]$^+$=395.1.

Example 24

(2R)—N-(4-Amino-3,4-dioxo-1-phenylbutan-2-yl)-1-(3,5-difluorobenzyl)-5-oxopyrrolidine-2-carboxamide Coupling of (R)-1-(3,5-difluoro-benzyl)-5-oxo-pyrrolidine-2-carboxylic acid with 3-amino-2-hydroxy-4-phenylbutanamide and oxidation of the resulting hydroxyamide intermediate to the corresponding ketoamide.
ESI-MS [M+H]$^+$=430.2;
$^1$H-NMR (500 MHz DMSO), δ [ppm]: 8.66-8.63 (m, 1H), 8.07 (d, 1H, J=5.0 Hz), 7.82 (s, 1H), 7.28-7.11 (m, 6H), 6.87 (s, 0.5H), 6.86 (s, 0.5H), 6.79 (s, 0.5H), 6.78 (s, 0.5H), 5.22-5.19 (m, 1H), 4.77 (d, 0.5H, J=20.0 Hz), 4.77 (d, 0.5H, J=20.0 Hz), 3.99-3.96 (m, 1H), 3.62 (d, 0.5H, J=15.0 Hz), 3.47 (d, 0.5H, J=15.0 Hz), 3.20-3.16 (m, 1H), 2.78-2.75 (m, 1H), 2.31-2.11 (m, 3H), 1.76 (m, 0.5H), 1.56 (m, 0.5H). The $^1$H-NMR analysis indicated a diastereomeric ratio of about 1:1.

The following compounds of examples 25 to 35 were prepared in a manner analogous to the synthesis of (2R)-1-benzyl-N-(3-hydroxy-4-oxo-1-phenyl-4-(pyridin-2-ylmethylamino)butan-2-yl)-5-oxopyrrolidine-2-carboxamide (Example 20.3) followed by oxidation to the corresponding ketoamide as described in step 1.2 of Example 1.

Example 25

(2R)-1-Benzyl-N-(4-(methylamino)-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenylbutanoic acid with methylamine and oxidation of the resulting hydroxyamide intermediate to the corresponding ketoamide.

ESI-MS [M+H]⁺=408.2.
¹H-NMR (500 MHz, DMSO) ~1.5:1 mixture of diastereomers: δ [ppm]: 8.71-8.68 (m, 1H), 8.65-8.63 (m, 1H), 7.36-7.03 (m, 10H), 5.26-5.19 (m, 1H), 4.86 (d, 0.6H), 4.76 (d, 0.4H), 3.92-3.88 (m, 1H), 3.52 (d, 0.6H), 3.37 (d, 0.4H), 3.24-3.15 (m, 1H), 2.80-2.75 (m, 1H), 2.72-2.70 (m, 3H), 2.31-2.22 (m, 2H), 2.15-2.05 (m, 1H), 1.75-1.72 (m, 0.4H), 1.58-1.53 (m, 0.6H).

Example 26

(2R)-1-Benzyl-N-(3,4-dioxo-1-phenyl-4-(propylamino)butan-2-yl)-5-oxopyrrolidine-2-carboxamide Coupling of 3-((R)-1-benzyl-5-oxopyrrolidine-2-carboxamido)-2-hydroxy-4-phenyl-butanoic acid with propylamine and oxidation of the resulting hydroxyamide intermediate to the corresponding ketoamide.
ESI-MS [M+H]⁺=436.2.
¹H-NMR (500 MHz, DMSO) ~2:1 mixture of diastereomers: δ [ppm]: 8.83-8.81 (m, 1H), 8.69-8.67 (m, 1H), 7.37-7.04 (m, 10H), 5.29-5.22 (m, 1H), 4.86 (d, 0.7H), 4.77 (d, 0.3H), 3.93-3.91 (m, 1H), 3.53 (d, 1H), 3.23-3.13 (m, 3H), 2.82-2.77 (m, 1H), 2.29-2.23 (m, 2H), 2.12-2.06 (m, 1H), 1.57-1.49 (m, 3H), 0.98-0.86 (m, 3H).

Example 27

(2R)-1-Benzyl-N-(4-(cyclopropylamino)-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenyl-butanoic acid with cyclopropylamine and oxidation of the resulting hydroxyamide intermediate to the corresponding ketoamide.
ESI-MS [M+H]⁺=434.2.
¹H-NMR (500 MHz, DMSO) ~1:1 mixture of diastereomers: δ [ppm]: 8.86-8.83 (m, 1H), 8.69-8.67 (m, 1H), 7.36-7.04 (m, 10H), 5.26-5.18 (m, 1H), 4.86 (d, 0.5H), 4.77 (d, 0.5H), 3.91-3.89 (m, 1H), 3.52 (d, 0.5H), 3.39-3.35 (d, 0.5H, hidden under solvent signal), 3.23-3.19 (m, 1H), 2.84-2.74 (m, 2H), 2.33-2.21 (m, 2H), 2.17-2.01 (m, 1H), 1.76-1.70 (m, 0.5H), 1.59-1.52 (m, 0.5H), 0.72-0.59 (m, 4H).

Example 28

(2R)-1-Benzyl-N-(4-(isobutylamino)-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenyl-butanoic acid with isobutylamine and oxidation of the resulting hydroxyamide intermediate to the corresponding ketoamide.
ESI-MS [M+H]⁺=450.2.
¹H-NMR (500 MHz, DMSO) ~1:1 mixture of diastereomers: δ [ppm]: 8.81-8.78 (m, 1H), 8.68-8.67 (m, 1H), 7.33-7.03 (m, 10H), 5.30-5.22 (m, 1H), 4.86 (d, 0.5H), 4.76 (d, 0.5H), 3.92-3.91 (m, 1H), 3.26-3.16 (m, 1H), 3.08-2.94 (m, 2H), 2.86-2.74 (m, 1H), 2.36-2.05 (m, 3.5H), 1.88-1.70 (m, 2H), 1.52-1.61 (m, 0.5H), 0.95-0.83 (m, 6H).

Example 29

(2R)-1-Benzyl-N-(4-(cyclobutylamino)-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenyl-butanoic acid with cyclobutylamine and oxidation of the resulting hydroxyamide intermediate to the corresponding ketoamide.
ESI-MS [M+H]⁺=448.2.
¹H-NMR (500 MHz, DMSO) ~2:1 mixture of diastereomers: δ [ppm]: 9.05-9.03 (m, 1H), 8.70-8.68 (m, 1H), 7.36-7.03 (m, 10H), 5.21-5.15 (m, 1H), 4.85 (d, 0.7H), 4.75 (d, 0.3H), 4.31-4.25 (m, 1H), 3.91-3.88 (m, 1H), 3.50 (d, 0.7H), 3.38-3.33 (d, 0.3H, hidden under solvent signal), 3.21-3.17 (m, 1H), 2.79-2.74 (m, 1H), 2.29-2.04 (m, 6H), 1.72-1.53 (m, 4H)

Example 30

(2R)-1-Benzyl-N-(4-(methoxyamino)-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenyl-butanoic acid with O-methylhydroxylamine and oxidation of the resulting hydroxyamide intermediate to the corresponding ketoamide using 2-iodoxybenzoic acid (IBX):

IBX (293 mg, 0.472 mmol) was added to a solution of (2R)-1-benzyl-N-(3-hydroxy-4-(methoxyamino)-4-oxo-1-phenylbutan-2-yl)-5-oxopyrrolidine-2-carboxamide (143 mg, 0.337 mmol) in DMSO (5 mL). After stirring for 2 h more IBX (105 mg, 0.169 mmol) was added and the stirring continued overnight. The saturated aqueous NaHCO₃ solution was added and the reaction mixture was diluted with water and DCM. The organic layer was separated and the aqueous layer was extracted with DCM. The combined organic layers were washed with water and dried (MgSO₄). The crude product obtained was dissolved in a minimal amount of DCM and diethylether was added. The precipitate formed was isolated and dried in vacuo. The title compound was obtained as a colourless solid (12 mg, 8%)
ESI-MS [M+H]⁺=424.2.
¹H-NMR (500 MHz, DMSO) single diastereomers, absolute configuration not determined: δ [ppm]: 8.24-8.22 (m, 1H), 7.31-7.22 (m, 9H), 7.02-7.00 (m, 2H), 5.52-5.47 (m, 1H), 4.74-4.70 (m, 1H), 3.95-3.93 (m, 1H), 3.65 (s, 3H), 2.70-2.44 (m, 2H, hidden under solvent signal), 2.36-2.09 (m, 4H), 1.79-1.72 (m, 1H).

Example 31

(2R)-1-Benzyl-N-(3,4-dioxo-1-phenyl-4-(2-(pyridin-2-yl)-ethylamino)butan-2-yl)-5-oxopyrrolidine-2-carboxamide Coupling of 3-((R)-1-benzyl-5-oxopyrrolidine-2-carboxamido)-2-hydroxy-4-phenyl-butanoic acid with 2-(pyridin-2-yl)ethanamine and oxidation of the resulting hydroxyamide intermediate to the corresponding ketoamide.
ESI-MS [M+H]⁺=499.2.
¹H-NMR (500 MHz, DMSO) ~1:1 mixture of diastereomers: δ [ppm]: 8.84-8.79 (m, 1H), 8.59-8.56 (m, 1H), 8.47-8.46 (m, 1H), 7.69-7.65 (m, 1H), 7.31-7.19 (m, 10H), 7.12-7.10 (m, 1H), 7.01-6.99 (m, 1H), 5.27-5.18 (m, 1H), 4.82 (d, 0.5H), 4.73 (d, 0.5H), 3.89-3.86 (m, 1H), 3.56-3.47 (m, 3H), 3.15-3.11 (m, 1H), 2.96-2.92 (m, 2H), 2.74-2.69 (m, 1H), 2.30-2.19 (m, 2H), 2.11-2.01 (m, 1H), 1.72-1.70 (m, 0.5H), 1.55-1.51 (m, 0.5H).

Example 32

(2R)-1-Benzyl-N-(3,4-dioxo-1-phenyl-4-(3-(pyridin-2-yl)propylamino)butan-2-yl)-5-oxopyrrolidine-2-carboxamide Coupling of 3-((R)-1-benzyl-5-oxopyrrolidine-2-carboxamido)-2-hydroxy-4-phenyl-butanoic acid with 3-(pyridin-2- yl)propan-1-amine and oxidation of the resulting hydroxyamide intermediate to the corresponding ketoamide.

ESI-MS [M+H]$^+$=513.2.

$^1$H-NMR (500 MHz, DMSO) ~4:3 mixture of diastereomers: δ [ppm]: 8.84-8.79 (m, 1H), 8.61-8.59 (m, 1H), 8.45-8.43 (m, 1H), 7.67-7.63 (m, 1H), 7.31-7.14 (m, 10H), 7.11 (d, 1H), 7.00 (d, 1H), 5.27-5.18 (m, 1H), 4.82 (d, 0.6H), 4.73 (d, 0.4H), 3.89-3.86 (m, 1H), 3.50 (d, 0.6H), 3.35 (d, 0.4H), 3.21-3.16 (m, 3H), 2.78-2.70 (m, 3H), 2.29-1.99 (m, 3H), 1.91-1.84 (m, 2H), 1.73-1.68 (m, 0.4H), 1.55-1.49 (m, 0.6H).

Example 33

(2R)-1-Benzyl-N-(3,4-dioxo-1-phenyl-4-(3-phenylpropylamino)butan-2-yl)-5-oxopyrrolidine-2-carboxamide Coupling of 3-((R)-1-benzyl-5-oxopyrrolidine-2-carboxamido)-2-hydroxy-4-phenyl-butanoic acid with 3-phenylpropan-1-amine and oxidation of the resulting hydroxyamide intermediate to the corresponding ketoamide.

ESI-MS [M+H]$^+$=512.3.

$^1$H-NMR (500 MHz, DMSO) ~4:3 mixture of diastereomers: δ [ppm]: 8.89-8.85 (m, 1H), 8.70-8.67 (m, 1H), 7.36-6.98 (m, 15H), 5.30-5.21 (m, 1H), 4.86 (d, 0.6H), 4.76 (d, 0.4H), 3.89-3.86 (m, 1H), 3.53 (d, 0.6H), 3.24-3.05 (m, 3H), 2.82-2.67 (m, 1H), 2.64-1.53 (m, 2H), 2.33-2.05 (m, 3H), 1.84-1.71 (m, 2.4H), 1.59-1.54 (m, 0.6H).

Example 34

(2R)-1-Benzyl-N-(4-(ethyl(methyl)amino)-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenyl-butanoic acid with N-methyl-ethanamine and oxidation of the resulting hydroxyamide intermediate to the corresponding ketoamide.

ESI-MS [M+H]$^+$=436.2.

$^1$H-NMR (500 MHz, DMSO) ~2:1 mixture of diastereomers: δ [ppm]: 8.82-8.79 (m, 1H), 7.35-7.22 (m, 8H), 7.10-7.08 (m, 1.5H), 7.01-7.00 (m, 0.5H), 4.90-4.87 (m, 1H), 4.82-4.75 (m, 1H), 3.86-3.84 (m, 1H), 3.44-3.19 (m, 4H), 2.99-2.87 (m, 4H), 2.37-2.17 (m, 2H), 2.14-2.04 (m, 1H), 1.67-1.60 (m, 0.3H), 1.53-1.43 (m, 0.6H), 1.16-1.05 (m, 3H).

Example 35

(2R)-1-Benzyl-N-(4-(2-chlorobenzylamino)-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenyl-butanoic acid with (2-chlorophenyl)methanamine and oxidation of the resulting hydroxyamide intermediate to the corresponding ketoamide.

ESI-MS [M+H]$^+$=518.2.

$^1$H-NMR (500 MHz, DMSO) ~1:1 mixture of diastereomers: δ [ppm]: 9.36 (brs, 1H), 8.76-8.75 (m, 1H), 7.47-7.05 (m, 14H), 5.29-5.19 (m, 1H), 4.89-4.86 (m, 0.5H), 4.78-4.75 (m, 0.5H), 3.92 (brs, 1H), 3.57-3.52 (d, 0.5H), 3.38-3.32 (0.5H hidden under solvent signal), 3.25-3.23 (m, 1H), 2.87-2.83 (m, 1H), 2.53-2.51 (m, 1H), 2.34-2.05 (m, 4H), 1.76-1.71 (m, 0.5H), 1.58-1.55 (m, 0.5H).

Example 36

(2R)—N-(4-(Cyclopropylamino)-3,4-dioxo-1-phenylbutan-2-yl)-5-oxo-1-(2-(trifluoromethyl)benzyl)pyrrolidine-2-carboxamide 36.1 2-Hydroxy-3-((R)-5-oxo-1-(2-(trifluoromethyl)benzyl)pyrrolidine-2-carboxamido)-4-phenylbutanoic acid The title compound was prepared in a manner analogous to the synthesis of ethyl 3-((R)-1-benzyl-5-oxopyrrolidine-2-carboxamido)-2-hydroxy-4-phenylbutanoate followed by saponification providing 3-((R)-1-benzyl-5-oxopyrrolidine-2-carboxamido)-2-hydroxy-4-phenylbutanoic acid as described in steps 20.1 and 20.2 of Example 20.

ESI-MS [M+H]$^+$=465.1.

36.2 (2R)—N-(4-(Cyclopropylamino)-3,4-dioxo-1-phenylbutan-2-yl)-5-oxo-1-(2-(trifluoromethyl)benzyl)pyrrolidine-2-carboxamide Coupling of 2-hydroxy-3-((R)-5-oxo-1-(2-(trifluoromethyl)benzyl)pyrrolidine-2-carboxamido)-4-phenylbutanoic acid with cyclopropylamine and oxidation of the resulting hydroxyamide intermediate to the corresponding ketoamide.

ESI-MS [M+H]$^+$=502.2.

$^1$H-NMR (500 MHz, DMSO) ~3:1 mixture of diastereomers: δ [ppm]: 8.78-8.77 (m, 1H), 8.60-8.57 (m, 1H), 7.76-7.50 (m, 4H), 7.35-7.18 (m, 5H), 5.27-5.22 (m, 1H), 4.99-4.90 (m, 1H), 4.00-3.98 (m, 1H), 3.90-3.81 (m, 1H), 3.20-3.16 (m, 1H), 2.82-2.69 (m, 2H), 2.35-2.15 (m, 3H), 1.84-1.80 (m, 0.3H), 1.62-1.55 (m, 0.7H), 0.70-0.61 (m, 4H).

Example 37

(2R)—N-(4-(Ethylamino)-3,4-dioxo-1-phenylbutan-2-yl)-5-oxo-1-(2-(trifluoromethyl)-benzyl)pyrrolidine-2-carboxamide Coupling of 2-hydroxy-3-((R)-5-oxo-1-(2-(trifluoromethyl)benzyl)pyrrolidine-2-carboxamido)-4-phenylbutanoic acid with ethylamine and oxidation of the resulting hydroxyamide intermediate to the corresponding ketoamide.

ESI-MS [M+H]$^+$=490.2.

$^1$H-NMR (500 MHz, DMSO) ~2:1 mixture of diastereomers: δ [ppm]: 8.74-8.72 (m, 1H), 8.60-8.57 (m, 1H), 7.75-7.50 (m, 4H), 7.34-7.17 (m, 5H), 5.28-5.24 (m, 1H), 4.98-4.90 (m, 1H), 4.00-3.99 (m, 1H), 3.88 (d, 0.7H), 3.83 (d, 0.3H), 3.20-3.16 (m, 3H), 2.79-2.70 (m, 1H), 2.34-2.13 (m, 3H), 1.84-1.80 (0.3H), 1.60-1.56 (m, 0.7H), 1.10-1.06 (m, 3H).

Example 38

(2R)—N-(4-(Benzylamino)-3,4-dioxo-1-phenylbutan-2-yl)-5-oxo-1-(2-(trifluoromethyl)benzyl)pyrrolidine-2-carboxamide Coupling of 2-hydroxy-3-((R)-5-oxo-1-(2-(trifluoromethyl)benzyl)pyrrolidine-2-carboxamido)-4-phenylbutanoic acid with phenylmethanamine and oxidation of the resulting hydroxyamide intermediate to the corresponding ketoamide.

ESI-MS [M+H]$^+$=552.2.

$^1$H-NMR (500 MHz, DMSO) ~3:2 mixture of diastereomers: δ [ppm]: 9.26-9.25 (m, 1H), 8.64-8.60 (m, 1H), 7.75-7.48 (m, 3H), 7.35-7.16 (m, 11H), 5.27-5.21 (m, 1H), 4.94 (t, 1H), 4.37-4.34 (m, 2H), 4.01-4.00 (m, 1H), 3.89-3.81 (m, 1H), 3.21-3.14 (m, 1H), 2.83-2.72 (m, 1H), 2.36-2.13 (m, 3H), 1.81-1.77 (0.4H), 1.61-1.54 (m, 0.6H).

Example 39

(2R)—N-(4-(Isopropylamino)-3,4-dioxo-1-phenylbutan-2-yl)-5-oxo-1-(2-(trifluoromethyl)benzyl)pyrrolidine-2-carboxamide Coupling of 2-hydroxy-3-((R)-5-oxo-1-(2-(trifluoromethyl)benzyl)pyrrolidine-2-carboxamido)-4-phenylbutanoic acid with propan-2-amine and oxidation of the resulting hydroxyamide intermediate to the corresponding ketoamide.

ESI-MS [M+H]$^+$=504.2.

$^1$H-NMR (500 MHz, DMSO) ~1:1 mixture of diastereomers: δ [ppm]: 8.64-8.60 (m, 2H), 7.77-7.49 (m, 3H), 7.35-7.18 (m, 6H), 5.30-5.23 (m, 1H), 4.99-4.91 (m, 1H), 4.02-3.80 (m, 3H), 3.19-3.16 (m, 1H), 3.79-3.70 (m, 1H), 2.35-2.26 (m, 3H), 1.85-1.81 (0.5H), 1.59-1.55 (m, 0.5H), 1.15-1.12 (m, 6H).

Example 40

(2R)—N-(3,4-Dioxo-1-phenyl-4-(2-(pyridin-2-yl)ethylamino)butan-2-yl)-5-oxo-1-(2-(trifluoromethyl)benzyl)pyrrolidine-2-carboxamide Coupling of 2-hydroxy-3-((R)-5-oxo-1-(2-(trifluoromethyl)benzyl)pyrrolidine-2-carboxamido)-4-phenylbutanoic acid with 2-(pyridin-2-yl)ethanamine and oxidation of the resulting hydroxyamide intermediate to the corresponding ketoamide.

ESI-MS [M+H]$^+$=567.2.

$^1$H-NMR (500 MHz, DMSO) ~1:1 mixture of diastereomers: δ [ppm]: 8.84-8.81 (m, 1H), 8.58-8.54 (m, 1H), 8.51-8.50 (m, 1H), 7.74-7.59 (m, 3H), 7.53-7.48 (m, 1H), 7.34-7.15 (m, 8H), 5.28-5.24 (m, 1H), 4.97-4.90 (m, 1H), 4.00-3.97 (m, 1H), 3.89 (d, 0.7H), 3.83 (d, 0.3H), 3.60-3.46 (m, 2H), 3.15-3.09 (m, 1H), 2.98-2.95 (m, 2H), 2.76-2.65 (m, 1H), 2.34-2.13 (m, 3H), 1.84-1.80 (m, 0.3H), 1.60-1.55 (m, 0.7H).

Example 41

(2R)—N-(3,4-Dioxo-1-phenyl-4-(3-(pyridin-2-yl)propylamino)butan-2-yl)-5-oxo-1-(2-(trifluoromethyl)benzyl)pyrrolidine-2-carboxamide Coupling of 2-hydroxy-3-((R)-5-oxo-1-(2-(trifluoromethyl)benzyl)pyrrolidine-2-carboxamido)-4-phenylbutanoic acid with 3-(pyridin-2-yl)propan-1-amine and oxidation of the resulting hydroxyamide intermediate to the corresponding ketoamide. ESI-MS [M+H]$^+$=581.2.

$^1$H-NMR (500 MHz, DMSO) ~1:1 mixture of diastereomers: δ [ppm]: 8.84-8.83 (m, 1H), 8.61-8.58 (m, 1H), 8.48-8.47 (m, 1H), 7.74-7.58 (m, 3H), 7.52-7.48 (m, 1H), 7.34-7.17 (m, 8H), 5.28-5.25 (m, 1H), 4.98-4.90 (m, 1H), 4.01-3.99 (m, 1H), 3.90 (d, 0.6H), 3.83 (d, 0.4H), 3.23-3.13 (m, 2H), 2.80-2.70 (m, 3H), 2.54-2.52 (m, 1H), 2.33-2.15 (m, 3H), 1.93-1.80 (m, 2.4H), 1.60-1.56 (m, 0.6H).

Example 42

(2R)—N-(4-(Ethylamino)-3,4-dioxo-1-phenylbutan-2-yl)-1-(2-methoxy-6-(trifluoromethyl)benzyl)-5-oxopyrrolidine-2-carboxamide 42.1 2-Hydroxy-3-((R)-1-(2-methoxy-6-(trifluoromethyl)benzyl)-5-oxopyrrolidine-2-carboxamido)-4-phenylbutanoic acid The title compound was prepared in a manner analogous to the synthesis of ethyl 3-((R)-1-benzyl-5-oxopyrrolidine-2-carboxamido)-2-hydroxy-4-phenylbutanoate followed by saponification providing 3-((R)-1-benzyl-5-oxopyrrolidine-2-carboxamido)-2-hydroxy-4-phenylbutanoic acid as described in steps 20.1 and 20.2 of Example 20.

ESI-MS [M+H]$^+$=495.2

42.2 (2R)—N-(4-(Ethylamino)-3,4-dioxo-1-phenylbutan-2-yl)-1-(2-methoxy-6-(trifluoromethyl)benzyl)-5-oxopyrrolidine-2-carboxamide Coupling of 2-hydroxy-3-((R)-1-(2-methoxy-6-(trifluoromethyl)benzyl)-5-oxopyrrolidine-2-carboxamido)-4-phenylbutanoic acid with ethylamine and oxidation of the resulting hydroxyamide intermediate to the corresponding ketoamide.

ESI-MS [M+H]$^+$=520.2.

$^1$H-NMR (500 MHz, DMSO) ~1:1 mixture of diastereomers: δ [ppm]: 8.79-8.70 (m, 1H), 8.32-8.31 (m, 1H), 7.52-7.46 (m, 1H), 7.33-7.16 (m, 7H), 5.45-5.41 (m, 0.5H), 5.20-5.17 (m, 0.5H), 4.93-4.86 (m, 1H), 3.99-3.95 (m, 1H), 3.71 (s, 2H), 3.40 (s, 3H), 3.23-3.13 (m, 2H), 2.76-2.70 (m, 1H), 2.15-2.11 (m, 1H), 2.04-1.96 (m, 1.5H), 1.89-1.80 (m, 1H), 1.41-1.37 (m, 0.5H), 1.11-1.04 (m, 3H).

Example 43

(2R)—N-(3,4-Dioxo-1-phenyl-4-(pyridin-2-ylmethylamino)butan-2-yl)-1-(2-methoxy-6-(trifluoromethyl)benzyl)-5-oxopyrrolidine-2-carboxamide Coupling of 2-hydroxy-3-((R)-1-(2-methoxy-6-(trifluoromethyl)benzyl)-5-oxopyrrolidine-2-carboxamido)-4-phenylbutanoic acid with pyridin-2-ylmethanamine and oxidation of the resulting intermediate hydroxyamide to the corresponding ketoamide.

ESI-MS [M+H]$^+$=583.2.

$^1$H-NMR (500 MHz, DMSO) ~3:4 mixture of diastereomers: δ [ppm]: 9.32-9.22 (m, 1H), 8.53-8.51 (m, 1H), 8.37-8.33 (m, 1H), 7.80-7.74 (m, 1H), 7.53-7.47 (m, 1H), 7.35-7.19 (m, 9H), 5.47-5.41 (m, 0.5H), 5.24-5.19 (m, 0.5H), 4.95-4.87 (m, 1H), 4.50-4.45 (m, 2H), 3.99 (d, 1H), 3.73 (s, 3H), 3.26-3.15 (m, 1H), 2.82-2.61 (m, 1H), 2.18-1.91 (m, 3H), 1.90-1.77 (m, 1H), 1.45-1.39 (m, 1H).

Example 44

(2R)—N-(4-(Benzylamino)-3,4-dioxo-1-phenylbutan-2-yl)-1-(2-methoxy-6-(trifluoromethyl)benzyl)-5-oxopyrrolidine-2-carboxamide Coupling of 2-hydroxy-3-((R)-1-(2-methoxy-6-(trifluoromethyl)benzyl)-5-oxopyrrolidine-2-carboxamido)-4-phenylbutanoic acid with phenylmethanamine and oxidation of the resulting intermediate hydroxyamide to the corresponding ketoamide.

ESI-MS [M+H]⁺=582.3.

¹H-NMR (500 MHz, DMSO) ~1:1 mixture of diastereomers: δ [ppm]: 9.39-9.31 (m, 1H), 8.40-8.36 (m, 1H), 7.53-7.48 (m, 1H), 7.37-7.19 (m, 12H), 5.46-5.43 (m, 0.5H), 5.22-5.18 (m, 0.5H), 4.95-4.88 (m, 1H), 4.39-4.35 (m, 2H), 4.99 (d, 1H), 3.72 (s, 3H), 3.41-3.38 (m, 1H, hidden under solvent signal), 3.22-3.16 (m, 1H), 2.81-2.76 (m, 1H), 2.14-2.11 (m, 1H), 2.04-1.96 (m, 1.5H), 1.87-1.77 (m, 1H). 1.41-1.40 (m, 0.5H).

Example 45

(2R)—N-(3,4-Dioxo-1-phenyl-4-(2-(pyridin-2-yl)ethylamino)butan-2-yl)-5-oxo-1-(2-(trifluoromethoxy)benzyl)pyrrolidine-2-carboxamide 45.1 2-Hydroxy-3-((R)-5-oxo-1-(2-(trifluoromethoxy)benzyl)pyrrolidine-2-carboxamido)-4-phenylbutanoic acid The title compound was prepared in a manner analogous to the synthesis of ethyl 3-((R)-1-benzyl-5-oxopyrrolidine-2-carboxamido)-2-hydroxy-4-phenylbutanoate followed by saponification providing 3-((R)-1-benzyl-5-oxopyrrolidine-2-carboxamido)-2-hydroxy-4-phenylbutanoic acid as described in steps 20.1 and 20.2 of Example 20.

ESI-MS [M+H]⁺=481.1

45.2 (2R)—N-(3,4-Dioxo-1-phenyl-4-(2-(pyridin-2-yl)ethylamino)butan-2-yl)-5-oxo-1-(2-(trifluoromethoxy)benzyl)pyrrolidine-2-carboxamide Coupling of 2-hydroxy-3-((R)-5-oxo-1-(2-(trifluoromethoxy)benzyl)pyrrolidine-2-carboxamido)-4-phenylbutanoic acid with 2-(pyridin-2-yl)ethanamine and oxidation of the resulting intermediate hydroxyamide to the corresponding ketoamide; ESI-MS [M+H]⁺=583.2.

¹H-NMR (500 MHz, DMSO) ~3:2 mixture of diastereomers: δ [ppm]: 8.86-8.84 (m, 1H), 8.59-8.57 (m, 1H), 8.50-8.49 (m, 1H), 7.72-7.69 (m, 1H), 7.46-7.12 (m, 11H), 5.29-5.25 (m, 1H), 4.89-4.82 (m, 1H), 3.93-3.86 (m, 1H), 3.72 (d, 0.6H), 3.65 (d, 0.4H), 3.60-3.49 (m, 2H), 3.17-3.12 (m, 1H), 3.01-2.91 (m, 2H), 2.76-2.70 (m, 1H), 2.33-2.07 (m, 3H), 1.79-1.74 (m, 0.4H), 1.59-1.53 (m, 0.6H).

Example 46

(2R)-1-(2-Chlorobenzyl)-N-(4-(cyclopropylamino)-3,4-dioxo-1-phenylbutan-2-yl)-5-oxopyrrolidine-2-carboxamide 46.1 3-((R)-1-(2-Chlorobenzyl)-5-oxopyrrolidine-2-carboxamido)-2-hydroxy-4-phenylbutanoic acid The title compound was prepared in a manner analogous to the synthesis of ethyl 3-((R)-1-benzyl-5-oxopyrrolidine-2-carboxamido)-2-hydroxy-4-phenylbutanoate followed by saponification providing 3-((R)-1-benzyl-5-oxopyrrolidine-2-carboxamido)-2-hydroxy-4-phenylbutanoic acid as described in steps 20.1 and 20.2 of Example 20.

ESI-MS [M+H]⁺=431.1.

46.2 (2R)-1-(2-Chlorobenzyl)-N-(4-(cyclopropylamino)-3,4-dioxo-1-phenylbutan-2-yl)-5-oxopyrrolidine-2-carboxamide Coupling of 3-((R)-1-(2-chlorobenzyl)-5-oxopyrrolidine-2-carboxamido)-2-hydroxy-4-phenylbutanoic acid with cyclopropylamine and oxidation of the resulting intermediate hydroxyamide to the corresponding ketoamide.

ESI-MS [M+H]⁺=468.2.

¹H-NMR (500 MHz, DMSO) ~3:2 mixture of diastereomers: δ [ppm]: 8.85-8.84 (m, 1H), 8.67-8.66 (m, 1H), 7.48-7.11 (m, 9H), 5.27-5.21 (m, 1H), 4.86-4.78 (m, 1H), 3.99-3.96 (m, 1H), 3.79 (d, 0.6H), 3.70 (d, 0.4H), 3.22-3.19 (m, 1H), 2.82-2.74 (m, 2H), 2.33-2.12 (m, 3H), 1.80-1.76 (m, 0.4H), 1.60-1.56 (m, 0.6H), 0.71-0.55 (m, 4H).

Example 47

(2R)-1-(2-Chlorobenzyl)-N-(4-(ethylamino)-3,4-dioxo-1-phenylbutan-2-yl)-5-oxopyrrolidine-2-carboxamide Coupling of 3-((R)-1-(2-chlorobenzyl)-5-oxopyrrolidine-2-carboxamido)-2-hydroxy-4-phenylbutanoic acid with ethylamine and oxidation of the resulting intermediate hydroxyamide to the corresponding ketoamide.

ESI-MS [M+H]⁺=456.2.

¹H-NMR (500 MHz, DMSO) ~1:1 mixture of diastereomers: δ [ppm]: 8.81-8.79 (m, 1H), 8.67-8.64 (m, 1H), 7.49-7.09 (m, 9H), 5.26-5.24 (m, 1H), 4.83 (d, 0.5H), 4.78 (d, 0.5H), 4.02-3.98 (m, 1H), 3.81-3.35 (m, 2H, hidden under solvent signal), 3.23-3.17 (m, 2H), 2.79-2.73 (m, 1H), 2.32-2.11 (m, 3H), 1.79-1.76 (m, 0.5H), 1.59-1.55 (m, 0.5H), 1.10-1.07 (m, 3H).

Example 48

(2R)—N-(4-(Cyclopropylamino)-3,4-dioxo-1-phenylbutan-2-yl)-1-(2,6-difluorobenzyl)-5-oxopyrrolidine-2-carboxamide 48.1 3-((R)-1-(2,6-Difluorobenzyl)-5-oxopyrrolidine-2-carboxamido)-2-hydroxy-4-phenylbutanoic acid The title compound was prepared in a manner analogous to the synthesis of ethyl 3-((R)-1-benzyl-5-oxopyrrolidine-2-carboxamido)-2-hydroxy-4-phenylbutanoate followed by saponification providing 3-((R)-1-benzyl-5-oxopyrrolidine-2-carboxamido)-2-hydroxy-4-phenylbutanoic acid as described in steps 20.1 and 20.2 of Example 20.

ESI-MS [M+H]⁺=433.1.

48.2 (2R)—N-(4-(Cyclopropylamino)-3,4-dioxo-1-phenylbutan-2-yl)-1-(2,6-difluorobenzyl)-5-oxopyrrolidine-2-carboxamide Coupling of 3-((R)-1-(2,6-difluorobenzyl)-5-oxopyrrolidine-2-carboxamido)-2-hydroxy-4-phenylbutanoic acid with cyclopropylamine and oxidation of the resulting intermediate hydroxyamide to the corresponding ketoamide.

ESI-MS [M+H]⁺=470.2.

¹H-NMR (500 MHz, DMSO) ~3:2 mixture of diastereomers: δ [ppm]: 8.85-8.81 (m, 1H), 8.64-8.60 (m, 1H), 7.43-6.98 (m, 8H), 5.28-5.19 (m, 1H), 4.86-4.76 (m, 1H), 3.97-3.80 (m, 2H), 3.24-3.16 (m, 1H), 2.81-2.72 (m, 2H), 2.25-2.00 (m, 3H), 1.77-1.73 (m, 0.6H), 1.50-1.46 (m, 0.4H), 0.70-0.55 (m, 4H).

Example 49

(2R)-1-(2,6-Difluorobenzyl)-N-(4-(ethylamino)-3,4-dioxo-1-phenylbutan-2-yl)-5-oxopyrrolidine-2-carboxamide Coupling of 3-((R)-1-(2,6-difluorobenzyl)-5-oxopyrrolidine-2-carboxamido)-2-hydroxy-4-phenylbutanoic acid with ethylamine and oxidation of the resulting intermediate hydroxyamide to the corresponding ketoamide.
ESI-MS [M+H]$^+$=458.2.
$^1$H-NMR (500 MHz, DMSO) ~1:1 mixture of diastereomers: δ [ppm]: 8.82-8.77 (m, 1H), 8.64-8.60 (m, 1H), 7.42-6.99 (m, 8H), 5.30-5.19 (m, 1H), 4.84 (d, 0.5H), 4.78 (d, 0.5H), 3.97-3.92 (m, 1H), 3.84-3.81 (m, 1H), 3.23-3.15 (m, 3H), 2.82-2.73 (m, 1H), 2.24-2.00 (m, 3H), 1.77-1.35 (m, 0.5H), 1.49-1.46 (m, 0.5H), 1.14-1.04 (m, 3H).

Example 50

(2R)—N-(4-Amino-3,4-dioxo-1-phenylbutan-2-yl)-5-oxo-1-[2-methoxy-6-(trifluoromethyl)benzyl]pyrrolidine-2-carboxamide Coupling of (R)-5-oxo-1-(2-methoxy-6-trifluoromethylbenzyl)-pyrrolidine-2-carboxylic acid with 3-amino-2-hydroxy-4-phenylbutanamide and oxidation of the resulting hydroxyamide intermediate to the corresponding ketoamide.
ESI-MS [M+H]$^+$=492.1

Example 51

(2R)—N-(4-Amino-3,4-dioxo-1-phenylbutan-2-yl)-5-oxo-1-(2,6-difluorobenzyl)-pyrrolidine-2-carboxamide Coupling of (R)-5-oxo-1-(2,6-difluorobenzyl)-pyrrolidine-2-carboxylic acid with 3-amino-2-hydroxy-4-phenylbutanamide and oxidation of the resulting hydroxyamide intermediate to the corresponding ketoamide.
ESI-MS [M+H]$^+$=430.1

Example 52

(2R)-1-Benzyl-N-(3,4-dioxo-1-phenyl-4-(thiazol-5-ylmethylamino)butan-2-yl)-5-oxopyrrolidine-2-carboxamide Coupling of 3-((R)-1-benzyl-5-oxopyrrolidine-2-carboxamido)-2-hydroxy-4-phenylbutanoic acid with C-thiazol-5-yl-methyl amine (5-thiazolmethylamine) and oxidation of the resulting intermediate hydroxyamide to the corresponding ketoamide in a manner as described above.
ESI-MS [M+H]$^+$=491.1.
$^1$H-NMR (500 MHz DMSO) ~5:3 mixture of diastereomers: δ [ppm]: 9.47-9.46 (m, 1H), 9.00 (s, 1H), 8.71-8.70 (m, 1H), 7.81 (s, 1H), 7.34-7.04 (m, 10H), 5.30-5.21 (m, 1H), 5.87-5.75 (m, 1H), 5.65-4.48 (m, 2H), 3.91-3.90 (m, 1H), 3.54-3.20 (m, 2H), 2.83-2.79 (m, 1H), 2.33-2.01 (m, 3H), 1.74-1.69 (m, 0.3H), 1.57-1.51 (m, 0.5H).

Example 53

(2R)—N-(4-(Benzo[d]thiazol-2-ylmethylamino)-3,4-dioxo-1-phenylbutan-2-yl)-1-benzyl-5-oxopyrrolidine-2-carboxamide Coupling of 3-((R)-1-benzyl-5-oxopyrrolidine-2-carboxamido)-2-hydroxy-4-phenylbutanoic acid with benzo[d]thiazol-2-ylmethanamine hydrochloride and oxidation of the resulting intermediate hydroxyamide to the corresponding ketoamide in a manner as described above.
ESI-MS [M+H]$^+$=541.2.
$^1$H-NMR (500 MHz DMSO), one diastereomer: δ [ppm]: 9.77-9.74 (m, 1H), 8.74-8.73 (m, 1H), 8.08 (d, 1H), 7.98 (d, 1H), 7.55-7.08 (m, 12H), 5.27-5.22 (m, 1H), 4.88-4.79 (m, 2H), 3.93 (m, 1H), 3.57-3.54 (m, 1H), 3.32-3.22 (m, 1H), 2.88-2.83 (m, 1H), 2.28-2.05 (m, 3H), 1.59-1.56 (m, 1H).

Example 54

(2R)-1-Benzyl-N-(4-morpholino-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenylbutanoic acid with morpholine and oxidation of the resulting intermediate hydroxyamide to the corresponding ketoamide in a manner as described above.
ESI-MS [M+H]$^+$=464.2.
$^1$H-NMR (500 MHz DMSO) ~1:2 mixture of diastereomers: δ [ppm]: 8.89-8.88 (m, 1H), 7.34-7.03 (m, 10H), 4.92-4.79 (m, 2H), 3.87-3.86 (m, 1H), 3.63-3.26 (m, 10H), 2.98-2.93 (m, 1H), 2.33-2.11 (m, 3H), 1.72-1.60 (m, 0.3H), 1.57-1.50 (m, 0.6H).

Example 55

(2R)—N-(4-(ethylamino)-3,4-dioxo-1-phenylbutan-2-yl)-5-oxo-1-(4-(trifluoromethyl)benzyl)pyrrolidine-2-carboxamide 55.1 2-Hydroxy-3-((R)-5-oxo-1-(4-(trifluoromethyl)benzyl)pyrrolidine-2-carboxamido)-4-phenylbutanoic acid The title compound was prepared in a manner analogous to the preparation of ethyl 3-((R)-1-benzyl-5-oxopyrrolidine-2-carboxamido)-2-hydroxy-4-phenylbutanoate described in example 20.1 followed by saponification providing 3-((R)-1-benzyl-5-oxopyrrolidine-2-carboxamido)-2-hydroxy-4-phenylbutanoic acid described in example 20.2.
ESI-MS [M+H]$^+$=504.2

55.2 (2R)—N-(4-(ethylamino)-3,4-dioxo-1-phenylbutan-2-yl)-5-oxo-1-(4-(trifluoromethyl)benzyl)pyrrolidine-2-carboxamide Coupling of 2-hydroxy-3-((R)-5-oxo-1-(4-(trifluoromethyl)benzyl)pyrrolidine-2-carboxamido)-4-phenylbutanoic acid with ethylamine and oxidation of the resulting intermediate hydroxyamide to the corresponding ketoamide in a manner as described above.
ESI-MS [M+H]$^+$=490.2.
$^1$H-NMR (500 MHz DMSO) ~1:1 mixture of diastereomers: δ [ppm]: 8.80-8.79 (m, 1H), 8.68-8.67 (m, 1H), 7.72-7.65 (m, 2H), 7.40-7.25 (m, 7H), 5.28-5.23 (m, 1H), 4.91-4.88 (m, 0.5H), 4.79-4.76 (m, 0.5H), 3.95-3.94 (m, 1H), 3.71-3.68 (m, 1H), 3.55-3.52 (m, 1H), 3.25-3.14 (m, 2H), 2.79-2.74 (m, 1H), 2.38-2.05 (m, 3H), 1.83-1.72 (m, 0.5H), 1.65-1.56 (m, 0.5H), 1.14-1.05 (m, 3H).

Example 56

(2R)-1-Benzyl-N-(4-(cyclohexylamino)-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenylbutanoic acid with cyclohexylamine and oxidation of the resulting intermediate hydroxyamide to the corresponding ketoamide in a manner as described above.

ESI-MS [M+H]⁺=476.2.

¹H-NMR (400 MHz DMSO), ~4:3 mixture of diastereomers: δ [ppm]: 8.64-8.57 (m, 2H), 7.36-7.05 (m, 8H), 7.16-7.14 (m, 1H), 7.05-7.03 (m, 1H), 5.31-5.21 (m, 1H), 4.86 (d, 0.6H), 4.77 (d, 0.4H), 3.93-3.89 (m, 1H), 3.63-3.51 (m, 1.5H), 3.40-3.32 (m, 0.5H), 3.23-3.17 (m, 1H), 2.82-2.76 (m, 1H), 2.36-2.02 (m, 3H), 1.74-1.59 (m, 6H), 1.37-1.27 (m, 5H).

Example 57

(2R)—N-(4-(2-Benzoylhydrazinyl)-3,4-dioxo-1-phenylbutan-2-yl)-1-benzyl-5-oxopyrrolidine-2-carboxamide Coupling of 3-((R)-1-benzyl-5-oxopyrrolidine-2-carboxamido)-2-hydroxy-4-phenylbutanoic acid with benzoylhydrazine and oxidation of the resulting intermediate hydroxyamide to the corresponding ketoamide in a manner as described above.

ESI-MS [M+H]⁺=513.2.

¹H-NMR (500 MHz DMSO), ~1:1 mixture of diastereomers: δ [ppm]: 10.86 (d, 1H), 10.59 (d, 1H), 8.70-8.67 (m, 1H), 7.92-7.91 (m, 2H), 7.1-7.09 (m, 13H), 5.34-5.24 (m, 1H), 4.87 (d, 0.5H), 4.78 (d, 0.5H), 3.94-3.93 (m, 1H), 3.58 (d, 1H), 3.44-3.28 (d, 1H, hidden under solvent signal), 2.87-2.82 (m, 1H), 2.40-2.33 (m, 3H), 1.83-1.77 (m, 0.5H), 1.66-1.59 (m, 0.5H).

Example 58

(2R)—N-(4-(Cyclopropylamino)-3,4-dioxo-1-phenylbutan-2-yl)-5-oxo-1-(4-(trifluoromethyl)benzyl)pyrrolidine-2-carboxamide Coupling of 2-hydroxy-3-((R)-5-oxo-1-(4-(trifluoromethyl)benzyl)pyrrolidine-2-carboxamido)-4-phenylbutanoic acid with cyclopropanamine and oxidation of the resulting intermediate hydroxyamide to the corresponding ketoamide in a manner as described above.

ESI-MS [M+H]⁺=502.2.

¹H-NMR (500 MHz DMSO), ~2:1 mixture of diastereomers: δ [ppm]: 8.84-8.83 (m, 1H), 8.69-8.67 (m, 1H), 7.71-7.65 (m, 2H), 7.40-7.23 (m, 7H), 5.23-5.20 (m, 1H), 4.89 (d, 0.6H), 4.77 (d, 0.3H), 3.95-3.92 (m, 1H), 3.70-3.52 (m, 1H), 3.22-3.19 (m, 1H), 2.82-2.74 (m, 2H), 2.34-2.09 (m, 3H), 1.79-1.74 (m, 0.3H), 1.60-1.56 (m, 0.6H), 0.70-0.62 (m, 4H).

Example 59

(2R)-1-Benzyl-N-(3,4-dioxo-1-phenyl-4-(thiazol-2-ylmethylamino)butan-2-yl)-5-oxopyrrolidine-2-carboxamide Coupling of 3-((R)-1-benzyl-5-oxopyrrolidine-2-carboxamido)-2-hydroxy-4-phenylbutanoic acid with 2-aminomethylthiazole and oxidation of the resulting intermediate hydroxyamide to the corresponding ketoamide in a manner as described above.

ESI-MS [M+H]⁺=491.2.

¹H-NMR (500 MHz DMSO), ~5:3 mixture of diastereomers: δ [ppm]: 9.64-9.64 (m, 1H), 8.73-8.72 (m, 1H), 7.76-7.66 (m, 2H), 7.3-7.05 (m, 10H), 5.31-5.24 (m, 1H), 4.89-4.57 (m, 3H), 3.93-3.92 (m, 1H), 3.55 (d, 1H), 3.24 (d, 1H), 2.86-2.82 (m, 1H), 2.33-1.98 (m, 3H), 1.77-1.72 (m, 0.4H), 1.58-1.57 (m, 0.7H).

Example 60

(2R)-1-Benzyl-N-(3,4-dioxo-1-phenyl-4-(thiophen-2-ylmethylamino)butan-2-yl)-5-oxopyrrolidine-2-carboxamide Coupling of 3-((R)-1-benzyl-5-oxopyrrolidine-2-carboxamido)-2-hydroxy-4-phenylbutanoic acid with 2-thiophenemethylamine and oxidation of the resulting intermediate hydroxyamide to the corresponding ketoamide in a manner as described above.

ESI-MS [M+H]⁺=490.2.

¹H-NMR (500 MHz DMSO), ~2:1 mixture of diastereomers: δ [ppm]: 9.44-9.42 (m, 1H), 8.72-8.69 (m, 1H), 7.44-6.98 (m, 13H), 5.32-5.22 (m, 1H), 4.91-4.75 (m, 1H), 4.54 (s, 2H), 3.94-3.92 (m, 1H), 3.57-3.41 (m, 1H), 3.27-3.21 (m, 1H), 2.85-2.79 (m, 1H), 2.36-2.02 (m, 3H), 1.81-1.69 (m, 0.3H), 1.63-1.49 (m, 0.6H).

Example 61

(2R)—N-(4-(Cyclopropylamino)-3,4-dioxo-1-phenylbutan-2-yl)-1-(2,6-dichlorobenzyl)-5-oxopyrrolidine-2-carboxamide 61.1 3-((R)-1-(2,6-Dichlorobenzyl)-5-oxopyrrolidine-2-carboxamido)-2-hydroxy-4-phenylbutanoic acid The title compound was prepared in a manner analogous to the preparation of ethyl 3-((R)-1-benzyl-5-oxopyrrolidine-2-carboxamido)-2-hydroxy-4-phenylbutanoate described in example 20.1 followed by saponification providing 3-((R)-1-benzyl-5-oxopyrrolidine-2-carboxamido)-2-hydroxy-4-phenylbutanoic acid described in example 20.2.

ESI-MS [M+H]⁺=492.1

61.2 (2R)—N-(4-(Cyclopropylamino)-3,4-dioxo-1-phenylbutan-2-yl)-1-(2,6-dichlorobenzyl)-5-oxopyrrolidine-2-carboxamide Coupling of 3-((R)-1-(2,6-dichlorobenzyl)-5-oxopyrrolidine-2-carboxamido)-2-hydroxy-4-phenylbutanoic acid with cyclopropanamine and oxidation of the resulting intermediate hydroxyamide to the corresponding ketoamide in a manner as described above.

ESI-MS [M+H]⁺=502.1.

¹H-NMR (500 MHz DMSO), ~1:1 mixture of diastereomers: δ [ppm]: 8.85-8.81 (m, 1H), 8.53-8.49 (m, 1H), 7.47-7.23 (m, 8H), 5.38-5.33 (m, 0.5H), 5.23-5.21 (m, 0.5H), 5.00-4.92 (m, 1H), 4.11-4.08 (m, 1H), 3.80-3.75 (m, 1H), 3.22-3.16 (m, 1H), 2.82-2.72 (m, 2H), 2.22-1.92 (m, 3H), 1.81-1.78 (m, 0.5H), 1.47-1.43 (m, 0.5H), 0.73-0.63 (m, 4H).

Example 62

(2R)-1-(2,6-Dichlorobenzyl)-N-(4-(ethylamino)-3,4-dioxo-1-phenylbutan-2-yl)-5-oxopyrrolidine-2-carboxamide Coupling of 3-((R)-1-(2,6-dichlorobenzyl)-5-oxopyrrolidine-2-carboxamido)-2-hydroxy-4-phenylbutanoic acid with ethylamine and oxidation of the resulting intermediate hydroxyamide to the corresponding ketoamide in a manner as described above.

ESI-MS [M+H]⁺=490.1.

¹H-NMR (500 MHz DMSO), ~1:1 mixture of diastereomers: δ [ppm]: 8.82-8.79 (m, 1H), 8.54-8.49 (m, 1H), 7.47-7.24 (m, 8H), 5.38 (vs, 0.5H), 5.23 (vs, 0.5H), 5.01-4.92 (m, 1H), 4.11-4.05 (m, 1H), 3.81-3.76 (m, 1H), 3.22-3.17 (m, 3H), 2.75 (vs, 1H), 2.21-1.93 (m, 3H), 1.81-1.79 (m, 0.5H), 1.44-1.43 (m, 0.5H), 1.22-1.09 (m, 3H).

Example 63

(2R)-1-Benzyl-N-(3,4-dioxo-1-phenyl-4-(pyridin-4-ylmethylamino)butan-2-yl)-5-oxopyrrolidine-2-carboxamide Coupling of 3-((R)-1-benzyl-5-oxopyrrolidine-2-carboxamido)-2-hydroxy-4-phenylbutanoic acid with 4-(aminomethyl)pyridine and oxidation of the resulting intermediate hydroxyamide to the corresponding ketoamide in a manner as described above.

ESI-MS [M+H]⁺=485.2.

¹H-NMR (500 MHz DMSO), ~4:1 mixture of diastereomers: δ [ppm]: 9.41-9.40 (m, 1H), 8.75-8.74 (m, 1H), 8.52-8.51 (m, 2H), 7.33-7.04 (m, 12H), 5.28-5.21 (m, 1H), 4.86 (d, 0.2H), 4.76 (d, 0.8H), 4.40 (s, 2H), 3.92-3.90 (m, 1H), 3.55-3.52 (m, 1H), 2.23-3.21 (m, 1H), 2.87-2.82 (m, 1H), 2.31-2.02 (m, 3H), 1.74-1.69 (m, 0.2H), 1.56-1.55 (m, 0.8H).

Example 64

(2R)-1-Benzyl-N-(4-(oxazol-2-ylmethylamino)-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenylbutanoic acid with oxazol-2-ylmethylamine and oxidation of the resulting intermediate hydroxyamide to the corresponding ketoamide in a manner as described above.

ESI-MS [M+H]⁺=475.2.

Example 65

(2R)-1-Benzyl-N-(3,4-dioxo-1-phenyl-4-(phenylamino)butan-2-yl)-5-oxopyrrolidine-2-carboxamide Coupling of 3-((R)-1-benzyl-5-oxopyrrolidine-2-carboxamido)-2-hydroxy-4-phenylbutanoic acid with aniline and oxidation of the resulting intermediate hydroxyamide to the corresponding ketoamide in a manner as described above.

ESI-MS [M+H]⁺=470.2.

¹H-NMR (500 MHz DMSO), ~1:1 mixture of diastereomers: δ [ppm]: 10.70 (s, 1H), 8.83 (d, 1H), 7.84 (s, 2H), 7.40-6.99 (m, 13H), 5.28-5.27 (m, 1H), 4.87 (s, 0.5H), 4.75 (d, 0.5H), 3.92-3.90 (m, 1H), 3.55-3.29 (m, 2H), 2.92-2.87 (m, 1H), 2.33-2.02 (m, 3H), 1.76-1.71 (m, 0.5H), 1.58-1.55 (m, 0.5H).

Example 66

(2R)—N-(4-(Benzo[d][1,3]dioxol-5-ylmethylamino)-3,4-dioxo-1-phenylbutan-2-yl)-1-benzyl-5-oxopyrrolidine-2-carboxamide Coupling of 3-((R)-1-benzyl-5-oxopyrrolidine-2-carboxamido)-2-hydroxy-4-phenylbutanoic acid with 3,4-methylenedioxybenzylamine and oxidation of the resulting intermediate hydroxyamide to the corresponding ketoamide in a manner as described above.

ESI-MS [M+H]⁺=528.3.

¹H-NMR (500 MHz DMSO), ~1:1 mixture of diastereomers: δ [ppm]: 9.27 (d, 1H), 8.72-8.6 (m, 1H), 7.32-6.78 (m, 13H), 6.00 (2xs, 2H), 5.29-2.18 (m, 1H), 4.85 (d, 0.5H), 4.75 (d, 0.5H), 4.33-4.31 (m, 2H), 3.91-3.89 (m, 1H), 3.56 (d, 0.5H), 3.38-3.35 (m, 0.5H, hidden under solvent signal), 3.23-3.20 (m, 1H), 2.84-2.79 (m, 1H), 2.29-2.04 (m, 3H), 1.73-1.68 (m, 0.5H), 1.55-1.51 (m, 0.5H).

Example 67

(2R)-1-Benzyl-N-(4-(4-fluorobenzylamino)-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenylbutanoic acid with 4-fluorobenzylamine and oxidation of the resulting intermediate hydroxyamide to the corresponding ketoamide in a manner as described above.

ESI-MS [M+H]⁺=502.2.

¹H-NMR (500 MHz DMSO), ~3:2 mixture of diastereomers: δ [ppm]: 9.36-9.35 (m, 1H), 8.72 (s, 1H), 7.34-7.04 (m, 14H), 5.29-5.22 (m, 1H), 4.86 (d, 0.6H), 4.76 (d, 0.4H), 4.36 (s, 2H), 3.92-3.90 (m, 1H), 3.55-3.52 (m, 1H), 3.24-3.21 (m, 1H), 2.85-2.80 (m, 1H), 2.33-2.05 (m, 3H), 1.74-1.69 (m, 0.4H), 1.55-1.53 (m, 0.6H).

Example 68

(2R)-1-Benzyl-N-(3,4-dioxo-1-phenyl-4-(4-(trifluoromethyl)benzylamino)butan-2-yl)-5-oxopyrrolidine-2-carboxamide Coupling of 3-((R)-1-benzyl-5-oxopyrrolidine-2-carboxamido)-2-hydroxy-4-phenylbutanoic acid with 4-(trifluoromethyl)benzylamine and oxidation of the resulting intermediate hydroxyamide to the corresponding ketoamide in a manner as described above.

ESI-MS [M+H]⁺=552.3.

¹H-NMR (500 MHz DMSO), ~1:1 mixture of diastereomers: δ [ppm]: 9.44-9.42 (m, 1H), 8.74-8.72 (m, 1H), 7.72-7.71 (m, 2H), 7.53-7.50 (2H), 7.33-7.03 (m, 10H), 5.28-5.18 (m, 1H), 4.86 (d, 0.5H), 4.75 (d, 0.5H), 4.46-4.45 (m, 2H), 3.91-3.89 (m, 1H), 3.54-3.51 (m, 1H), 3.24-3.21 (m, 1H), 2.85-2.81 (m, 1H), 2.29-2.02 (m, 3H), 1.72-1.67 (m, 0.5H), 1.57-1.48 (m, 0.5H).

Example 69

(2R)-1-Benzyl-N-(3,4-dioxo-1-phenyl-4-(((R)-tetrahydrofuran-2-yl)methylamino)-butan-2-yl)-5-oxopyrrolidine-2-carboxamide Coupling of 3-((R)-1-benzyl-5-oxopyrrolidine-2-carboxamido)-2-hydroxy-4-phenylbutanoic acid with (R)-(−)-tetrahydrofurfurylamine using 2-(7-aza-1H-benzotriazole-1-yl)-1,1,3,3-tetramethyluronium hexafluorophosphate (HATU) and N,N-diisopropylethylamine (DIPEA) followed by oxidation of the resulting intermediate hydroxyamide to the corresponding ketoamide in a manner as described above.

ESI-MS [M+H]⁺=478.2.

¹H-NMR (500 MHz DMSO), ~1:1 mixture of diastereomers: δ [ppm]: 8.77-8.65 (m, 2H), 7.37-7.04 (m, 10H), 5.33-5.23 (m, 1H), 4.86 (d, 0.5H), 4.77 (d, 0.5H), 3.97-3.90 (m, 2H), 3.80-3.75 (m, 1H), 3.66-3.60 (m, 1H), 3.54 (d, 0.5H), 3.36-3.35 (m, 0.5H, hidden under solvent signal), 3.27-3.18 (m, 3H), 2.82-2.76 (m, 1H), 2.34-2.16 (m, 2H), 2.18-2.04 (m, 1H), 1.92-1.72 (m, 3H), 1.61-1.56 (m, 2H).

Example 70

(2R)-1-Benzyl-N-(3,4-dioxo-1-phenyl-4-(((S)-tetrahydrofuran-2-yl)methylamino)-butan-2-yl)-5-oxopyrrolidine-2-carboxamide Coupling of 3-((R)-1-benzyl-5-oxopyrrolidine-2-carboxamido)-2-hydroxy-4-phenylbutanoic acid with (S)-(+)-tetrahydrofurfurylamine using HATU and DIPEA followed by oxidation of the resulting intermediate hydroxyamide to the corresponding ketoamide in a manner as described above.

ESI-MS [M+H]$^+$=478.2.

$^1$H-NMR (500 MHz DMSO), only one diastereomer: δ [ppm]: 8.75-8.66 (m, 2H), 7.37-7.15 (m, 10H), 5.26-5.22 (m, 1H), 4.86 (d, 1H), 3.98-3.90 (m, 2H), 3.80-3.76 (m, 1H), 3.66-3.62 (m, 1H), 3.53 (d, 1H), 3.33-3.16 (m, 3H), 2.81-2.76 (m, 1H), 2.27-2.23 (m, 2H), 2.12-2.02 (m, 1H), 1.93-1.78 (m, 3H), 1.61-1.52 (m, 2H).

Example 71

(2R)-1-Benzyl-N-(3,4-dioxo-1-phenyl-4-(2-(thiophen-3-yl)ethylamino)butan-2-yl)-5-oxopyrrolidine-2-carboxamide Coupling of 3-((R)-1-benzyl-5-oxopyrrolidine-2-carboxamido)-2-hydroxy-4-phenylbutanoic acid with 2-(thiophen-3-yl)ethanamine hydrochloride using HATU and DIPEA followed by oxidation of the resulting intermediate hydroxyamide to the corresponding ketoamide in a manner as described above.

ESI-MS [M+H]$^+$=504.2.

$^1$H-NMR (500 MHz DMSO), only one diastereomer (absolute configuration not determined): δ [ppm]: 8.90 (s, 1H), 8.67 (s, 1H), 7.47-7.04 (m, 13H), 5.27 (m, 1H), 4.89.4.86 (m, 1H), 3.94-3.93 (m, 1H), 3.56-3.42 (m, 3H, hidden under solvent signal), 3.19-3.17 (m, 1H), 2.86-2.75 (m, 3H), 2.31-2.06 (m, 3H), 1.58-1.57 (m, 1H).

Example 72

(2R)-1-Benzyl-N-(4-(furan-2-ylmethylamino)-3,4-dioxo-1-phenylbutan-2-yl)-5-oxopyrrolidine-2-carboxamide Coupling of 3-((R)-1-benzyl-5-oxopyrrolidine-2-carboxamido)-2-hydroxy-4-phenylbutanoic acid with furan-2-ylmethanamine using HATU and DIPEA followed by oxidation of the resulting intermediate hydroxyamide to the corresponding ketoamide in a manner as described above.

ESI-MS [M+H]$^+$=474.2.

$^1$H-NMR (500 MHz DMSO)), ~3:1 mixture of diastereomers: δ [ppm]: 9.26 (d, 1H), 8.70 (d, 1H), 7.59 (s, 1H), 7.35-7.04 (m, 10H), 6.41 (s, 1H), 6.28 (s, 1H), 5.27-5.21 (m, 1H), 4.86 (d, 0.7H), 4.76 (d, 0.3H), 4.42-4.32 (m, 2H), 3.91-3.89 (m, 1H), 3.53 (d, 1H), 3.23-3.20 (m, 1H), 2.83-2.78 (m, 1H), 2.31-2.01 (m, 3H), 1.74-1.69 (m, 0.3H), 1.55-1.54 (m, 0.7H).

Example 73

(2R)-1-Benzyl-N-(4-(2-benzylhydrazinyl)-3,4-dioxo-1-phenylbutan-2-yl)-5-oxopyrrolidine-2-carboxamide•Trifluoroacetic acid

73.1 (2R)-1-benzyl-N-(4-(2-benzylhydrazinyl)-3-hydroxy-4-oxo-1-phenylbutan-2-yl)-5-oxopyrrolidine-2-carboxamide Coupling of 3-((R)-1-benzyl-5-oxopyrrolidine-2-carboxamido)-2-hydroxy-4-phenylbutanoic acid with benzylhydrazine dihydrochloride analogous to step 1.1 of Example 1 provided the corresponding hydroxy amide.

ESI-MS [M+H]$^+$=501.3.

73.2 tert-Butyl 1-benzyl-2-(3-((R)-1-benzyl-5-oxopyrrolidine-2-carboxamido)-2-hydroxy-4-phenylbutanoyl)hydrazinecarboxylate NaOH (1 M in water, 2 mL, 2 mmol) and di-tert-butyldicarbonate (Boc$_2$O) (144 mg, 0.659 mmol) were added to a mixture of (2R)-1-benzyl-N-(4-(2-benzylhydrazinyl)-3-hydroxy-4-oxo-1-phenylbutan-2-yl)-5-oxopyrrolidine-2-carboxamide (300 mg, 0.599 mmol) in t-BuOH (6 mL). After stirring overnight water (20 mL) was added and the mixture was extracted with EtOAc. The combined organic layers were washed with saturated aqueous NaHCO$_3$ solution, water and dried (MgSO$_4$). Purification by flash column chromatography (gradient 1-10% MeOH in DCM) provided the title compound (130 mg, 36%).

ESI-MS [M+Na]$^+$=623.3, [M-Boc+H]$^+$=501.2.

73.3 tert-butyl 1-Benzyl-2-(3-((R)-1-benzyl-5-oxopyrrolidine-2-carboxamido)-2-oxo-4-phenylbutanoyl)hydrazinecarboxylate IBX (189 mg, 0.303 mmol, 45 wt %) was added a solution of tert-butyl 1-benzyl-2-(3-((R)-1-benzyl-5-oxopyrrolidine-2-carboxamido)-2-hydroxy-4-phenylbutanoyl)-hydrazinecarboxylate (130 mg, 0.216 mmol) in DMSO (3 mL). After stirring overnight saturated aqueous NaHCO$_3$ solution (15 mL) and water (15 mL) were added. The mixture was extracted with EtOAc, the combined organic layers were washed with saturated aqueous NaHCO$_3$ solution, water and dried (MgSO$_4$). Purification by flash column chromatography (gradient 1-10% MeOH in DCM) provided the title compound (110 mg, 85%).

ESI-MS [M+Na]$^+$=621.3, [M-Boc+H]$^+$=499.2.

73.4 (2R)-1-Benzyl-N-(4-(2-benzylhydrazinyl)-3,4-dioxo-1-phenylbutan-2-yl)-5-oxopyrrolidine-2-carboxamide•Trifluoroacetic acid Trifluoroacetic acid (TFA) (0.2 mL, 2.60 mmol) was added to a solution of tert-butyl 1-benzyl-2-(3-((R)-1-benzyl-5-oxopyrrolidine-2-carboxamido)-2-oxo-4-phenylbutanoyl)hydrazinecarboxylate (110 mg, 0.184 mmol) in DCM (2 mL). After stirring for 4 h the solvent was removed in vacuo and the residue obtained was triturated with diethyl ether providing the title compound (48 mg, 43%).

ESI-MS [M+H]$^+$=499.2.

Example 74

(2R)—N-(4-(Cyclopropylamino)-3,4-dioxo-1-phenylbutan-2-yl)-1-(2-methoxy-6-(trifluoromethyl)benzyl)-5-oxopyrrolidine-2-carboxamide

74.1 Ethyl 3-(tert-butoxycarbonylamino)-2-hydroxy-4-phenylbutanoate

Et$_3$N (6 ml, 43.00 mmol) was added to suspension of 4-ethoxy-3-hydroxy-4-oxo-1-phenylbutan-2-aminium chloride (4.7 g, 18.10 mmol) in THF (50 mL) at 10° C. A solution of di-tert-butyldicarbonate (4.2 g, 19.24 mmol) in THF (30 mL) was added within 10 min at 10° C. The reaction mixture was allowed to warm to room temperature and stirred overnight. The solvent was reduced in vacuo and the residue was extracted with DCM. The combined organic layers were washed with saturated aqueous NaCl solution and dried over MgSO$_4$. Purification by flash column chromatography (DCM/MeOH) provided the title compound (4.5 g, 77%).
ESI-MS [M+H]$^+$=224.1.

74.2 Tert-butyl 4-(cyclopropylamino)-3-hydroxy-4-oxo-1-phenylbutan-2-ylcarbamate EDC (8.3 g, 43.3 mmol), HOBT (6.6 g, 43.1 mmol) and Et$_3$N (7 ml, 50.2 mmol) were added to a mixture of 3-(tert-butoxycarbonylamino)-2-hydroxy-4-phenylbutanoic acid (10.6 g, 35.9 mmol) and cyclopropylamine (3.3 ml, 47.6 mmol) in DCM (300 mL) at 5° C. The reaction mixture was allowed to warm to room temperature and stirred overnight. After cooling to 5° C. more cyclopropylamine (2 ml, 28.5 mmol), EDC (5 g, 26.1 mmol), HOBT (4 g, 26.1 mmol) and Et$_3$N (3.5 ml, 25.1 mmol) were added, the mixture was allowed to warm to room temperature and the stirring was continued overnight. DCM (300 mL) was added, followed by washing with 0.5 M aqueous HCl solution, brine and drying with MgSO$_4$. The crude product was recrystallized from methyl-tert-butylether, the crystals obtained were washed with n-pentane and dried providing the title compound (10.2 g, 85%).
ESI-MS [M-Boc+H]$^+$=231.1.

74.3 3-Amino-N-cyclopropyl-2-hydroxy-4-phenylbutanamide Hydrochloride

HCl (4 M in dioxane, 16 mL, 64.00 mmol) was added dropwise to a solution of tert-butyl 4-(cyclopropylamino)-3-hydroxy-4-oxo-1-phenylbutan-2-ylcarbamate (7.5 g, 22.43 mmol) in DCM (130 mL). After stirring for 5 h additional HCl (4 M in dioxane, 5 mL, 20.00 mmol) was added and the stirring was continued overnight. The solvent was reduced in vacuo and methyl-tert-butyl-ether (200 mL) was added. The precipitate obtained was filtered, washed with methyl-tert-butyl-ether and n-pentane and dried providing the title compound (5.8 g, 96%).
ESI-MS [M+H]$^+$=236.1.

74.4 (2R)—N-(4-(Cyclopropylamino)-3-hydroxy-4-oxo-1-phenylbutan-2-yl)-1-(2-methoxy-6-(trifluoromethyl)benzyl)-5-oxopyrrolidine-2-carboxamide DIPEA (0.8 ml, 4.58 mmol) was added to a mixture of (R)-1-(2-methoxy-6-(trifluoromethyl)benzyl)-5-oxopyrrolidine-2-carboxylic acid (234 mg, 0.74 mmol) and 3-amino-N-cyclopropyl-2-hydroxy-4-phenylbutanamide hydrochloride (200 mg, 0.74 mmol) in DCM (50 mL). After stirring for 10 min HATU (337 mg, 0.89 mmol) was added and the stirring was continued overnight. The reaction mixture was diluted with DCM and water was added. The organic layer was separated and the aqueous layer was extracted with DCM. The combined organic layers were washed with saturated aqueous NaHCO$_3$ solution, saturated aqueous NaCl solution and dried over MgSO$_4$. Removal of the solvent in vacuo provided the title compound (498 mg, 95%, ca. 75% purity).
ESI-MS [M+H]$^+$=534.3.

74.5 (2R)—N-(4-(Cyclopropylamino)-3,4-dioxo-1-phenylbutan-2-yl)-1-(2-methoxy-6-(trifluoromethyl)benzyl)-5-oxopyrrolidine-2-carboxamide (2R)—N-(4-(cyclopropylamino)-3-hydroxy-4-oxo-1-phenylbutan-2-yl)-1-(2-methoxy-6-(trifluoromethyl)benzyl)-5-oxopyrrolidine-2-carboxamide (498 mg, 95%, ca. 75% purity) was oxidized to the corresponding ketoamide as described in step 1.2 of Example 1.
ESI-MS [M+H]$^+$=532.2.
$^1$H-NMR (500 MHz DMSO)), ~1:1 mixture of diastereomers: δ [ppm]: 8.87-8.80 (m, 1H), 8.35-8.32 (m, 1H), 7.53-7.48 (m, 1H), 7.35-7.18 (m, 7H), 5.46-5.42 (m, 0.5H), 5.20-5.16 (m, 0.5H), 4.96-4.88 (m, 1H), 4.01-3.96 (m, 1H), 3.72 (s, 3H), 3.22-3.16 (m, 1H), 2.84-2.71 (m, 2H), 2.16-1.81 (m, 4H), 1.42-1.19 (m, 1H), 0.72-0.62 (m, 4H).

Example 75

(2R)-1-Benzyl-N-(3,4-dioxo-1-phenyl-4-(2-phenylethylamino)butan-2-yl)-5-oxopyrrolidine-2-carboxamide Coupling of 3-((R)-1-benzyl-5-oxopyrrolidine-2-carboxamido)-2-hydroxy-4-phenyl-butanoic acid with 2-phenylethyl-1-amine and oxidation of the resulting hydroxyamide intermediate to the corresponding ketoamide.

Example 76

(2R)-1-benzyl-N-(4-(ethoxyamino)-3,4-dioxo-1-phenylbutan-2-yl)-5-oxopyrrolidine-2-carboxamide The building block (R)-1-Benzyl-5-oxo-pyrrolidine-2-carboxylic acid which was used in the following example is commercially available.

76.1 Ethyl 3-((R)-1-benzyl-5-oxopyrrolidine-2-carboxamido)-2-hydroxy-4-phenylbutanoate The reaction was carried out in analogy to reaction step 20.1 of Example 20 by reacting (R)-1-benzyl-5-oxopyrrolidine-2-carboxylic acid and 4-ethoxy-3-hydroxy-4-oxo-1-phenylbutan-2-aminium chloride. ESI-MS [M+H]$^+$=425.2.

76.2 3-((R)-1-benzyl-5-oxopyrrolidine-2-carboxamido)-2-hydroxy-4-phenylbutanoic acid Ethyl 3-((R)-1-benzyl-5-oxopyrrolidine-2-carboxamido)-2-hydroxy-4-phenylbutanoate was saponified in analogy to reaction step 20.2 of example 20 ESI-MS [M+H]$^+$=397.2.

76.3 (2R)-1-benzyl-N-(4-(ethoxyamino)-3-hydroxy-4-oxo-1-phenylbutan-2-yl)-5-oxopyrrolidine-2-carboxamide The reaction was carried out in analogy to reaction step 20.3 of Example 20 by reacting 3-((R)-1-benzyl-5-oxopyrrolidine-2-carboxamido)-2-hydroxy-4-phenylbutanoic acid with O-ethylhydroxylamine hydrochloride using HATU (1.2 equivalents) as coupling reagent and DIPEA (6.8 equivalents) as base. ESI-MS [M+H]$^+$=440.2

76.4 (2R)-1-benzyl-N-(4-(ethoxyamino)-3,4-dioxo-1-phenylbutan-2-yl)-5-oxopyrrolidine-2-carboxamide IBX (2-iodoxybenzoic acid 432 mg, 0.694 mmol) was added to a solution of (2R)-1-benzyl-N-(4-(ethoxyamino)-3-hydroxy-4-oxo-1-phenylbutan-2-yl)-5-oxopyrrolidine-2-carboxamide (218 mg, 0.496 mmol) in DMSO (2 ml). After stirring for 2 h at room temperature more IBX (123 mg, 0.198 mmol) was added and the stirring was continued overnight. Saturated aqueous NaHCO$_3$ solution was added and the reaction mixture was diluted with water and dichloromethane. The precipitate formed was filtered off, the organic layer was separated and the aqueous layer extracted with dichloromethane. The combined organic layers were washed with water and dried (MgSO$_4$). The solvent was removed in vacuo, the resulting residue was redissolved in a small amount of dichloromethane and diethylether was added. The white precipitate formed was filtered, washed with diethylether and dried in vacuo. The crude product was dissolved in dichloromethane and treated with three drops of aqueous HCl (4M in dioxane). Removal of the solvent provided the title compound (8.2 mg, 0.015 mmol, 3.02% yield). ESI-MS [M+H]$^+$= 438.2

Example 77

(2R)-1-benzyl-N-(4-(isopropoxyamino)-3,4-dioxo-1-phenylbutan-2-yl)-5-oxopyrrolidine-2-carboxamide The building block (R)-1-Benzyl-5-oxo-pyrrolidine-2-carboxylic acid used in the following example is commercially available.

77.1 Ethyl 3-((R)-1-benzyl-5-oxopyrrolidine-2-carboxamido)-2-hydroxy-4-phenylbutanoate The reaction was carried out in analogy to reaction step 20.1 by reacting (R)-1-benzyl-5-oxopyrrolidine-2-carboxylic acid and 4-ethoxy-3-hydroxy-4-oxo-1-phenylbutan-2-aminium chloride. ESI-MS [M+H]$^+$=425.2.

77.2 3-((R)-1-benzyl-5-oxopyrrolidine-2-carboxamido)-2-hydroxy-4-phenylbutanoic acid Ethyl 3-((R)-1-benzyl-5-oxopyrrolidine-2-carboxamido)-2-hydroxy-4-phenylbutanoate was saponified in analogy to reaction step 20.2 ESI-MS [M+H]$^+$=397.2.

77.3 (2R)-1-benzyl-N-(3-hydroxy-4-(isopropoxyamino)-4-oxo-1-phenylbutan-2-yl)-5-oxopyrrolidine-2-carboxamide The reaction can be carried out in analogy to reaction step 20.3 by reacting 3-((R)-1-benzyl-5-oxopyrrolidine-2-carboxamido)-2-hydroxy-4-phenylbutanoic acid with O-isopropylhydroxylamine.

77.4 (2R)-1-benzyl-N-(4-(isopropoxyamino)-3,4-dioxo-1-phenylbutan-2-yl)-5-oxopyrrolidine-2-carboxamide (2R)-1-benzyl-N-(3-hydroxy-4-(isopropoxyamino)-4-oxo-1-phenylbutan-2-yl)-5-oxopyrrolidine-2-carboxamide can be oxidized in analogy to reaction step 20.4.

Example 78

(2R)-1-benzyl-N-(4-(cyclopropylmethoxyamino)-3,4-dioxo-1-phenylbutan-2-yl)-5-oxopyrrolidine-2-carboxamide The building block (R)-1-Benzyl-5-oxo-pyrrolidine-2-carboxylic acid is commercially available.

78.1 Ethyl 3-((R)-1-benzyl-5-oxopyrrolidine-2-carboxamido)-2-hydroxy-4-phenylbutanoate The reaction was carried out in analogy to reaction step 20.1 by reacting (R)-1-benzyl-5-oxopyrrolidine-2-carboxylic acid and 4-ethoxy-3-hydroxy-4-oxo-1-phenylbutan-2-aminium chloride. ESI-MS [M+H]$^+$=425.2.

78.2 3-((R)-1-benzyl-5-oxopyrrolidine-2-carboxamido)-2-hydroxy-4-phenylbutanoic acid Ethyl 3-((R)-1-benzyl-5-oxopyrrolidine-2-carboxamido)-2-hydroxy-4-phenylbutanoate was saponified in analogy to reaction step 20.2. ESI-MS [M+H]$^+$=397.2.

78.3 (2R)-1-benzyl-N-(4-(cyclopropylmethoxyamino)-3-hydroxy-4-oxo-1-phenylbutan-2-yl)-5-oxopyrrolidine-2-carboxamide The reaction can be carried out in analogy to reaction step 20.3 by reacting 3-((R)-1-benzyl-5-oxopyrrolidine-2-carboxamido)-2-hydroxy-4-phenylbutanoic acid with O-(cyclopropylmethyl)hydroxylamine.

78.4 (2R)-1-benzyl-N-(4-(cyclopropylmethoxyamino)-3,4-dioxo-1-phenylbutan-2-yl)-5-oxopyrrolidine-2-carboxamide (2R)-1-benzyl-N-(4-(cyclopropylmethoxyamino)-3-hydroxy-4-oxo-1-phenylbutan-2-yl)-5-oxopyrrolidine-2-carboxamide can be oxidized in analogy to reaction step 20.4.

Example 79

(2R)-1-(2-fluorobenzyl)-N-(4-(methoxyamino)-3,4-dioxo-1-phenylbutan-2-yl)-5-oxopyrrolidine-2-carboxamide The building block (R)-1-(2-fluorobenzyl)-5-oxopyrrolidine-2-carboxylic acid was prepared in analogy to the procedure published by S. Marchalin et al., *Synthetic Communications* 28(19), 3619 (1998),

79.1 Ethyl 3-((R)-1-(2-fluorobenzyl)-5-oxopyrrolidine-2-carboxamido)-2-hydroxy-4-phenylbutanoate The reaction was carried out in analogy to reaction step 20.1 by reacting (R)-1-(2-fluorobenzyl)-5-oxopyrrolidine-2- carboxylic acid and 4-ethoxy-3-hydroxy-4-oxo-1-phenylbutan-2-aminium chloride. ESI-MS [M+H]$^+$=443.2.

79.2 3-((R)-1-(2-fluorobenzyl)-5-oxopyrrolidine-2-carboxamido)-2-hydroxy-4-phenylbutanoic acid Ethyl 3-((R)-1-(2-fluorobenzyl)-5-oxopyrrolidine-2-carboxamido)-2-hydroxy-4-phenylbutanoate was saponified in analogy to reaction step 20.2. ESI-MS [M+H]$^+$=415.2.

79.3 (2R)-1-(2-fluorobenzyl)-N-(3-hydroxy-4-(methoxyamino)-4-oxo-1-phenylbutan-2-yl)-5-oxopyrrolidine-2-carboxamide The reaction can be carried out in analogy to reaction step 20.3 by reacting 3-((R)-1-(2-fluorobenzyl)-5-oxopyrrolidine-2-carboxamido)-2-hydroxy-4-phenylbutanoic acid with O-methylhydroxylamine.

79.4 (2R)-1-(2-fluorobenzyl)-N-(4-(methoxyamino)-3,4-dioxo-1-phenylbutan-2-yl)-5-oxopyrrolidine-2-carboxamide (2R)-1-(2-fluorobenzyl)-N-(3-hydroxy-4-(methoxyamino)-4-oxo-1-phenylbutan-2-yl)-5-oxopyrrolidine-2-carboxamide can be oxidized in analogy to reaction step 20.4.

Example 80

(2R)-1-(2-chlorobenzyl)-N-(4-(methoxyamino)-3,4-dioxo-1-phenylbutan-2-yl)-5-oxopyrrolidine-2-carboxamide The building block (R)-1-(2-chlorobenzyl)-5-oxopyrrolidine-2-carboxylic acid was prepared in analogy to the procedure published by S. Marchalin et al., *Synthetic Communications* 28(19), 3619 (1998),

80.1 Ethyl 3-((R)-1-(2-chlorobenzyl)-5-oxopyrrolidine-2-carboxamido)-2-hydroxy-4-phenylbutanoate The reaction was carried out in analogy to reaction step 20.1 by reacting (R)-1-(2-chlorobenzyl)-5-oxopyrrolidine-2-carboxylic acid and 4-ethoxy-3-hydroxy-4-oxo-1-phenylbutan-2-aminium chloride. ESI-MS [M+H]$^+$=459.2.

80.2 3-((R)-1-(2-chlorobenzyl)-5-oxopyrrolidine-2-carboxamido)-2-hydroxy-4-phenylbutanoic acid Ethyl 3-((R)-1-(2-chlorobenzyl)-5-oxopyrrolidine-2-carboxamido)-2-hydroxy-4-phenylbutanoate was saponified in analogy to reaction step 20.2. ESI-MS [M+H]$^+$=431.1.

80.3 (2R)-1-(2-chlorobenzyl)-N-(3-hydroxy-4-(methoxyamino)-4-oxo-1-phenylbutan-2-yl)-5-oxopyrrolidine-2-carboxamide The reaction can be carried out in analogy to reaction step 20.3 by reacting 3-((R)-1-(2-chlorobenzyl)-5-oxopyrrolidine-2-carboxamido)-2-hydroxy-4-phenylbutanoic acid with O-methylhydroxylamine.

80.4 (2R)-1-(2-chlorobenzyl)-N-(4-(methoxyamino)-3,4-dioxo-1-phenylbutan-2-yl)-5-oxopyrrolidine-2-carboxamide (2R)-1-(2-chlorobenzyl)-N-(3-hydroxy-4-(methoxyamino)-4-oxo-1-phenylbutan-2-yl)-5-oxopyrrolidine-2-carboxamide can be oxidized in analogy to reaction step 20.4.

Example 81

(2R)—N-(4-(cyclopropylamino)-3,4-dioxo-1-phenylbutan-2-yl)-1-(2-fluorobenzyl)-5-oxopyrrolidine-2-carboxamide The building block (R)-1-(2-fluorobenzyl)-5-oxopyrrolidine-2-carboxylic acid was prepared in analogy to the procedure published by S. Marchalin et al., *Synthetic Communications* 28(19), 3619 (1998),

81.1 Ethyl 3-((R)-1-(2-fluorobenzyl)-5-oxopyrrolidine-2-carboxamido)-2-hydroxy-4-phenylbutanoate The reaction was carried out in analogy to reaction of step 20.1 by reacting (R)-1-(2-fluorobenzyl)-5-oxopyrrolidine-2-carboxylic acid and 4-ethoxy-3-hydroxy-4-oxo-1-phenylbutan-2-aminium chloride. ESI-MS [M+H]$^+$=443.2.

81.2 3-((R)-1-(2-fluorobenzyl)-5-oxopyrrolidine-2-carboxamido)-2-hydroxy-4-phenylbutanoic acid Ethyl 3-((R)-1-(2-fluorobenzyl)-5-oxopyrrolidine-2-carboxamido)-2-hydroxy-4-phenylbutanoate was saponified in analogy to reaction step 20.2. ESI-MS [M+H]$^+$=415.2.

81.3 (2R)—N-(4-(cyclopropylamino)-3-hydroxy-4-oxo-1-phenylbutan-2-yl)-1-(2-fluorobenzyl)-5-oxopyrrolidine-2-carboxamide The reaction was carried out in analogy to reaction step 20.3 by reacting 3-((R)-1-(2-fluorobenzyl)-5-oxopyrrolidine-2-carboxamido)-2-hydroxy-4-phenylbutanoic acid with cyclopropanamine using HATU (1.2 equivalents) as coupling reagent and DIPEA (3 equivalents) as base. ESI-MS [M+H]$^+$=454.2.

81.4 (2R)—N-(4-(cyclopropylamino)-3,4-dioxo-1-phenylbutan-2-yl)-1-(2-fluorobenzyl)-5-oxopyrrolidine-2-carboxamide (2R)—N-(4-(cyclopropylamino)-3-hydroxy-4-oxo-1-phenylbutan-2-yl)-1-(2-fluorobenzyl)-5-oxopyrrolidine-2-carboxamide was oxidized in analogy to reaction step 20.4. The reaction mixture was stirred overnight. Water was added, the precipitate formed was filtered, washed with water and dried in vacuo. The residue obtained was redissolved in dichloromethane, a few drops of HCl (4M in dioxane) and a few drops of diethylether were added. The resulting precipitate was filtered, washed with diethylether and dried in vacuo providing the title compound. ESI-MS [M+H]$^+$=452.2.

$^1$H-NMR (500 MHz, DMSO)—4:3 mixture of diastereomers: δ [ppm]: 8.89-8.82 (m, 1H), 8.74-8.65 (m, 1H), 7.41-7.06 (m, 9H), 5.30-5.22 (m, 1H), 4.87-4.75 (m, 1H), 4.03-3.95 (m, 1H), 3.75-3.60 (m, 1H), 3.30-3.19 (m, 1H), 2.87-2.74 (m, 2H), 2.34-2.09 (m, 3H), 1.77-1.75 (m, 0.5H), 1.60-1.55 (m, 0.6H), 0.76-0.58 (m, 4H).

Biological investigation of inhibition of calpain and cathepsins

The following solutions and buffers were employed:
HBS (for 40 ml): 800 µl 1M HEPES; 2.16 ml 100 mM KCl; 4.8 ml 1M NaCl; 3.59 ml 5% glucose; 60 µl 1M MgSO$_4$; 400 µl 100 mM Na pyruvate, 28.19 ml water; pH 7.2-7.5.
lysis buffer (for 20 ml): 400 µl 1M Tris pH 8.2; 2.74 ml 1M NaCl; 520 µl 0.5M EDTA; 2 ml 10% triton X-100; 0.8 ml (=1:25) CompletePlus (1 tablet/2 ml H$_2$O); 200 µl 100 mM Pefabloc; 13.34 ml water, pH 8.2.
TBST (10×) (for 1 l): 100 mM Tris (12.1 g); 1.5M NaCl (87 g); 1% Tween 20 (10 g), adjusted to pH 8.

I. Enzyme Inhibition In Vitro:

Testing for blockade of the corresponding enzymic activities was carried out by means of kinetic fluorescence assays (excitation 390 nm, emission 460 nm).

Apparent Ki values were calculated from the experimentally determined IC$_{50}$ values by the Cheng-Prussoff relation assuming a reversible competitive enzyme inhibition. The Km values of the substrates used under the assay conditions indicated above were: 90 µM (Z-Phe-Arg-AMC, cathepsin B), 10 µM (Z-Gly-Pro-Arg-AMC, cathepsin K), 2 µM (Z-Phe-Arg-AMC, cathepsin L), and 30 µM (Z-Val-Val-Arg-AMC, cathepsin S).

The indicated Ki values are averages of the inhibition constants calculated on the basis of 2 to 4 independent dose-effect plots.

The following assays were used:

1. Calpain I:
   20 nM calpain-I—isolated from human erythrocytes (Calbiochem #208713), 100 µM Suc-Leu-Tyr-AMC (Bachem #I-1355) as substrate in buffer with 62 mM imidazole, 0.3 mM CaCl$_2$, 0.10% CHAPS, 0.05% BSA, 1 mM DTT at pH 7.3 and room temperature.

2. Cathepsin B:
   0.25 nM cathepsin B—isolated from human liver (Calbiochem #219362), 100 µM Z-Phe-Arg-AMC (Bachem #I-1160) as substrate 50 mM MES, 2 mM EDTA, 0.05% Brij 35, 2.5 mM L-cysteine, pH 6.0, room temperature.

3. Cathepsin K:
   3 nM cathepsin K—activated from recombinant human procathepsin K from *E. coli* (Calbiochem #342001), 10 µM Z-Gly-Pro-Arg-AMC (Biomol #P-142) as substrate in 50 mM MES, 2 mM EDTA, 0.05% Brij 35, 2.5 mM L-cysteine, pH 6.0, room temperature.

4. Cathepsin L:
   1 nM cathepsin L—isolated from human liver (Calbiochem #219402), 2 µM Z-Phe-Arg-AMC (Bachem #I-1160) as substrate in 50 mM MES, 2 mM EDTA, 0.05% Brij 35, 2.5 mM L-cysteine, pH 6.0, room temperature.

5. Cathepsin S:
   0.5 nM recombinant human cathepsin S from *E. coli* (Calbiochem #219343), 20 µM Z-Val-Val-Arg-AMC (Bachem #I-1540) as substrate in 50 mM MES, 2 mM EDTA, 0.05% Brij 35, 2.5 mM L-cysteine, pH 6.0, room temperature.

The results of the in vitro determination are indicated in Table 1. The following abbreviations are used in Table 1:

In the "Calpain activity" column, +++ stands for a calpain Ki (Ki(calpain)) of <50 nM, ++ means 50 nM≦Ki(Calpain)<100 nM and + means 100 nM≦Ki(Calpain)<600 nM.

The "Sel. cat. B" column indicates the Ki(cathepsin B)/Ki (calpain) ratio. In this connection, +++ means a Ki(cathepsin B)/Ki(calpain) ratio of >30, ++ means 10<Ki(cathepsin B)/Ki(calpain)≦30 and + means 5<Ki(cathepsin B)/Ki(calpain)≦10.

The "Sel. cat. K" column indicates the Ki(cathepsin K)/Ki (calpain) ratio. In this connection, +++ means a Ki(cathepsin K)/Ki(calpain) ratio of >30, ++ means 10<Ki(cathepsin B)/Ki(calpain)≦30 and + means 5<Ki(cathepsin K)/Ki (calpain)≦10.

The "Sel. cat. L" column indicates the Ki(cathepsin L)/Ki (calpain) ratio. In this connection, +++ means a Ki(cathepsin L)/Ki(calpain) ratio of >30, ++ means 10<Ki(cathepsin B)/Ki (calpain)≦30 and + means 5<Ki(cathepsin L)/Ki(calpain) ≦10.

The "Sel. cat. S" column indicates the Ki(cathepsin S)/Ki (calpain) ratio. In this connection, +++ means a Ki(cathepsin S)/Ki(calpain) ratio of >100, ++ means 30<Ki(cathepsin B)/Ki(calpain)≦100 and + means 10<Ki(cathepsin S)/Ki (calpain)≦30.

TABLE 1

| Example | Calpain activity | Sel cat. B | Sel cat. K | Sel cat. L | Sel cat. S | human cytCL | cyno cytCL |
|---|---|---|---|---|---|---|---|
| 1 | +++ | ++ | ++ | ++ | +++ | | |
| 2 | + | | ++ | + | | | |
| 3 | +++ | ++ | +++ | ++ | +++ | | |
| 4 | ++ | ++ | | | + | | |
| 5 | ++ | ++ | ++ | ++ | ++ | | |
| 6 | +++ | + | +++ | | ++ | | |
| 8 | ++ | +++ | ++ | ++ | +++ | | |
| 9 | ++ | | +++ | +++ | +++ | | |
| 10 | +++ | +++ | | ++ | | | |
| 11 | +++ | ++ | +++ | | ++ | | |
| 12 | +++ | | + | | + | | |
| 13 | + | + | +++ | | ++ | | |
| 14 | ++ | ++ | | ++ | ++ | | |
| 15 | | ++ | + | + | + | | |
| 16 | + | ++ | +++ | ++ | + | | |
| 17 | ++ | ++ | +++ | +++ | +++ | | |
| 18 | + | +++ | | | | | |
| 19 | +++ | ++ | | ++ | | | |
| 20 | ++ | +++ | +++ | ++ | +++ | ++ | ++ |
| 21 | + | +++ | +++ | +++ | ++ | ++ | ++ |
| 25 | + | +++ | +++ | +++ | ++ | ++ | ++ |
| 26 | + | +++ | +++ | ++ | | | |
| 27 | + | +++ | +++ | +++ | ++ | ++ | ++ |
| 28 | + | +++ | +++ | +++ | ++ | ++ | ++ |
| 31 | + | | ++ | | ++ | | |
| 32 | ++ | ++ | + | | ++ | | |
| 33 | ++ | ++ | ++ | | ++ | | |
| 36 | ++ | ++ | +++ | +++ | +++ | ++ | ++ |
| 37 | + | ++ | ++ | +++ | + | ++ | ++ |
| 42 | | ++ | ++ | ++ | | ++ | ++ |
| 43 | + | +++ | +++ | +++ | ++ | ++ | ++ |
| 46 | ++ | ++ | +++ | +++ | +++ | | |
| 47 | + | +++ | +++ | +++ | ++ | | |
| 48 | + | +++ | | ++ | | | |
| 49 | + | +++ | | ++ | | | |
| 50 | +++ | +++ | +++ | +++ | +++ | + | + |
| 51 | ++ | ++ | +++ | ++ | +++ | | |
| 52 | + | | | | | | |
| 53 | ++ | | | | | | |
| 54 | + | | | | | | |
| 55 | + | | | | | | |
| 56 | ++ | ++ | + | | ++ | | |
| 57 | ++ | + | ++ | | +++ | | |
| 58 | + | + | + | | ++ | | |
| 59 | + | +++ | +++ | ++ | +++ | | |
| 60 | ++ | +++ | +++ | ++ | +++ | | |
| 61 | + | + | +++ | +++ | +++ | | |
| 62 | + | ++ | ++ | ++ | ++ | | |
| 63 | ++ | +++ | +++ | +++ | +++ | | |
| 64 | + | ++ | +++ | ++ | +++ | | |
| 65 | ++ | +++ | +++ | +++ | +++ | | |
| 66 | ++ | +++ | ++ | ++ | +++ | | |
| 67 | +++ | +++ | +++ | +++ | +++ | | |
| 68 | + | +++ | +++ | ++ | +++ | | ++ |
| 69 | + | | | | | | |
| 70 | ++ | | | | | | |
| 71 | +++ | | | | | | |

TABLE 1-continued

| Example | Calpain activity | Sel cat. B | Sel cat. K | Sel cat. L | Sel cat. S | human cytCL | cyno cytCL |
|---|---|---|---|---|---|---|---|
| 72 | ++ | | | | | | |
| 74 | + | | | | | | |

II. Spectrin Molt-4 Assay to Determine Cellular Calpain Inhibition:

The assay design and procedure were as disclosed by Chatterjee; BMC 1998, 6, pp. 509-522; the $EC_{50}$ values are calculated from the percentage degradation of spectrin as a function of the dose.

Cell culture conditions: the molt-4 cells are maintained in RPMI 1640+Glutamax™ I medium (Gibco) with 10% FCS and 50 µg/ml gentamicin at 37° C., 5% $CO_2$ and split 1:15 twice a week.

Preparation of the molt-4 cells: the cells are washed, counted and taken up in a concentration of $2 \times 10^7$ cells/ml in HBS buffer.

Dilution of the inhibitor substances: all the inhibitors are dissolved in a concentration of $10^{-2}$ M in DMSO. The stock solution is then diluted 1:15 in DMSO (=$6.67 \times 10^{-4}$ M). Thereafter the stock solution diluted 1:15 is diluted 1:4 in DMSO in two steps (=$1.67 \times 10^{-4}$ M and $4.17 \times 10^{-5}$ M). Thereafter, these three solutions are further diluted 1:50 in HBS buffer to give solutions having a concentration of $1.33 \times 10^{-5}$ M, $3.36 \times 10^{-6}$ M and $8.34 \times 10^{-7}$ M.

Test mixture: for each mixture, $10^6$ cells (see above) are introduced into a 1.5 ml Eppendorf tube. To these are added in each case 150 µl of the diluted substances (final conc. $10^{-5}$ M; $2.5 \times 10^{-6}$ M and $6.25 \times 10^{-7}$ M) and thoroughly mixed. A negative control and a positive control are used as controls. In this case, initially only 150 µl of HBS buffer is pipetted onto the cells. All the mixtures are incubated at 37° C., 5% $CO_2$ in an incubator for 10 mM Thereafter, except for the negative control, in each case $CaCl_2$ (final conc. 5 mM) and ionomycin (final conc. 5 µM) are added, thoroughly mixed and incubated at 37° C., 5% $CO_2$ in an incubator for 30 mM Then centrifuge at 700 g for 5 mM The supernatants are discarded and the pellets are taken up in 20 µl of lysis buffer. The mixtures are subsequently placed on ice for 30-60 mM and then centrifuged at 15000 g for 15 mM The supernatants are removed and put into new Eppendorf tubes. The protein determination is then carried out thereon, e.g. with a MicroB CA assay (Pierce).

SDS-PAGE electrophoresis: 10 µg of total protein from each mixture are put into a new Eppendorf tube and, after pipetting in the same volume of 2× Tris-glycine SDS sample buffer (Invitrogen) and 1/10 volume of 1M DTT, thoroughly mixed and heated at 95° C. for 15 mM The solutions are briefly centrifuged and loaded onto a 6% SDS gel (Invitrogen). The gel is run at 100V with 1× Tris-glycine laemmli buffer (Biomol) until the lower band of the marker has reached the base of the gel.

Western blotting: the gel is removed from the apparatus and blotted onto nitrocellulose in 1× Tris-glycine transfer buffer (Invitrogen)+20% methanol with 1.5 A/cm² in a Fast-Blot chamber (Biometra) for 30 mM The nitrocellulose filter is removed, briefly washed in TBST buffer and blocked in TBST/5% milk powder for 1 h at RT (room temperature). The blocked nitrocellulose is then incubated with an anti-spectrin Ab (Chemicon) (1:10000 in TBST/5% milk powder) at RT for 3 h or at 4° C. overnight. The nitrocellulose is washed 3× in TBST buffer. It is then incubated with anti-mouse IgG (POD) antibody (Sigma) (1:10000 in TBST/5% milk powder) at room temperature for 1 h.

The nitrocellulose is then washed 5× in TBST buffer. In the next step, 5 ml of prepared solution of the SuperSignal® West Pico chemiluminescence substrate (Pierce) are put on the filter and incubated for 5 mM The nitrocellulose is then taken out of the solution, gently dabbed dry and inserted into a development folder film (Tropix). A digital image analysis system (VersaDoc, Biorad) is used to record and quantify the ECL (QuantityOne), and the percentage degradation of spectrin is calculated from the data. Graph-pad prism is used to fit the percentage spectrum degradation as a function of the dose to a sigmoidal dose-effect plot (top fixed at 100% and bottom at 0%), and the EC 50% is calculated.

III Assay for Determining Cytosolic Clearance of Compounds of Formula I:

For comparison purposes data measured with human liver cytosol were contrasted with those obtained with cynomolgus monkey liver cytosol.

0.5 µM of a compound to be tested was incubated with 1 mg/ml of human liver cytosol as well as monkey liver cytosol at 37° C. in 0.5 M of phosphate buffer at pH 7.5 while shaking (commercial sources: female cynomolgus liver cytosol from Tebu bio, human liver cytosol from BDgentest).

In each case aliquots of 65 µl were taken after 0, 5, 10 and 15 min and transferred into wells of a wellplate which were immediately filled with 130 µl of ethanol to stop the reaction. The samples were kept frozen until analysis on a LC/MS/MS system (Applied Biosystems SCIEX 4000).

Read out parameters were the loss of parent compounds, from which the half life periods ($T_{1/2}$) were calculated from. Based on these data the parameters cytosolic clearance (cytCL), scaled clearance (CLs) and predicted clearance (CLp) were calculated using the following equations:

$$cytCL = (\ln 2/T_{1/2}) \times [\text{cytosolic protein}] \times 1000 \quad 1)$$

$$CLs = cytCL \times [\text{cytosolic yield}]/1{,}000{,}000 \times 60 \quad 2)$$

$$CLp = (CLs + \text{hepatic plasma flow})/\text{hepatic plasma flow}/CLs \quad 3)$$

To assess the stability of the compounds tested the clearance ranges were adjusted to the hepatic plasma flow of the different species according to the following scheme:

stable=from 0 to about ⅓ of the hepatic plasma flow;
moderately stable=from about ⅓ to about ⅔ of the hepatic plasma flow;
instable=more than ⅔ of the hepatic plasma flow.

Based on this adjustment the following qualifiers were assigned to evaluate the cytosolic stabilities of the compounds tested:

| cytCL | symbol | human | cynomolgus monkey (cyno) |
|---|---|---|---|
| stable | ++ | 0-14 µl/min/mg | 0-18 µl/min/mg |
| moderately stable | + | 14-70 µl/min/mg | 18-90 µl/min/mg |
| instable | − | >70 µl/min/mg | >90 µl/min/mg |

The cytCL data obtained this way for the inventive compounds are depicted in Table 1 above.

The invention claimed is:
1. A carboxamide compound of the formula I

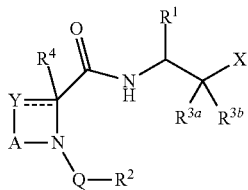

in which --- indicates a single bond or, if $R^4$ is absent, indicates a double bond;

$R^1$ is hydrogen, $C_1$-$C_{10}$-alkyl, $C_2$-$C_{10}$-alkenyl, $C_2$-$C_{10}$-alkynyl, where the last 3 radicals mentioned may be partly or completely halogenated and/or have 1, 2 or 3 substituents $R^{1a}$,
  $C_3$-$C_7$-cycloalkyl, $C_3$-$C_7$-cycloalkyl-$C_1$-$C_4$-alkyl, where a $CH_2$ group in the cycloalkyl moiety of the last two radicals mentioned may be replaced by O, NH, or S, or two adjacent C atoms may form a double bond, where the cycloalkyl moiety may further have 1, 2, 3 or 4 radicals $R^{1b}$,
  aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, where aryl and hetaryl in the last 6 radicals mentioned may be unsubstituted or carry 1, 2, 3 or 4 identical or different radicals $R^{1c}$; where
    $R^{1a}$ is selected independently of one another from OH, SH, COOH, CN, OCH$_2$COOH, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, COOR$^{a1}$, CONR$^{a2}$R$^{a3}$, SO$_2$NR$^{a2}$R$^{a3}$, —NR$^{a2}$—SO$_2$—R$^{a4}$, NR$^{a2}$—CO—R$^{a5}$, SO$_2$—R$^{a4}$ and NR$^{a6}$R$^{a7}$;
    $R^{1b}$ is selected independently of one another from OH, SH, COOH, CN, OCH$_2$COOH, halogen, phenyl which optionally has 1, 2 or 3 substituents $R^{1d}$, $C_1$-$C_6$-alkyl, $C_1$-$C_6$-alkoxy, $C_1$-$C_6$-alkylthio, where the alkyl moieties in the last 3 substituents mentioned may be partly or completely halogenated and/or have 1, 2 or 3 substituents $R^{1a}$,
    COOR$^{b1}$, CONR$^{b2}$R$^{b3}$, SO$_2$NR$^{b2}$R$^{b3}$, NR$^{b2}$SO$_2$R$^{b4}$, NR$^{b2}$—CO—R$^{b5}$, SO$_2$—R$^{b4}$ and NR$^{b6}$R$^{b7}$,
    in addition two $R^{1b}$ radicals may together form a $C_1$-$C_4$-alkylene group, or 2 $R^{1b}$ radicals bonded to adjacent C atoms of cycloalkyl may form together with the carbon atoms to which they are bonded also a benzene ring;
    $R^{1c}$ is selected independently of one another from OH, SH, halogen, NO$_2$, NH$_2$, CN, COOH, OCH$_2$COOH, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the alkyl moieties in the last 4 substituents mentioned may be partly or completely halogenated and/or have 1, 2 or 3 substituents $R^{1a}$, $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 $R^{1b}$ radicals, and where 1 or 2 CH$_2$-groups in the cycloalkyl moiety may be replaced by O, NH or S,
    aryl, hetaryl, O-aryl, O—CH$_2$-aryl, where the last three radicals mentioned are unsubstituted in the aryl moiety or may carry 1, 2, 3 or 4 radicals $R^{1d}$, COOR$^{c1}$, CONR$^{c2}$R$^{c3}$, SO$_2$NR$^{c2}$R$^{c3}$, NR$^{c2}$—SO$_2$—R$^{c4}$, NR$^{c2}$—CO—R$^{c5}$, SO$_2$—R$^{c4}$, —(CH$_2$)$_p$—NR$^{c6}$R$^{c7}$ with p=0, 1, 2, 3, 4, 5 or 6 and
    O—(CH$_2$)$_q$—NR$^{c6}$R$^{c7}$ with q=2, 3, 4, 5 or 6; where
      $R^{a1}$, $R^{b1}$ and $R^{c1}$ are independently of one another H, $C_1$-$C_6$-alkyl, $C_1$-$C_6$-haloalkyl, $C_1$-$C_6$-alkyl which has 1, 2 or 3 substituents selected from the group consisting of OH, SH, COOH, CN, OCH$_2$COOH, $C_1$-$C_6$-alkoxy, $C_1$-$C_6$-haloalkoxy, $C_3$-$C_7$-cycloalkyloxy, $C_1$-$C_6$-alkylthio and $C_1$-$C_6$-haloalkylthio", or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$,
      $R^{a2}$, $R^{b2}$ and $R^{c2}$ are independently of one another H, $C_1$-$C_6$-alkyl, $C_1$-$C_6$-haloalkyl, $C_1$-$C_6$-alkyl which has 1, 2 or 3 substituents selected from the group consisting of OH, SH, COOH, CN, OCH$_2$COOH, $C_1$-$C_6$-alkoxy, $C_1$-$C_6$-haloalkoxy, $C_3$-$C_7$-cycloalkyloxy, $C_1$-$C_6$-alkylthio and $C_1$-$C_6$-haloalkylthio, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, and
      $R^{a3}$, $R^{b3}$ and $R^{c3}$ are independently of one another H, $C_1$-$C_6$-alkyl, $C_1$-$C_6$-haloalkyl, $C_1$-$C_6$-alkyl which has 1, 2 or 3 substituents selected from the group consisting of OH, SH, COOH, CN, OCH$_2$COOH, $C_1$-$C_6$-alkoxy, $C_1$-$C_6$-haloalkoxy, $C_3$-$C_7$-cycloalkyloxy, $C_1$-$C_6$-alkylthio and $C_1$-$C_6$-haloalkylthio, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, or the two radicals $R^{a2}$ and $R^{a3}$, or $R^{b2}$ and $R^{b3}$ or $R^{c2}$ and $R^{c3}$ form together with the N atom a 3 to 7-membered, optionally substituted nitrogen heterocycle which may optionally have 1, 2 or 3 further different or identical heteroatoms from the group of O, N, S as ring members,
      $R^{a4}$, $R^{b4}$ and $R^{c4}$ are independently of one another $C_1$-$C_6$-alkyl, $C_1$-$C_6$-haloalkyl, $C_1$-$C_6$-alkyl which has 1, 2 or 3 substituents selected from the group consisting of OH, SH, COOH, CN, OCH$_2$COOH, $C_1$-$C_6$-alkoxy, $C_1$-$C_6$-haloalkoxy, $C_3$-$C_7$-cycloalkyloxy, $C_1$-$C_6$-alkylthio and $C_1$-$C_6$-haloalkylthio, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, and
      $R^{a5}$, $R^{b5}$ and $R^{c5}$ have independently of one another one of the meanings mentioned for $R^{a1}$, $R^{b1}$ and $R^{c1}$,
      $R^{a6}$, $R^{b6}$ and $R^{c6}$ are independently of one another H, $C_1$-$C_6$-alkyl, $C_1$-$C_6$-alkoxy, $C_1$-$C_6$-haloalkyl, $C_1$-$C_6$-alkyl which has 1, 2 or 3 substituents selected from the group consisting of OH, SH, COOH, CN, OCH$_2$COOH, $C_1$-$C_6$-alkoxy, $C_1$-$C_6$-haloalkoxy, $C_3$-$C_7$-cycloalkyloxy, $C_1$-$C_6$-alkylthio and $C_1$-$C_6$-haloalkylthio", or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, aryl, hetaryl, O-aryl, $OCH_2$-aryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$— (aryl-$C_1$-$C_4$-alkyl) or $SO_2$—(hetaryl-$C_1$-$C_4$-alkyl), where aryl and hetaryl in the last 18 radicals mentioned are unsubstituted or have 1, 2 or 3 substituents $R^{1d}$, and $R^{a7}$, $R^{b7}$ and $R^{c7}$ are independently of one another H, $C_1$-$C_6$-alkyl, $C_1$-$C_6$-haloalkyl, $C_1$-$C_6$-alkyl which has 1, 2 or 3 substituents selected from the group consisting of OH, SH, COOH, CN, $OCH_2COOH$, $C_1$-$C_6$-alkoxy, $C_1$-$C_6$-haloalkoxy, $C_3$-$C_7$-cycloalkyloxy, $C_1$-$C_6$-alkylthio and $C_1$-$C_6$-haloalkylthio, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, or the two radicals $R^{a6}$ and $R^{a7}$ or $R^{b6}$ and $R^{b7}$ or $R^{c6}$ and $R^{c7}$ form together with the N atom a 3 to 7-membered, optionally substituted nitrogen heterocycle which may optionally have 1, 2 or 3 further different or identical heteroatoms from the group of O, N and S as ring members, or two radicals $R^{1b}$ or $R^{1c}$ bonded to adjacent C atoms form together with the C atoms to which they are bonded a 4-, 5-, 6- or 7-membered, optionally substituted carbocycle or an optionally substituted heterocycle which has 1, 2 or 3 different or identical heteroatoms from the group of O, N and S as ring members;

$R^{1d}$ is selected from halogen, OH, SH, $NO_2$, COOH, $C(O)NH_2$, CHO, CN, $NH_2$, $OCH_2COOH$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—$C(O)C_1$-$C_6$-alkyl, and $SO_2$—$C_1$-$C_6$-alkyl or two radicals $R^{1d}$ bonded to adjacent carbon atoms may together form a moiety —O-Alk"-O—, where Alk" is linear $C_1$-$C_2$-alkandiyl, which is unsubstituted or wherein 1 or 2 hydrogen atoms may be replaced by fluorine, chlorine or methyl;

$R^2$ is phenyl, which is unsubstituted or carries 1, 2, 3 or 4 identical or different radicals $R^{2b}$ where $R^{2b}$ has one of the meanings indicated for $R^{1c}$;

$R^{3a}$ and $R^{3b}$ are independently of one another hydroxy or $C_1$-$C_4$-alkoxy, or together with the carbon atom to which they are bonded are C=O or C=$NR^3$; or $R^{3a}$ and $R^{3b}$ together form a moiety S-Alk-S, O-Alk-S or O-Alk-O, wherein Alk is linear $C_2$-$C_5$-alkandiyl, which may be unsubstituted or substituted with 1, 2, 3 or 4 radicals selected from $C_1$-$C_4$-alkyl or halogen;

$R^3$ is H, $C_1$-$C_6$-alkyl, $C_1$-$C_6$-alkoxy, $C_2$-$C_6$-alkenyl, $C_3$-$C_6$-cycloalkyl, $C_3$-$C_6$-cycloalkyl-$C_1$-$C_4$-alkyl, $C_2$-$C_6$-alkenyloxy, $C_3$-$C_6$-cycloalkyloxy or $C_3$-$C_6$-cycloalkyl-$C_1$-$C_4$-alkyloxy;

$R^4$ is absent or indicates hydrogen;

A is C=O;

Q is $CH_2$ or $CH_2CH_2$;

X is hydrogen or a radical of the formulae C(=O)—O—$R^{x1}$, C(=O)—$NR^{x2}R^{x3}$, C(=O)—N($R^{x4}$)—($C_1$-$C_6$-alkylene)-$NR^{x2}R^{x3}$ or C(=O)—N($R^{x4}$)$NR^{x2}R^{x3}$, in which $R^{x1}$ is hydrogen, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, where alkyl, alkenyl, alkoxy, alkynyl, cycloalkyl, heterocycloalkyl in the last 6 radicals mentioned are unsubstituted or have 1, 2 or 3 substituents $R^{xa}$, or aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{xd}$, $R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, O—$C_1$-$C_6$-alkyl, where alkyl, alkoxy, alkenyl, alkynyl, cycloalkyl, heterocycloalkyl in the last 10 radicals mentioned are unsubstituted or have 1, 2 or 3 substituents $R^{xa}$, aryl, O-aryl, O—$CH_2$-aryl, hetaryl, O—-$CH_2$-hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$-(hetaryl-$C_1$-$C_4$-alkyl), where aryl and hetaryl in the last 19 radicals mentioned are unsubstituted or have 1, 2 or 3 substituents $R^{xd}$, and $R^{x3}$ is H, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, where alkyl, alkenyl, alkoxy, alkynyl, cycloalkyl, heterocycloalkyl in the last 6 radicals mentioned are unsubstituted or have 1, 2 or 3 substituents $R^{xa}$, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{xd}$, or the two radicals $R^{x2}$ and $R^{x3}$ form together with the N atom a 3 to 7-membered nitrogen heterocycle which may optionally have 1, 2 or 3 further different or identical heteroatoms from the group of 0, N, S as ring members, and which may have 1, 2 or 3 substituents $R^{xb}$, $R^{x4}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, where alkyl, alkenyl, alkoxy, alkynyl, cycloalkyl, heterocycloalkyl in the last 9 radicals mentioned are unsubstituted or have 1, 2 or 3 substituents $R^{xa}$, aryl, O-aryl, O—$CH_2$-aryl, hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$-

(hetaryl-$C_1$-$C_4$-alkyl), where aryl and hetaryl in the last 18 radicals mentioned are unsubstituted or have 1, 2 or 3 substituents $R^{xd}$, and where $R^{xa}$ has one of the meanings indicated for $R^{1a}$, $R^{xb}$ has one of the meanings indicated for $R^{1b}$, and $R^{xd}$ has one of the meanings indicated for $R^{1d}$;

Y is $CH_2$, $CH_2$—$CH_2$, $CH_2CH_2CH_2$, $N(R^{y\#})$—$CH_2$ or $N(R^{y\#})$—$CH_2$—$CH_2$ or, if $R^4$ is absent, a moiety $CH$=$CH$—$CH$=, where in the aforementioned moieties, 1 or 2 hydrogen atoms may be replaced by a radical $R^y$, $R^y$ is selected independently of one another from hydrogen, OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{ya}$, $C_3$-$C_7$-cycloalkyl, $C_3$-$C_7$-cycloalkyl-$C_1$-$C_4$-alkyl, $C_3$-$C_7$-cycloalkyl-O, where the cycloalkyl moiety in the last three radicals mentioned may have 1, 2, 3 or 4 $R^{yb}$ radicals, and where 1 or 2 $CH_2$-groups in the cycloalkyl moiety may be replaced by O, NH or S, aryl, hetaryl, O-aryl, $CH_2$-aryl, O—$CH_2$-aryl, where the last 4 radicals mentioned are unsubstituted in the aryl moiety or may carry 1, 2, 3 or 4 radicals $R^{yd}$, $COOR^{y1}$, $CONR^{y2}R^{y3}$, $SO_2NR^{y2}R^{y3}$, —NH—$SO_2$—$R^{y4}$, NH—CO—$R^{y5}$, $SO_2$—$R^{y4}$, —$(CH_2)_p$—$NR^{y6}R^{y7}$ with p=0, 1, 2, 3, 4, 5 or 6 and O—$(CH_2)_q$—$NR^{y6}R^{y7}$ with q=2, 3, 4, 5 or 6;

where $R^{ya}$ has one of the meanings indicated for $R^{1a}$,
$R^{yb}$ has one of the meanings indicated for $R^{1b}$,
$R^{yd}$ has one of the meanings indicated for $R^{1d}$,
$R^{y1}$ has one of the meanings indicated for $R^{c1}$,
$R^{y2}$ has one of the meanings indicated for $R^{c2}$,
$R^{y3}$ has one of the meanings indicated for $R^{c3}$,
$R^{y4}$ has one of the meanings indicated for $R^{c4}$,
$R^{y5}$ has one of the meanings indicated for $R^{c5}$,
$R^{y6}$ has one of the meanings indicated for $R^{c6}$, and
$R^{y7}$ has one of the meanings indicated for $R^{c7}$;

$R^{y\#}$ is selected independently of one another from hydrogen, $NH_2$, CN, $CF_3$, $CHF_2$, $CH_2F$, O—$CF_3$, O—$CHF_2$, O—$CH_2F$, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{ya}$, $C_3$-$C_7$-cycloalkyl, $C_3$-$C_7$-cycloalkyl-$C_1$-$C_4$-alkyl, $C_3$-$C_7$-cycloalkyl-O, where the cycloalkyl moiety in the last three radicals mentioned may have 1, 2, 3 or 4 $R^{yb}$ radicals, and where 1 or 2 $CH_2$-groups in the cycloalkyl moiety may be replaced by O, NH or S, aryl, hetaryl, O-aryl, $CH_2$-aryl, O—$CH_2$-aryl, where the last 4 radicals mentioned are unsubstituted in the aryl moiety or may carry 1, 2, 3 or 4 radicals $R^{yd}$, $COOR^{y1}$, $CONR^{y2}R^{y3}$, $SO_2NR^{y2}R^{y3}$, —NH—$SO_2$—$R^{y4}$, NH—CO—$R^{y5}$, $SO_2$—$R^{y4}$, —$(CH_2)_p$—$NR^{y6}R^{y7}$ with p=0, 1, 2, 3, 4, 5 or 6 and O—$(CH_2)_q$—$NR^{y6}R^{y7}$ with q=2, 3, 4, 5 or 6;

or a tautomer thereof or a pharmaceutically acceptable salt thereof.

2. The carboxamide compound of claim 1, in which $R^1$ is selected from:

$C_3$-$C_{10}$-alkyl which is unsubstituted or may be partly or completely halogenated and/or have substituents $R^{1a}$, phenyl-$C_1$-$C_4$-alkyl and hetaryl-$C_1$-$C_4$-alkyl, where phenyl and hetaryl in the last 2 radicals mentioned may be unsubstituted or carry 1, 2, 3 or 4 identical or different radicals $R^{1c}$.

3. The carboxamide compound of claim 1, in which X in the formula I is a C(=O)—$NR^{x2}R^{x3}$ radical in which $R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$, and $R^{x3}$ is H, $C_1$-$C_6$-alkyl, $C_1$-$C_6$-haloalkyl or $C_1$-$C_6$-alkyl which has 1, 2 or 3 substituents $R^{xa}$, or $NR^{x2}R^{x3}$ is a nitrogen heterocycle of the following formulae:

in which $R^{x5}$ is hydrogen or has the meaning indicated in claim 1 for $R^{xb}$.

4. The carboxamide compound as claimed in claim 3, in which X is C(O)—$NH_2$.

5. The carboxamide compound of claim 3, in which X is C(O)—$NHR^{x2}$, where $R^{x2}$ is CN, $C_1$-$C_6$-alkyl, $C_1$-$C_6$-haloalkyl, $C_1$-$C_6$-alkyl which has 1, 2 or 3 substituents $R^{xa}$, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$.

6. The carboxamide compound of claim 5, in which $R^{x2}$ is $C_1$-$C_4$-alkyl, $C_3$-$C_6$-cycloalkyl, phenyl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$ and hetaryl is a 5- or 6-membered heteroaromatic radical which has as ring members 1 or 2 heteroatoms selected from O, S and N.

7. The carboxamide compound of claim 1, in which $R^{3a}$ and $R^{3b}$ are hydroxy or together with the carbon atom to which they are bonded are C=O.

8. The carboxamide compound of claim 1, wherein $R^4$ is hydrogen.

9. The carboxamide compound of claim 8, wherein the carbon atom, which carries the radical $R^4$ has predominantly R-configuration.

10. The carboxamide compound of claim 1, which corresponds to the formula I-A, $$\text{(I-A)}$$

in which X, Q, $R^1$, $R^2$, $R^{3a}$, $R^{3b}$ and $R^y$ have the aforementioned meanings, n is 0, 1 or 2, q is 2 or 3, and the asterisk (*) indicates a center of chirality, the tautomers thereof and the pharmaceutically suitable salts thereof.

11. The carboxamide compound as claimed in claim 10, wherein q is 2.

12. The carboxamide compound of claim 1, which corresponds to the formula I-B, $$\text{(I-B)}$$

in which X, Q, $R^1$, $R^2$, $R^{3a}$, $R^{3b}$, $R^y$ and $R^{y\#}$ have the aforementioned meanings, n is 0, 1 or 2, s is 1 or 2, and the asterisk (*) indicates a center of chirality, the tautomers thereof and or a tautomer thereof or a pharmaceutically acceptable salt thereof.

13. The carboxamide compound as claimed of claim 10, wherein the carbon atom indicated with an asterisk has predominantly R-configuration.

14. The carboxamide compound of claim 1, which corresponds to the formula I-C, $$\text{(I-C)}$$

in which X, Q, $R^1$, $R^2$, $R^{3a}$, $R^{3b}$ and $R^y$ have the aforementioned meanings, n is 0, 1 or 2, or a tautomer thereof or a pharmaceutically acceptable salt thereof.

15. The carboxamide compound of claim 10, in which Q is $CH_2$.

16. The carboxamide compound of claim 10, in which Q is $CH_2CH_2$.

17. The carboxamide compound of claim 10, in which $R^1$ is selected from:

$C_3$-$C_{10}$-alkyl which is unsubstituted or may be partly or completely halogenated and/or have 1, 2 or 3 substituents $R^{1a}$, phenyl-$C_1$-$C_4$-alkyl and hetaryl-$C_1$-$C_4$-alkyl, where phenyl and hetaryl in the last 2 radicals mentioned may be unsubstituted or carry 1, 2, 3 or 4 identical or different radicals $R^{1c}$.

18. The carboxamide compound of claim 10, in which X is $C(O)$—$NHR^{x2}$, where $R^{x2}$ is hydrogen, CN, $C_1$-$C_6$-alkyl, $C_1$-$C_6$-haloalkyl, $C_1$-$C_6$-alkyl which has 1, 2 or 3 substituents $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$.

19. The carboxamide compound of claim 10, in which $R^{3a}$ and $R^{3b}$ are hydroxy or together with the carbon atom to which they are bonded are C=O.

20. The carboxamide compound of claim 1, which are selected from the group consisting of N-(4-amino-3,4-dioxo-1-phenylbutan-2-yl)-1-benzyl-5-oxopyrrolidine-2-carboxamide, N-(4-amino-3,4-dioxo-1-phenylbutan-2-yl)-1-(3-chlorobenzyl)-5-oxopyrrolidine-2-carboxamide, N-(4-amino-3,4-dioxo-1-phenylbutan-2-yl)-1-(4-fluorobenzyl)-5-oxopyrrolidine-2-carboxamide, N-(4-amino-3,4-dioxo-1-phenylbutan-2-yl)-1-(3-methoxybenzyl)-5-oxopyrrolidine-2-carboxamide, N-(4-amino-3,4-dioxo-1-phenylbutan-2-yl)-1-(3-trifluoromethyl-benzyl)-5-oxopyrrolidine-2-carboxamide, N-(4-amino-3,4-dioxo-1-phenylbutan-2-yl)-1-(3-fluorobenzyl)-5-oxopyrrolidine-2-carboxamide, N-(4-amino-3,4-dioxo-1-phenylbutan-2-yl)-5-oxo-1-[2-(trifluoromethoxy)benzyl]pyrrolidine-2-carboxamide, N-(4-amino-3,4-dioxo-1-phenylbutan-2-yl)-5-oxo-1-[3-(trifluoromethoxy)benzyl]pyrrolidine-2-carboxamide, N-(4-amino-3,4-dioxo-1-phenylbutan-2-yl)-1-benzyl-6-oxopiperidine-2-carboxamide, N-(4-amino-3,4-dioxo-1-phenylbutan-2-yl)-1-(3-cyanobenzyl)-5-oxopyrrolidine-2-carboxamide, N-(4-amino-3,4-dioxo-1-phenylbutan-2-yl)-5-oxo-1-[2-(trifluoromethyl)benzyl]pyrrolidine-2-carboxamide, N-(4-amino-3,4-dioxo-1-phenylbutan-2-yl)-1-benzyl-4-methyl-5-oxopyrrolidine-2-carboxamide, 1-benzyl-N-{3,4-dioxo-1-phenyl-4-[(pyridin-2-ylmethyl)amino]butan-2-yl}-5-oxopyrrolidine-2-carboxamide, 1-benzyl-N-[4-(ethylamino)-3,4-dioxo-1-phenylbutan-2-yl]-5-oxopyrrolidine-2-carboxamide, N-(4-amino-3,4-dioxo-1-phenylbutan-2-yl)-1-(3,5-dimethoxybenzyl)-5-oxopyrrolidine-2-carboxamide, N-(4-amino-3,4-dioxo-1-phenylbutan-2-yl)-1-(3,5-difluorobenzyl)-5-oxopyrrolidine-2-carboxamide, 1-benzyl-N-(4-(methylamino)-3,4-dioxo-1-phenylbutan-2-yl)-5-oxopyrrolidine-2-carboxamide, 1-benzyl-N-(3,4-dioxo-1-phenyl-4-(propylamino)butan-2-yl)-5-oxopyrrolidine-2-carboxamide, 1-benzyl-N-(4-(cyclopropylamino)-3,4-dioxo-1-phenylbutan-2-yl)-5-oxopyrrolidine-2-carboxamide, 1-benzyl-N-(4-(isobutylamino)-3,4-dioxo-1-phenylbutan-2-yl)-5-oxopyrrolidine-2-carboxamide, 1-benzyl-N-(4-(cyclobutylamino)-3,4-dioxo-1-phenylbutan-2-yl)-5-oxopyrrolidine-2-carboxamide, 1-benzyl-N-(4-(methoxyamino)-3,4-dioxo-1-phenylbutan-2-yl)-5-oxopyrrolidine-2-carboxamide, 1-benzyl-N-(3,4-dioxo-1-phenyl-4-(2-(pyridin-2-yl)ethylamino)butan-2-yl)-5-oxopyrrolidine-2-carboxamide, 1-benzyl-N-(3,4-dioxo-1-phenyl-4-(3-(pyridin-2-yl)propylamino)butan-2-yl)-5-oxopyrrolidine-2-carboxamide, 1-benzyl-N-(3,4-dioxo-1-phenyl-4-(3-phenylpropylamino)butan-2-yl)-5-oxopyrrolidine-2-carboxamide,
1-benzyl-N-(4-(ethyl(methyl)amino)-3,4-dioxo-1-phenylbutan-2-yl)-5-oxopyrrolidine-2-carboxamide,
1-benzyl-N-(4-(2-chlorobenzylamino)-3,4-dioxo-1-phenylbutan-2-yl)-5-oxopyrrolidine-2-carboxamide,
N-(4-(cyclopropylamino)-3,4-dioxo-1-phenylbutan-2-yl)-5-oxo-1-(2-(trifluoromethyl)benzyl)pyrrolidine-2-carboxamide,
N-(4-(ethylamino)-3,4-dioxo-1-phenylbutan-2-yl)-5-oxo-1-(2-(trifluoromethyl)benzyl)pyrrolidine-2-carboxamide,
N-(4-(benzylamino)-3,4-dioxo-1-phenylbutan-2-yl)-5-oxo-1-(2-(trifluoromethyl)benzyl)pyrrolidine-2-carboxamide,
N-(4-(isopropylamino)-3,4-dioxo-1-phenylbutan-2-yl)-5-oxo-1-(2-(trifluoromethyl)benzyl)pyrrolidine-2-carboxamide,
N-(3,4-dioxo-1-phenyl-4-(2-(pyridin-2-yl)ethylamino)butan-2-yl)-5-oxo-1-(2-(trifluoromethyl)benzyl)pyrrolidine-2-carboxamide,
N-(3,4-dioxo-1-phenyl-4-(3-(pyridin-2-yl)propylamino)butan-2-yl)-5-oxo-1-(2-(trifluoromethyl)benzyl)pyrrolidine-2-carboxamide,
N-(4-(ethylamino)-3,4-dioxo-1-phenylbutan-2-yl)-1-(2-methoxy-6-(trifluoromethyl)benzyl)-5-oxopyrrolidine-2-carboxamide,
N-(3,4-dioxo-1-phenyl-4-(pyridin-2-ylmethylamino)butan-2-yl)-1-(2-methoxy-6-(trifluoromethyl)benzyl)-5-oxopyrrolidine-2-carboxamide,
N-(4-(benzylamino)-3,4-dioxo-1-phenylbutan-2-yl)-1-(2-methoxy-6-(trifluoromethyl)benzyl)-5-oxopyrrolidine-2-carboxamide,
N-(3,4-dioxo-1-phenyl-4-(2-(pyridin-2-yl)ethylamino)butan-2-yl)-5-oxo-1-(2-(trifluoromethoxy)benzyl)pyrrolidine-2-carboxamide,
1-(2-chlorobenzyl)-N-(4-(cyclopropylamino)-3,4-dioxo-1-phenylbutan-2-yl)-5-oxopyrrolidine-2-carboxamide,
1-(2-chlorobenzyl)-N-(4-(ethylamino)-3,4-dioxo-1-phenylbutan-2-yl)-5-oxopyrrolidine-2-carboxamide,
N-(4-(cyclopropylamino)-3,4-dioxo-1-phenylbutan-2-yl)-1-(2,6-difluorobenzyl)-5-oxopyrrolidine-2-carboxamide,
1-(2,6-difluorobenzyl)-N-(4-(ethylamino)-3,4-dioxo-1-phenylbutan-2-yl)-5-oxopyrrolidine-2-carboxamide,
N-(4-amino-3,4-dioxo-1-phenylbutan-2-yl)-5-oxo-1-[2-methoxy-6-(trifluoromethyl)benzyl]pyrrolidine-2-carboxamide,
N-(4-amino-3,4-dioxo-1-phenylbutan-2-yl)-5-oxo-1-(2,6-difluorobenzyl)pyrrolidine-2-carboxamide and,
1-benzyl-N-(3,4-dioxo-1-phenyl-4-(2-phenylethylamino)butan-2-yl)-5-oxopyrrolidine-2-carboxamide,
or a tautomer thereof or a pharmaceutically acceptable salt thereof.

21. The carboxamide compound of claim 1, which are selected from the group consisting of
1-benzyl-N-(3,4-dioxo-1-phenyl-4-(thiazol-5-ylmethylamino)butan-2-yl)-5-oxopyrrolidine-2-carboxamide,
N-(4-(benzo[d]thiazol-2-ylmethylamino)-3,4-dioxo-1-phenylbutan-2-yl)-1-benzyl-5-oxopyrrolidine-2-carboxamide,
1-benzyl-N-(4-morpholino-3,4-dioxo-1-phenylbutan-2-yl)-5-oxopyrrolidine-2-carboxamide,
N-(4-(ethylamino)-3,4-dioxo-1-phenylbutan-2-yl)-5-oxo-1-(4-(trifluoromethyl)benzyl)pyrrolidine-2-carboxamide,
1-benzyl-N-(4-(cyclohexylamino)-3,4-dioxo-1-phenylbutan-2-yl)-5-oxopyrrolidine-2-carboxamide,
N-(4-(2-benzoylhydrazinyl)-3,4-dioxo-1-phenylbutan-2-yl)-1-benzyl-5-oxopyrrolidine-2-carboxamide,
N-(4-(cyclopropylamino)-3,4-dioxo-1-phenylbutan-2-yl)-5-oxo-1-(4-(trifluoromethyl)benzyl)pyrrolidine-2-carboxamide,
1-benzyl-N-(3,4-dioxo-1-phenyl-4-(thiazol-2-ylmethylamino)butan-2-yl)-5-oxopyrrolidine-2-carboxamide,
1-benzyl-N-(3,4-dioxo-1-phenyl-4-(thiophen-2-ylmethylamino)butan-2-yl)-5-oxopyrrolidine-2-carboxamide,
N-(4-(cyclopropylamino)-3,4-dioxo-1-phenylbutan-2-yl)-1-(2,6-dichlorobenzyl)-5-oxopyrrolidine-2-carboxamide,
1-(2,6-dichlorobenzyl)-N-(4-(ethylamino)-3,4-dioxo-1-phenylbutan-2-yl)-5-oxopyrrolidine-2-carboxamide,
1-benzyl-N-(3,4-dioxo-1-phenyl-4-(pyridin-4-ylmethylamino)butan-2-yl)-5-oxopyrrolidine-2-carboxamide,
1-benzyl-N-(4-(oxazol-2-ylmethylamino)-3,4-dioxo-1-phenylbutan-2-yl)-5-oxopyrrolidine-2-carboxamide,
1-benzyl-N-(3,4-dioxo-1-phenyl-4-(phenylamino)butan-2-yl)-5-oxopyrrolidine-2-carboxamide,
N-(4-(benzo[d][1,3]dioxol-5-ylmethylamino)-3,4-dioxo-1-phenylbutan-2-yl)-1-benzyl-5-oxopyrrolidine-2-carboxamide,
1-benzyl-N-(4-(4-fluorobenzylamino)-3,4-dioxo-1-phenylbutan-2-yl)-5-oxopyrrolidine-2-carboxamide,
1-benzyl-N-(3,4-dioxo-1-phenyl-4-(4-(trifluoromethyl)benzylamino)butan-2-yl)-5-oxopyrrolidine-2-carboxamide,
1-benzyl-N-(3,4-dioxo-1-phenyl-4-(((R)-tetrahydrofuran-2-yl)methylamino)butan-2-yl)-5-oxopyrrolidine-2-carboxamide,
1-benzyl-N-(3,4-dioxo-1-phenyl-4-(((S)-tetrahydrofuran-2-yl)methylamino)butan-2-yl)-5-oxopyrrolidine-2-carboxamide,
1-benzyl-N-(3,4-dioxo-1-phenyl-4-(2-(thiophen-3-yl)ethylamino)butan-2-yl)-5-oxopyrrolidine-2-carboxamide,
1-benzyl-N-(4-(furan-2-ylmethylamino)-3,4-dioxo-1-phenylbutan-2-yl)-5-oxopyrrolidine-2-carboxamide,
1-benzyl-N-(4-(2-benzylhydrazinyl)-3,4-dioxo-1-phenylbutan-2-yl)-5-oxopyrrolidine-2-carboxamide and,
N-(4-(cyclopropylamino)-3,4-dioxo-1-phenylbutan-2-yl)-1-(2-methoxy-6-(trifluoromethyl)benzyl)-5-oxopyrrolidine-2-carboxamide
or a tautomer thereof or a pharmaceutically acceptable salt thereof.

* * * * *